(12) United States Patent
Serino et al.

(10) Patent No.: US 9,511,130 B2
(45) Date of Patent: Dec. 6, 2016

(54) ESCHERICHIA COLI VACCINE COMBINATION

(75) Inventors: Laura Serino, Siena (IT); Mariagrazia Pizza, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 34 days.

(21) Appl. No.: 14/344,892

(22) PCT Filed: Sep. 14, 2012

(86) PCT No.: PCT/IB2012/054825
§ 371 (c)(1),
(2), (4) Date: Nov. 10, 2014

(87) PCT Pub. No.: WO2013/038385
PCT Pub. Date: Mar. 21, 2013

(65) Prior Publication Data
US 2015/0118261 A1   Apr. 30, 2015

(30) Foreign Application Priority Data

Sep. 14, 2011 (GB) .................................. 1115906.8
Jul. 25, 2012 (GB) .................................. 1213251.0

(51) Int. Cl.
| A61K 39/108 | (2006.01) |
| C07K 14/245 | (2006.01) |
| A61K 39/00 | (2006.01) |

(52) U.S. Cl.
CPC ......... *A61K 39/0258* (2013.01); *C07K 14/245* (2013.01); *A61K 2039/54* (2013.01); *A61K 2039/541* (2013.01); *A61K 2039/542* (2013.01); *A61K 2039/543* (2013.01); *A61K 2039/55516* (2013.01); *A61K 2039/55544* (2013.01)

(58) Field of Classification Search
CPC ............ A61K 39/0258; A61K 2039/54; A61K 2039/55544; A61K 2039/542; A61K 2039/543; A61K 2039/55516; A61K 2039/541; C07K 14/245
See application file for complete search history.

(56) References Cited

U.S. PATENT DOCUMENTS

| 5,057,540 | A | 10/1991 | Kensil et al. |
| 5,916,588 | A | 6/1999 | Popescu et al. |
| 6,090,406 | A | 7/2000 | Popescu et al. |
| 6,207,646 | B1 | 3/2001 | Krieg et al. |
| 6,239,116 | B1 | 5/2001 | Krieg et al. |
| 6,429,199 | B1 | 8/2002 | Krieg et al. |

FOREIGN PATENT DOCUMENTS

| EP | 0626169 A2 | 11/1994 |
| EP | 0735898 A1 | 10/1996 |
| EP | 0761231 A1 | 3/1997 |
| EP | 0835318 A2 | 4/1998 |
| WO | 90/14837 A1 | 12/1990 |
| WO | 94/00153 A1 | 1/1994 |
| WO | 98/40100 A1 | 9/1998 |
| WO | 98/57659 A1 | 12/1998 |
| WO | 99/11241 A1 | 3/1999 |
| WO | 99/27960 A1 | 6/1999 |
| WO | 99/40936 A2 | 8/1999 |
| WO | 99/44636 A2 | 9/1999 |
| WO | 99/52549 A1 | 10/1999 |
| WO | 02/081653 A2 | 10/2002 |
| WO | 03/024480 A2 | 3/2003 |
| WO | 03/024481 A2 | 3/2003 |
| WO | 2005/103073 A2 | 11/2005 |
| WO | 2006/089264 A2 | 8/2006 |
| WO | 2006/091517 A2 | 8/2006 |
| WO | 2009/104092 A2 | 8/2009 |
| WO | 2011/004263 A2 | 1/2011 |
| WO | 2011/007257 A1 | 1/2011 |
| WO | 2011/080595 A2 | 7/2011 |

OTHER PUBLICATIONS

Search Report received for Great Britain Patent Application No. 1115906.8, mailed on Jan. 11, 2012, 2 pages.
International Preliminary Report on Patentability received for PCT Patent Application No. PCT/IB2012/054825, mailed on Mar. 27, 2014, 13 pages.
International Search Report and Written Opinion received for PCT Patent Application No. PCT/IB2012/054825, mailed on Apr. 5, 2013, 18 pages.
Andrianov et al., "Preparation of Hydrogel Microspheres by Coacervation of Aqueous Polyphosphazene Solutions", Biomaterials, vol. 19, No. 1-3, Jan. 1998, pp. 109-115.
Andrianov at al., "Protein Release from Polyphosphazene Matrices", Advanced Drug Delivery Reviews, vol. 31, No. 3, May 1998, pp. 185-196.
Beignon et al., "The LTR72 Mutant of Heat-Labile Enterotoxin of *Escherichia coli* Enhances the Ability of Peptide Antigens to Elicit CD4+ T Cells and Secrete Gamma Interferon after Coapplication onto Bare Skin", Infection and Immunity, vol. 70, No. 6, Jun. 2002, pp. 3012-3019.
Durant et al., "Identification of Candidates for a Subunit Vaccine against Extraintestinal Pathogenic *Escherichia coli*", Infection and Immunity. vol. 75, No. 4, Apr. 2007, pp. 1916-1925.
Evans et al., "Enhancement of Antigen-Specific immunity via the TLR4 Ligands MPL™ Adjuvant and Ribi.529", Expert Review of Vaccines, vol. 2, No. 2, Apr. 2003, pp. 219-229.
Gerber et al., "Human Papillomavirus Virus-Like Particles are Efficient Oral Immunogens when Coadministered with *Escherichia coli* Heat-Labiie Enterotoxin Mutant R192G or CpG DNA", Journal of Virology, vol. 75, No. 10, May 2001, pp. 4752-4760.
Glück et al., "New Technology Platforms in the Development of Vaccines for the Future", Vaccine, vol. 20, Suppl. 5, Dec. 20, 2002, pp. B10-B16.

(Continued)

Primary Examiner — Padma V Baskar
(74) Attorney, Agent, or Firm — Morrison & Foerster LLP

(57) ABSTRACT

The invention provides an immunogenic composition comprising a combination of (i) bacterial Ig-like domain protein fragment (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto.

7 Claims, 15 Drawing Sheets

(56) References Cited

OTHER PUBLICATIONS

Ibba, Michael, "Strategies for in Vitro and in Vivo Translation with Non-natural Amino Acids", Biotechnology and Genetic Engineering Reviews, vol. 13, Dec. 1995, pp. 197-216.

Johnson et al., "Synthesis and Biological Evaluation of a New Class of Vaccine Adjuvants: Aminoalkyl Glucosaminide 4-Phosphates (AGPs)", Bioorganic & Medicinal Chemistry Letters, vol. 9, No. 15, Aug. 1999, pp. 2273-2278.

Jones, Taff, "Resiquimod 3M (PMID:12669385)", Current Opinion in Investigational Drugs, vol. 4, No. 2, Feb. 2003, pp. 214-218.

Krieg, Arthur M., "CpG Motifs: The Active Ingredient in Bacterial Extracts?", Nature Medicine, vol. 9, 2003, pp. 831-835.

Lenz et al., "Papillomavirus-Like Particles Induce Acute Activation of Dendritic Cells", The Journal of immunology, vol. 166, No. 9, 2001, pp. 5346-5355.

McCluski et al., "Parenteral and Mucosal Prime-Boost Immunization Strategies in Mice with Hepatitis B Surface Antigen and CpG DNA", FEMS Immunology and Medical Microbiology, vol. 32,. 2002, pp. 179-185.

Mellmann et al., "Prospective Genomic Characterization of the German Enterohemorrhagic *Escherichia coli* O104:H4 Outbreak by Rapid Next Generation Sequencing Technology", PLoS One, vol. 6, No. 7, e22751, Jul. 2011, pp. 1-9.

Meraldi et al., "OM-174, a New Adjuvant with a Potential for Human Use, Induces a Protective Response when Administered with the Synthetic C-Terminal Fragment 242-310 from the Circumsporozoite Protein of Plasmodium Berghei", Vaccine, vol. 21, No. 19-20, Jun. 2, 2003, pp. 2485-2491.

Moriel et al., "Identification of Protective and Broadly Conserved Vaccine Antigens from the Genome of Extraintestinal Pathogenic *Escherichia coli*", Proceedings of the National Academy of Sciences of the United States of America, vol. 107, No. 20, May 18, 2010, pp. 9072-9077.

Niikura et al., "Chimeric Recombinant Hepatitis E Virus-like Particles as an Oral Vaccine Vehicle Presenting Foreign Epitopes", Virology, vol. 293, 2002, pp. 273-280.

O'Hagan, Derek T., "Vaccine Adjuvants: Preparation Methods and Research Protocols", Methods in Molecular Medicine, vol. 42, 2000, 353 pages.

Pajak et al., "The Adjuvant OM-174 Induces both the Migration and Maturation of Murine Dendritic Cells in Vivo", Vaccine, vol. 21, No, 9-10, Feb. 14, 2003, pp. 836-842.

Partidos et al., "Heat-Labile Enterotoxin of *Escherichia coli* and Its Site-Directed Mutant LTK63 Enhance the Proliferative and Cytotoxic T-Cell Responses to Intranasally Co-Immunized Synthetic Peptides", Immunology Letters, vol. 67, No. 3, Apr. 1999, pp. 209-216.

Peppoloni et al., "Mutants of the *Escherichia coli* Heat-Labile Enterotoxin as Safe and Strong Adjuvants for Intranasal Delivery of Vaccines", Expert Review of Vaccines, vol. 2, No. 2, Apr. 2003, pp. 285-293.

Pine et al., "Intranasal Immunization with Influenza Vaccine and a Detoxified Mutant of Heat Labile Enterotoxin from *Escherichia coli* (LTK63)", Journal of Controlled Release, vol. 85, No. 1, Dec. 2002, pp. 263-270.

Pinto et al., "Cellular Immune Responses to Human Papilomavirus (HPV)—16 L1 in Healthy Valunteers Immunized with Recombinant HPV-16 L1 Virus-Like Particles", The Journal of Infectious Deseases, vol. 188, No. 2, Jul. 15, 2003, pp. 327-338.

Pizza et al., "LTK63 and LTR72, Two Mucosal Adjuvants Ready for Clinical Trials", International Journal of Medical Microbiology, vol. 295, No, 4-5, Oct. 2000, pp. 455-461.

Pizza et al., "Mucosal Vaccines: Non Toxic Derivatives of LT and CT as Mucosal Adjuvants", Vaccine, vol. 19, No. 17-19,, Mar. 2001, pp. 2534-2541.

Podda at al., "MF59-Adjuvanted Vaccines: Increased Immunogenicity with an Optimal Safety Profile", Expert Review of Vaccines, vol. 2, No. 2, Apr. 2003, pp. 197-204.

Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells", Infection and Immunity, vol. 67, No. 12, Dec. 1999, pp. 6270-6280.

Scharton-Kersten et al., "Transcutaneous Immunization with Bacterial ADP-Ribosylating Exotoxins, Subunits, and Unrelated Adjuvants", Infection and Immunity, vol. 68, No. 9, Sep. 2000, pp. 5306-5313.

Schellack et al,, "IC31, A Novel Adjuvant Signaling via TLR9, Induces Potent Cellular and Humoral Immune Responses", Vaccine, vol. 24, No. 26, Jun. 2006, pp. 5461-5472.

Singh at al., "A Novel Bioadhesive Intranasal Delivery System for Inactivated Influenza Vaccines", Journal of Controlled Release, vol. 70, No, 3, Feb. 2001, pp. 267-276.

Stanley, M. A., "Imiquirnod and the lmidazoquinolones: Mechanism of Action and Therapeutic Potential", Clinical and Experimental Dermatology, vol. 27, No. 7, Oct. 2002, pp. 571-577.

Welch et al., "Extensive Mosaic Structure Revealed by the Complete Genome Sequence of Uropathogenic *Escherichia coli*", PNAS, vol. 99, No. 26, 2002, pp, 17020-17024.

Podda, Audino, "The Adjuvanted Influenza Vaccines with Novel Adjuvants: Experience with the MF59-Adjuvanted Vaccine", Vaccine, vol. 19, 2001, pp. 2673-2680.

Male et al., "Introduction to the Immune System", Immunology, Seventh Edition, 2006, 4 pages.

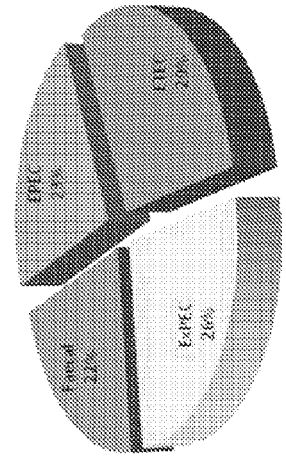
Fig. 2(a)
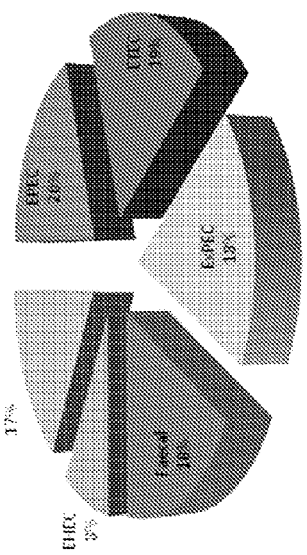
Fig. 2(b)
Fig. 2(c)

| Sample | MW (kDa) | Conc (µM) | Buffer | Batch | Zinc content (mol %) |
|---|---|---|---|---|---|
| ΔG3526TL | 164 | 4.3 | 10mM KH$_2$PO$_4$, 150mM NaCl | ExPEC_102 | 70 |
| ΔG3526 his | 165 | 3 | PBS+ 40% glycerol | ExPEC_115 | 68 |
| 3526 A his | 81 | 4.9 | PBS | ExPEC_092 | 33 |
| 3526 B his | 86 | 4.4 | PBS+ 40% glycerol | ExPEC_086 | 5 |
| ΔG3526 C his | 140 | 3.2 | PBS | ExPEC_112 | 18 |
| ΔG3526E1305-his | 165 | 3.3 | PBS+ 40% glycerol | ExPEC_099 | 43 |
| ΔG3526TL3M | 164 | 3.1 | 10mM KH$_2$PO$_4$, 150mM NaCl | ExPEC_117 | 8 |

ESCHERICHIA COLI VACCINE COMBINATION

CROSS REFERENCE TO RELATED APPLICATIONS

This application is a U.S. National Phase patent application of PCT/IB2012/054825, filed Sep. 14, 2012, which claims priority to United Kingdom patent No. 1115906.8, filed Sep. 14, 2011, and United Kingdom patent No. 1213251.0, filed Jul. 25, 2012, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 529552004800SubSequenceListing.txt, date recorded: Oct. 30, 2014, size: 225 KB).

TECHNICAL FIELD

The present invention relates generally to the field of immunisation against _E. coli_ and _E. coli_ vaccines. More specifically, the invention relates to combinations of polypeptides useful in the preparation of prophylactic and therapeutic vaccine combinations for use in immunisation against pathogenic _E. coli_ pathotypes. In particular, it relates to a vaccine useful in protecting humans against a broad spectrum of _E. coli_ strains.

BACKGROUND TO THE INVENTION

Several publications and patent documents are referenced in this application in order to describe more fully the state of the art to which this invention pertains. The disclosure of each of these publications is incorporated herein by reference.

_Escherichia coli_ is a common colonizer of the human gastrointestinal tract and although _E. coli_ strains are largely regarded as commensal, some isolates have the potential to cause diseases. Two distinct pathogenic categories of _E. coli_ are recognized depending on whether they cause intestinal or extraintestinal infections. The extraintestinal pathogenic _E. coli_ (ExPEC) group includes human pathogenic strains causing urinary tract infections (UPEC), neonatal meningitis (NMEC) and septicemia. Other ExPEC strains are instead pathogenic for avian species (APEC). The intestinal pathogenic _E. coli_ (InPEC) group includes many pathotypes such as enterotoxigenic (ETEC), enteropathogenic (EPEC), enterohemorrhagic (EHEC), enteroinvasive, adherent invasive, and diffusely adherent _E. coli_, all causing infections to the human intestinal tract. These pathogenic strains of _Escherichia coli_ are the most common cause of bacterial infections presenting a recurrent global threat that kills over two million of people in the world every year.

Vaccination would undoubtedly be the most cost-effective preventive measure against morbidity and death from pathogenic _E. coli_ strains. However, primary studies have focused attention on the identification of candidates for use in vaccines protective against individual pathogenic categories, for example against UPEC alone or NMEC alone. In an earlier publication based on a comparative genome analysis and using the complete genome sequences of three ExPEC strains (IHE3034, CFT073 and 536), the Inventors identified nine potential vaccine candidates able to confer protection from sepsis (PNAS 2010; 107:20, p 9072-9077).

Whilst vaccines for use against individual diseases or illnesses are useful, it would be desirable to provide broad spectrum vaccines that provide protective immunity in animals, particularly humans, against all, or a large number, of infections caused by _E. coli_. For example, once vaccinated an individual could be covered or protected against all, or a high percentage, of the different diseases that _E. coli_ can cause. A broadly protective vaccine would be of further benefit due to the spread of antibiotic resistant bacteria (CTX-M β-lactamase and carbepenemases) in hospitals and communities as a whole. However, the development of such a 'universal' or 'pan _E. coli_' vaccine is challenging because of the need to selectively prevent against subtypes of _E. coli_ strains that are not normally part of the commensal flora. There is thus a need for improved _E. coli_ vaccines, including a need to move away from crude cell lysates and towards better-defined molecules, and a need to identify antigens that are suitable for inclusion in a 'universal' vaccine, particularly antigens that are prevalent among clinically relevant strains without also being found in commensal strains.

In addition, a needle-free or mucosally administered vaccine would be preferable for reasons of improved patient comfort and ease of administration, as well as reducing the risk of contamination and other adverse effects while promoting patient compliance and increasing the safety of vaccination.

The present Inventors have discovered a combination of antigens suitable for use in the preparation of a broad spectrum vaccine against pathogenic _E. coli_. Surprisingly, the vaccine combination provides protection against disease/illness caused by pathogenic strains of _E. coli_ from both ExPEC and InPEC groups.

BRIEF DESCRIPTION OF THE INVENTION

In a first aspect, the invention provides an immunogenic composition comprising a combination of (i) bacterial Ig-like domain protein fragment (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto.

In certain embodiments the immunogenic compositions further comprise (iii) upec1232 having the amino acid sequence set forth in SEQ ID NO:4 or a protein having at least 80% similarity thereto.

In further embodiments the immunogenic compositions further comprise (iv) gspK (orf3515) having the amino acid sequence set forth in SEQ ID NO:30 or a protein having at least 80% similarity thereto.

In other embodiments the immunogenic compositions further comprise at least one bacterial toxin. Particularly, the bacterial toxin is an _Escherichia coli_ toxin. More particularly, the bacterial toxin is modified heat-labile toxin of _Escherichia coli_ (LTK63), yet more particularly detoxified heat-labile toxin of _Escherichia coli_ (LTK63).

Protein components of the compositions of the invention may be fragments of the proteins or amino acid sequences mentioned herein.

In certain embodiments, the putative Lipoprotein (orf3526) utilised in the immunogenic compositions is a mutant protein wherein at least one amino acid (e.g., 1, 2, 3, 4 or 5 amino acids) at positions 1304, 1305, 1306, 1307 and/or 1308 with reference to SEQ ID 8 is/are substituted by another amino acid. In certain embodiments, the putative Lipoprotein (orf3526) is a mutant orf3526 protein wherein the zinc binding activity is reduced by at least 50% relative to wild-type orf3526. In certain embodiments, the mutant has a zinc content which is at least 50% lower than the content of an equivalent amount of wild-type orf3526. The mutant polypeptides may be lipidated e.g. at an N-terminal cysteine. The mutant polypeptides may be prepared having a reduced zinc ion content or substantially free from zinc ions, relative to other variants of orf3526 polypeptide or fragments thereof, for example relative to wild-type orf3526 polypeptide. A mutant orf3526 protein having such reduced the zinc binding activity may have one or more (e.g., 2, 3, 4 or 5) of the aforementioned amino acid substitutions at positions 1304, 1305, 1306, 1307 and/or 1308. Particular mutant orf3526 proteins comprise the amino acid sequence of SEQ ID: 31, or immunogenic fragments thereof, which include mutations at positions 1304, 1305 and 1308. One such fragment includes mutations at positions 1304, 1305 and 1308 and comprises amino acid residues 24-1520, or residues 34-1520, of SEQ ID 31. The mutant polypeptides, or immunogenic fragments thereof, may be prepared having a reduced zinc ion content or substantially free from zinc ions, relative to other variants of orf3526 polypeptide or fragments thereof, for example relative to wild-type orf3526 polypeptide.

In certain embodiments, isoform B (corresponding to peak B in FIG. 9a) of orf3526, or an immunogenic fragment thereof, is preferred. One such exemplary immunogenic fragments is isoform B of a polypeptide that includes mutations at positions 1304, 1305 and 1308 and comprises amino acid residues 24-1520, or residues 34-1520, of SEQ ID 31.

In other embodiments, isoform A (corresponding to peak A in FIG. 9a) of orf3526, or an immunogenic fragment thereof, is preferred. One such exemplary immunogenic fragments is isoform A of a polypeptide that includes mutations at positions 1304, 1305 and 1308 and comprises amino acid residues 24-1520, or residues 34-1520, of SEQ ID 31.

In other embodiments, isoform C (corresponding to peak C in FIG. 9a) of orf3526, or an immunogenic fragment thereof, is preferred.

In further embodiments, a combination of at least two of isoforms A, B and C of orf3526, or immunogenic fragments thereof, is preferred. In particular, a combination of isoform A and B of orf3526, or immunogenic fragments thereof, is preferred. For example, a combination of isoforms A and B of a polypeptide that includes mutations at positions 1304, 1305 and 1308 and comprises amino acid residues 24-1520, or residues 34-1520, of SEQ ID 31, is preferred.

The immunogenic compositions of the invention may comprise one or more pharmaceutically acceptable carriers, diluents and/or adjuvants. The immunogenic compositions of the invention may comprise propane-1,2,3-triol (glycerol). The immunogenic compositions of the invention may be vaccines, or vaccine compositions.

In other aspects there is provided a method for treating or preventing E. coli infection in a mammal, which comprises administering to said mammal an effective amount of an immunogenic composition according to the invention. In certain embodiments the immunogenic composition will be administered to a mucosal surface such as nasal epithelium, oral mucosa or luminal surface of a gastrointestinal organ selected from the group consisting of: stomach, small intestine, large intestine, and rectum. Preferably, immunogenic compositions of the present invention are administered by parenteral administration.

In other aspects there is provided the use of immunogenic compositions of the invention in medicine, e.g. for treating or preventing E. coli infections in a mammal, in particular for providing broad protection against pathogenic E. coli, e.g. extraintestinal or intraintestinal pathogenic E. coli, in particular for treating or preventing infections by more than one E. coli pathotype, e.g. infections by both extraintestinal and intraintestinal pathogenic E. coli, i.e. both ExPEC and InPEC pathotypes, such as NMEC, APEC, UPEC, EHEC, AIEC, EPEC, EAEC, EIEC, ETEC and DAEC pathotypes. Thus the subject may be protected against diseases including, but not limited to peritonitis, pyelonephritis, cystitis, endocarditis, prostatitis, urinary tract infections (UTIs), meningitis (particularly neonatal meningitis), sepsis (or SIRS), dehydration, pneumonia, diarrhea (infantile, travellers', acute, persistent, etc.), bacillary dysentery, hemolytic uremic syndrome (HUS), pericarditis, bacteriuria, etc. Thus, the invention provides the use of immunogenic compositions of the invention for the manufacture of a medicament for treating or preventing E. coli infections, e.g. extraintestinal or intraintestinal pathogenic E. coli, in particular infections by more than one E. coli pathotype, e.g. infections by both extraintestinal and intraintestinal pathogenic E. coli, i.e. both ExPEC and InPEC pathotypes, such as NMEC, APEC, UPEC, EHEC, AIEC, EPEC, EAEC, EIEC, ETEC and DAEC pathotypes, or any of the aforementioned diseases.

The invention also provides orf3526 mutant polypeptides wherein at least one amino acid (e.g., 1, 2, 3, 4 or 5 amino acids) at positions 1304, 1305, 1306, 1307 and/or 1308 (numbered with reference to SEQ ID: 8) is/are substituted by another amino acid. In certain embodiments, the mutant has a zinc content which is at least 50% lower than the content of an equivalent amount of wild-type orf3526. Particular mutant orf3526 polypeptides comprise the amino acid sequence of SEQ ID: 31, or immunogenic fragments thereof which include said amino acid positions 1304, 1305 and 1308. One such fragment comprises amino acid residues 24-1520, or residues 34-1520, of SEQ ID 31. The mutant polypeptides may be lipidated e.g. at an N-terminal cysteine. The mutant polypeptides may be prepared having a reduced zinc ion content or substantially free from zinc ions, relative to other variants of orf3526 polypeptide or fragments thereof, for example relative to wild-type orf3526 polypeptide.

The invention also provides isoform B of the 3526 polypeptide (corresponding to peak B in FIG. 9a), or an immunogenic fragment thereof, obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C. In further embodiments, isoform B is of a 3526 polypeptide that includes mutations at positions 1304, 1305 and 1308 and, optionally, lacks amino acid residues 1-23, or residues 1-33, of SEQ ID 31.

The invention also provides isoform A of the 3526 polypeptide (corresponding to peak A in FIG. 9a), or an immunogenic fragment thereof, obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C. In further embodiments, isoform A is of a 3526 polypeptide that includes mutations at positions 1304, 1305 and 1308 and, optionally, lacks amino acid residues 1-23, or residues 1-33, of SEQ ID 31.

The invention also provides isoform C of the 3526 polypeptide (corresponding to peak C in FIG. 9a), or an immunogenic fragment thereof, obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B. In further embodiments, isoform C is of a 3526 polypeptide that includes mutations at positions 1304, 1305 and 1308 and, optionally, lacks amino acid residues 1-23, or residues 1-33, of SEQ ID 31.

In further embodiments, the invention provides a combination of at least two of isoforms A, B and C of orf3526, or immunogenic fragments thereof, obtainable by purification using size exclusion chromatography (e.g. CaptoQ and/or butyl sepharose chromatography) from a composition comprising recombinant 3526 polypeptide(s) of a fraction that elutes at around 16 mins for isoform A, at around 17 mins for isoform B, and around 19 mins for isoform C; or of a fraction that elutes before isoform B and/or before isoform C for isoform A, or that elutes after isoform A and/or before isoform C for isoform B, or that elutes after isoform A and/or after isoform B for isoform C. For example, a combination of isoform A and B of orf3526, or immunogenic fragments thereof, such as a combination of isoforms A and B of a polypeptide that includes mutations at positions 1304, 1305 and 1308 and comprises amino acid residues 24-1520, or residues 34-1520, of SEQ ID 31.

"Isoform C" is used as a synonym for "fragment C".

The invention also provides a protein which binds to an antibody which antibody does bind to isoform B of the 3526 polypeptide obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C, but which antibody does not bind to isoform A of the 3526 polypeptide obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C, or to isoform C of the 3526 polypeptide, obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B. In further embodiments, isoform B is of a 3526 polypeptide that includes mutations at positions 1304, 1305 and 1308 and, optionally, lacks amino acid residues 1-23, or residues 1-33, of SEQ ID 31.

The invention also provides a protein which binds to an antibody which antibody does bind to isoform A of the 3526 polypeptide obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C, but which antibody does not bind to isoform B of the 3526 polypeptide obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C, or to isoform C of the 3526 polypeptide obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B. In further embodiments, isoform B is of a 3526 polypeptide that includes mutations at positions 1304, 1305 and 1308 and, optionally, lacks amino acid residues 1-23, or residues 1-33, of SEQ ID 31.

The invention also provides a protein which binds to an antibody which antibody does bind to isoform C of the 3526 polypeptide obtainable by purification using size exclusion chromatography (e.g. CaptoQ and/or butyl sepharose chromatography) from a composition comprising recombinant 3526 polypeptide(s) of a fraction that elutes at around 19 mins, or that elutes after isoform A and/or after isoform B, but which antibody does not bind to isoform A of the 3526 polypeptide obtainable by purification using size exclusion chromatography (e.g. CaptoQ and/or butyl sepharose chromatography) from a composition comprising recombinant 3526 polypeptide(s) of a fraction that elutes at around 16 mins, or of a fraction that elutes before isoform B and/or before isoform C, or to obtainable by purification using size exclusion chromatography (e.g. CaptoQ and/or butyl sepharose chromatography) from a composition comprising recombinant 3526 polypeptide(s) of a fraction that elutes at around 17 mins, or that elutes after isoform A and/or before isoform C. In further embodiments, isoform B is of a 3526 polypeptide that includes mutations at positions 1304, 1305 and 1308 and, optionally, lacks amino acid residues 1-23, or residues 1-33, of SEQ ID 31.

Such antibodies can be prepared by screening methods known in the art (e.g. chromatography using isoforms for positive and negative selection; phage display).

The invention also provides immunogenic compositions comprising one or more of these isoforms, and their use in a method for treating or preventing *E. coli* infection, for example in a mammal.

BRIEF DESCRIPTION OF FIGURES

FIG. 2: Gene distribution analysis—Gene presence of best protective candidates was evaluated in 603 *E. coli* strains by PCR amplification and blast searches on sequenced genomes. ExPEC: APEC=Avian, UPEC=Uropathogenic, NMEC=Newborn meningitic, SEPEC=Septicaemia, pathogenic *E. coli*. EPEC=Enteropathogenic *E. coli*. ETEC=Enterotoxigenic *E. coli*. EHEC=Enterohaemorrhagic *E. coli*. Faecal *E. coli* and Other Pathovars=Lab.Strains, STEC=Toxinproducing *E. coli*, EIEC=enteroinvasive *e. coli*, AIEC=adhesive invasive *E. coli*, EAEC=enteroagregative *E. coli*. AREC=ampicillin resistant *E. coli*. orf3526 (ECOK1_3385) expression was assessed by immunoblotting analysis on supernatant fractions using polyclonal rabbit serum.

FIG. 11: Zinc content of various orf3526 derivatives was determined by atomic absorption spectroscopy. Results suggest the presence of a single zinc ion per protein molecule. The unexpected low zinc content of 3526 B his, actually containing the zinc binding motif, could be explained by misfolding of this truncated derivative, while the single amino acid exchange in the E1305 mutant apparently is not sufficient to completely abolish zinc binding (red boxes). In contrast, zinc affinity is completely lost in the TL3M triple mutant.

DETAILED DESCRIPTION OF THE INVENTION

Figure 1A:
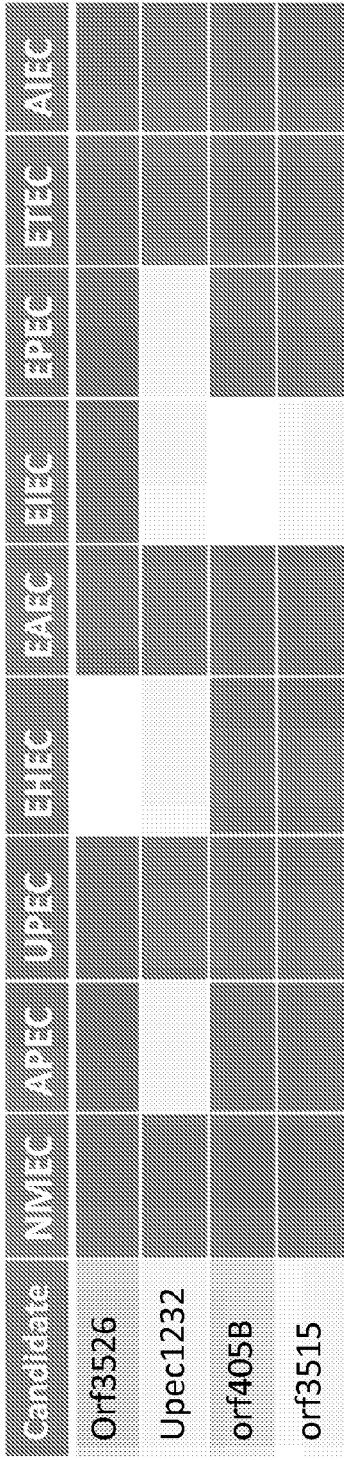
FIG. 1: (A) Presence of each of the antigens utilised in compositions of the present invention were determined in most pathogenic strains, specifically NMEC, APEC, UPEC, EHEC, EAEC, EIEC, EPEC, ETEC and AIEC; (B) Gene presence of protective candidates was evaluated in sequenced genomes (based on >85% sequence homology) and in clinical isolates (by PCR amplification).
Figure 1B:
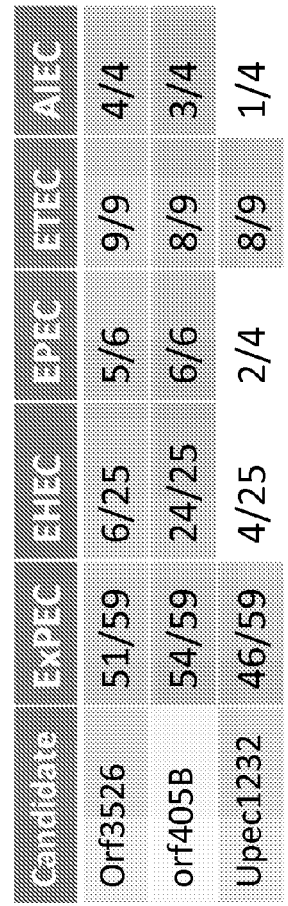

The invention provides immunogenic compositions comprising an immunogenic component of *Escherichia coli* wherein the immunogenic component is selected from the group consisting of bacterial Ig-like domain protein fragment (orf405B) having the amino acid sequence set forth in SEQ ID NO:2 or a protein having at least 80% similarity thereto, upec1232 having the amino acid sequence set forth in SEQ ID NO:4 or a protein having at least 80% similarity thereto, putative Lipoprotein (orf3526) having the amino acid sequence set forth in SEQ ID NO:8 or a protein having at least 80% similarity thereto and gspK (orf3515) having the amino acid sequence set forth in SEQ ID NO:30 or a protein having at least 80% similarity thereto. A composition of the invention may comprise e.g. one, two, three or four of the aforementioned components, e.g.

orf405B and upec1232; orf405B and orf3526; orf405B and orf3515;
upec1232 and orf3526; upec1232 and orf3515;
orf3526 and orf3515;
orf405B, upec1232 and orf3526; orf405B, orf3526 and orf3515; or upec1232, orf3526s and
orf3515;

or proteins having at least 80% similarity to any thereof.

Preferably, an immunogenic composition of the invention comprises one, two or three components selected from orf405B, upec1232, orf3526, or proteins having at least 80% similarity to any thereof. For example, an immunogenic composition of the invention may comprise the three components orf405B, upec1232 and orf3526, or proteins having at least 80% similarity to any thereof. More preferably, an immunogenic composition of the invention comprises one or two components selected from orf405B and orf3526, or proteins having at least 80% similarity to any thereof. For example, an immunogenic composition of the invention may comprise the two components orf405B and orf3526, or proteins having at least 80% similarity to any thereof. Alternatively, an immunogenic composition of the invention may comprise orf405B, upec1232, orf3526, and orf3515, or proteins having at least 80% similarity to any thereof.

Components of compositions of the invention may be isolated or purified.

As used herein, the term "immunogenic" means that, for example the polypeptide(s), composition and the like, is/are capable of eliciting a humoral or cellular immune response, and preferably both. For example, the term "immunogenic composition" refers to any composition able, once it has been administered to a subject, such as an animal for example a human, to induce or stimulate an immune response against *E. coli*.

An immunogenic polypeptide is also antigenic. A molecule is "antigenic" when it is capable of specifically interacting with an antigen recognition molecule of the immune system, such as an immunoglobulin (antibody) or T cell antigen receptor. An antigenic polypeptide contains an epitope of at least about five, and particularly at least about 10, at least 15, at least 20 or at least 50 amino acids. An antigenic portion of a polypeptide, also referred to as an epitope, can be that portion that is immunodominant for antibody or T cell receptor recognition, or it can be a portion used to generate an antibody to the molecule by conjugating the antigenic portion to a carrier polypeptide for immunization. The skilled person will recognise that a molecule that is antigenic need not be itself immunogenic, for example, some antigens require the presence of an adjuvant or carrier to render them capable of eliciting an immune response.

The term "antigen" refers to a molecule against which a subject can initiate a humoral and/or cellular immune response. An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the subject will display either a therapeutic or protective immunological response such that resistance to new infection will be enhanced and/or the clinical severity of the disease reduced. Such protection will be demonstrated by either a reduction or lack of symptoms normally displayed by an infected subject, a quicker recovery time and/or a lowered viral titre in the infected host. The term "immunogenic" protein or polypeptide as used herein also refers to an amino acid sequence which elicits an immunological response as described above.

When said immunogenic compositions prevent, ameliorate, palliate or eliminate disease from an animal then the immunogenic composition may optionally be referred to as a vaccine.

The term "vaccine" as used herein refers to a vaccine composition that comprises either purified antigenic determinants, nucleic acids encoding the purified antigenic determinants or fragments thereof, in the absence of the disease-causing organism. Such vaccines may also be referred to as a "sub-unit vaccine". The terms are not intended to encompass "whole-cell vaccines", for example those derived from whole bacterial cells that have been killed and which may contain the antigenic determinants in un-purified form as part of a complex and uncharacterised composition.

As used herein, the term "multivalent", means that the vaccine contains structurally similar or 'related' antigenic determinants from at least two strains or isolates, the antigenic determinants being homologues having minor differences between their amino acid sequences.

The terms "variant", "homologue", "derivative" or "fragment" in relation to polypeptides or antigens include any substitution of, variation of, modification of, replacement of, deletion of or addition of one (or more) amino acid or nucleotide from or to a sequence. Unless the context admits otherwise, references to particular antigens includes references to such variants, homologues, derivatives and fragments.

Preferred variants of an antigen can elicit antibodies which bind to that antigen. In particular, the antibodies bind to wild-type antigens as present in an *E. coli* cell.

In particular, the term "homologue" covers identity with respect to structure and/or function providing the resultant amino acid sequence has antigenic or immunogenic activity. With respect to sequence identity (i.e. similarity), there may be at least 70%, at least 75%, at least 80%, at least 85%, at least 90% sequence identity. There may be, e.g., at least 91%, 92%, 93%, or 94%, sequence identity. There may also be at least 95%, 96%, 97%, 98%, 99%, or 99.5% sequence identity. These terms also encompass polypeptides derived from amino acids which are allelic variations of nucleic acid or amino acid sequence(s). Percentage sequence identity and similarity between a sequence A and a sequence B is calculated as (x/y)*100, wherein x is the number of amino acids that are identical between A and B and y is the number of amino acids of the longest sequence selected from A and B. For example, in the case of 10 identical residues between a first sequence A consisting of 50 amino acids and a second sequence B consisting of 200 amino acids, the sequence identity between the two sequences is 5%.

Where reference is made to the "activity" or "biological activity" of a polypeptide, these terms are intended to refer to the antigenic and immunogenic activities of the polypeptide. Examples of such activities, and methods of assaying and quantifying these activities, are known in the art, and are described in detail elsewhere in this document.

As used herein a "deletion" is defined as a change in either nucleotide or amino acid sequence in which one or more nucleotides or amino acid residues, respectively, are absent. As used herein an "insertion" or "addition" is that change in a nucleotide or amino acid sequence which has resulted in the addition of one or more nucleotides or amino acid residues, respectively, as compared to the naturally occurring substance. As used herein "substitution" results from the replacement of one or more nucleotides or amino acids by different nucleotides or amino acids, respectively.

The terms "antigen" and "amino acid sequence", as they are used in this document, should be taken to include reference to each of the above sequences, as well as to their fragments, homologues, derivatives and variants.

The term "fragment" as used herein refers to partial nucleotide or amino acid sequences according to the present invention. In certain embodiments amino acid sequence or polypeptide fragments may include polypeptides comprising an amino acid sequence of at least 'n' consecutive amino acids derived from the listed sequence identifiers, for example at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100, at least 150, at least 200 or at least 250 amino acid residues of the amino acid sequence. In certain embodiments amino acid fragments may include polypeptides comprising an amino acid sequence of no more than 50, no more than 60, no more than 75, no more than 100, no more than 150, no more than 200, no more than 250, no more than 300, no more than 350, no more than 400 amino acid residues. Preferred fragments comprise an epitope or are immunogenic fragments. Preferred fragments lack an amino-terminal portion of the polypeptides of the invention, such as residues 1-23 or residues 1-33 of SEQ ID NO: 8 or SEQ ID NO:31, or corresponding residues in other orf3526 polypeptides of the invention. Sequence identity and similarity between a fragment and a longer sequence is calculated according to the same method as described above, i.e. based on identical residues relative to the longest sequence.

As used herein, the term "purified" or "to purify" refers to the removal of contaminants from a sample. For example, antigens are purified by removal of contaminating proteins. The removal of contaminants results in an increase in the percent of antigen (e.g., antigen of the present invention) in the sample.

"Isolated" and "purified" as used herein describe certain molecules, proteins, polysaccharides, lipids, antigens, and the like, and refers to a state beyond that in which the molecules, proteins, polysaccharides, lipids, or antigens exist naturally in cells. Particularly the term as used herein means removed from its naturally occurring environment such as a cell, for example. In preferred embodiments, the isolated molecules, proteins, polysaccharides, lipids, antigens, and the like, are separated from greater than 20%, 30%, 40%, 50%, 60%, 70%, 80%, 90%, 95% or 99% of the proteins and/or the lipids with which the molecules, proteins, polysaccharides, lipids, antigens, and the like are normally associated naturally in cells. If the isolated molecules, proteins, polysaccharides, lipids, antigens, and the like are synthesized, they are contaminated with less than 50%, 40%, 30%, 20%, 10%, 5%, 1% or 0.1% of the chemical precursors or synthesis reagents used to synthesize the lipid antigen. In preferred embodiments, the molecules, proteins, polysaccharides, lipids or antigens are at least 1% pure, 5% pure, 10% pure, 20% pure, 30% pure, 40% pure, 50% pure, 60% pure, 70% pure, 80% pure, 90% pure, 95% pure, 99% pure, or 100% pure. As used herein, the term "% pure" indicates the percentage of a composition that is made up of the molecule of interest, by weight. Thus, a composition of 100 grams containing 50 grams of a molecule of interest is 50% pure with respect to the molecule of interest.

The term "treating" includes both therapeutic treatment and prophylactic or preventative treatment, wherein the object is to prevent or lessen infection. For example, treating may include directly affecting or curing, suppressing, inhibiting, preventing, reducing the severity of, delaying the onset of, reducing symptoms associated with, for example, infection, or a combination thereof "Preventing" may refer, inter alia, to delaying the onset of symptoms, preventing relapse to a disease, and the like. Treating may also include "suppressing" or "inhibiting" an infection or illness, for example reducing severity, number, incidence or latency of symptoms, ameliorating symptoms, reducing secondary symptoms, reducing secondary infections, prolonging patient survival, or combinations thereof.

Polypeptides used in the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [1,2]. Solid-phase peptide synthesis is particularly preferred, such as methods based on tBoc or Fmoc [3] chemistry. Enzymatic synthesis [4] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [5]. Where D-amino acids are included, however, it is preferred to use chemical synthesis. Polypeptides may have covalent modifications at the C-terminus and/or N-terminus.

Polypeptides can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides are preferably provided in purified or substantially purified form. Polypeptides may be attached to a solid support. Polypeptides may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides can be naturally or non-naturally glycosylated (i.e. the polypeptide has a glycosylation pattern that differs from the glycosylation pattern found in the corresponding naturally occurring polypeptide).

Polypeptides used in the present invention may be produced by culturing a host cell under conditions which induce polypeptide expression. Expression of the polypeptide may take place in a heterologous host for expression. The heterologous host may be prokaryotic (e.g. a bacterium) or eukaryotic. Suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

Particular polypeptides used in combinations of the invention may comprise an amino acid sequence that is derived from bacterial Ig-like domain (group 1) protein fragment (orf405B), gspK (orf3515), upec-1232 and putative Lipoprotein (orf3526) each as more fully described herein.

Bacterial Ig-Like Domain Protein Fragment 'orf405B'

Bacterial Ig-like domain (group 1) protein, from *E. coli* NMEC, is disclosed in WO2006/089264 (SEQ IDs 809 and 810) and is referred to therein as 'orf405', the protein is also referred to as orf284' from *E. coli* NMEC strain IHE3034, 'c0415' from CFT073 and 'ecp_0367' from 536. Fragments of this orf405 protein were first disclosed in WO2011/004263 (for example in SEQ IDs 641 and 642). Compositions according to the present invention preferably comprise bacterial Ig-like domain protein fragment 'orf405B'. The nucleotide and amino acid sequences of this protein fragment, referred to herein, as SEQ IDs 1 and 2 are:

>orf405B (SEQ ID 1)
GTTGCTGATGGTCAGCAAGCCTACACGCTGACACTGACAGCGGTGGACT
CCGAGGGTAATCCGGTGACGGGAGAAGCCAGCCGCCTGCGACTTGTTCC
GCAAGACACTAATGGTGTAACCGTTGGTGCCATTTCGGAAATAAAACCA
GGGGTTTACAGCGCCACGGTTTCTTCGACCCGTGCCGGAAACGTTGTTG
TGCGTGCCTTCAGCGAGCAGTATCAGCTGGGCACATTACAACAAACGCT
GAAGTTTGTTGCCGGGCCGCTTGATGCAGCACATTCGTCCATCACACTG
AATCCTGATAAACCGGTGGTTGGCGGTACAGTTACGGCAATCTGGACGG
CAAAAGATGCTAATGACAACCCTGTAACTGGCCTCAATCCGGATGCACC
GTCATTATCGGGCGCAGCTGCTGCTGGTTCTACGGCATCAGGCTGGACG
GATAATGGCGACGGGACCTGGACTGCGCAGATTTCTCTCGGCACTACGG
CGGGTGAATTAGACGTTATGCCGAAGCTCAATGGGCAGGACGCGGCAGC
AAATGCGGCAAAAGTAACCGTGGTGGCTGATGCATTATCTTCAAACCAG
TCGAAAGTCTCTGTCGCAGAAGATCACGTAAAAGCCGGTGAAAGCACAA
CCGTAACGCTGGTGGCGAAAGATGCGCATGGCAACGCTATCAGTGGTCT
TTCGTTGTCGGCAAGTTTGACGGGGACCGCCTCTGAAGGGGCGACCGTT
TCCAGTTGGACCGAAAAAGGTGACGGTTCCTATGTTGCTACGTTAACTA
CAGGCGGAAAGACGGGCGAGCTTCGTGTCATGCCGCTCTTCAACGGCCA
GCCTGCAGCCACCGAAGCCGCGCAGCTGACTGTTATTGCCGGAGAGATG
TCATCAGCGAACTCTACGCTTGTTGCGGACAATAAAACTCCAACGGTTA
AAACGACGACGGAACTCACCTTCACCATGAAGGATGCGTACGGGAATCC
GGTCACCGGGCTGAAGCCAGATGCACCAGTGTTTAGTGGTGCCGCCAGC
ACGGGGAGTGAGCGTCCTTCAGCAGGAAACTGGACAGAGAAAGGTAATG
GGGTCTACGTGTCGACCTTAACGCTGGGATCTGCCGCGGGTCAGTTGTC
TGTGATGCCGCGAGTGAACGGCCAAAATGCCGTTGCTCAGCCACTGGTG
CTGAATGTTGCAGGTGACGCATCTAAGGCTGAGATTCGTGATATGACAG
TGAAGGTTAATAACCAA >orf405B (SEQ ID 2)
VADGQQAYTLTLTAVDSEGNPVTGEASRLRLVPQDTNGVTVGAISEIKP
GVYSATVSSTRAGNVVVRAFSEQYQLGTLQQTLKFVAGPLDAAHSSITL
NPDKPVVGGTVTAIWTAKDANDNPVTGLNPDAPSLSGAAAAGSTASGWT
DNGDGTWTAQISLGTTAGELDVMPKLNGQDAAANAAKVTVVADALSSNQ
SKVSVAEDHVKAGESTTVTLVAKDAHGNAISGLSLSASLTGTASEGATV
SSWTEKGDGSYVATLTTGGKTGELRVMPLFNGQPAATEAAQLTVIAGEM
SSANSTLVADNKTPTVKTTTELTFTMKDAYGNPVTGLKPDAPVFSGAAS
TGSERPSAGNWTEKGNGVYVSTLTLGSAAGQLSVMPRVNGQNAVAQPLV
LNVAGDASKAEIRDMTVKVNNQ When used according to the present invention, orf405B protein may take various forms. Particular orf405B sequences have 80% or more identity (e.g. 80%, 85%, 90%, 95%, 96%, 97%, 98%, 99% or more) to SEQ ID NOs 1 and/or 2. This includes variants (e.g. allelic variants, homologs, orthologs, paralogs, mutants etc).

Upec1232 Protein

'Upec1232' protein from *E. coli* UPEC is disclosed in WO2006/091517 (SEQ ID 138) and is also known as: 'c1275' from CFT073. When used according to the present invention, upec1232 protein may take various forms. Preferred upec1232 sequences have 80% or more identity (e.g. 80%, 85%, 90%, 95%, 96%, 97%, 98%, 99% or more) to SEQ ID NOs 3, 4, 5 or 6. This includes variants (e.g. allelic variants, homologs, orthologs, paralogs, mutants etc).

```
>upec-1232
                                                    (SEQ ID 3)
ATGATTCACCTGTTCAAAACCTGCATGATTACCGCCTTCATTCTGGGGT
TAACGTGGTCTGCCCCACTCCGGGCACAGGATCAACGTTACATCAGTAT
ACGCAATACAGATACGATATGGCTCCCGGGAAATATTTGTGCTTACCAG
TTCCGGCTGGATAATGGCGGAAACGATGAAGGATTTGGCCCCCTCACCA
TCACTCTGCAACTCAAAGACAAATATGGTCAGACGCTGGTGACCAGAAA
AATGGAAACGGAAGCCTTTGGTGACAGTAATGCCACGCGAACCACAGAC
GCATTTCTGGAAACGGAGTGCGTGGAAAATGTCGCCACAACCGAAATCA
TTAAAGCAACTGAAGAAAGTAACGGCCATCGTGTCAGTCTGCCGTTATC
GGTTTTCGATCCCCAGGACTACCATCCACTGCTGATTACCGTTTCCGGA
AAAAACGTTAAC
```

```
>upec-1232
                                                    (SEQ ID 4)
MIHLFKTCMITAFILGLTWSAPLRAQDQRYISIRNTDTIWLPGNICAYQ
FRLDNGGNDEGFGPLTITLQLKDKYGQTLVTRKMETEAFGDSNATRTTD
AFLETECVENVATTEIIKATEESNGHRVSLPLSVFDPQDYHPLLITVSG
KNVN
```

```
>pCFT-1232
                                                    (SEQ ID 5)
CAGGATCAACGTTACATCAGTATACGCAATACAGATACGATATGGCTCC
CGGGAAATATTTGTGCTTACCAGTTCCGGCTGGATAATGGCGGAAACGA
TGAAGGATTTGGCCCCCTCACCATCACTCTGCAACTCAAAGACAAATAT
GGTCAGACGCTGGTGACCAGAAAAATGGAAACGGAAGCCTTTGGTGACA
GTAATGCCACGCGAACCACAGACGCATTTCTGGAAACGGAGTGCGTGGA
AAATGTCGCCACAACCGAAATCATTAAAGCAACTGAAGAAAGTAACGGC
CATCGTGTCAGTCTGCCGTTATCGGTTTTCGATCCCCAGGACTACCATC
CACTGCTGATTACCGTTTCCGGAAAAAACGTTAAC
```

```
>pCFT-1232
                                                    (SEQ ID 6)
QDQRYISIRNTDTIWLPGNICAYQFRLDNGGNDEGFGPLTITLQLKDKY
GQTLVTRKMETEAFGDSNATRTTDAFLETECVENVATTEIIKATEESNG
HRVSLPLSVFDPQDYHPLLITVSGKNVN
```

Putative Lipoprotein Orf3526

Accessory colonization factor D (AcfD) precursor, also known as 'ECOK1_3385', also known as 'putative lipoprotein orf3526', also referred to as 'orf3526' protein from *E. coli* NMEC strain IHE3034 is disclosed in WO2006/089264. When used according to the present invention, orf3526 protein may take various forms. Preferred orf3526 sequences have 80% or more identity (e.g. 80%, 85%, 90%, 95%, 96%, 97%, 98%, 99% or more) to SEQ ID NOs 7-28. This includes variants (e.g. allelic variants, homologs, orthologs, paralogs, mutants etc).

```
>orf03526
                                                    (SEQ ID 7)
ATGAATAAGAAATTTAAATATAAGAAATCGCTTTTAGCGGCTATTTTAAGCGCAACCCTGTTAGCCGGTTGT
GATGGTGGTGGTTCAGGATCGTCCTCCGATACGCCGTCTGTAGATTCTGGATCAGGGACTTTGCCGGAAGTG
AAACCCGATCCAACACCAACCCCGGAGCCGACACCTGAGCCGACGCCGGACCCAGAACCTACGCCGGATCCA
ACACCTGATCCTGAGCCGACACCAGAACCGGAGCCAGAACCTGTTCCTACGAAAACGGGTTATCTGACCCTG
GGCGGAAGCCAGCGGGTAACTGGTGCTACCTGTAATGGTGAATCCAGCGATGGCTTTACCTTTACGCCAGGC
AATACCGTGAGTTGTGTGGTGGGCAGTACGACCATTGCAACATTCAACACCCAGTCAGAAGCTGCGCGTAGC
CTGCGTGCGGTTGACAAAGTGTCGTTTAGCCTGGAGGACGCGCAGGAGCTGGCGAATTCTGAAAATAAGAAA
ACCAACGCCATCTCTCTGGTGACGTCCAGCGACAGTTGCCCCGCAGATGCAGAACAGCTTTGTCTTACTTTC
TCGTCAGTGGTTGATCGCGCGCGATTTGAAAAACTGTATAAGCAAATTGATCTGGCAACAGACAATTTCAGC
AAGCTGGTCAATGAAGAGGTGGAAAACAATGCTGCGACTGATAAAGCGCCGTCCACCCATACCTCAACGGTA
GTGCCAGTCACGACGAGGGAACAAAACCGGATCTGAACGCGTCCTTCGTGTCGGCTAACGCGGAACAGTTT
TATCAGTATCAACCCACTGAAATCATTCTTTCCGAAGGCCAACTGGTGGATAGCCTGGGGAACGGTGTTGCT
GGCGTTGACTACTACACCAATTCAGGCCGTGGCGTAACTGACGAAAACGGTAAATTTTCCTTTAGCTGGGGC
GAAACCATCTCCTTTGGTATCGATACCTTTGAACTGGGCTCAGTACGTGGCAATAAGTCGACCATTGCGCTG
ACTGAATTGGGTGATGAAGTTCGCGGGGCAAATATCGATCAGCTCATTCATCGTTATTCGACGACTGGTCAA
AATAATACTCGTGTTGTTCCGGACGATGTACGCAAGGTCTTTGCCGAATATCCCAACGTGATCAACGAGATA
ATCAATCTTTCGTTATCCAACGGTGCGACGCTGGATGAAGGCGATCAAAACGTTGTGCTGCCTAACGAATTT
ATCGAGCAGTTTAAGACGGGTCAGGCCAAAGAGATCGATACCGCGATTTGTGCGAAAACCGACGGTTGTAAC
GAGGCTCGCTGGTTCTCGCTGACAACGCGCAATGTTAATGACGGCCAGATTCAGGGCGTTATTAACAAGCTG
TGGGGCGTGGATACGAACTATCAGTCTGTCAGCAAGTTCCACGTCTTCCATGACTCTACCAACTTCTATGGC
AGCACCGGTAACGCGCGCGGTCAGGCGGTGGTAAATATCTCCAACTCGGCATTCCCGATTCTGATGGCGCGT
AATGATAAAAACTACTGGCTGGCGTTTGGCGAAAAACGCGCCTGGGATAAAAATGAGCTGGCGTACATTACG
GAAGCGCCTTCCATTGTGCAGCCAGAGAACGTTACGCGCGATACTGCGACTTTCAACCTGCCGTTTATTTCG
CTGGGGCAAGTCGGTGAAGGCAAACTGATGGTTATCGGTAACCCGCACTACAACAGCATCCTGCGTTGCCCG
AACGGTTACAGTTGGGGCGGTGGTGTTAATAGTAAAGGTGAGTGTACGCTCAGCGGTGATTCTGATGACATG
AAGCACTTTATGCAGAACGTACTGCGCTACTTGTCAAATGACATCTGGCAGCCAAATACCAAGAGCATCATG
ACTGTCGGCACCAACCTGGAGAACGTTTATTTCAAAAAAGCGGGCCAGGTATTGGGAAATAGTGCACCATTT
GCTTTCCATGAGGATTTCACTGGTATCACGGTTAAACAGTTGACCAGCTATGGCGATCTGAATCCGGAAGAG
ATTCCGTTGCTGATCCTCAACGGCTTTGAATATGTGACTCAGTGGTTCGGCGATCCCTATGCTGTGCCTCTG
CGTGCAGATACCAGCAAACCGAAGCTGACTCAGCAGGATGTGACCGATCTGATCGCTTATCTGAACAAAGGT
GGCTCGGTGCTGATCATGGAAAACGTGATGAGCAATCTTAAGGAAGAGAGCGCGTCCAGTTTTGTGCGTCTG
CTGGATGCCGCGGGTCTGTCAATGGCTCTGAACAAATCGGTGGTGAACAACGATCCGCAAGGGTATCCGGAT
CGCGTTCGTCAGCGTCGCGCGACTGGCATTTGGGTTTATGAACGTTATCCTGCTGCAGACGGCGCGCAACCG
CCGTACACCATCGACCCAAATACAGGGGAAGTGACCTGGAAATACCAGCAAGACAACAAGCCTGATGACAAG
CCGAAACTGGAAGTTGCGAGCTGGCAGGAGGAAGTTGAGGGCAAACAGGTAACGCGTTATGCCTTTATTGAT
GAAGCGGAATACACAACAGAAGAATCTCTGGAAGCGCAAAGGCAAAATCTTTGAGAAGTTTCCTGGGTTA
CAGGAGTGTAAGGACTCGACTTACCATTACGAGATTAACTGTTTGGAGCGCCGCCCAGGCACGGATGTTCCG
GTAACAGGTGGCATGTATGTTCCGCGCTATACGCAACTGAATCTTGACGCCGACACCGCGAAAGCGATGGTG
CAGGCGGCGGATTTAGGCACCAACATTCAGCGCCTGTATCAGCATGAGCTTTATTTCCGTACCAAAGGCAGT
```

-continued

```
AAAGGTGAGCGTCTGAACAGTGTTGATCTGGAACGTCTGTACCAGAACATGTCGGTCTGGCTGTGGAACGAT
ACGAAATATCGTTACGAAGAGGGCAAGGAAGATGAGCTGGGCTTTAAAACGTTCACCGAGTTCCTGAACTGC
TACGCCAATGATGCCTATGCAGGCGGCACCAAGTGCTCCGCAGATCTGAAAAAATCGCTGGTCGATAACAAC
ATGATCTACGGTGACGGTAGCAGCAAAGCGGGCATGATGAACCCAAGCTATCCGCTCAACTATATGGAAAAA
CCGCTGACGCGTCTGATGCTGGGCCGTTCCTGGTGGGATCTGAACATTAAGGTTGATGTGGAGAAGTACCCA
GGATCCGTATCGGCAAAGGGTGAGAGCGTTACGGAAAACATCAGCCTGTACTCGAATCCGACCAAATGGTTT
GCGGGTAACATGCAGTCAACCGGCCTGTGGGCACCGGCCCAGCAGGACGTCACCATTAAGTCTTCGGCGTCA
GTCCCAGTGACTGTTACCGTGGCGCTGGCTGACGACCTGACTGGACGTGAGAAGCATGAAGTTGCGCTGAAC
CGTCCGCCAAGAGTGACTAAAACGTATACTCTGGAGGCTAACGGTGAAGTGACCTTCAAGGTGCCTTATGGT
GGTCTGATTTATATCAAGGGCGACAGTAAGGATGATGTTTCTGCTAACTTCACCTTTACCGGTGTAGTAAAA
GCGCCGTTCTATAAAGACGGCGAATGAAAAACGATCTGGACTCACCGGCGCCGCTGGGCGAGCTGGAGTCT
GCGTCGTTCGTCTATACCACGCCGAAGAAGAACCTTGAGGCCAGCAATTTCACTGGTGGTGTAGCAGAATTC
GCTAAAGATCTGGATACCTTTGCCAGCTCGATGAATGACTTCTACGGTCGTAATGATGAAGACGGTAAGCAC
CGGATGTTTACCTATAAAAACTTGACGGGGCACAAGCATCGTTTCACCAACGATGTGCAGATCTCCATCGGT
GATGCGCACTCGGGTTATCCGGTAATGAACAGCAGCTTCTCGACAACAGCACCACGCTGCCGACGACGCCG
CTGAACGACTGGCTGATTTGGCACGAAGTCGGTCATAACGCTGCAGAAACACCGCTGAACGTACCGGGTGCA
ACTGAAGTGGCGAACAACGTGCTGGCGCTGTACATGCAGGATCGCTATCTCGGTAAGATGAACCGTGTCGCT
GACGACATTACCGTCGCGCCGGAATATCTGGACGAGAGCAACGGTCAGGCCTGGGCGCGCGGCGGTGCGGGT
GACCGTCTGCTGATGTACGCACAGTTGAAGGAGTGGGCAGAGGAAAACTTTGATATCAAACAGTGGTATCCA
GATGGTGAGCTGCCTAAGTTCTACAGCGATCGTAAAGGGATGAAGGGCTGGAACCTGTTCCAGTTGATGCAC
CGTAAAGCGCGCGGCGATGATGTTGGTAACAGCACCTTTGGTGGCAAGAATTACTGTGCTGAATCCAATGGT
AACGCTGCCGACACGCTGATGCTGTGTGCATCCTGGGTCGCTCAGGCGGATCTTTCGGAATTCTTTAAGAAA
TGGAATCCGGGTGCAAGTGCTTACCAGTTGCCGGGAGCAACGGAGATGAGTTTCCAGGGCGGTGTGAGCTCT
TCGGCTTACAGCACGCTGGCGTCACTCAAGCTGCCGAAACCGGAAAAGGGCCGGAAACCATTAACAAGGTT
ACCGAGCATAAGATGTCTGCCGAG
```

>orf03526
(SEQ ID 8)

```
MNKKFKYKKSLLAAILSATLLAGCDGGGSGSSSDTPSVDSGSGTLPEVKPDPTPTPEPTPEPTPDPEPTPDP
TPDPEPTPEPEPEPVPTKTGYLTLGGSQRVTGATCNGESSDGFTFTPGNTVSCVVGSTTIATFNTQSEAARS
LRAVDKVSFSLEDAQELANSENKKTNAISLVTSSDSCPADAEQLCLTFSSVVDRARFEKLYKQIDLATDNFS
KLVNEEVENNAATDKAPSTHTSTVVPVTTEGTKPDLNASFVSANAEQFYQYQPTEIILSEGQLVDSLGNGVA
GVDYYTNSGRGVTDENGKFSFSWGETISFGIDTFELGSVRGNKSTIALTELGDEVRGANIDQLIHRYSTTGQ
NNTRVVPDDVRKVFAEYPNVINEIINLSLSNGATLDEGDQNVVLPNEFIEQFKTGQAKEIDTAICAKTDGCN
EARWFSLTTRNVNDGQIQGVINKLWGVDTNYQSVSKFHVFHDSTNFYGSTGNARGQAVVNISNSAFPILMAR
NDKNYWLAFGEKRAWDKNELAYITEAPSIVQPENVTRDTATFNLPFISLGQVGEGKLMVIGNPHYNSILRCP
NGYSWGGGVNSKGECTLSGDSDDMKHFMQNVLRYLSNDIWQPNTKSIMTVGTNLENVYFKKAGQVLGNSAPF
APFHEDFTGITVKQLTSYGDLNPEEIPLLILNGFEYVTQWSGDPYAVPLRADTSKPKLTQQDVTDLIAYLNKG
GSVLIMENVMSNLKEESASSFVRLLDAAGLSMALNKSVVNNDPQGYPDRVRQRRATGIWVYERYPAADGAQP
PYTIDPNTGEVTWKYQQDNKPDDKPKLEVASWQEEVEGKQVTRYAFIDEAEYTTEESLEAAKAKIFEKFPGL
QECKDSTYHYEINCLERRPGTDVPVTGGMYVPRYTQLNLDADTAKAMVQAADLGTNIQRLYQHELYFRTKGS
KGERLNSVDLERLYQNMSVWLWNDTKYRYEEGKEDELGFKTFTEFLNCYANDAYAGGTKCSADLKKSLVDNN
MIYGDGSSKAGMMNPSYPLNYMEKPLTRLMLGRSWWDLNIKVDVEKYPGSVSAKGESVTENISLYSNPTKWF
AGNMQSTGLWAPAQQDVTIKSSASVPVTVTVALADDLTGREKHEVALNRPPRVTKTYTLEANGEVTFPKVPYG
GLIYIKGDSKDDVSANFTFTGVVKAPFYKDGEWKNDLDSPAPLGELESASFVYTTPKKNLEASNFTGGVAEF
AKDLDTFASSMNDFYGRNDEDGKHRMFTYKNLTGHKHRFTNDVQISIGDAHSGYPVMNSSFSTNSTTLPTTP
LNDWLIWHEVGHNAAETPLNVPGATEVANNVLALYMQDRYLGKMNRVADDITVAPEYLDESNGQAWARGGAG
DRLLMYAQLKEWAEENFDIKQWYPDGELPKFYSDRKGMKGWNLFQLMHRKARGDDVGNSTFGGKNYCAESNG
NAADTLMLCASWVAQADLSEFFKKWNPGASAYQLPGATEMSFQGGVSSSAYSTLASLKLPKPEKGPETINKV
TEHKMSAE
```

>pK1-3526A
(SEQ ID 9)

```
TGTGATGGTGGTGGTTCAGGATCGTCCTCCGATACGCCGTCTGTAGATTCTGGATCAGGGACTTTGCCGGAA
GTGAAACCCGATCCAACACCAACCCCGGAGCCGACACCTGAGCCGACACCTCCAGAACCTACGCCGGAT
CCAACACCTGATCCTGAGCCGACACCAGAACCGGAGCCAGAACCTGTTCCTACGAAAACGGGTTATCTGACC
CTGGGCGGAAGCCAGCGGGTAACTGGTGCTACCTGTAATGGTGAATCCAGCGATGGCTTTACCTTTACGCCA
GGCAATACCGTGAGTTGTGTGGTGGGCAGTACGACCATTGCAACATTCAACACCCAGTCAGAAGCTGCGCGT
AGCCTGCGTGCGGTTGACAAAGTGTCGTTTAGCCTGGAGGACGCGCAGGAGCTGGCGAATTCTGAAAATAAG
AAAACCAACGCCATCTCTCTGGTGACGTCCAGCGACAGTTGCCCCGCAGATGCAGAACAGCTTTGTCTTACT
TTCTCGTCAGTGGTTGATCGCGCGCGATTTGAAAAACTGTATAAGCAAATTGATCTGGCAACAGACAATTTC
AGCAAGCTGGTCAATGAAGAGGTGGAAAACAATGCTGCGACTGATAAAGCGCCGTCCACCCATACCTCAACG
GTAGTGCCAGTCACGACAGAGGGAACAAAACCGGATCTGAACGCGTCCTTCGTGTCGGCTAACGCGGAACAG
TTTTATCAGTATCAACCCACTGAAATCATTCTTTCCGAAGGCCAACTGGTGGATAGCCTGGGGAACGGTGTT
GCTGGCGTTGACTACTACACCAATTCAGGCCGTGGCGTAACTGACGAAAACGGTAAATTTTCCTTTAGCTGG
GGCGAAACCATCTCCTTTGGTATCGATACCTTTGAACTGGGCTCAGTACGTGGCAATAAGTCGACCATTGCG
CTGACTGAATTGGGTGATGAAGTTCGCGGGCAAATATCGATCAGCTCATTCATCGTTATTCGACGACTGGT
CAAAATAATACTCGTGTTGTTCCGGACGATGTACGCAAGGTCTTTGCCGAATATCCCAACGTGATCAACGAG
ATAATCAATCTTTCGTTATCCAACGGTGCGACGCTGGATGAAGGCGATCAAAACGTTGTGCTGCCTAACGAA
TTTATCGAGCAGTTTAAGACGGGTCAGGCCAAAGAGATCGATACCGCGATTTGTGCGAAAACCGACGGTTGT
AACGAGGCTCGCTGGTTCTCGCTGACAACGCGCAATGTTAATGACGGCCAGATTCAGGGCGTTATTAACAAG
CTGTGGGGCGTGGATACGAACTATCAGTCTGTCAGCAAGTTCCACGTCTTCCATGACTCTACCAACTTCTAT
GGCAGCACCGGTAACGCGCGCGGTCAGGCGGTGGTAAATATCTCCAACTCGGCATTCCCGATTCTGATGGCG
CGTAATGATAAAAACTACTGGCTGGCGTTTGGCGAAAACGCGCCTGGGATAAAAATGAGCTGGCGTACATT
ACGGAAGCGCCTTCCATTGTGCAGCCAGAGAACGTTACGCGCGATACTGCGACTTTCAACCTGCCGTTTATT
TCGCTGGGGCAAGTCGGTGAAGGCAAACTGATGGTTATCGGTAACCCGCACTACAACAGCATCCTGCGTTGC
CCGAACGGTTACAGTTGGGGCGGTGGTGTTAATAGTAAAGGTGAGTGTACGCTCAGCGGTGATTCTGATGAC
ATGAAGCACTTTATGCAGAACGTACTGCGCTACTTGTCAAATGACATCTGGCAGCCAAATACCAAGAGCATC
ATGACTGTCGGCACCAACCTGGAGAACGTTTATTTCAAAAAAGCGGGCCAGGTATTGGGAAATAGTGCACCA
TTTGCTTTCCATGAGGATTTCACTGGTATCACGGTTAAACAGTTGACCAGCTATGGCGATCTGAATCCGGAA
GAGATTCCGTTGCTGATCCTCAACGGCTTTGAATATGTGACTCAGTGGTCTGGCGATCCCTATGCTGTGCCT
```

-continued
```
CTGCGTGCAGATACCAGCAAACCGAAGCTGACTCAGCAGGATGTGACCGATCTGATCGCTTATCTGAACAAA
GGTGGCTCGGTGCTGATCATGGAAAACGTGATGAGCAATCTTAAGGAAGAGAGCGCGTCCAGTTTTGTGCGT
CTGCTGGATGCCGCGGGTCTGTCAATGGCTCTGAACAAATCGGTGGTGAACAAC
```

>pK1-3526A                                                                   (SEQ ID 10)
```
CDGGGSGSSSDTPSVDSGSGTLPEVKPDPTPTPEPTPEPTPDPEPTPDPTPDPEPTPEPEPEPVPTKTGYLT
LGGSQRVTGATCNGESSDGFTFTPGNTVSCVVGSTTIATFNTQSEAARSLRAVDKVSFSLEDAQELANSENK
KTNAISLVTSSDSCPADAEQLCLTFSSVVDRARFEKLYKQIDLATDNFSKLVNEEVENNAATDKAPSTHTST
VVPVTTEGTKPDLNASFVSANAEQFYQYQPTEIILSEGQLVDSLGNGVAGVDYYTNSGRGVTDENGKFSFSW
GETISFGIDTFELGSVRGNKSTIALTELGDEVRGANIDQLIHRYSTTGQNNTRVVPDDVRKVFAEYPNVINE
IINLSLSNGATLDEGDQNVVLPNEFIEQFKTGQAKEIDTAICAKTDGCNEARWFSLTTRNVNDGQIQGVINK
LWGVDTNYQSVSKFHVFHDSTNFYGSTGNARGQAVVNISNSAFPILMARNDKNYWLAFGEKRAWDKNELAYI
TEAPSIVQPENVTRDTATFNLPFISLGQVGEGKLMVIGNPHYNSILRCPNGYSWGGGVNSKGECTLSGDSDD
MKHFMQNVLRYLSNDIWQPNTKSIMTVGTNLENVYFKKAGQVLGNSAPFAFHEDFTGITVKQLTSYGDLNPE
EIPLLILNGFEYVTQWSGDPYAVPLRADTSKPKLTQQDVTDLIAYLNKGGSVLIMENVMSNLKEESASSFVR
LLDAAGLSMALNKSVVNN
```

>pK1-3526B                                                                   (SEQ ID 11)
```
GATCCGCAAGGGTATCCGGATCGCGTTCGTCAGCGTCGCGCGACTGGCATTTGGGTTTATGAACGTTATCCT
GCTGCAGACGGCGCGCAACCGCCGTACACCATCGACCCAAATACGAGCGGGAAGTGACCTGGAAATACCAGCA
GACAACAAGCCTGATGACAAGCCGAAACTGGAAGTTGCGAGCTGGCAGGAGGAAGTTGAGGGCAAACAGGTA
ACGCGTTATGCCTTTATTGATGAAGCGGAATACACAACAGAAGAATCTCTGGAAGCGGCAAAGGCAAAAATC
TTTGAGAAGTTTCCTGGGTTACAGGAGTGTAAGGACTCGACTTACCATTACGAGATTAACTGTTTGGAGCGC
CGCCCAGGCACGGATGTTCCGGTAACAGGTGGCATGTATGTTCCGCGCTATACGCAACTGAATCTTGACGCC
GACACCGCGAAAGCGATGGTGCAGGCGGCGGATTTAGGCACCAACATTCAGCGCCTGTATCAGCATGAGCTT
TATTTCCGTACCAAAGGCAGTAAAGGTGAGCGTCTGAACAGTGTTGATCTGGAACGTCTGTACCAGAACATG
TCGGTCTGGCTGTGGAACGATACGAAATATCGTTACGAAGAGGGCAAGGAAGATGAGCTGGGCTTTAAAACG
TTCACCGAGTTCCTGAACTGCTACGCCAATGATGCCTATGCGGCGGCACCAAGTGCTCCGCAGATCTGAAA
AAATCGCTGGTCGATAACAACATGATCTACGGTGACGGTAGCAGCAAAGCGGGCATGATGAACCCAAGCTAT
CCGCTCAACTATATGGAAAAACCGCTGACGCGTCTGATGCTGGGCCGTTCCTGGTGGGATCTGAACATTAAG
GTTGATGTGGAGAAGTACCCAGGATCCGTATCGGCAAAGGGTGAGAGCGTTACGGAAAACATCAGCCTGTAC
TCGAATCCGACCAAATGGTTTGCGGGTAACATGCAGTCAACCGGCCTGTGGGCACCGGCCCAGCAGGACGTC
ACCATTAAGTCTTCGGCGTCAGTCCCAGTGACTGTTACCGTGGCGCTGGCTGACGACCTGACTGGACGTGAG
AAGCATGAAGTTGCGCTGAACCGTCCGCCAAGAGTGACTAAAACGTATACTCTGGAGGCTAACGGTGAAGTG
ACCTTCAAGGTGCCTTATGGTGGTCTGATTTATATCAAGGGCGACAGTAAGGATGATGTTTCTGCTAACTTC
ACCTTTACCGGTGTAGTAAAAGCGCCGTTCTATAAAGACGGCGAATGGAAAAACGATCTGGACTCACCGGCG
CCGCTGGGCGAGCTGGAGTCTGCGTCGTTCGTCTATACCACGCCGAAGAAGAACCTTGAGGCCAGCAATTTC
ACTGGTGGTGTAGCAGAATTCGCTAAAGATCTGGATACCTTTGCCAGCTCGATGAATGACTTCTACGGTCGT
AATGATGAAGACGGTAAGCACCGGATGTTTACCTATAAAAACTTGACGGGGCACAAGCATCGTTTCACCAAC
GATGTGCAGATCTCCATCGGTGATGCGCACTCGGGTTATCCGGTAATGAACAGCAGCTTCTCGACGAACAGC
ACCACGCTGCCGACGACGCCGCTGAACGACTGGCTGATTTGGCACGAAGTCGGTCATAACGCTGCAGAAACA
CCGCTGAACGTACCGGGTGCAACTGAAGTGGCGAACAACGTGCTGGCGCTGTACATGCAGGATCGCTATCTC
GGTAAGATGAACCGTGTCGCTGACGACATTACCGTCGCGCCGGAATATCTGGACGAGAGCAACGGTCAGGCC
TGGGCGCGCGGCGGTGCGGGTGACCGTCTGCTGATGTACGCACAGTTGAAGGAGTGGGCAGAGGAAAACTTT
GATATCAAACAGTGGTATCCAGATGGTGAGCTGCCTAAGTTCTACAGCGATCGTAAAGGGATGAAGGGCTGG
AACCTGTTCCAGTTGATGCACCGTAAAGCGCGCGGCGATGATGTTGGTAACAGCACCTTTGGTGGCAAGAAT
TACTGTGCTGAATCAATGGTAACGCTGCCGACACGCTGATGCTGTGTGCATCCTGGGTCGCTCAGGCGGAT
CTTTCGGAATTCTTTAAGAAATGGAATCCGGGTGCAAGTGCTTACCAGTTGCCGGGAGCAACGGAGATGAGT
TTCCAGGGCGGTGTGAGCTCTTCGGCTTACAGCACGCTGGCGTCACTCAAGCTGCCGAAACCGGAAAAGGG
CCGGAAACCATTAACAAGGTTACCGAGCATAAGATGTCTGCCGAG
```

>pK1-3526B                                                                   (SEQ ID 12)
```
DPQGYPDRVRQRRATGIWVYERYPAADGAQPPYTIDPNTGEVTWKYQQDNKPDDKPKLEVASWQEEVEGKQV
TRYAFIDEAEYTTEESLEAAKAKIFEKFPGLQECKDSTYHYEINCLERRPGTDVPVTGGMYVPRYTQLNLDA
DTAKAMVQAADLGTNIQRLYQHELYFRTKGSKGERLNSVDLERLYQNMSVWLWNDTKYRYEEGKEDELGFKT
FTEFLNCYANDAYAGGTKCSADLKKSLVDNNMIYGDGSSKAGMMNPSYPLNYMEKPLTRLMLGRSWWDLNIK
VDVEKYPGSVSAKGESVTENISLYSNPTKWFAGNMQSTGLWAPAQQDVTIKSSASVPVTVTVALADDLTGRE
KHEVALNRPPRVTKTYTLEANGEVTFKVPYGGLIYIKGDSKDDVSANFTFTGVVKAPFYKDGEWKNDLDSPA
PLGELESASFVYTTPKKNLEASNFTGGVAEFAKDLDTFASSMNDFYGRNDEDGKHRMFTYKNLTGHKHRFTN
DVQISIGDAHSGYPVMNSSFSTNSTTLPTTPLNDWLIWHEVGHNAAETPLNVPGATEVANNVLALYMQDRYL
GKMNRVADDITVAPEYLDESNGQAWARGGAGDRLLMYAQLKEWAEENFDIKQWYPDGELPKFYSDRKGMKGW
NLFQLMHRKARGDDVGNSTFGGKNYCAESNGNAADTLMLCASWVAQADLSEFFKKWNPGASAYQLPGATEMS
FQGGVSSSAYSTLASLKLPKPEKGPETINKVTEHKMSAE
```

>pK1-3526dG                                                                  (SEQ ID 13)
```
GATACGCCGTCTGTAGATTCTGGATCAGGGACTTTGCCGGAAGTGAAACCCGATCCAACACCAACCCCGGAG
CCGACACCTGAGCCGACGCCGGACCCAGAACCTACGCCGGATCCAACACCTGATCCTGAGCCGACACCAGAA
CCGGAGCCAGAACCTGTTCCTACGAAAACGGGTTATCTGACCCTGGGCGGAAGCCAGCGGGTAACTGGTGCT
ACCTGTAATGGTGAATCCAGCGATGGCTTTACCTTTACGCCAGGCAATACCGTGAGTTGTGTGGTGGGCAGT
ACGACCATTGCAACATTCAACACCCAGTCAGAAGCTGCGCGTAGCCTGCGTGCGGTTGACAAAGTGTCGTTT
AGCCTGGAGGACGCGCAGGAGCTGGCGAATTCTGAAAATAAGAAAACCAACGCCATCTCTCTGGTGACGTCC
AGCGACGTTGCCCCGCAGATGCAGAACAGCTTTGTCTTACTTTCTGTCAGTGGTTGATCGCGGCGGATT
GAAAAACTGTATAAGCAAATTGATCTGGCAACAGACAATTTCAGCAAGCTGGTCAATGAAGAGGTGGAAAAC
AATGCTGCGACTGATAAAGCGCCGTCCACCCATACCTCAACGGTAGTGCCAGTCACGACAGAGGGAACAAAA
CCGGATCTGAACGCGTCCTTCGTGTCGGCTAACGCGGAACAGTTTTATCAGTATCAACCCACTGAAATCATT
CTTTCCGAAGGCCAACTGGTGGATAGCCTGGGGAACGGTGTTGCTGGCGTTGACTACTACACCAATTCAGGC
CGTGGCGTAACTGACGAAAACGGTAAATTTTCCTTTAGCTGGGGCGAAACCATCTCCTTTGGTATCGATACC
```

-continued

```
TTTGAACTGGGCTCAGTACGTGGCAATAAGTCGACCATTGCGCTGACTGAATTGGGTGATGAAGTTCGCGGG
GCAAATATCGATCAGCTCATTCATCGTTATTCGACGACTGGTCAAAATAATACTCGTGTTGTTCCGGACGAT
GTACGCAAGGTCTTTGCCGAATATCCCAACGTGATCAACGAGATAATCAATCTTTCGTTATCCAACGGTGCG
ACGCTGGATGAAGGCGATCAAAACGTTGTGCTGCCTAACGAATTTATCGAGCAGTTTAAGACGGGTCAGGCC
AAAGAGATCGATACCGCGATTTGTGCGAAAACCGACGGTTGTAACGAGGCTCGCTGGTTCTCGCTGACAACG
CGCAATGTTAATGACGGCCAGATTCAGGGCGTTATTAACAAGCTGTGGGGCGTGGATACGAACTATCAGTCT
GTCAGCAAGTTCCACGTCTTCCATGACTCTACCAACTTCTATGGCAGCACCGGTAACGCGCGCGGTCAGGCG
GTGGTAAATATCTCCAACTCGGCATTCCCGATTCTGATGGCGCGTAATGATAAAAACTACTGGCTGGCGTTT
GGCGAAAAACGCGCCTGGGATAAAAATGAGCTGGCGTACATTACGGAAGCGCCTTCCATTGTGCAGCCAGAG
AACGTTACGCGCGATACTGCGACTTTCAACCTGCCGTTTATTTCGCTGGGGCAAGTCGGTGAAGGCAAACTG
ATGGTTATCGGTAACCCGCACTACAACAGCATCCTGCGTTGCCCGAACGGTTACAGTTGGGGCGGTGGTGTT
AATAGTAAAGGTGAGTGTACGCTCAGCGGTGATTCTGATGACATGAAGCACTTTATGCAGAACGTACTGCGC
TACTTGTCAAATGACATCTGGCAGCCAAATACCAAGAGCATCATGACTGTCGGCACCAACCTGGAGAACGTT
TATTTCAAAAAAGCGGGCCAGGTATTGGGAAATAGTGCACCATTTGCTTTCCATGAGGATTTCACTGGTATC
ACGGTTAAACAGTTGACCAGCTATGGCGATCTGAATCCGGAAGAGATTCCGTTGCTGATCCTCAACGGCTTT
GAATATGTGACTCAGTGGTCTGGCGATCCCTATGCTGTGCCTCTGCGTGCAGATACCAGCAAACCGAAGCTG
ACTCAGCAGGATGTGACCGATCTGATCGCTTATCTGAACAAAGGTGGCTCGGTGCTGATCATGGAAAACGTG
ATGAGCAATCTTAAGGAAGAGAGCGCGTCCAGTTTTTGTCGTCTGCTGGATGCCGCGGGTCTGTCAATGGCT
CTGAACAAATCGGTGGTGAACAACGATCCGCAAGGGTATCCGGATCGCGTTCGTCAGCGTCGCGCGACTGGC
ATTTGGGTTTATGAACGTTATCCTGCTGCAGACGGCGCGCAACCGCCGTACACCATCGACCCAAATACAGGG
GAAGTGACCTGGAAATACCAGCAAGACAACAAGCCTGATGACAAGCCGAAACTGGAAGTTGCGAGCTGGCAG
GAGGAAGTTGAGGGCAAACAGGTAACGCGTTATGCCTTTATTGATGAAGCGGAATACAACAGAAGAATCT
CTGGAAGCGGCAAAGGCAAAAATCTTTGAGAAGTTTCCTGGGTTACAGGAGTGTAAGGACTCGACTTACCAT
TACGAGATTAACTGTTTGGAGCGCCGCCCAGGCACGGATGTTCCGGTAACAGGTGGCATGTATGTTCCGCGC
TATACGCAACTGAATCTTGACGCCGACACCGCGAAAGCGATGGTGCAGGCGGCGGATTTAGGCACCAACATT
CAGCGCCTCTATCAGCATGAGCTTTATTTCCGTACCAAAGGCAGTAAAGGTGAGCGTCTGAACAGTGTTGAT
CTGGAACGTCTGTACCAGAACATGTCGGTCTGGCTGTGGAACGATACGAAATATCGTTACGAAGAGGGCAAG
GAAGATGAGCTGGGCTTTAAAACGTTCACCGAGTTCCTGAACTGCTACGCCAATGATGCCTATGCAGGCGGC
ACCAAGTGCTCCGCAGATCTGAAAAAATCGCTGGTCGATAACAACATGATCTACGGTGACGGTAGCAGCAAA
GCGGGCATGATGAACCCAAGCTATCCGCTCAACTATATGGAAAAACGCTGACGCTCTGATGCTGGGCCGT
TCCTGGTGGGATCTGAACATTAAGGTTGATGTGGAGAAGTACCCAGGATCCGTATCGGCAAAGGGTGGAGAGC
GTTACGGAAAACATCAGCCTGTACTCGAATCCGACCAAATGGTTTGCGGGTAACATGCAGTCAACCGGCCTG
TGGGCACCGGCCCAGCAGGACGTCACCATTAAGTCTTCGGCGTCAGTCCCAGTGACTGTTACCGTGGCGCTG
GCTGACGACCTGACTGGACGTGAGAAGCATGAAGTTGCGCTGAACCGTCCGCCAAGAGTGACTAAAACGTAT
ACTCTGGAGGCTAACGGTGAAGTGACCTTCAAGGTGCCTTATGGTGGTCTGATTTATATCAAGGGCGACAGT
AAGGATGATGTTTCTGCTAACTTCACCTTTACCGGTGTAGTAAAAGCGCCGTTCTATAAAGACGGCGAATGG
AAAAACGATCTGGACTCACCGGCGCCGCTGGGCGAGCTGGAGTCTGCGTCGTTCGTCTATACCACGCCGAAG
AAGAACCTTGAGGCCAGCAATTTCACTGGTGGTGTAGCAGAATTCGCTAAAGATCTGGATACCTTTGCCAGC
TCGATGAATGACTTCTACGGTCGTAATGATGAAGACGGTAAGCACCGGATGTTTACCTATAAAAACTTGACG
GGGCACAAGCATCGTTTCACCAACGATGTGCAGATCTCCATCGGTGATGCGCACTGGGTTATCCGGTAATG
AACAGCAGCTTCTCGACGAACAGCACCACGCTGCCGACGACGCCGCTGAACGACTGGCTGATTTGGCACGAA
GTCGGTCATAACGCTGCAGAAACACCGCTGAACGTACCGGGTGCAACTGAAGTGGCGAACAACGTGCTGGCG
CTGTACATGCAGGATCGCTATCTCGGTAAGATGAACCGTGTCGCTGACGACATTACCGTCGCGCGCCGGAATAT
CTGGACGAGAGCAACGGTCAGGCCTGGGCGCGCGGCGGTGCGGGTGACCGTCTGCTGATGTACGCACAGTTG
AAGGAGTGGGCAGAGGAAAACTTTGATATCAAACAGTGGTATCCAGATGGTGAGCTGCCTAAGTTCTACAGC
GATCGTAAAGGGATGAAGGGCTGGAACCTGTTCCAGTTGATGCACCGTAAAGCGCGCGGCGATGATGTTGGT
AACAGCACCTTTGGTGGCAAGAATTACTGTGCTGAATCCAATGGTAACGCTGCCGACACGCTGATGCTGTGT
GCATCCTGGGTCGCTCAGGCGGATCTTTCGGAATTCTTTAAGAAATGGAATCCGGGTGCAAGTGCTTACCAG
TTGCCGGGAGCAACGGAGATGAGTTTCCAGGGCGGTGTGAGCTCTTCGGCTTACAGCACGCTGGCGTCACTC
AAGCTGCCGAAACCGGAAAAGGGCCGGAAACCATTAACAAGGTTACCGAGCATAAGATGTCTGCCGAG
```

>pK1-3526dG                                                    (SEQ ID 14)

DTPSVDSGSGTLPEVKPDPTPTPEPTPEPTPDPEPTPDPTPDPEPTPEPEPEPVPTKTGYLTLGGSQRVTGA
TCNGESSDGFTFTPGNTVSCVVGSTTIATFNTQSEAARSLRAVDKVSFSLEDAQELANSENKKTNAISLVTS
SDSCPADAEQLCLTFSSVVDRARFEKLYKQIDLATDNFSKLVNEEVENNAATDKAPSTHTSTVVPVTTEGTK
PDLNASFVSANAEQFYQYQPTEIILSEGQLVDSLGNGVAGVDYYTNSGRGVTDENGKFSFSWGETISFGIDT
FELGSVRGNKSTIALTELGDEVRGANIDQLIHRYSTTGQNNTRVVPDDVRKVFAEYPNVINEIINLSLSNGA
TLDEGDQNVVLPNEFIEQFKTGQAKEIDTAICAKTDGCNEARWFSLTTRNVNDGQIQGVINKLWGVDTNYQS
VSKFHVFHDSTNFYGSTGNARGQAVVNISNSAFPILMARNDKNYWLAFGEKRAWDKNELAYITEAPSIVQPE
NVTRDTATFNLPFISLGQVGEGKLMVIGNPHYNSILRCPNGYSWGGGVNSKGECTLSGDSDDMKHFMQNVLR
YLSNDIWQPNTKSIMTVGTNLENVYFKKAGQVLGNSAPFAFHEDFTGITVKQLTSYGDLNPEEIPLLILNGF
EYVTQWSGDPYAVPLRADTSKPKLTQQDVTDLIAYLNKGGSVLIMENVMSNLKEESASSFVRLLDAAGLSMA
LNKSVVNNDPQGYPDRVRQRRATGIWVYERYPAADGAQPPYTIDPNTGEVTWKYQQDNKPDDKPKLEVASWQ
EEVEGKQVTRYAFIDEAEYTTEESLEAAKAKIFEKFPGLQECKDSTYHYEINCLERRPGTDVPVTGGMYVPR
YTQLNLDADTAKAMVQAADLGTNIQRLYQHELYFRTKGSKGERLNSVDLERLYQNMSVWLWNDTKYRYEEGK
EDELGFKTFTEFLNCYANDAYAGGTKCSADLKKSLVDNNMIYGDGSSKAGMMNPSYPLNYMEKPLTRLMLGR
SWWDLNIKVDVEKYPGSVSAKGESVTENISLYSNPTKWFAGNMQSTGLWAPAQQDVTIKSSASVPVTVTVAL
ADDLTGREKHEVALNRPPRVTKTYTLEANGEVTFKVPYGGLIYIKGDSKDDVSANFTFTGVVKAPFYKDGEW
KNDLDSPAPLGELESASFVYTTPKKNLEASNFTGGVAEFAKDLDTFASSMNDFYGRNDEDGKHRMFTYKNLT
GHKHRFTNDVQISIGDAHSGYPVMNSSFSTNSTTLPTTPLNDWLIWHEVGHNAAETPLNVPGATEVANNVLA
LYMQDRYLGKMNRVADDITVAPEYLDESNGQAWARGGAGDRLLMYAQLKEWAEENFDIKQWYPDGELPKFYS
DRKGMKGWNLFQLMHRKARGDDVGNSTFGGKNYCAESNGNAADTLMLCASWVAQADLSEFFKKWNPGASAYQ
LPGATEMSFQGGVSSSAYSTLASLKLPKPEKGPETINKVTEHKMSAE

>pK1-3526dP                                                    (SEQ ID 15)

AAAACGGGTTATCTGACCCTGGGCGGAAGCCAGCGGGTAACTGGTGCTACCTGTAATGGTGAATCCAGCGAT
GGCTTTACCTTTACGCCAGGCAATACCGTGAGTTGTGTGGTGGGCAGTACGACCATTGCAACATTCAACACC
CAGTCAGAAGCTGCGCGTAGCCTGCGTGCGGTTGACAAAGTGTCGTTTAGCCTGGAGGACGCGCAGGAGCTG
GCGAATTCTGAAAATAAGAAAACCAACGCCATCTCTCTGGTGACGTCCAGCGACAGTTGCCCCGCAGATGCA
```

-continued
```
GAACAGCTTTGTCTTACTTTCTCGTCAGTGGTTGATCGCGCGCGATTTGAAAAACTGTATAAGCAAATTGAT
CTGGCAACAGACAATTTCAGCAAGCTGGTCAATGAAGAGGTGGAAAACAATGCTGCGACTGATAAAGCGCCG
TCCACCCATACCTCAACGGTAGTGCCAGTCACGACAGAGGGAACAAAACCGGATCTGAACGCGTCCTTCGTG
TCGGCTAACGCGGAACAGTTTTATCAGTATCAACCCACTGAAATCATTCTTTCCGAAGGCCAACTGGTGGAT
AGCCTGGGGAACGGTGTTGCTGGCGTTGACTACTACACCAGTTCAGGCGCGTGGCGTAACTGACGAAAACGGT
AAATTTTCCTTTAGCTGGGGCGAAACCATCTCCTTTGGTATCGATACCTTTGAACTGGGCTCAGTACGTGGC
AATAAGTCGACCATTGCGCTGACTGAATTGGGTGATGAAGTTCGCGGGGCAAATATCGATCAGCTCATTCAT
CGTTATTCGACGACTGGTCAAAATAATACTCGTGTTGTTCCGGACGATGTACGCAAGGTCTTTGCCGAATAT
CCCAACGTGATCAACGAGATAATCAATCTTTCGTTATCCAACGGTGCGACGCTGGATGAAGGCGATCAAAAC
GTTGTGCTGCCTAACGAATTTATCGAGCAGTTTAAGACGGGTCAGGCCAAAGAGATCGATACCGCGATTTGT
GCGAAAACCGACGGTTGTAACGAGGCTCGCTGGTTCTCGCTGACAACGCGCAATGTTAATGACGGCCAGATT
CAGGGCGTTATTAACAAGCTGTGGGGCGTGGATACGAACTATCAGTCTGTCAGCAAGTTCCACGTCTTCCAT
GACTCTACCAACTTCTATGGCAGCACCGGTAACGCGCGCGGTCAGGCGGTGGTAAATATCTCCAACTCGGCA
TTCCCGATTCTGATGGCGCGTAATGATAAAAACTACTGGCTGGCGTTTGGCGAAAAACGCGCTGGGATAAA
AATGAGCTGGCGTACATTACGGAAGCGCCTTCCATTGTGCAGCCAGAGAACGTTACGCGCGATACTGCGACT
TTCAACCTGCCGTTTATTTCGCTGGGGCAAGTCGGTGAAGGCAAACTGATGGTTATCGGTAACCCGCACTAC
AACAGCATCCTGCGTTGCCCGAACGGTTACAGTTGGGGCGGTGGTGTTAATAGTAAAGGTGAGTGTACGCTC
AGCGGTGATTCTGATGACATGAAGCACTTTATGCAGAACGTACTGCGCTACTTGTCAAATGACATCTGGCAG
CCAAATACCAAGAGCATCATGACTGTCGGCACCAACCTGGAGAACGTTTATTTCAAAAAAGCGGGCCAGGTA
TTGGGAAATAGTGCACCATTTGCTTTCCATGAGGATTTCACTGGTATCACGGTTAAACAGTTGACCAGCTAT
GGCGATCTGAATCCGGAAGAGATTCCGTTGCTGATCCTCAACGGCTTTGAATATGTGACTCAGTGGTCTGGC
GATCCCTATGCTGTGCCTCTGCGTGACAGATACCAGCAAACCGAAGCTGACTCAGGATGTGACCGATCTG
ATCGCTTATCTGAACAAAGGTGGCTCGGTGCTGATCATGGAAAACGTGATGAGCAATCTTAAGGAAGAGAGC
GCGTCCAGTTTTGTGCGTCTGCTGGATGCCGCGGGTCTGTCAATGGCTCTGAACAAATCGGTGGTGAACAAC
GATCCGCAAGGGTATCCGGATCGCGTTCGTCAGCGTCGCGCGACTGGCATTTGGGTTTATGAACGTTATCCT
GCTGCAGACGGCGCGCAACCGCCGTACACCATCGACCCAAATACAGGGGAAGTGACCTGGAAATACCAGCAA
GACAACAAGCCTGATGACAAGCCGAAACTGGAAGTTGCGAGCTGGCAGGAGGAAGTTGAGGGCAAACAGGTA
ACGCGTTATGCCTTTATTGATGAAGCGGAATACACAACAGAAGAATCTCTGGAAGCGGCAAAGGCAAAAATC
TTTGAGAAGTTTCCTGGGTTACAGGAGTGTAAGGACTCGACTTACCATTACGAGATTAACTGTTTGGAGCGC
CGCCCAGGCACGGATGTTCCGGTAACAGGTGGCATGTATGTTCCGCGCTATACGCAACTGAATCTTGACGCC
GACACCGCGAAAGCGATGGTGCAGGCGGCGGATTTAGGCACCAACATTCAGCGCCTGTATCAGCATGAGCTT
TATTTCCGTACCAAAGGCAGTAAAGGTGAGCGTCTGAACAGTGTTGATCTGGAACGTCTGTACCAGAACATG
TCGGTCTGGCTGTGGAACGATACGAAATATCGTTACGAAGAGGGCAAGGAAGATGAGCTGGGCTTTAAAACG
TTCACCGAGTTCCTGAACTGCTACGCCAATGATGCCTATGCAGGCGGCACCAAGTGCTCCGCAGATCTGAAA
AAATCGCTGGTCGATAACAACATGATCTACGGTGACGGTAGCAGCAAAGCGGGCATGATGAACCCAAGCTAT
CCGCTCAACTATATGGAAAAACCGCTGACGCGTCTGATGCTGGGCCGTTCCTGGTGGGATCTGAACATTAAG
GTTGATGTGGAGAAGTACCCAGGATCCGTATCGGCAAAGGGTGAGAGCGTTACGGAAAACATCAGCCTGTAC
TCGAATCCGACCAAATGGTTTGCGGGTAACATGCAGTCAACCGGCCTGTGGGCACCGGCCCAGCAGGACGTC
ACCATTAAGTCTTCGGCGTCAGTCCCAGTGACTGTTACCGTGGCGCTGGCTGACGACCTGACTGGACGTGAG
AAGCATGAAGTTGCGCTGAACCGTCCGCCAAGAGTGACTAAAACGTATACTCTGGAGGCTAACGGTGAAGTG
ACCTTCAAGGTGCCTTATGGTGGTCTGATTTATATCAAGGGCGACAGTAAGGATGATGTTTCTGCTAACTTC
ACCTTTACCGGTGTAGTAAAAGCGCCGTTCTATAAAGACGGCGAATGGAAAACGATCTGGACTCACCGGCG
CCGCTGGGCGAGCTGGAGTCTGCGTCGTTCGTCTATACCACGCCGAAGAAGAACCTTGAGGCCAGCAATTTC
ACTGGTGGTGTAGCAGAATTCGCTAAAGATCTGGATACCTTTGCCAGCTCGATGAATGACTTCTACGGTCGT
AATGATGAAGACGGTAAGCACCGGATGTTTACCTATAAAAACTTGACGGGGCACAAGCATCGTTTCACCAAC
GATGTGCAGATCTCCATCGGTGATGCGCACTCGGGTTATCCGGTAATGAACAGCAGCTTCTCGACGAACAGC
ACCACGCTGCCGACGACGCCGCTGAACGACTGGCTGATTTGGCACGAAGTCGGTCATAACGCTGCAGAAACA
CCGCTGAACGTACCGGGTGCAACTGAAGTGGCGAACAACGTGCTGGCGCTGTACATGCAGGATCGCTATCTC
GGTAAGATGAACCGTGTCGCTGACGACATTACCGTCGCGCCGGAATATCTGGACGAGAGCAACGGTCAGGCC
TGGGCGCGCGGCGGTGCGGGTGACCGTCTGCTGATGTACGCACAGTTGAAGGAGTGGGCAGAGGAAACTTT
GATATCAAACAGTGGTATCCAGATGGTGAGCTGCCTAAGTTCTACAGCGATCGTAAAGGGATGAAGGGCTGG
AACCTGTTCCAGTTGATGCACCGTAAAGCGCGCGGCGATGATGTTGGTAACAGCACCTTTGGTGGCAAGAAT
TACTGTGCTGAATCCAATGGTAACGCTGCCGACACGCTGATGCTGTGTGCATCCTGGGTCGCTCAGGCGGAT
CTTTCGGAATTCTTTAAGAAATGGAATCCGGGTGCAAGTGCTTACCAGTTGCCGGGAGCAACGGAGATGAGT
TTCCAGGGCGGTGTGAGCTCTTCGGCTTACAGCACGCTGGCGTCACTCAAGCTGCCGAAACCGGAAAAAGGG
CCGGAAACCATTAACAAGGTTACCGAGCATAAGATGTCTGCCGAG
```

>pK1-3526dP (SEQ ID 16)
```
KTGYLTLGGSQRVTGATCNGESSDGFTFTPGNTVSCVVGSTTIATFNTQSEAARSLRAVDKVSFSLEDAQEL
ANSENKKTNAISLVTSSDSCPADAEQLCLTFSSVVDRARFEKLYKQIDLATDNFSKLVNEEVENNAATDKAP
STHTSTVVPVTTEGTKPDLNASFVSANAEQFYQYQPTEIILSEGQLVDSLGNGVAGVDYYTNSGRGVTDENG
KFSFSWGETISFGIDTFELGSVRGNKSTIALTELGDEVRGANIDQLIHRYSTTGQNNTRVVPDDVRKVFAEY
PNVINEIINLSLSNGATLDEGDQNVVLPNEFIEQFKTGQAKEIDTAICAKTDGCNEARWFSLTTRNVNDGQI
QGVINKLWGVDTNYQSVSKFHVFHDSTNFYGSTGNARGQAVVNISNSAFPILMARNDKNYWLAFGEKRAWDK
NELAYITEAPSIVQPENVTRDTATFNLPFISLGQVGEGKLMVIGNPHYNSILRCPNGYSWGGGVNSKGECTL
SGDSDDMKHFMQNVLRYLSNDIWQPNTKSIMTVGTNLENVYFKKAGQVLGNSAPFAFHEDFTGITVKQLTSY
GDLNPEEIPLLILNGFEYVTQWSGDPYAVPLRADTSKPKLTQQDVTDLIAYLNKGGSVLIMENVMSNLKEES
ASSFVRLLDAAGLSMALNKSVVNNDPQGYPDRVRQRRATGIWVYERYPAADGAQPPYTIDPNTGEVTWKYQQ
DNKPDDKPKLEVASWQEEVEGKQVTRYAFIDEAEYTTEESLEAAKAKIFEKFPGLQECKDSTYHYEINCLER
RPGTDVPVTGGMYVPRYTQLNLDADTAKAMVQAADLGTNIQRLYQHELYFRTKGSKGERLNSVDLERLYQNM
SVWLWNDTKYRYEEGKEDELGFKTFTEFLNCYANDAYAGGTKCSADLKKSLVDNNMIYGDGSSKAGMMNPSY
PLNYMEKPLTRLMLGRSWWDLNIKVDVEKYPGSVSAKGESVTENISLYSNPTKWFAGNMQSTGLWAPAQQDV
TIKSSASVPVTVTVALADDLTGREKHEVALNRPPRVTKTYTLEANGEVTFKVPYGGLIYIKGDSKDDVSANF
TFTGVVKAPFYKDGEWKNDLDSPAPLGELESASFVYTTPKKNLEASNFTGGVAEFAKDLDTFASSMNDFYGR
NDEDGKHRMFTYKNLTGHKHRFTNDVQISIGDAHSGYPVMNSSFSTNSTTLPTTPLNDWLIWHEVGHNAAET
PLNVPGATEVANNVLALYMQDRYLGKMNRVADDITVAPEYLDESNGQAWARGGAGDRLLMYAQLKEWAEENF
DIKQWYPDGELPKFYSDRKGMKGWNLFQLMHRKARGDDVGNSTFGGKNYCAESNGNAADTLMLCASWVAQAD
LSEFFKKWNPGASAYQLPGATEMSFQGGVSSSAYSTLASLKLPKPEKGPETINKVTEHKMSAE
```

-continued

>pK1-3526 (SEQ ID 17)
TGTGATGGTGGTGGTTCAGGATCGTCCTCCGATACGCCGTCTGTAGATTCTGGATCAGGGACTTTGCCGGAA
GTGAAACCCGATCCAACACCAACCCCGGAGCCGACACCTGAGCCGACGCCGGACCCAGAACCTACGCCGGAT
CCAACACCTGATCCTGAGCCGACACCAGAACCGGAGCCAGAACCTGTTCCTACGAAAACGGGTTATCTGACC
CTGGGCGGAAGCCAGCGGGTAACTGGTGCTACCTGTAATGGTGAATCCAGCGATGGCTTTACCTTTACGCCA
GGCAATACCGTGAGTTGTGTGGTGGGCAGTACGACCATTGCAACATTCAACACCCAGTCAGAAGCTGCGCGT
AGCCTGCGTGCGGTTGACAAAGTGTCGTTTAGCCTGGAGGACGCGCAGGAGCTGGCGAATTCTGAAAATAAG
AAAACCAACGCCATCTCTCTGGTGACGTCCAGCGACAGTTGCCCCGCAGATGCAGAACAGCTTTGTCTTACT
TTCTCGTCAGTGGTTGATCGCGCGCGATTTGAAAAACTGTATAAGCAAATTGATCTGGCAACAGACAATTTC
AGCAAGCTGGTCAATGAAGAGGTGGAAAACAATGCTGCGACTGATAAAGCGCCGTCCACCCATACCTCAACG
GTAGTGCCAGTCACGACAGAGGGAACAAAACCGGATCTGAACGCGTCCTTCGTGTCGGCTAACGCGGAACAG
TTTTATCAGTATCAACCCACTGAAATCATTCTTTCCGAAGGCCAACTGGTGGATAGCCTGGGGAACGGTGTT
GCTGGCGTTGACTACTACACCAATTCAGGCCGTGGCGTAACTGACGAAAACGGTAAATTTTCCTTTAGCTGG
GGCGAAACCATCTCCTTTGGTATCGATACCTTTGAACTGGGCTCAGTACGTGGCAATAAGTCGACCATTGCG
CTGACTGAATTGGGTGATGAAGTTCGCGGGCAAATATCGATCAGCTCATTCATCGTTATTCGACGACTGGT
CAAAATAATACTCGTGTTGTTCCGGACGATGTACGCAAGGTCTTTGCCGAATATCCCAACGTGATCAACGAG
ATAATCAATCTTTCGTTATCCAACGGTGCGACGCTGGATGAAGGCGATCAAAACGTTGTGCTGCCTAACGAA
TTTATCGAGCAGTTTAAGACGGGTCAGGCCAAAGAGATCGATACCGCGATTTGTGCGAAAACCGACGGTTGT
AACGAGGCTCGCTGGTTCTCGCTGACAACGCGCAATGTTAATGACGGCCAGATTCAGGGCGTTATTAACAAG
CTGTGGGGCGTGGATACGAACTATCAGTCTGTCAGCAAGTTCCACGTCTTCCATGACTCTACCAACTTCTAT
GGCAGCACCGGTAACGCGCGCGGTCAGGCGGTGGTAAATATCTCCAACTCGGCATTCCCGATTCTGATGGCG
CGTAATGATAAAAACTACTGGCTGGCGTTTGGCGAAAAACGCGCCTGGGATAAAAATGAGCTGGCGTACATT
ACGGAAGCGCCTTCCATTGTGCAGCCAGAGAACGTTACGCGCGATACTGCGACTTTCAACCTGCCGTTTATT
TCGCTGGGGCAAGTCGGTGAAGGCAAACTGATGGTTATCGGCAATCCGCACTACAACAGCATCCTGCGTTGC
CCGAACGGTTACAGTTGGGGCGGTGGTGTTAATAGTAAAGGTGAGTGTACGCTCAGCGGTGATTCTGATGAC
ATGAAGCACTTTATGCAGAACGTACTGCGCTACTTGTCAAATGACATCTGGCAGCCAAATACCAAGAGCATC
ATGACTGTCGGCACCAACCTGGAGAACGTTTATTTCAAAAAAGCGGGCCAGGTATTGGGAAATAGTGCACCA
TTTGCTTTCCATGAGGATTTCACTGGTATCACGGTTAAACAGTTGACCAGCTATGGCGATCTGAATCCGGAA
GAGATTCCGTTGCTGATCCTCAACGGCTTTGAATATGTGACTCAGTGGTCTGGCGATCCCTATGCTGTGCCT
CTGCGTGCAGATACCAGCAAACCGAAGCTGACTCAGCAGGATGTGACCGATCTGATCGCTTATCTGAACAAA
GGTGGCTCGGTGCTGATCATGGAAAACGTGATGAGCAATCTTAAGGAAGAGAGCGCGTCCAGTTTTGTGCGT
CTGCTGGATGCCGCGGGTCTGTCAATGGCTCTGAACAAATCGGTAGTTAACAACGATCCGCAAGGGTATCCG
GATCGCGTTCGTCAGCGTCGCGCGACTGGCATTTGGGTTTATGAACGTTATCCTGCTGCAGACGGCGCGCAA
CCGCCGTACACCATCGACCCAAATACAGGGGAAGTGACCTGGAAATACCAGCAAGACAACAAGCCTGATGAC
AAGCCGAAACTGGAAGTTGCGAGCTGGCAGGAGGAAGTTGAGGGCAAACAGGTAACGCGTTATGCCTTTATT
GATGAAGCGGAATACACAACAGAAGAATCTCTGGAAGCGGCAAAGGCAAAAATCTTTGAGAAGTTTCCTGGG
TTACAGGAGTGTAAGGACTCGACTTACCATTACGAGATTAACTGTTTGGAGCTCCGCCCAGGCACGGATGTT
CCGGTAACAGGTGGCATGTATGTTCCGCGCTATACGCAACTGAATCTTGACGCCGACACCGCGAAAGCGATG
GTGCAGGCGGCGGATTTAGGCACCAACATTCAGCGCCTGTATCAGCATGAGCTTTATTTCCGTACCAAAGGC
AGTAAAGGTGAGCGTCTGAACAGTGTTGATCTGGAACGTCTGTACCAGAACATGTCGGTCTGGCTGTGGAAC
GATACGAAATATCGTTACGAAGAGGGCAAGGAAGATGAGCTGGGCTTTAAAACGTTCACCGAGTTCCTGAAA
TGCTACGCCAATGATGCCTATGCAGGCGGCACCAAGTGCTCCGCAGATCTGAAAAAATCGCTGGTCGATAAC
AACATGATCTACGGTGACGGTAGCAGCAAAGCGGGCATGATGAACCCAAGCTATCCGCTCAACTATATGGAA
AAACCGCTGACGCGTCTGATGCTGGGCCGTTCCTGGTGGGATCTGAACATTAAGGTTGATGTGGAGAAGTAC
CCAGGATCCGTATCGGCAAAGGGTGAGAGCGTTACGGAAAACATCAGCCTGTACTCGAATCCGACCAAATGC
TTTGCGGGTAACATGCAGTCAACCGGCCTGTGGGCACCGGCCCAGCAGGACGTCACCATTAAGTCTTCGGCG
TCAGTCCCAGTGACTGTTACCGTGGCGCTGGCTGACACCGACTGGACGTGAGAAGCATGAAGTTGCGCTG
AACCGTCCGCCAAGAGTGACTAAAACGTATACTCTGGAGGCTAACGGTGAAGTGACCTTCAAGGTGCCTTAT
GGTGGTCTGATTTATATCAAGGGCGAACGTAAGGATGATGTTTCTGCTAACTTCACCTTTACCGGTGTAGTA
AAAGCGCCGTTCTATAAAGACGGCGAATGGAAAAACGATCTGGACTCACCGGCGCCGCTGGGCGAGCTGGAG
TCTGCGTCGTTCGTCTATACCACGCCGAAGAAGAACCTTGAGGCCAGCAATTTCACTGGTGGTAGCAGAA
TTCGCTAAAGATCTGGATACCTTTGCCAGCTCGATGAATGACTTCTACGGTCGTAATGATGAAGACGGTAAG
CACCGGATGTTTACCTATAAAAACTTGACGGGGCACAAGCATCGTTTCACCAACGATGTCGACATCTCCATC
GGTGATGCGCACTCGGGTTATCCGGTAATGAACAGCAGCTTCTCGACGAACAGCACCACGCTGCCGACGACG
CCGCTGAACGACTGGCTGATTGGCACGAAGTCGGTCATAACGCTGCAGAAACACCGCTGAACGTACCGGGT
GCAACTGAAGTGGCGAACAACGTGCTGGCGCTGTACATGCAGGATCGCTATCTCGGTAAGATGAACCGTGTC
GCTGACGACATTACCGTCGCGCGCGGAATATCTGGACGAGAGCAACGGTCAGGCCTGGGCGCGCGGTGCG
GGTGACCGTCTGCTGATGTACGCACAGTTGAAGGAGTGGGCAGAGGAAAACTTTGATATCAAACAGTGGTAT
CCAGATGGTGAGCTGCCTAAGTTCTACAGCGATCGTAAAGGGATGAAGGGCTGGAACCTGTTCCAGTTGATG
CACCGTAAAGCGCGCGGCGATGATGTTGGTAACAGCACCTTTGGTGGCAAGAATTACTGTGCTGAATCCAAT
GGTAACGCTGCCGACACGCTGATGCTGTGTGCATCCTGGGTCGCTCAGGCGGATCTTTCGGAATTCTTTAAG
AAATGGAATCCAGGTGCAAGTGCTTACCAGTTGCCGGGAGCAACGGAAGATGAGTTTCCAGGGCGGTGTGAGC
TCTTCGGCTTACACGCGTGGCGTCATCAAGCTGCCGAAACCGGAAAAAGGGCCGGAAACCATTAACAAG
GTTACCGAGCATAAGATGTCTGCCGAG

>pK1-3526 (SEQ ID 18)
CDGGGSGSSSDTPSVDSGSGTLPEVKPDPTPTPEPTPEPTPDPEPTPDPTPDPEPTPEPEPEPVPTKTGYLT
LGGSQRVTGATCNGESSDGFTFTPGNTVSCVVGSTTIATFNTQSEAARSLRAVDKVSFSLEDAQELANSENK
KTNAISLVTSSDSCPADAEQLCLTFSSVVDRARFEKLYKQIDLATDNFSKLVNEEVENNAATDKAPSTHTST
VVPVTTEGTKPDLNASFVSANAEQFYQYQPTEIILSEGQLVDSLGNGVAGVDYYTNSGRGVTDENGKFSFSW
GETISFGIDTFELGSVRGNKSTIALTELGDEVRGANIDQLIHRYSTTGQNNTRVVPDDVRKVFAEYPNVINE
IINLSLSNGATLDEGDQNVVLPNEFIEQFKTGQAKEIDTAICAKTDGCNEARWFSLTTRNVNDGQIQGVINK
LWGVDTNYQSVSKFHVPHDSTNFYGSTGNARGQAVVNISNSAFPILMARNDKNYWLAFGEKRAWDKNELAYI
TEAPSIVQPENVTRDTATFNLPFISLGQVGEGKLMVIGNPHYNSILRCPNGYSWGGGVNSKGECTLSGDSDD
MKHFMQNVLRYLSNDIWQPNTKSIMTVGTNLENVYFKKAGQVLGNSAPFAHEDFTGITVKQLTSYGDLNPE
EIPLLILNGFEYVTQWSGDPYAVPLRADTSKPKLTQQDVTDLIAYLNKGGSVLIMENVMSNLKEESASSFVR
LLDAAGLSMALNKSVVNNDPQGYPDRVRQRRATGIWVYERYPAADGAQPPYTIDPNTGEVTWKYQQDNKPDD
KPKLEVASWQEEVEGKQVTRYAFIDEAEYTTEESLEAAKAKIFEKFPGLQECKDSTYHYEINCLERRPGTDV

-continued

PVTGGMYVPRYTQLNLDADTAKAMVQAADLGTNIQRLYQHELYFRTKGSKGERLNSVDLERLYQNMSVWLWN
DTKYRYEEGKEDELGFKTFTEFLNCYANDAYAGGTKCSADLKKSLVDNNMIYGDGSSKAGMMNPSYPLNYME
KPLTRLMLGRSWWDLNIKVDVEKYPGSVSAKGESVTENISLYSNPTKWFAGNMQSTGLWAPAQQDVTIKSSA
SVPVTVTVALADDLTGREKHEVALNRPPRVTKTYTLEANGEVTFKVPYGGLIYIKGDSKDDVSANFTFTGVV
KAPFYKDGEWKNDLDSPAPLGELESASFVYTTPKKNLEASNPTGGVAEFAKDLDTFASSMNDFYGRNDEDGK
HRMFTYKNLTGHKHRFTNDVQISIGDAHSGYPVMNSSFSTNSTTLPTTPLNDWLIWHEVGHNAAETPLNVPG
ATEVANNVLALYMQDRYLGKMNRVADDITVAPEYLDESNGQAWARGGAGDRLLMYAQLKEWAEENFDIKQWY
PDGELPKFYSDRKGMKGWNLFQLMHRKARGDDVGNSTFGGKNYCAESNGNAADTLMLCASWVAQADLSEFFK
KWNPGASAYQLPGATEMSFQGGVSSSAYSTLASLKLPKPEKGPETINKVTEHKMSAE

>pK1-3526E1305A
(SEQ ID 19)
TGTGATGGTGGTGGTTCAGGATCGTCCTCCGATACGCCGTCTGTAGATTCTGGATCAGGGACTTTGCCGGAA
GTGAAACCCGATCCAACACCCAACCCCGGAGCCGACACCTGAGCCGACGCCGGACCCAGAACCTACGCCGGAT
CCAACACCTGATCCTGAGCCGACACCAGAACCGGAGCCAGAACCTGTTCCTACGAAAACGGGTTATCTGACC
CTGGGCGGAAGCCAGCGGGTAACTGGTGCTACCTGTAATGGTGAATCCAGCGATGGCTTTACCTTTACGCCA
GGCAATACCGTGAGTTGTGTGGTGGGCAGTACGACCATTGCAACATTCAACACCCAGTCAGAAGCTGCGCGT
AGCCTGCGTGCGGTTGACAAAGTGTCGTTTAGCCTGGAGGACGCGCAGGAGCTGGCGAATTCTGAAAATAAG
AAAACCAACGCCATCTCTCTGGTGACGTCCAGCGACAGTTGCCCCGCAGATGCAGAACAGCTTTGTCTTACT
TTCTCGTCAGTGGTTGATCGCGCGCGATTTGAAAAACTGTATAAGCAAATTGATCTGGCAACAGACAATTTC
AGCAAGCTGGTCAATGAAGAGGTGGAAAACAATGCTGCGACTGATAAAGCGCCGTCCACCCATACCTCAACG
GTAGTGCCAGTCACGACAGAGGGAACAAAACCGGATCTGAACGCGTCCTTCGTGTCGGCTAACGCGGAACAG
TTTTATCAGTATCAACCCACTGAAATCATTCTTTCCGAAGGCCAACTGGTGGATAGCTGGGGAACGGTGTT
GCTGGCGTTGACTACTACACCAATTCAGGCCGTGGCGTAACTGACGAAAACGGTAAATTTTCCTTTAGCTGG
GGCGAAACCATCTCCTTTGGTATCGATACCTTTGAACTGGGCTCAGTACGTGGCAATAAGTCGACCATTGCG
CTGACTGAATTGGGTGATGAAGTTCGCGGGGCAAATATCGATCAGCTCATTCATCGTTATTCGACGACTGGT
CAAAATAATACTCGTGTTGTTCCGGACGATGTACGCAAGGTCTTTGCCGAATATCCCAACGTGATCAACGGA
ATAATCAATCTTTCGTTATCCAACGGTGCGACGCTGGATGAAGGCGATCAAAACGTTGTGCTGCCTAACGAA
TTTATCGAGCAGTTTAAGACGGGTCAGGCCAAAGAGATCGATACCGCGATTTGTGCGAAAACCGACGGTTGT
AACGAGGCTCGCTGGTTCTCGCTGACAACGCGCAATGTTAATGACAGTCGACCAGATTCAGGGCGTTATTAACAAG
CTGTGGGGCGTGGATACGAACTATCAGTCTGTCAGCAAGTTCCACGTCTTCCATGACTCTACCAACTTCTAT
GGCAGCACCGGTAACGCGCGCGGTCAGGCGGTGGTAAATATCTCCAACTCGGCATTCCCGATTCTGATGGCG
CGTAATGATAAAAACTACTGGCTGGCGTTTGGCGAAAAACGCGCCTGGGATAAAAATGAGCTGGCGTACATT
ACGGAAGCGCCTTCCATTGTGCAGCCAGAGAACGTTACGCGCGATACTGCGACTTTCAACCTGCCGTTTATT
TCGCTGGGGCAAGTCGGTGAAGGCAAACTGATGGTTATCGGTAACCCGCACTACAACAGCATCCTGCGTTGC
CCGAACGGTTACAGTTGGGCGGTGGTGTTAATAGTAAAGGTGAGTGTACGCTCAGCGGTGATTCTGATGAC
ATGAAGCACTTTATGCAGAACGTACTGCGCTACTTGTCAAATGACATCTGGCAGCCAAATACCAAGAGCATC
ATGACTGTCGGCACCAACCTGGAGAACGTTTATTTCAAAAAAGCGGGCCAGGTATTGGGAAATAGTGCACCA
TTTGCTTTCCATGAGGATTTCACTGGTATCACGGTTAAACAGTTGACCAGCTATCGGCGATCTGAATCCGGAA
GAGATTCCGTTGCTGATCCTCAACGGCTTTGAATATGTGACTCAGTGGTCTGGCGATCCCTATGCTGTGCCT
CTGCGTGCAGATACCAGCAAACCGAAGCTGACTCAGCAGGATGTGACCGATCTGATCGCTTATCTGAACAAA
GGTGGCTCGGTGCTGATCATGGAAAACGTGATGAGCAATCTTAAGGAAGAGAGCGCGTCCAGTTTTGTGCGT
CTGCTGGATGCCGCGGGTCTGTCAATGGCTCTGAACAAATCGGTGGTGAACAACGATCCGCAAGGGTATCCG
GATCGCGTTCGTCAGCGTCGCGCGACTGGCATTTGGGTTTATGAACGTTATCCTGCTGCAGACGGCGCGCAA
CCGCCGTACACCATCGACCCAAATACAGGGGAAGTGACCTGGAAATACCAGCAAGACAACAAGCCTGATGAC
AAGCCGAAACTGGAAGTTGCGAGCTGGCAGGAGGAAGTTGAGGGCAAACAGGTAACGCGTTATGCCTTTATT
GATGAAGCGGAATACAACAAGAAGAATCTCTGGAAGCGGCAAAGGCAAAATCTTTGAGAAGTTTCCTGGG
TTACAGGAGTGTAAGGACTCGACTTACCATTACGAGATTAACTGTTTGGAGCGCCGCCCAGGCACGGATGTT
CCGGTAACAGGTGGCATGTATGTTCCGCGCTATACGCAACTGAATCTTGACGCCGACACCGCGAAAGCGATG
GTGCAGGCGGCGGATTTAGGCACCAACATTCAGCGCCTGTATCAGCATGAGCTTTATTTCCGTACCAAAGGC
AGTAAAGGTGAGCGTCTGAACAGTGTTGATCTGGAACGTCTGTACCAGAACATGTCGGTCTGGCTGTGGAAC
GATACGAAATATCGTTACGAAGAGGGCAAGGAAGATGAGCTGGGCTTTAAAACGTTCACCGAGTTCCTGAAC
TGCTACGCCAATGATGCCTATGCAGGCGGCACCAAGTGCTCCGCAGATCTGAAAAATCGCTGGTCGATAAC
AACATGATCTACGGTGACGGTAGCAGCAAAGCGGGCATGATGAACCCAAGCTATCCGCTCAACTATATGGAA
AAACCGCTGACGCGTCTGATGCTGGGCCGTTCCTGGTGGGATCTGAACATTAAGGTTGATGTGGAGAAGTAC
CCAGGATCCGTATCGGCAAAGGGTGAGAGCGTTACGGAAAACATCAGCCTGTACTCGAATCCGACCAAATGG
TTTGCGGGTAACATGCAGTCAACCGGCCTGTGGGCACCGGCCCAGCAGGACGTCACCATTAAGTCTTCGGCG
TCAGTCCCAGTGACTGTTACCGTGGCGCTGGCTGACGACCTGACTGGACGTGAGAAGCATGAAGTTGCGCTG
AACCGTCCGCCAAGAGTGACTAAAACGTATACTCTGGAGGCTAACGGTGAAGTGACCTTCAAGGTGCCTTAT
GGTGGTCTGATTTATATCAAGGGCGACAGTAAGGATGATGTTTCTGCTAACTTCACCTTTACCGGTGTAGTA
AAAGCGCCGTTCTATAAAGACGGCGAATGGAAAAACGATCTGGACTCACCGGCGCCGCTGGGCGAGCTGGAG
TCTGCTTCGTTCGTCTATACCACGCCGAAGAAGAACCTTGAGGCCAGCAATTTCACTGGTGGTGTAGCAGAA
TTCGCTAAAGATCTGGATACCTTTGCCAGCTCGATGAATGACTTCTACGGTCGTAATGATGAAGACGGTAAG
CACCGGATGTTTACCTATAAAAACTTGACGGGGCACAAGCATCGTTTCACCAACGATGTGCAGATCTCCATC
GGTGATGCGCACTCGGGTTATCCGGTAATGAACAGCAGCTTCTCGACGAACAGCACCACGCTGCCGACGACG
CCGCTGAACGACTGGCTGATTTGGCACGCAGTCGGTCATAACGCTGCAGAAAACACCGCTGAACGTACCGGT
GCAACTGAAGTGGCGAACAACGTGCTGGCGCTGTACATGCAGGATCGCTATCTCGGTAAGATGAACCGTGTC
GCTGACGACATTACCGTCGCGCCGGAATATCTGGACGAGAGCAACGGTCAGGCCTGGGCGCGCGGCGGTGCG
GGTGACCGTCTGCTGATGTACGCACAGTTGAAGGAGTGGGCAGAGGAAAATTTCGATATCAAACAGTGGTAT
CCAGATGGTGAGCTGCCTAAGTTCTACAGCGATCGTAAAGGGATGAAGGGCTGGAACCTGTTCCAGTTGATG
CACCGTAAAGCGCGCGGCGATGATGTTGGTAACAGCACCTTTGGTGGCAAGAATTACTGTGCTGAATCCAAT
GGTAACGCTGCCGACACGCTGATGCTGTGTGCATCCTGGGTTGCTCAGGCGGATCTTTCGGAATTCTTTAAG
AAATGGAATCCGGGTGCAAGTGCTTACCAGTTGCCGGGAGCAACGGAGATGAGTTTCCAGGGCGGTGTGAGC
TCTTCGGCTTACAGCACGCTGGCGTCACTCAAGCTGCCGAAACCGGAAAAGGGCCGGAAACCATTAACAAG
GTTACCGAGCATAAGATGTCTGCCGAG

>pK1-3526E1305A
(SEQ ID 20)
CDGGGSGSSSDTPSVDSGSGTLPEVKPDPTPTPEPTPEPTPDPEPTPDPTPDPEPTPEPEPEPVPTKTGYLT
LGGSQRVTGATCNGESSDGFTFTPGNTVSCVVGSTTIATFNTQSEAARSLRAVDKVSFSLEDAQELANSENK
KTNAISLVTSSDSCPADAEQLCLTFSSVVDRARFEKLYKQIDLATDNFSKLVNEEVENNAATDKAPSTHTST

-continued

```
VVPVTTEGTKPDLNASFVSANAEQFYQYQPTEIILSEGQLVDSLGNGVAGVDYYTNSGRGVTDENGKFSFSW
GETISFGIDTFELGSVRGNKSTIALTELGDEVRGANIDQLIHRYSTTGQNNTRVVPDDVRKVFAEYPNVINE
IINLSLSNGATLDEGDQNVVLPNEFIEQFKTGQAKEIDTAICAKTDGCNEARWFSLTTRNVNDGQIQGVINK
LWGVDTNYQSVSKFHVFHDSTNFYGSTGNARGQAVVNISNSAFPILMARNDKNYWLAFGEKRAWDKNELAYI
TEAPSIVQPENVTRDTATFNLPFISLGQVGEGKLMVIGNPHYNSILRCPNGYSWGGGVNSKGECTLSGDSDD
MKHFMQNVLRYLSNDIWQPNTKSIMTVGTNLENVYFKKAGQVLGNSAPFAFHEDFTGITVKQLTSYGDLNPE
EIPLLILNGFEYVTQWSGDPYAVPLRADTSKPKLTQQDVTDLIAYLNKGGSVLIMENVMSNLKEESASSFVR
LLDDAAGLSMALNKSVVNNDPQGYPDRVRQRRATGIWVYERYPAADGAQPPYTIDPNTGEVTWKYQQDNKPDD
KPKLEVASWQEEVEGKQVTRYAFIDEAEYTTEESLEAAKAKIFEKFPGLQECKDSTYHYEINCLERRPGTDV
PVTGGMYVPRYTQLNLDADTAKAMVQAADLGTNIQRLYQHELYFRTKGSKGERLNSVDLERLYQNMSVWLWN
DTKYRYEEGKEDELGFKTFTEFLNCYANDAYAGGTKCSADLKKSLVDNNMIYGDGSSKAGMMNPSYPLNYME
KPLTRLMLGRSWWDLNIKVDVEKYPGSVSAKGESVTENISLYSNPTKWFAGNMQSTGLWAPAQQDVTIKSSA
SVPVTVTVALADDLTGREKHEVALNRPPRVTKTYTLEANGEVTFKVPYGGLIYIKGDSKDDVSANFTFTGVV
KAPFYKDGEWKNDLDSPAPLGELESASFVYTTPKKNLEASNFTGGVAEFAKDLDTFASSMNDFYGRNDEDGK
HRMFTYKNLTGHKHRFTNDVQISIGDAHSGYPVMNSSFSTNSTTLPTTPLNDWLIWHAVGHNAAETPLNVPG
ATEVANNVLALYMQDRYLGKMNRVADDITVAPEYLDESNGQAWARGGAGDRLLMYAQLKEWAEENFDIKQWY
PDGELPKFYSDRKGMKGWNLFQLMHRKARGDDVGNSTFGGKNYCAESNGNAADTLMLCASWVAQADLSEFFK
KWNPGASAYQLPGATEMSFQGGVSSSAYSTLASLKLPKPEKGPETINKVTEHKMSAE
```

>pK1-3526D1422A
(SEQ ID 21)
```
TGTGATGGTGGTGGTTCAGGATCGTCCTCCGATACGCCGTCTGTAGATTCTGGATCAGGGACTTTGCCGGAA
GTGAAACCCGATCCAACACCAACCCCGGAGCCGACACCTGAGCCGACGCCGGACCCAGAACCTACGCCGGAT
CCAACACCTGATCCTGAGCCGACACCAGAACCGGAGCCAGAACCTGTTCCTACGAAAACGGGTTATCTGACC
CTGGGCGGAAGCCAGCGGGTAACTGGTGCTACCTGTAATGGTGAATCCAGCGATGGCTTTACCTTTACGCCA
GGCAATACCGTGAGTTGTGTGGTGGGCAGTACGACCATTGCAACATTCAACACCCAGTCAGAAGCTGCGCGT
AGCCTGCGTGCCGGTTGACAAAGTGTCGTTTAGCCTGGAGGACGCGCAGGAGCTGGCGAATTCTGAAAATAAG
AAAACCAACGCCATCTCTCTGGTGACGTCCAGCGACAGTTGCCCCGCAGATGCAGAACAGCTTTGTCTTACT
TTCTCGTCAGTGGTTGATCGCGCGCGATTTGAAAAACTGTATAAGCAAATTGATCTGGCAACAGACAATTTC
AGCAAGCTGGTCAATGAAGAGGTGGAAAACAATGCTGCGACTGATAAAGCGCCGTCCACCCATACCTCAACG
GTAGTGCCAGTCACGACAGAGGGAACAAAACCGGATCTGAACGCGTCCTTCGTGTCGGCTAACGCGGAACAG
TTTTATCAGTATCAACCCACTGAAATCATTCTTTCCGAAGGCCAACTGGTGGATAGCCTGGGGAACGGTGTT
GCTGGCGTTGACTACTACACCAATTCAGGCCGTGGCGTAACTGACGAAAACGGTAAATTTTCCTTTAGCTGG
GGCGAAACCATCTCCTTTGGTATCGATACCTTTGAACTGGGCTCAGTACGTGGCAATAAGTCGACCATTGCG
CTGACTGAATTGGGTGATGAAGTTCGCGGGGCAAATATCGATCAGCTCATTCATCGTTATTCGACGACTGGT
CAAAATAATACTCGTGTTGTTCCGGACGATGTACGCAAGGTCTTTGCCGAATATCCCAACGTGATCAACGAG
ATAATCAATCTTTCGTTATCCAACGGTGCGACGCTGGATGAAGGCGATCAAAACGTTGTGCTGCCTAACGAA
TTTATCGAGCAGTTTAAGACGGGTCAGGCCAAAGAGATCGATACCGCGATTTGTGCGAAAACCGACGGTTGT
AACGAGGCTCGCTGGTTCTCGCTGACAACGCGCAATGTTAATGACGGCCAGATTCAGGGCGTTATTAACAAG
CTGTGGGGCGTGGATACGAACTATCAGTCTGTCAGCAAGTTCCACGTCTTCCATGACTCTACCAACTTCTAT
GGCAGCACCGGTAACGCGCGCGGTCAGGCGGTGGTAAATATCTCCAACTCGGCATTCCCGATTCTGATGGCG
CGTAATGATAAAAACTACTGGCTGGCGTTTGGCGAAAAACGCGCCTGGGATAAAAATGAGCTGGCGTACATT
ACGGAAGCGCCTTCCATTGTGCAGCCAGAGAACGTTACGCGCGATACTGCCATTTCAACCTGCCGTTTATT
TCGCTGGGGCAAGTCGGTGAAGGCAAACTGATGGTTATCGGTAACCCGCACTACAACAGCATCCTGCGTTGC
CCGAACGGTTACAGTTGGGGCGGTGGTGTTAATAGTAAAGGTGAGTGTACGCTCAGCGGTGATTCTGATGAC
ATGAAGCACTTTATGCAGAACGTACTGCGCTACTTGTCAAATGACATCTGGCAGCCAAATACCAAGAGCATC
ATGACTGTCGGCACCAACCTGGAGAACGTTATTTCAAAAAGCGGGCCAGGTATTGGGAAATAGTGCACCA
TTTGCTTTCCATGAGGATTTCACTGGTATCACGGTTAAACAGTTGACCAGCTATGGCGATCTGAATCCGGAA
GAGATTCCGTTGCTGATCCTCAACGGCTTTGAATATGTGACTCAGTGGTCTGGCGATCCCTATGCTGTGCCT
CTGCGTGCAGATACCAGCAAACCGAAGCTGACTCAGCAGGATGTGACCGATCTGATCGCTTATCTGAACAAA
GGTGGCTCGGTGCTGATCATGGAAAACGTGATGAGCAATCTTAAGGAAGAGGAGCGCGTCCAGTTTTGTCGT
CTGCTGGATGCCGCGGGTCTGTCAATGGCTCTGAACAAATCGGTGGTGAACAACGATCCGCAAGGGTATCCG
GATCGCGTTCGTCAGCGTCGCGCGACTGGCATTTGGGTTTATGAACGTTATCCTGCTGCAGACGGCGCGCAA
CCGCCGTACACCATCGACCCAAATACAGGGGAAGTGACCTGGAAATACCAGCAAGACAACAAGCCTGATGAC
AAGCCGAAACTGGAAGTTGCGAGCTGGCAGGAGGAAGTTGAGGGCAAACAGGTAACGCGTTATGCCTTTATT
GATGAAGCGGAATACAACAACGAAGAATCTCTGGAAGCGGCAAAGGCAAAAATCTTTGAGAAGTTTCCTGGG
TTACAGGAGTGTAAGGACTCGACTTACCATTACGAGATTAACTGTTTGGAGCGCCGCCCAGGCACGGATGTT
CCGGTAACAGGTGGCATGTATGTTCCGCGCTATACGCAACTGAATCTTGACGCCGACACCGCGAAAGCGATG
GTGCAGGCGGCGGATTTAGGCACCAACATTCAGCGCCTGTATCAGCATGAGCTTTATTTCCGTACCAAAGGC
AGTAAAGGTGAGCGTCTGAACAGTGTTGATCTGGAACGTCTGTACCAGAACATGTCGGTCTGGCTGTGGAAC
GATACGAAATATCGTTACGAAGAGGGCAAGGAAGATGAGCTGGGCTTTAAAACGTTCACCGAGTTCCTGAAC
TGCTACGCCAATGATGCCTATGCAGGCGGCACCAAGTGCTCCGCAGATCTGAAAAAATCGCTGGTCGATAAC
AACATGATCTACGGTGACGGTAGCAGCAAAGCGGGCATGATGAACCCAAGCTATCCGCTCAACTATATGGAA
AAACCGCTGACGCGTCTGATGCTGGGCCGTTCCTGGTGGGATCTGAACATTAAGGTTGATGTGGAGAAGTAC
CCAGGATCCGTATCGGCAAAGGGTGAGAGCGTTACGGAAAACATCAGCCTGTACTCGAATCCGACCAAATGG
TTTGCGGGTAACATGCAGTCAACCGGCCTGTGGGCACCGGCCCAGCAGGACGTCACCATTAAGTCTTCGGCG
TCAGTCCCAGTGACTGTTACCGTGGCGCTGGCTGACGACCTGACTGGACGTGAGAAGCATGAAGTTGCGCTG
AACCGTCCGCCAAGAGTGACTAAAACGTATACTCTGGAGGCTAACGGTGAAGTGACCTTCAAGGTGCCTTAT
GGTGGTCTGATTTATATCAAGGGCGACAGTAAGGATGATGTTTCTGCTAACTTCACCTTTACCGGTGTAGTA
AAAGCGCCGTTCTATAAAGACGGCGAATGGAAAAACGATCTGGACTCACCGGCGCCGCTGGGCGAGCTGGAG
TCTGCGTCGTTCGTCTATACCACGCCGAAGAAGAACCTTGAGGCCAGCAATTTCACTGGTGGTGTAGCAGAA
TTCGCTAAAGATCTGGATACCTTTGCCAGCTCGATGAATGACTTCTACGGTCGTAATGATGAAGACGGTAAG
CACCGGATGTTTACCTATAAAAACTTGACGGGGCACAAGCATCGTTTCACCAACGATGTGCAGATCTCCATC
GGTGATGCGCACTCGGGTTATCCGGTAATGAACAGCAGCTTCTCGACAACAGCACCACGCTGCCGACGACG
CCGCTGAACGACTGGCTGATTTGGCACGAAGTCGGTCATAACGCTGCAGAAACACCGCTGAACGTACCGGGT
GCAACTGAAGTGGCGAACAACGTGCTGGCGCTGTACATGCAGGATCGCTATCTCGGTAAGATGAACGTGTC
GCTGACGACATTACCGTCGCGCCGGAATATCTGGACGAGAACAACGGTCAGGCCTGGGCGCGGCGGTGCG
GGTGACCGTCTGCTGATGTACGCACAGTTGAAGGAGTGGGCAGAGGAAAACTTTGATATCAAACAGTGGTAT
CCAGATGGTGAGCTGCCTAAGTTCTACAGCGATCGTAAAGGGATGAAGGGCTGGAACCTGTTCCAGTTGATG
CACCGTAAAGCGCGCGGCGCTGATGTTGGTAACAGCACCTTTGGTGGCAAGAATTACTGTGCTGAATCCAAT
GGTAACGCTGCCGACACGCTGATGCTGTGTGCATCCTGGGTCGCTCAGGCGGATCTTTCGGAATTCTTTAAG
```

```
AAATGGAATCCGGGTGCAAGTGCTTACCAGTTGCCGGGAGCAACGGAGATGAGTTTCCAGGGCGGTGTGAGC
TCTTCGGCTTACAGCACGCTGGCGTCACTCAAGCTGCCGAAACCGGAAAAAGGGCCGGAAACCATTAACAAG
GTTACCGAGCATAAGATGTCTGCCGAG

>pK1-3526D1422A
                                                              (SEQ ID 22)
CDGGGSGSSSDTPSVDSGSGTLPEVKPDPTPTPEPTPEPTPDPEPTPDPTPDPEPTPEPEPEPVPTKTGYLT
LGGSQRVTGATCNGESSDGFTFTPGNTVSCVVGSTTIATFNTQSEAARSLRAVDKVSFSLEDAQELANSENK
KTNAISLVTSSDSCPADAEQLCLTFSSVVDRARFEKLYKQIDLATDNFSKLVNEEVENNAATDKAPSTHTST
VVPVTTEGTKPDLNASFVSANAEQFYQYQPTEIILSEGQLVDSLGNGVAGVDYYTNSGRGVTDENGKFSFSW
GETISFGIDTFELGSVRGNKSTIALTELGDEVRGANIDQLIHRYSTTGQNNTRVVPDDVRKVFAEYPNVINE
IINLSLSNGATLDEGDQNVVLPNEFIEQFKTGQAKEIDTAICAKTDGCNEARWFSLTTRNVNDGQIQGVINK
LWGVDTNYQSVSKFHVFHDSTNFYGSTGNARGQAVVNISNSAFPILMARNDKNYWLAFGEKRAWDKNELAYI
TEAPSIVQPENVTRDTATFNLPFISLGQVGEGKLMVIGNPHYNSILRCPNGYSWGGGVNSKGECTLSGDSDD
MKHFMQNVLRYLSNDIWQPNTKSIMTVGTNLENVYFKKAGQVLGNSAPFAHEDFTGITVKQLTSYGDLNPE
EIPLLILNGFEYVTQWSGDPYAVPLRADTSKPKLTQQDVTDLIAYLNKGGSVLIMENVMSNLKEESASSFVR
LLDAAGLSMALNKSVVNNDPQGYPDRVRQRRATGIWVYERYPAADGAQPPYTIDPNTGEVTWKYQQDNKPDD
KPKLEVASWQEEVEGKQVTRYAFIDEAEYTTEESLEAAKAKIFEKFPGLQECKDSTYHYEINCLERRPGTDV
PVTGGMYVPRYTQLNLDADTAKAMVQAADLGTNIQRLYQHELYFRTKGSKGERLNSVDLERLYQNMSVWLWN
DTKYRYEEGKEDELGFKTFTEFLNCYANDAYAGGTKCSADLKKSLVDNNMIYGDGSSKAGMMNPSYPLNYME
KPLTRLMLGRSWWDLNIKVDVEKYPGSVSAKGESVTENISLYSNPTKWFAGNMQSTGLWAPAQQDVTIKSSA
SVPVTVTVALADDLTGREKHEVALNRPPRVTKTYTLEANGEVTFKVPYGGLIYIKGDSKDDVSANFTFTGVV
KAPFYKDGEWKNDLDSPAPLGELESASFVYTTPKKNLEASNFTGGVAEFAKDLDTFASSMNDFYGRNDEDGK
HRMFTYKNLTGHKHRFTNDVQISIGDAHSGYPVMNSSFSTNSTTLPTTPLNDWLIWHEVGHNAAETPLNVPG
ATEVANNVLALYMQDRYLGKMNRVADDITVAPEYLDESNGQAWARGGAGDRLLMYAQLKEWAEENFDIKQWY
PDGELPKFYSDRKGMKGWNLFQLMHRKARGADVGNSTFGGKNYCAESNGNAADTLMLCASWVAQADLSEFFK
KWNPGASAYQLPGATEMSFQGGVSSSAYSTLASLKLPKPEKGPETINKVTEHKMSAE

>pK1-3526AdG
                                                              (SEQ ID 23)
GATACGCCGTCTGTAGATTCTGGATCAGGGACTTTGCCGGAAGTGAAACCCGATCCAACACCAACCCCGGAG
CCGACACCTGAGCCGACGCCGGACCCAGAACCTACGCCGGATCCAACACCTGATCCTGAGCCGACACCAGAA
CCGGAGCCAGAACCTGTTCCTACGAAAACGGGTTATCTGACCCTGGGCGGAAGCCAGCGGGTAACTGGTGCT
ACCTGTAATGGTGAATCCAGCGATGGCTTTACCTTTACGCCAGGCAATACCGTGAGTTGTGTGGTGGGCAGT
ACGACCATTGCAACATTCAACACCCAGTCAGAAGCTGCGCGTAGCCTGCGTGCGGTTGACAAAGTGTCGTTT
AGCCTGGAGGACGCGCAGGAGCTGGCGAATTCTGAAAATAAGAAAACCAACGCCATCTCTCTGGTGACGTCC
AGCGACAGTTGCCCCGCAGATGCAGAACAGCTTTGTCTTACTTTCTCGTCAGTGGTTGATCGCGCGCGATTT
GAAAAACTGTATAAGCAAATTGATCTGGCAACAGACAATTTCAGCAAGCTGGTCAATGAAGAGGTGGAAAAC
AATGCTGCGACTGATAAAGCGCCGTCCACCCATACCTCAACGGTAGTGCCAGTCACGACAGGAGGGACAAAA
CCGGATCTGAACGCGTCCTTCGTGTCGGCTAACGCGAACAGTTTTATCAGTATCAACCCACTGAAATCATT
CTTTCCGAAGGCCAACTGGTGGATAGCCTGGGGAACGGTGTTGCTGGCGTTGACTACTACACCAATTCAGGC
CGTGGCGTAACTGACGAAAACGGTAAATTTTCCTTTAGCTGGGGCGAAACCATCTCCTTTGGTATCGATACC
TTTGAACTGGGCTCAGTACGTGGCAATAAGTCGACCATTGCGCTGACTGAATTGGGTGATGAAGTTCGCGGG
GCAAATATCGATCAGCTCATTCATCGTTATTCGACGACTGGTCAAAATAATACTCGTGTTGTTCCGGACGAT
GTACGCAAGGTCTTTGCCGAATATCCCAACGTGATCAACGAGATAATCAATCTTTCGTTATCCAACGGTGCG
ACGCTGGATGAAGGCGATCAAAACGTTGTGCTGCCTAACGAATTTATCGAGCAGTTTAAGACGGGTCAGGCC
AAAGAGATCGATACCGCGATTTGTGCGAAAACCGACGGTTGTAACGAGGCTCGCTGGTTCTCGCTGACAACG
CGCAATGTTAATGACGGCCAGATTCAGGGCGTTATTAACAAGCTGTGGGGCGTGGATACGAACTATCAGTCT
GTCAGCAAGTTCCACGTCTTCATGACTCTACCAACTTCTATGGCAGCACCGGTAACGCGCGCGGTCAGGCG
GTGGTAAATATCTCCAACTCGGCATTCCCGATTCTGATGGCGCGTAATGATAAAAACTACTGGCTGGCGTTT
GGCGAAAAACGCGCCTGGGATAAAAATGAGCTGGCGTACATTACGGAAGCGCCTTCCATTGTGCAGCCAGAG
AACGTTACGCGCGATACTGCGACTTTCAACCTGCCGTTTATTTCGCTGGGGCAAGTCGGTGAAGGCAAACTG
ATGGTTATCGGTAACCCGCACTACAACAGCATCCTGCGTTGCCCGAACGGTTACAGTTGGGGCGGTGGTGTT
AATAGTAAAGGTGAGTGTACGCTCAGCGGTGATTCTGATGACATGAAGCACTTTATGCAGAACGTACTGCGC
TACTTGTCAAATGACATCTGGCAGCCAAATACCAAGAGCATCATGACTGTCGGCACCAACCTGGAGAACGTT
TATTTCAAAAAAGCGGGCCAGGTATTGGGAAATAGTGCACCATTTGCTTTCCATGAGGATTTCACTGGTATC
ACGGTTAAACAGTTGACCAGCTATGGCGATCTGAATCCGGAAGAGATTCCGTTGCTGATCCTCAACGGCTTT
GAATATGTGACTCAGTGGTCTGGCGATCCCTATGCTGTGCCTCTGCGTGCAGATACCAGCAAACCGAAGCTG
ACTCAGCAGGATGTGACCGATCTGATCGCTTATCTGAACAAAGGTGGCTCGGTGCTGATCATGGAAAACGTG
ATGAGCAATCTTAAGGAAGAGAGCGCGTCCAGTTTTGTGCGTCTGCTGGATGCCGCGGGTCTGTCAATGGCT
CTGAACAAATCGGTGGTGAACAAC

>pK1-3526AdG
                                                              (SEQ ID 24)
DTPSVDSGSGTLPEVKPDPTPTPEPTPEPTPDPEPTPDPTPDPEPTPEPEPEPVPTKTGYLTLGGSQRVTGA
TCNGESSDGFTFTPGNTVSCVVGSTTIATFNTQSEAARSLRAVDKVSFSLEDAQELANSENKKTNAISLVTS
SDSCPADAEQLCLTFSSVVDRARFEKLYKQIDLATDNFSKLVNEEVENNAATDKAPSTHTSTVVPVTTEGTK
PDLNASFVSANAEQFYQYQPTEIILSEGQLVDSLGNGVAGVDYYTNSGRGVTDENGKFSFSWGETISFGIDT
FELGSVRGNKSTIALTELGDEVRGANIDQLIHRYSTTGQNNTRVVPDDVRKVFAEYPNVINEIINLSLSNGA
TLDEGDQNVVLPNEFIEQFKTGQAKEIDTAICAKTDGCNEARWFSLTTRNVNDGQIQGVINKLWGVDTNYQS
VSKFHVFHDSTNFYGSTGNARGQAVVNISNSAFPILMARNDKNYWLAFGEKRAWDKNELAYITEAPSIVQPE
NVTRDTATFNLPFISLGQVGEGKLMVIGNPHYNSILRCPNGYSWGGGVNSKGECTLSGDSDDMKHFMQNVLR
YLSNDIWQPNTKSIMTVGTNLENVYFKKAGQVLGNSAPFAHEDFTGITVKQLTSYGDLNPEEIPLLILNGF
EYVTQWSGDPYAVPLRADTSKPKLTQQDVTDLIAYLNKGGSVLIMENVMSNLKEESASSFVRLLDAAGLSMA
LNKSVVNN

>pK1-3526CdG
                                                              (SEQ ID 25)
GATACGCCGTCTGTAGATTCTGGATCAGGGACTTTGCCGGAAGTGAAACCCGATCCAACACCAACCCCGGAG
CCGACACCTGAGCCGACGCCGGACCCAGAACCTACGCCGGATCCAACACCTGATCCTGAGCCGACACCAGAA
CCGGAGCCAGAACCTGTTCCTACGAAAACGGGTTATCTGACCCTGGGCGGAAGCCAGCGGGTAACTGGTGCT
```

-continued

```
ACCTGTAATGGTGAATCCAGCGATGGCTTTACCTTTACGCCAGGCAATACCGTGAGTTGTGTGGTGGGCAGT
ACGACCATTGCAACATTCAACACCCAGTCAGAAGCTGCGCGTAGCCTGCGTGCGGTTGACAAAGTGTCGTTT
AGCCTGGAGGACGCGCAGGAGCTGGCGAATTCTGAAAATAAGAAAACCAACGCCATCTCTCTGGTGACGTCC
AGCGACAGTTGCCCCGCAGATGCAGAACAGCTTTGTCTTACTTTCTCGTCAGTGGTTGATCGCGCGCGATTT
GAAAAACTGTATAAGCAAATTGATCTGGCAACAGACAATTTCGACAAGCTGGTCAATGAAGAGGTGGAAAAC
AATGCTGCGACTGATAAAGCGCCGTCCACCCATACCTCAACGGTAGTGCCAGTCACGACAGAGGGAACAAAA
CCGGATCTGAACGCGTCCTTCGTGTCGGCTAACGCGGAACAGTTTTATCAGTATCAACCCACTGAAATCATT
CTTTTCCGAAGGCCAACTGGTGGATAGCCTGGGGAACGGTGTTGCTGGCGTTGACTACTACACCAATTCAGGC
CGTGGCGTAACTGACGAAAACGGTAAATTTTCCTTTAGCTGGGGCGAAACCATCTCCTTTGGTATCGATACC
TTTGAACTGGGCTCAGTACGTGGCAATAAGTCGACCATTGCGCTGACTGAATTGGGTGATGAAGTTCGCGGG
GCAAATATCGATCAGCTCATTCATCGTTATTCGACGACTGGTCAAATAATACTCGTGTTGTTCCGGACGAT
GTACGCAAGGTCTTTGCCGAATATCCCAACGTGATCAACGAGATAATCATCTTTCGTTATCCAACGGTGCG
ACGCTGGATAAGGCGATCAAAACGTTGTGCTGCCTAACGAATTTATCGAGCAGTTTAAGACGGGTCAGGCC
AAAGAGATCGATACCGCGATTTGTGCGAAAACCGACGGTTGTAACGAGGCTCGCTGGTTCTCGCTGACAACG
CGCAATGTTAATGACGGCCAGATTCAGGGCGTTATTAACAAGCTGTGGGCGTGGATACGAACTATCAGTCT
GTCAGCAAGTTCCACGTCTTCCATGACTCTACCAACTTCTATGGCAGCACCGGTAACGCGCGCGGTCAGGCG
GTGGTAAATATCTCCAACTCGGCATTCCCGATTCTGATGGCGCGTAATGATAAAAACTACTGGCTGGCGTTT
GGCGAAAAACGCGCCTGGGATAAAAATGAGCTGGCGTACATTACGGAAGCGCCTTCCATTGTGCAGCCAGAG
AACGTTACGCGCGATACTGCGACTTTCAACCTGCCGTTTATTTCGCTGGGGCAAGTCGGTGAAGGCAAACTG
ATGGTTATCGGTAACCCGCACTACAACAGCATCCTGCGTTGCCCGAACGGTTACAGTTGGGGCGGTGGTGTT
AATAGTAAAGGTGAGTGTACGCTCAGCGGTGATTCTGATGACATGAAGCACTTTATGCAGAACGTACTGCGC
TACTTGTCAATGACATCTGGCAGCCAAATACCAAGAGCATCGATGTGTCGGCACCAACCTGGAGAACGTT
TATTTCAAAAAAGCGGGCCAGGTATTGGGAAATAGTGCACCATTTGCTTTCCATGAGGATTTCACTGGTATC
ACGGTTAAACGTTGACCAGCTATGGCGATCGAATCCGGAAGAGATTCCGTTGCTGATCCTCAACGGCTTTT
GAATATGTGACTCAGTGGTCTGGCGATCCCTATGCTGTGCCTCTGCGTGCAGATACCAGCAAACCGAAGCTG
ACTCAGCAGGATGTGACCGATCTGATCGCTTATCTGAACAAAGGTGGCTCGGTGCTGATCATGGAAAACGTG
ATGAGCAATCTTAAGGAAGAGAGCGCGTCCAGTTTTGTGCGTCTGCTGGATGCCGCGGGTCTGTCAATGGCT
CTGAACAAATCGGTGGTGAACAACGATCCGCAAGGGTATCCGGATCGCGTTCGTCAGCGTCGCGCGACTGGC
ATTTGGGTTTATGAACGTTATCCTGCTGCAGACGGCGCGCAACCGCCGTACACCATCGACCCAAATACAGGG
GAAGTGACCTGGAAATACCAGCAAGACAACAAGCCTGATGACAAGCCGAAACTGGAAGTTGCGAGCTGGCAG
GAGGAAGTTGAGGGCAAACAGGTAACGCGTTATGCCTTTATTGATGAAGCGGAATACACAACAGAAGAATCT
CTGGAAGCGGCAAAGGCAAAAATCTTTGAGAAGTTTCCTGGGTTACAGGAGTGTAAGGACTCGACTTACCAT
TACGAGATTAACTGTTTGGAGCGCCGCCCAGGCACGGATGTTCCGGTAACAGGTGGCATGTATGTTCCGCGC
TATACGCAACTGAATCTTGACGCCGACACCGCGAAAGCGATGGTGCAGGCGGCGGATTTAGGCACCAACATT
CAGCGCCTGTATCAGCATGAGCTTTATTTCCGTACCAAAGGCAGTAAAGGTGAGCGTCTGAACAGTGTTGAT
CTGGAACGTCTGTACCAGAACATGTCGGTCTGGCTGTGGAACGATACGAAATATCGTTACGAAGAGGGCAAG
GAAGATGAGCTGGGCTTTAAAACGTTCACCGAGTTCCTGAACTGCTACGCCAATGATGCCTATGCAGGCGGC
ACCAAGTGCTCCGCAGATCTGAAAAAATCGCTGGTCGATAACAACATGATCTACGGTGACGGTAGCAGCAAA
GCGGGCATGATGAACCCAAGCTATCCGCTCAACTATATGGAAAAACCGCTGACGCGTCTGATGCTGGGCCGT
TCCTGGTGGGATCTGAACATTAAGGTTGATGTGGAGAAGTACCCAGGATCCGTATCGGCAAAGGGTGGAGAGC
GTTACGGAAAACATCAGCCTGTACTCGAATCCGACCAAATGTTTGCGGGTAACATGCAGTCAACCGGCCTG
TGGGCACCGGCCCAGCAGGACGTCACCATTAAGTCTTCGGCGTCAGTCCCAGTGACTGTTACCGTGGCGCTG
GCTGACGACCTGACTGGACGTGAGAAGCATGAAGTTGCGCTGAACCGTCCGCCTAAAGATCTGACCAAGACTTAT
ACTCTGGAGGCTAACGGTGAAGTGACCTTCAAGGTGCCTTATGGTGGTCTGATTTATATCAAGGGCGACAGT
AAGGATGATGTTTCTGCTAACTTCACCTTTACCGGTGTAGTAAAAGCGCCGTTCTATAAGACGGCGAATGG
AAAAACGATCTGGACTCACCGGCGCCGCTGGGCGAGCTGGAGTCTGCGTCGTTCGTCTATACCACGCCGAAG
AAGAACCTTGAGGCCAGCAATTTCACTGGTGGTGTAGCAGAATTCGCTAAAGATCTGGATACCTTTGCCAGC
TCGATGAATGACTTCTACGGTCGTAATGATGAAGACGGTAAGCACCGGATGTTTACCTATAAAAACTTGACG
GGGCACAAGCATCGTTTCACCAACGATGTGCAGATCTCCATCGGTGATGCGCACTCGGGTTATCCGGTAATG
AACAGCAGCTTCTCGACGAACAGCACCACGCTGCCGACGACGCCGCTGAACGACTGGCTGATTTGG
``` pK1-3526CdG (SEQ ID 26)

```
DTPSVDSGSGTLPEVKPDPTPTPEPTPEPTPDPEPTPDPTPDPEPTPEPEPEPVPTKTGYLTLLGGSQRVTGA
TCNGESSDGFTTPGNTVSCVVGSTTIATFNTQSEAARSLRAVDKVSFSLEDAQELANSENKKTNAISLVTS
SDSCPADAEQLCLTFSSVVDRARFEKLYKQIDLATDNFSKLVNEEVENNAATDKAPSTHTSTVVPVTTEGTK
PDLNASFVSANAEQFYQYQPTEIILSEGQLVDSLGNGVAGVDYYTNSGRGVTDENGKFSFSWGETISFGIDT
FELGSVRGNKSTIALTELGDEVRGANIDQLIHRYSTTGQNNTRVVPDDVRKVFAEYPNVINEIINLSLSNGA
TLDEGDQNVVLPNEFIEQFKTGQAKEIDTAICAKTDGCNEARWFSLTTRNVNDGQIQGVINKLWGVDTNYQS
VSKFHVFHDSTNFYGSTGNARGQAVVNISNSAFPILMARNDKNYWLAFGEKRAWDKNELAYITEAPSIVQPE
NVTRDTATFNLPFISLGQVGEGKLMVIGNPHYNSILRCPNGYSWGGGVNSKGECTLSGDSDDMKHFMQNVLR
YLSNDIWQPNTKSIMTVGTNLENVYFKKAGQVLGNSAPFAFHEDFTGITVKQLTSYGDLNPEEIPLLILNGF
EYVTQWSGDPYAVPLRADTSKPKLTQQDVTDLIAYLNKGGSVLIMENVMSNLKEESASSFVRLLDAAGLSMA
LNKSVVNNDPQGYPDRVRQRRATGIWVYERYPAADGAQPPYTIDPNTGEVTWKYQQDNKPDDKPKLEVASWQ
EEVEGKQVTRYAFIDEAEYTTEESLEAAKAKIFEKFPGLQECKDSTYHYEINCLERRPGTDVPVTGGMYVPR
YTQLNLDADTAKAMVQAADLGTNIQRLYQHELYFRTKGSKGERLNSVDLERLYQNMSVWLWNDTKYRYEEGK
EDELGFKTFTEFLNCYANDAYAGGTKCSADLKKSLVDNNMIYGDSSKAGMMNPSYPLNYMEKPLTRLMLGR
SWWDLNIKVDVEKYPGSVSAKGESVTENISLYSNPTKWFAGNMQSTGLWAPAQQDVTIKSSASVPVTVTVAL
ADDLTGREKHEVALNRPPRVTKTYTLEANGEVTFKVPYGGLIYIKGDSKDDVSANFTFTGVVKAPFYKDGEW
KNDLDSPAPLGELESASFVYTTPKKNLEASNFTGGVAEFAKDLDTFASSMNDFYGRNDEDGKHRMFTYKNLT
GHKHRFTNDVQISIGDAHSGYPVMNSSFSTNSTTLPTTPLNDWLIW
```

>pK1-L3526-2stop (SEQ ID 27)

```
ATGAATAAGAAATTTAAATATAAGAAATCGCTTTTAGCGGCTATTTTAAGCGCAACCCTGTTAGCCGGTTGT
GATGGTGGTGGTTCAGGATCGTCCTCCGGATACGCCGTCTGTGAGATTCTGGATCAGGGGACTTTGCCGGAAGTG
AAACCCGATCCAACACCAACCCCCGGAGCCGACACCTGAGCCGACGCCGGACCCAGAACCTACGCCGGATCCA
ACACCTGATCCTGAGCCGACACCAGAACCGGAGCCAGAACCTGTTCCTACGAAAACGGGTTATCTGACCCTG
GGCGGAAGCCAGCGGGTAACTGGTGCTACCTGTAATGGTGAATCCAGCGATGGCTTTACCTTTACGCCAGGC
AATACCGTGAGTTGTGTGGTGGGCAGTACGACCATTGCAACATTCAACACCCAGTCAGAAGCTGCGCGTAGC
CTGCGTGCGGTTGACAAAGTGTCGTTTAGCCTGGAGGACGCGCAGGAGCTGGCGAATTCTGAAAATAAGAAA
```

-continued

```
ACCAACGCCATCTCTCTGGTGACGTCCAGCGACAGTTGCCCCGCAGATGCAGAACAGCTTTGTCTTACTTTC
TCGTCAGTGGTTGATCGCGCGCGATTTGAAAAACTGTATAAGCAAATTGATCTGGCAACAGACAATTTCAGC
AAGCTGGTCAATGAAGAGGTGGAAAACAATGCTGCGACTGATAAAGCGCCGTCCACCCATACCTCAACGGTA
GTGCCAGTCACGACAGAGGGAACAAAACCGGATCTGAACGCGTCCTTCGTGTCGGCTAACGCGGAACAGTTT
TATCAGTATCAACCCACTGAAATCATTCTTTCCGAAGGCCAACTGGTGGATAGCCTGGGGAACGGTGTTGCT
GGCGTTGACTACTACACCAATTCAGGCCGTGGCGTAACTGACGAAAACGGTAAATTTTCCTTTAGCTGGGGC
GAAACCATCTCCTTTGGTATCGATACCTTTGAACTGGGCTCAGTACGTGGCAATAAGCTGACCATTGCGCTG
ACTGAATTGGGTGATGAAGTTCGCGGGGCAAATATCGATCAGCTCATTCATCGTTATTCGACGACTGGTCAA
AATAACTCGTGTTGTTCCGGACGATGTACGCAAGGTCTTTGCCGAATATCCCAACGTGATCAACGAGATA
ATCAATCTTTCGTTATCCAACGGTGCGACGCTGGATGAAGGCGATCAAAACGTTGTGCTGCCTAACGAATTT
ATCGAGCAGTTTAAGACGGGTCAGGCCAAAGAGATCGATACCGCGATTTGTGCGAAAACCGACGGTTGTAAC
GAGGCTCGCTGGTTCTCGCTGACAACGCGCAATGTTAATGACGGCCAGATTCAGGGCGTTATTAACAAGCTG
TGGGGCGTGGATACGAACTATCAGTCTGTCAGCAAGTTCCACGTCTTCCATGACTCTACCAACTTCTATGGC
AGCACCGGTAACGCGCGGTCAGGCGGTGGTAAATATCTCCAACTCGGCATTCCCGATTCTGATGGCGCGT
AATGATAAAAACTACTGGCTGGCGTTTGGCGAAAAACGCGCCTGGGATAAAATGAGCTGGCGTACATTACG
GAAGCGCCTTCCATTGTGCAGCCAGAGAACGTTACGCGCGATACTGCGACTTTCAACCTGCCGTTTATTTCG
CTGGGGCAAGTCGGTGAAGGCAAACTGATGGTTATCGGTAACCCGCACTACAACAGCATCCTGCGTTGCCCG
AACGGTTACAGTTGGGGCGGTGGTGTTAATAGTAAAGGTGAGTGTACGCTCAGCGGTGATTCTGATGACATG
AAGCACTTTATGCAGAACGTACTGCGCTACTTGTCAAATGACATCTGGCAGCCAAATACCAAGAGCATCATG
ACTGTCGGCACCAACCTGGAGAACGTTTATTTCAAAAAAGCGGGCCAGGTATTGGGAAATAGTGCACCATTT
GCTTTCCATGAGGATTTCACTGGTATCACGGTTAAACAGTTGACCAGCTATGGCGATCTGAATCCGGAAGAG
ATTCCGTTGCTGATCCTCAACGGCTTTGAATATGTGACTCAGTGGTTCTGGCGATCCCTATGCTGTGCCTCTG
CGTGCAGATACCAGCAAACCGAAGCTGACTCAGCAGGATGTGACCGATCTGATCGCTTATCTGAACAAAGGT
GGCTCGGTGCTGATCATGGAAAACGTGATGAGCAATCTTAAGGAAGAGAGCGCGTCCAGTTTTGTGCGTCTG
CTGGATGCCGCGGGTCTGTCAATGGCTCTGAACAAATCGGTGGTGAACAACGATCCGCAAGGGTATCCGGAT
CGCGTTCGTCAGCGTCGCGCGACTGGCATTTGGGTTTATGAACGTTATCCTGCTGCAGACGGCGCGCAACCG
CCGTACACCATCGACCCAAATACAGGGGAAGTGACCTGGAAATACCAGCAAGACAACAAGCCTGATGACAAC
CCGAAACTGGAAGTTGCGAGCTGGCAGGAGGAAGTTGAGGGCAAACAGGTAACGCGTTATGCCTTTATTGAT
GAAGCGGAATACACAACAGAAGAATCTCTGGAAGCGGCAAAGGCAAAATCTTTGAGAAGTTTCCTGGGTTA
CAGGAGTGTAAGGACTCGACTTACCATTACGAGATTAACTGTTTGGAGCGCCGCCCAGGCACGGATGTTCCG
GTAACAGGTGGCATGTATGTTCCGCGCTATACGCAACTGAATCTTGACGCCGACACCGCGAAAGCGATGGTG
CAGGCGGCGGATTTAGGCACCAACATTCAGCGCCTGTATCAGCATGAGCTTTATTTCCGTACCAAAGGCAGT
AAAGGTGAGCGTCTGAACAGTGTTGATCTGGAACGTCTGTACCAGAACATGTCGGTCTGGCTGTGGAACGAT
ACGAAATATCGTTACGAAGAGGGCAAGGAAGATGAGCTGGGCTTTAAAACGTTCACCGAGTTCCTGAACTGC
TACGCCAATGATGCCTATGCAGGCGGCACCAAGTGCTCCGCAGATCTGAAAAAATCGCTGGTCGATAACAAC
ATGATCTACGGTGACGGTAGCAGCAAAGCGGGCATGATGAACCCAAGCTATCCGCTAACTATATGGAAAAA
CCGCTGACGCGTCTGATGCTGGGCCGTTCCTGGTGGGATCTGAACATTAAGGTTGATGTGGAGAAGTACCCA
GGATCCGTATCGGCAAAGGGTGAGAGCGTTACGGAAAACATCAGCCTGTACTCGAATCCGACCAAATGGTTT
GCGGGTAACATGCAGTCAACCGGCCTGTGGGCACCGGCCCAGCAGGACGTCACCATTAAGTCTTCGGCGTCA
GTCCCAGTGACTGTTACCGTGGCGCTGGCTGACGACCTGACTGGACGTGAGAAGCATGAAGTTGCGCTGAAC
CGTCCGCCAAGAGTGACTAAAACGTATACTCTGGAGGCTAACGGTGAAGTGACCTTCAAGGTGCCTTATGGT
GGTCTGATTTATATCAAGGGCGACAGTAAGGATGATGTTTCTGCTAACTTCACCTTTACCGGTGTAGTAAAA
GCGCCGTTCTATAAAGACGGCGAATGGAAAAACGATCTGGACTCACCGGCGCCGTGGGCGAGCTGGAGTCT
GCGTCGTTCGTCTATACCACGCCGAAGAAGAACCTTGAGGCCAGCAATTTCACTGGTGGTGTAGCAGAATTC
GCTAAAGATCTGGATACCTTTGCCAGCTCGATGAATGACTTCTACGGTCGTAATGATGAAGACGGTAAGCAC
CGGATGTTTACCTATAAAAACTTGACGGGGCACAAGCATCGTTTCACCAACGATGTGCAGATCTCCATCGGT
GATGCGCACTCGGGTTATCCGGTAATGAACAGCAGCTTCTCGACGAACAGCACCACGCTGCCGACGACGCCG
CTGAACGACTGGCTGATTTGGCACGAAGTCGGTCATAACGCTGCAGAAACACCGCTGAACGTACCGGGTGCA
ACTGAAGTGGCGAACAACGTGCTGGCGCTGTACATGCAGGATCGCTATCTCGGTAAGATGAACCGTGTCGCT
GACGACATTACCGTCGCGCCGGAATATCTGGACGAGAGCAACGGTCAGGCCTGGGCGCGCGGCGGTGCGGGT
GACCGTCTGCTGATGTACGCACAGTTGAAGGAGTGGGCAGAGGAAAACTTTGATATCAAACAGTGGTATCCA
GATGGTGAGCTGCCTAAGTTCTACAGGCGATCGTAAAGGGATGAAGGGCTGGAACCTGTTCCAGTTGATGCAC
CGTAAAGCGCGCGCGATGATGTTGGTAACAGCACCTTTGGTGGCAAGAATTACTGTGCTGAATCCAATGGT
AACGCTGCCGACACGCTGATGCTGTGCATCCTGGGTCGCTCAGGCGGATCTTTCGGAATTCTTTAAGAAA
TGGAATCCGGGTGCAAGTGCTTACCAGTTGCCGGGAGCAACGGAGATGAGTTTCAGGGCGGTGTGAGCTCT
TCGGCTTACAGCACGCTGGCGTCACTCAAGCTGCCGAAACCGGAAAAAGGGCCGGAAACCATTAACAAGGTT
ACCGAGCATAAGATGTCTGCCGAGTAA
```

>pK1-L3526-2stop (SEQ ID 28)

```
MNKKFKYKKSLLAAILSATLLAGCDGGGSGSSSDTPSVDSGSGTLPEVKPDPTPTPEPTPEPTPDPEPTPDP
TPDPEPTPEPEPEPVPTKTGYLTLGGSQRVTGATCNGESSDGFTFTPGNTVSCVVGSTTIATFNTQSEAARS
LRAVDKVSFSLEDAQELANSENKKTNAISLVTSSDSCPADAEQLCLTFSSVVDRARFEKLYKQIDLATDNFS
KLVNEEVENNAATDKAPSTHTSTVVPVTTEGTKPDLNASFVSANAEQFYQYQPTEIILSEGQLVDSLGNGVA
GVDYYTNSGRGVTDENGKFSFSWGETISFGIDTFELGSVRGNKSTIALTELGDEVRGANIDQLIHRYSTTGQ
NNTRVVPDDVRKVFAEYPNVINEIINLSLSNGATLDEGDQNVVLPNEFIEQFKTGQAKEIDTAICAKTDGCN
EARWFSLTTRNVNDGQIQGVINKLWGVDTNYQSVSKFHVFHDSTNFYGSTGNARGQAVVNISNSAFPILMAR
NDKNYWLAFGEKRAWDKNELAYITEAPSIVQPENVTRDTATFNLPFISLGQVGEGKLMVIGNPHYNSILRCP
NGYSWGGGVNSKGECTLSGDSDDMKHFMQNVLRYLSNDIWQPNTKSIMTVGTNLENVYFKKAGQVLGNSAPF
AFHEDFTGITVKQLTSYGDLNPEEIPLLILNGFEYVTQWSGDPYAVPLRADTSKPKLTQQDVTDLIAYLNKG
GSVLIMENVMSNLKEESASSFVRLLDAAGLSMALNKSVVNNDPQGYPDRVRQRRATGIWVYERYPAADGAQP
PYTIDPNTGEVTWKYQQDNKPDDKPKLEVASWQEEVEGKQVTRYAFIDEAEYTTEESLEAAKAKIFEKFPGL
QECKDSTYHYEINCLERRPGTDVPVTGGMYVPRYTQLNLDADTAKAMVQAADLGTNIQRLYQHELYFRTKGS
KGERLNSVDLERLYQNMSVWLWNDTKYRYEEGKEDELGFKTFTEFLNCYANDAYAGGTKCSADLKKSLVDNN
MIYGDGSSKAGMMNPSYPLNYMEKPLTRLMLGRSWWDLNIKVDVEKYPGSVSAKGESVTENISLYSNPTKWF
AGNMQSTGLWAPAQQDVTIKSSASVPVTVTVALADDLTGREKHEVALNRPPRVTKTYTLEANGEVTFKVPYG
GLIYIKGDSKDDVSANFTFTGVVKAPFYKDGEWKNDLDSPAPLGELESASFVYTTPKKNLEASNFTGGVAEF
AKDLDTFASSMNDFYGRNDEDGKHRMFTYKNLTGHKHRFTNDVQISIGDAHSGYPVMNSSFSTNSTTLPTTP
LNDWLIWHEVGHNAAETPLNVPGATEVANNVLALYMQDRYLGKMNRVADDITVAPEYLDESNGQAWARGGAG
```

```
DRLLMYAQLKEWAEENFDIKQWYPDGELPKFYSDRKGMKGWNLFQLMHRKARGDDVGNSTFGGKNYCAESNG
NAADTLMLCASWVAQADLSEFFKKWNPGASAYQLPGATEMSFQGGVSSSAYSTLASLKLPKPEKGPETINKV
TEHKMSAE*
```

Preferred orf3526 sequences of the invention match the consensus sequence as recited in SEQ ID NO:54, or are immunogenic fragments thereof. Other preferred orf3526 sequences of the invention match the consensus sequence as recited in SEQ ID NO:55, or are immunogenic fragments thereof. X represents any amino acid. Other preferred orf3526 sequences further contain a sequence motif at those positions that correspond to positions 1304-1308 of SEQ ID NO:8, selected from: XEVGH, XXVGH, XEVGX, HXVGX and XXVGX, wherein in any such sequence motif X is not H or E; or X is not H, E or D; or X is not H, E, D, N, Q or C; or X is a non-polar amino acid, or X is selected from A or G, or X is preferably A. In further embodiments, residues 1-23 or 1-33 of SEQ ID NO:54 or SEQ ID NO:55 are lacking.

When used according to the present invention, orf3515 protein may take various forms. Preferred orf3515 sequences have 80% or more identity (e.g. 80%, 85%, 90%, 95%, 96%, 97%, 98%, 99% or more) to SEQ ID NOs 29 and 30. This includes variants (e.g. allelic variants, homologs, orthologs, paralogs, mutants etc).

```
>orf03515
                                                       (SEQ ID 29)
ATGATCACCTCACCACCAAAACGCGGAATGGCACTGGTCGTGGTGCTGG
TATTGCTGGCGGTTATGATGCTGGTGACCATCACGCTTTCCGGGCGGAT
GCAGCAACAACTTGGGCGAACGCGCAGCCAGCAGGAGTACCAGCAGGCG
CTGTGGTACAGCGCCAGTGCAGAAAGCCTGGCGCTGAGCGCGCTCAGTC
TGAGCCTGAAAAATGAAAAGCGTGTGCATCTGGCACAACCGTGGGCTTC
```

```
>consensus_sequence_75%
                                                   (SEQ ID NO: 54)
MNKKFKYKKSLLAAILSATLLAGCDGGGSGSSSDTPXVDSGXGXLPEVKPDPTPXPEPTPDPEPTPXPTPDP
EPTPEPEPEPVPTKTGYLTLGGSQRVTGATCNGESSDGFTFTPGXVXCVXGXXTTIATFBTQSEAARSLRAVXKVS
FSLEDAQELAXSXBKKXNAXSLVTSXBSCPABXEQXCLXFSSVXXXXRFXXLYKQIDLAXXXFXKLVNEEVENNAA
TDKAPSTHTSXVVPVTTXGTKPDLNASFVSANAEQFYQYQPTEIILSEGXLVDSXGXGVXGVBYYTXSGRGVTXEN
GXFSFSWGETISFGIDTFELGSVRGNKSTIALTELGDEVRGANIDQLIHRYSXXGXNBTRVVPDXVRKVFAEYPNV
INEIINLSLSNGATLXEGXQXVXLPNEFIEQFXTGQAKEIDTAICAKTXGCNEARWFSLTTRNVNDGQIQGVINKL
WGVDXBYXSVXKFHVFHDSTNFYGSTGNARGQAVVNISNAAFPILMARNDKNYWLAFGEKRAWDKNELAYITEAPS
JVZPENVTRDTATFNLPFISLGQVGXGKLMVIGNPHYNSILRCPNGYSWXGGVNXXGZCTLXXDXDDMKXFMZNVL
RYLSBDXWXPBXKXXMTVGTNLXXVYFKXHGQVXGNSAXFXFHXDFXGIXVXXLXSYGDLBPZEXPLLILNGFEYV
TQXGXPDYAXPLRADTSKPKLTQQDVTDLIAYLNKGGSVLIMENVMSNLKEESASXFVRLLDAAGLSMALNKSVVN
NDPQGYPBRVRQXRATGIWVYERYPAXDGXXXPYTIDXXTGEVXWKYQXXNKPDDKPKLEVASWXEXVXGKQXTRY
AFIDEAXXXTXXSLXAAKXKIXXXFPGLXECKDXXYHYEXNCLEXRPGTXVPVTGGMYVPXYTQLXLXADTAKAMV
QAADLGTNIQRLYQHELYFRTNGXKGERLXSVDLERLYQNMSVWLWNXXXYRYEXXKXDELGFKTFTEFLNCYAND
AYXXGTXCSAXLKKSLVDNXMIYGXXSXKAGMMNPSYPLNYMEKPLTRLMLGRSWWDLNIKVDVEKYPGXVSXXGZ
XVTEXISLYSNPTKWFAGNMQSTLGLWAPAQXEVITXSXAXVPVTVTVALADDLTGREKHEVALNRPPXVTKTYXL
XAXGXVXFKVPYGGLIYIKGBSXXBXSAXFTFTGVVKAPFYKDGXWKNXLBSPAPLGELESXXFVYTTPKKNLXAS
NXTGGXXZFAXDLDTFASSMNDFYGRBXEXGKHRMFTYKXLTGHKHRFTNDVQISIGDAHSGYPVMNSSFSTNSTT
LPTTPLNDWLIWHEVGHNAAETPLXVPGATEVANNVLALYMQDRYLGKNMRVADDITVAPEYLXESNGQAWARGGA
GDRLLMYAQLKEWAEKNFDIKXWYPXGXLPXFYSXREGMKGWNLFQLMHRKARGDXVGXXXFGXXNYCAESNGNAA
TLMLCASWVAQTDLSEFFKKWNPGANAYQLPGAXEMSFEGGVSQSAYXTLAXLXLPKPZXGPETINXVTEHKMSAE
```

```
>consensus_sequence_100%
                                                   (SEQ ID NO: 55)
MNKKFKYKKSLLAAILSATLLAGCDGGGSGXSSDTPXXDSGXGXLPXVKPDPTPXXXXXXXXXXXXXXXXXXXXX
XXXXXPXXXPEXXXXPVXTKTGYLXLGGSXRXTGXXXCNXEXSDGFTFXXGXXVXCVXGXXTTIATFBTQSEAARS
LRAVXKVSFSLEDAXELAXSXBKKXNAXSLVTXXBSCPABXEQXCLXFSSVXXXXXRFXXLYKQIXLXXXXFXKLVN
EEVENNAATDKAPSTHTSXXVPXTTXGTXPDLNASFVSANAEQXYQYPXEIIXSEGXLVXSXGXGVXGVBYYTXXG
RGVTXENGXGXGSWGEXJSFGIDTFELGSVRGNKSTIALTELGDEVRGANIDQLIHRXSXXXXNXXRXVPXXVRXV
FAXYPNVINEIINLSLSNGXXLXEGXQXXXXXXNXFJEQXXXGQXXEIDTAICXXXXGCNXXRWFSLTXRNVNXGXI
QXVINKLWGVDXXYXSVXKFHVFHDSTNFYGSTGNARGQAVVNISNXAFPILMARNDKNYWLAFGEKRAWDKNXLA
YITEAPSJVXXENVTRXTAXFNLPFISLGQVGXGKLMVIGNPHYNSILRCPNGYSWXGXVBXXGZCTXXXDXBDMK
XFMZNVLRYLSBXXWXPBXKXXMTVGTNLXXVYFKXXGQVXGXXAXFXFHXDFXGIXXXXXXSYGBLBPXXXPLLI
LNGFEYVTQXXXDPYXXPLRADTSKPKLXQQDVTDLIAYXNKGGSVLIMENVMSNLKEESASXFVRLLDAAXLSMA
LNKSVVNXDPQGYPBRXRQXRXXXIWVYERYPXXXXXXXXPYTIBXXTXXXVXWXXXXKDXKPKLEVASWXEXVX
GXQXXXXXAFIDXAXXXTXXXLXAAKXXIXXXFXGLXXCXBXXYHYEXNCLEXRXGXXVPXTXXXXXGMXVPXYTQL
XLXADTAKAMXQAADXGTNIQRLYQHELYFRTXGXXGERLXXVDLERLYQNXSVWLWNXXXYXYXXXKXDELGFKT
FTEFLNCYXNBAYXXGTXCSXXLKXSLXDNXMIYGXXXXXKAGMMNPXYPLNYMEKPLTRLMLGRSWWDLNIKVDV
EXYPGXVXXXGZXVTZXIXLYSXPTKWFAGNMQSTGLXAPAXXXVXIXSXXXVXVTVAXADDLTGREKHEVXLN
RPPXVTKTYXLXAXXXVXFXVPYGGLIYIKXBSXXXXXSAXFTFXGVVKAPFYKBGXWXXXXSPAPLGELESXXF
VYTXPKXNLXAXXXSNXXXGXXZFAXXLDTFAXSMNDFXGRBXXXGXHXMFTXXXLXGHKHRFXNDVQISIGDAHS
GYPVMNSSFSXBSXTLPTXPLNDWLIWHEXGHNAAETPLXVPGATEVANXVLALYMQDRYLGKMNRVADDITVAPE
YLXESNXQAWARGGAGDRLLMYAQLKEWAEXNFDIXXWYPXGXLPXFSXRXGMKGWNLFQLMHRKAXGDXVXXXX
FGXXNYCAESNGNXADXLMLCASWVAQXDLSXFFKKWNPGAXAYQLPGXXEMFXXGXVXXSAYXTLAXXXLXKPXX
GPEXXNXVTEXXMXXE
``` gspK (Orf3515)

gspK general secretion pathway protein is referred to herein as 'orf3515.' orf3515' protein from *E. coli* NMEC is disclosed in WO2006/089264 (SEQ IDs 7029 & 7030) is also known as: 'orf3332' from *E. coli* NMEC strain IHE3034, 'c3702' from CFT073 and ecp_3039 from 536.

```
                                                       -continued
TGGCCCGCGTTTTTTCCCACTGCCGCAGGGCAAATTGCCGTCACTCTG
CGTGACGCACAGGCCTGCTTTAACCTGAATGCCCTCGCTCAGCCGACGA
CGGCGTCGCGTCCGCTCGCGGTACAACAACTGATTGCCCTGATCTCGCG
CCTCGATGTGCCTGCTTATCGGGCCGAACTGATAGCCGAAAGCCTGTGG
GAGTTTATTGACGAAGACCGCAGCGTGCAGACGCGTCTGGGTCGTGAAG
ACAGCGAGTATCTCGCCCGCTCGGTGCCGTTCTACGCCGCTAATCAACC
```

```
                              -continued
GCTGGCTGATATCAGCGAGATGCGCGTGGTGCAGGGAATGGACGCCGGG
CTTTATCAAAAACTGAAACCGTTGGTCTGTGCGCTGCCGATGGCCCGCC
AGCAAATCAACATCAATACATTAGATGTCACGCAAAGTGTGATTCTTGA
GGCGCTGTTTGACCCGTGGTTAAGCCCTGTTCAGGCGCGGGCATTATTA
CAACAACGTCCGGCGAAGGGCTGGGAAGATGTCGATCAGTTTCTTGCTC
AGCCGCTACTTGCAGACGTCGATGAGCGTACTAAAAAACAGCTAAAAAC
CATCCTGAGCGTGGACAGCAATTACTTCTGGCTGCGTTCAGATATCACC
GTGAATGAGATTGAACTGACGATGAATTCGTTAATTGTCCGCATGGGCC
CACAACACTTTTCTGTTCTCTGGCATCAGACAGGAGAAAGTGAG >orf03515
                                              (SEQ ID 30)
MITSPPKRGMALVVVLVLLAVMMLVTITLSGRMQQQLGRTRSQQEYQQA
LWYSASAESLALSALSLSLKNEKRVHLAQPWASGPRFFPLPQGQIAVTL
RDAQACFNLNALAQPTTASRPLAVQQLIALISRLDVPAYRAELIAESLW
EFIDEDRSVQTRLGREDSEYLARSVPFYAANQPLADISEMRVVQGMDAG
LYQKLKPLVCALPMARQQININTLDVTQSVILEALFDPWLSPVQARALL
QQRPAKGWEDVDQFLAQPLLADVDERTKKQLKTILSVDSNYFWLRSDIT
VNEIELTMNSLIVRMGPQHFSVLWHQTGESE
```

Particular compositions of the invention will comprise a combination of (i) bacterial Ig-like domain protein (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto.

Other particular compositions of the invention will further comprise (iii) upec1232 having the amino acid sequence set forth in SEQ ID NO:4 or a protein having at least 80% similarity thereto.

More particularly the immunogenic components of a composition of the invention will consist essentially of (i) bacterial Ig-like domain protein (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto. The composition can additionally include non-immunogenic components.

Other particular immunogenic components of a composition of the invention will consist essentially of (i) bacterial Ig-like domain protein (orf405B) having the amino acid sequence set forth in SEQ ID NO:2 or a protein having at least 80% similarity thereto, and (ii) putative Lipoprotein (orf3526) having the amino acid sequence set forth in SEQ ID NO:8 or a protein having at least 80% similarity thereto, and (iii) upec1232 having the amino acid sequence set forth in SEQ ID NO:4 or a protein having at least 80% similarity thereto. The composition can additionally include non-immunogenic components.

Particularly, the compositions of the invention may further comprise at least one bacterial toxin. Particularly, the toxin is derived from E. coli (i.e., E. coli heat labile enterotoxin "LT"), cholera ("CT"), or pertussis ("PT").

The use of detoxified ADP-ribosylating toxins as mucosal adjuvants is described in WO95/17211 and as parenteral adjuvants in WO98/42375.

Particular detoxified LT mutants include LT-K63, LT-R72, and LTR192G. Preferably, the bacterial toxin will be a mutant or modified bacterial toxin. In a preferred embodiment the bacterial toxin is the modified heat-labile toxin of Escherichia coli (LTK63).

The use of ADP-ribosylating toxins and detoxified derivatives thereof, particularly LT-K63 and LT-R72, as adjuvants can be found in the following references, each of which is specifically incorporated by reference herein in their entirety: Beignon, et al., "The LTR72 Mutant of Heat-Labile Enterotoxin of Escherichia coli Enahnces the Ability of Peptide Antigens to Elicit CD4 T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol. (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of Escherichia coli Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280; Partidos et al., "Heat-labile enterotoxin of Escherichia coli and its site-directed mutant LTK63 enhance the proliferative and cytotoxic T-cell responses to intranasally co-immunized synthetic peptides", Immunol Lett. (1999) 67(3):209-216; Peppoloni et al., "Mutants of the Escherichia coli heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from Escherichia coli (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol. (1995) 15(6):1165-1167, specifically incorporated herein by reference in its entirety.

Thus, in the context of the invention, the word "toxin" is intended to mean toxins that have been detoxified such that they are no longer toxic to humans, or a toxin subunit or fragment thereof that is substantially devoid of toxic activity in humans.

Other detoxified toxins include the B subunit from E. coli labile toxin (LT), the amino terminal domain of the anthrax lethal factor (LF), P. aeruginosa exotoxin A, adenylate cyclase A from B. Pertussis, a derived or mutant from a toxin which is a family of the ABS family, for example, the cholera toxin (CT), the Bordatella Pertussis toxin (PT) as well as the recently identified subtilase cytotoxins. (Paton et al, J Exp Med 2004, Vol 200 pp 35-46).

The labile toxin (LT) of E. coli consists of two subunits, a pentameric B subunit and a monomeric A subunit. The A subunit is responsible for toxicity, whilst the B subunit is responsible for transport into the cell. LT binds the G M1 ganglioside receptor.

A derivative of E. coli heat-labile toxin with equal or greater the 90% homology has greater than 90% homology at the amino acid level. In another embodiment the protein has equal or greater than 95% homology, for example 96, 97, 98 or 99%. For example, amino acid deletions may be made that do not affect function. In a further embodiment, a derivative is still able to bind the G M1 ganglioside receptor.

Thus, particular compositions of the invention include combinations of at least two, at least three, at least four or five E. coli antigens selected from the group consisting of orf405B, upec1232, orf3526, orf3515 and LTK63. Particular compositions of the invention include no more than two, no more than three, no more than four or no more than five antigens selected from the group consisting of orf405B, upec1232, orf3526, orf3515 and LTK63. Yet more particularly, compositions of the invention consist of, or consist essentially of, a combination of two, three, four or five antigens selected from the group consisting of orf405B, upec1232, orf3526, orf3515 and LTK63. Particular combinations include the following *E. coli* antigen(s)/immunogenic components:

Orf405B+orf3526
Orf405B+upec1232+orf3526
Orf405B+upec1232+orf3526+orf3515
Orf405B+orf3526+LTK63
Orf405B+upec1232+orf3526+LTK63
Orf405B+upec1232+orf3526+orf3515+LTK63

Antigen orf3526 comprises a zinc binding motif which encompasses amino acids at positions 1304-1308 (HEVGH underlined in SEQ ID 8) with reference to SEQ ID 8. Since this zinc binding motif may be associated with toxicity, orf3526 polypeptides which lack or have reduced zinc binding activity are particularly useful in combinations of the present invention. Preferably, zinc binding activity of a mutant orf3526 protein is either reduced by or reduced to at least 50%, at least 45%, at least 40%, at least 35%, at least 30%, at least 25%, at least 20%, at least 15%, at least 10% or at least 5% relative to or compared to wild-type orf3526. Zinc binding can be determined by atomic absorption and other assays will be known to one skilled in the art. Thus, mutations in the zinc binding motif are useful in reducing zinc binding and associated toxicity. For example, mutations in the zinc binding motif from wild-type HEVGH to AEVGH can reduce zinc binding to about 43% or more particularly, mutations from wild-type to AAVGA can reduce zinc binding to around 5%. Surprisingly an orf3526 mutant which comprises the AAVGA sequence has the added advantage that it co-elutes with native orf3526 and is present in only two isoforms (a monomer and truncated form) meaning that the efficiency of purification is simplified and significantly improved in comparison with other mutants tested. Compositions of the invention may comprise orf3526 mutants comprising a sequence motif selected from XEVGH, XXVGH, XEVGX, HXVGX or XXVGX, wherein in any such sequence motif X is not H or E; or X is not H, E or D; or X is not H, E, D, N, Q or C; or X is a non-polar amino acid, or X is selected from A or G, or X is preferably A.

Advantageously, vaccine combinations of the present invention may be used in combination with a Group B *Streptococcus* vaccine to prevent most cases of neonatal meningitis. Thus, in certain embodiments, the combinations of the invention may include: (i) one or more further, non *E. coli*, polypeptides that elicit antibody responses against Group B *Streptococcal* (GBS) proteins; (ii) a capsular saccharide from Group B *Streptococcus*; and/or (iii) one or more further immunogens that elicit antibody responses that recognise epitopes on non-GBS organisms. In other embodiments, the immunogenic combinations of the present invention are administered separately at substantially the same time as a GBS vaccine.

Particular GBS polypeptides include: 'GBS80' (SAG0645) a cell wall surface anchor family protein (see GI: 22533660); 'GBS1523' (SAN1518; SpbI), a cell wall surface anchor family protein (see GI: 77408651); 'GBS104' (SAG0649) (see GI: 22533664); 'GBS67' (SAG1408), a cell wall surface anchor family protein (see GI: 22534437); 'GBS59', a pilus backbone protein encoded by pathogenicity island 2a (BP-2a); 'GBS3' (SAG2603; BibA), a pathogenicity protein (see GI:22535109); 'SAN1485', a cell wall surface anchor family protein' (see GI: 77408233); 'GBS147' (SAG0416), a putative protease (see GI: GI:22533435); 'GBS328' (SAG1333) a 5'-nucleotidase family protein' (see GI: 22534359).

Immunogenic Compositions and Medicaments

The Polypeptides described above are useful as active ingredients (immunogens) in immunogenic compositions of the invention, and such compositions may be useful as vaccines. Immunogenic compositions will be pharmaceutically acceptable. They will usually include components in addition to the antigens e.g. they typically include one or more pharmaceutical carrier(s), excipient(s) and/or adjuvant(s). Thorough discussions of vaccine adjuvants are available in refs. 6 and 7.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To improve thermal stability, a composition may include a temperature protective agent. To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

In certain embodiments the vaccine composition will comprise one or more pharmaceutically acceptable carriers, diluents and/or adjuvants. Adjuvants which may be used in compositions of the invention include, but are not limited to:

mineral salts, such as aluminium salts and calcium salts, including hydroxides (e.g. oxyhydroxides), phosphates (e.g. hydroxyphosphates, orthophosphates) and sulphates, etc. [e.g. see chapters 8 & 9 of ref 8];

oil-in-water emulsions, such as squalene-water emulsions, including MF59 (5% Squalene, 0.5% Tween 80, and 0.5% Span 85, formulated into submicron particles using a microfluidizer) [Chapter 10 of ref 6, see also ref 9-12, chapter 10 of ref 13 and chapter 12 of ref 14], complete Freund's adjuvant (CFA) and incomplete Freund's adjuvant (IFA);

saponin formulations [chapter 22 of ref 6], such as QS21 [15] and ISCOMs [chapter 23 of ref 6];

virosomes and virus-like particles (VLPs) [16-22];

bacterial or microbial derivatives, such as non-toxic derivatives of enterobacterial lipopolysaccharide (LPS), Lipid A derivatives [23, 24], immunostimulatory oligonucleotides [25-30], such as IC-31™ [31] (deoxynucleotide comprising 26-mer sequence 5'-(IC)$_{13}$-3' (SEQ ID NO:56) and polycationic polymer peptide comprising 11-mer amino acid sequence KLKLLLLLKLK (SEQ ID NO:57)) and ADP-ribosylating toxins and detoxified derivatives thereof [32-41];

human immunomodulators, including cytokines, such as interleukins (e.g. IL-1, IL-2, IL-4, IL-5, IL-6, IL-7, IL-12 [42, 43], interferons (e.g. interferon-γ), macrophage colony stimulating factor, and tumor necrosis factor;

bioadhesives and mucoadhesives, such as chitosan and derivatives thereof, esterified hyaluronic acid microspheres [44] or mucoadhesives, such as cross-linked derivatives of poly(acrylic acid), polyvinyl alcohol, polyvinyl pyrollidone, polysaccharides and carboxymethylcellulos [45];

microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.);

liposomes [Chapters 13 & 14 of ref 6, ref 46-48];

polyoxyethylene ethers and polyoxyethylene esters [49];

PCPP formulations [50 and 51];

muramyl peptides, including N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE); and imidazoquinolone compounds, including Imiquamod and its homologues (e.g. "Resiquimod 3M") [52 and 53].

The invention may also comprise combinations of one or more of the adjuvants identified above. For example, the following adjuvant compositions may be used in the invention: (1) a saponin and an oil-in-water emulsion [54]; (2) a saponin (e.g. QS21)+a non-toxic LPS derivative (e.g. 3dMPL) [55]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [56]; (5) combinations of 3dMPL with, for example, QS21 and/or oil-in-water emulsions [57]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref 6.

The use of an aluminium hydroxide and/or aluminium phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG & alum or resiquimod & alum. A combination of aluminium phosphate and 3dMPL may be used.

The compositions of the invention may elicit both a cell mediated immune response as well as a humoral immune response.

Two types of T cells, CD4 and CD8 cells, are generally thought necessary to initiate and/or enhance cell mediated immunity and humoral immunity CD8 T cells can express a CD8 co-receptor and are commonly referred to as Cytotoxic T lymphocytes (CTLs). CD8 T cells are able to recognized or interact with antigens displayed on MHC Class 1 molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β) an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

A composition may include a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Infections can affect various areas of the body and so the compositions of the invention may be prepared in various forms. For example, the compositions may be prepared for parenteral administration as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be formulated for administration using a 'vaccine patch' or plaster. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Delivery methods including parenteral injection (e.g., subcutaneous, intraperitoneal, intravenous, intramuscular, or interstitial injection) and rectal, oral (e.g., tablet, spray), vaginal, topical, transdermal are disclosed in WO 99/27961, transcutaneous methods in WO02/074244 and WO02/064162, intranasal in WO03/028760. Other routes of administration include ocular, aural, and pulmonary or other mucosal administration.

Particularly the compositions of the present invention may be administered via a systemic route or a mucosal route or a transdermal route or it may be administered directly into a specific tissue. As used herein, the term "transdermal delivery" includes intradermal (e.g., into the dermis or epidermis) and transdermal (e.g. "percutaneous") i.e., delivery by passage of an agent into or through at least a top layer of skin. As used herein, the term "systemic administration" includes but is not limited to any parenteral routes of administration. In particular, parenteral administration includes but is not limited to subcutaneous, intraperitoneal, intravenous, intraarterial, intramuscular, or intrasternal injection, intravenous, intraarterial, or kidney dialytic infusion techniques. Generally, the systemic, parenteral administration is intramuscular injection. As used herein, the term "mucosal administration" includes but is not limited to oral, intranasal, intravaginal, intrarectal, intratracheal, intestinal and ophthalmic administration. Novel direct delivery forms can also include transgenic expression of the combinations of polypeptides in foods, e.g., transgenic expression in a potato.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Pharmaceutically Acceptable Carriers

Compositions of the invention will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472. The compositions of the invention may be prepared in various forms (e.g., liquid, lyophilized), as is known in the art.

Methods of Treatment, and Administration of Immunogenic or Vaccine Compositions of the Invention The invention also provides a method for raising an immune response in a subject, particularly a mammal, comprising the step of administering an effective amount of a composition of the invention. The immune response is preferably protective and preferably involves antibodies and/or cell-mediated immunity. The method may raise a booster response.

The invention also provides immunogenic combinations or compositions for use as a medicament e.g. for use in raising an immune response in a subject, such as a mammal.

The invention also provides the use of a combination of polypeptides or a composition of the invention in the manufacture of a medicament for raising an immune response in a subject, such as a mammal.

The invention also provides a delivery device pre-filled with an immunogenic composition of the invention.

By raising an immune response in the subject by these uses and methods, the subject, for example a mammal, can be protected against *E. coli* infection, e.g. more than one *E. coli* pathotype, including ExPEC and non-ExPEC strains. The invention is particularly useful for providing broad protection against pathogenic ExPEC *E. coli*, including intestinal pathotypes such as EPEC, EAEC, EIEC, ETEC and DAEC (Diffuse-adhering *Escherichia coli*) pathotypes. Thus the subject may be protected against diseases including, but not limited to peritonitis, pyelonephritis, cystitis, endocarditis, prostatitis, urinary tract infections (UTIs), meningitis (particularly neonatal meningitis), sepsis (or SIRS), dehydration, pneumonia, diarrhea (infantile, travellers', acute, persistent, etc.), bacillary dysentery, hemolytic uremic syndrome (HUS), pericarditis, bacteriuria, etc.

The subject is preferably a mammal, particularly a human, but by way of non-limiting example, may also be a cow, a pig, a sheep, a horse, a cat or a dog since *E. coli* disease is also problematic in these species. In certain embodiments the subject may be an avian subject such as, for example, a chicken, goose, turkey and the like.

Where the vaccine is for prophylactic use, the human is particularly a child (e.g. a toddler or infant) or a teenager; where the vaccine is for therapeutic use, the human is particularly a teenager or an adult. A vaccine intended for children may also be administered to adults e.g. to assess safety, dosage, immunogenicity, etc.

One way of checking efficacy of therapeutic treatment involves monitoring *E. coli* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Typically, antigen-specific serum antibody responses are determined post-immunisation but pre-challenge whereas antigen-specific mucosal antibody responses are determined post-immunisation and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of compositions of the invention can also be determined in vivo by challenging animal models of *E. coli* infection, e.g., guinea pigs or mice, with the vaccine compositions. A murine model of ExPEC and lethal sepsis is described in reference 58. A cotton rat model is disclosed in ref 59

Dosage treatment can be a single dose schedule or a multiple dose schedule. In some embodiments, compositions of the invention are administered in combination with an antibiotic treatment regime. In one embodiment, the antibiotic is administered prior to administration of a composition of the invention. In another embodiment, the antibiotic is administered subsequent to the administration of a composition of the invention.

Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines of the invention may be used to treat both children and adults. Thus a human patient may be less than 1 year old, 1-5 years old, 5-15 years old, 15-55 years old, or at least 55 years old. Particular patient groups for receiving the vaccines are the elderly (e.g. ≥50 years old, ≥60 years old, and preferably ≥65 years), the young (e.g. ≤5 years old), hospitalised patients, healthcare workers, armed service and military personnel, travellers, pregnant women, the chronically ill, or immunodeficient patients. The vaccines are not suitable solely for these groups, however, and may be used more generally in a population.

Vaccines of the invention are particularly useful for patients who are expecting a surgical operation, or other hospital in-patients. They are also useful in patients who will be catheterized. They are also useful in adolescent females (e.g. aged 11-18) and in patients with chronic urinary tract infections.

Vaccines of the invention may be administered to patients at substantially the same time as (e.g. during the same medical consultation or visit to a healthcare professional or vaccination centre) or in combination with other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a *Streptococcal* vaccine such as a Group A *Streptococcal* vaccine or a Group B *Streptococcal* vaccine etc.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 60-61, etc.

In some implementations, the term "comprising" refers to the inclusion of the indicated active agent, such as recited polypeptides, as well as inclusion of other active agents, and pharmaceutically acceptable carriers, excipients, emollients, stabilizers, etc., as are known in the pharmaceutical industry. In some implementations, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. Use of the transitional phrase "consisting essentially" means that the scope of a claim is to be interpreted to encompass the specified materials or steps recited in the claim, and those that do not materially affect the basic and novel characteristic(s) of the claimed invention. See, In re Herz, 537F.2d 549, 551-52, 190 USPQ 461, 463 (CCPA 1976) (emphasis in the original); see also MPEP §2111.03. Thus, the term "consisting essentially of" when used in a claim of this invention is not intended to be interpreted to be equivalent to "comprising".

The term "about" in relation to a numerical value x means, for example, x±10%.

"GI" numbering is used herein. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

References to a percentage sequence identity between two amino acid sequences means that, when aligned, that percentage of amino acids are the same (i.e. identical) in comparing the two sequences, relative to the longest of the sequences. This alignment and the percent homology or sequence identity can be determined using software programs known in the art. A preferred alignment is determined by the Smith-Waterman homology search algorithm using an affine gap search with a gap open penalty of 12 and a gap extension penalty of 2, BLOSUM matrix of 62.

While certain embodiments of the present invention have been described and specifically exemplified above, it is not intended that the invention be limited to such embodiments. Various modifications may be made thereto without departing from the scope and spirit of the present invention as set forth in the following claims.

MODES FOR CARRYING OUT THE INVENTION

Example 1

Bacterial Ig-like domain (group 1) protein (orf405), gspK (orf3515), upec-1232, and orf3526, each as more fully described herein, have been expressed, sequenced and purified. Sequences were obtained for the orthologs in various other E. coli strains. Distribution of each of the candidate antigens were determined in most pathogenic strains, specifically NMEC, APEC, UPEC, EHEC, EAEC, EIEC, EPEC, ETEC and AIEC. The presence of each of the antigens is shown in FIGS. 1A and B.

Example 2

Antigens were PCR amplified from the genomic DNA templates, cloned in pET-21b vectors (Novagen) and transformed in DH5α-T1 chemically competent cells for propagation (Invitrogen). BL21 (DE3) chemically competent cells were used for expression. All candidates were cloned and expressed without the signal sequence and as His-tag fusion proteins. Candidates were purified by affinity chromatography.

| Antigen | Homology | Size (kDa) | Solubility | Yield (mg/L of growth) | % Purity |
|---|---|---|---|---|---|
| Orf3526 | IHE3034/ RS218/536 | 165 | + | 1.245 mg/L | 90% |
| Orf3515 | All | 31 | + | 16.7 mg/L | 95% |
| 405B | All | 46 | + | 5.3 mg/L | 95% |
| Upec1232 | CFT073 | | + | | 95% |

Example 3

Protection was evaluated in a sepsis animal model. CD1 out bred female mice (5 weeks old) from Charles River Italia were immunized by subcutaneous injections at the $1^{st}$, $21^{st}$ and $35^{th}$ days with 20 µg of recombinant protein in Freund's adjuvant. Positive control was immunized with $10^8$ heat-inactivated bacteria (65° C. for 30 minutes) in 0.15 ml of physiological solution in Freund's adjuvant (Sigma), while negative control was immunized with physiologic solution in Freund's adjuvant. Challenge was done at the $49^{th}$ day with a dose of $10^7$ of fresh bacterial culture/mouse ($LD_{80}$) by intraperitoneal (for strains IHE3034 and CFT073) or intravenous (for strain 536) injection. Heparinised-blood samples were collected from survived mice at 24 hours after challenge to determine bacteremia levels and the mortality was observed for four days after challenge.

| | Sepsis Animal Model | | |
|---|---|---|---|
| Candidate | Survival with vaccination (%) | Survival without vaccination (%) | P value |
| upec-1232 | 15/30 (50) | 3/36 (8) | 0.0002 |
| gspK (orf3515) | 30/110 (27) | 11/116 (9) | 0.0005 |
| 405B (bacterial Ig-like domain (group 1) protein fragment) | 17/63 (26) | 9/66 (13) | 0.07 |
| Orf3526 | 8/8 (100) | 2/8 (25) | — |

Example 3A

Protection was evaluated in a sepsis animal model. CD1 mice were immunized by subcutaneous injections at day 0, 21 and 35 with 20 µg of recombinant protein in Freund's complete adjuvant or alum. Positive control was immunized with $10^8$ heat-inactivated bacteria (65° C. for 30 minutes) in 0.15 ml of physiological solution in Freund's complete adjuvant or alum, while negative control was immunized with physiologic solution in Freund's complete adjuvant or alum. Challenge was done at the $49^{th}$ day with a dose of $10^7$ of fresh bacterial culture/mouse ($LD_{80}$) by intraperitoneal (for strains IHE3034 and CFT073) or intravenous (for strain 536) injection. Heparinised-blood samples were collected from survived mice at 24 hours after challenge to determine bacteremia levels and the mortality was observed for four days after challenge.

Protection Using Freud's Complete Adjuvant:

| | Sepsis Animal Model | | |
|---|---|---|---|
| Candidate | Survival with vaccination (%) | Protection rate | P value |
| upec-1232 | 15/30 (50) | 45% | 0.0002 |
| gspK (orf3515) | 30/110 (27) | 20% | 0.0009 |
| 405B | 25/81 (30) | 18% | 0.029 |
| Orf3526 | 125/149 (84) | 83% | <0.0001 |

Protection Using Alum—Homologous Challenge:

| | Sepsis Animal Model | | |
|---|---|---|---|
| Candidate | Survival with vaccination (%) | Protection rate | P value |
| upec-1232-His | 4/8 (50) | 43% | 0.28 |
| 405B-His | 11/40 (27.5) | 19% | 0.046 |
| Orf3526-native | 7/8 (87.5) | 87.5% | 0.0014 |
| Orf3526-His | 74/102 (72.5) | 70% | <0.0001 |

Protection Using Alum—Heterologous Challenge:

| | Sepsis Animal Model | | |
|---|---|---|---|
| Candidate | Survival with vaccination (%) | Protection rate | P value |
| Orf3526-His | 14/23 (61) | 48% | 0.018 |

Protection rate=((% dead control−% dead immune)/(% dead control))×100

Example 3C

Cross-protection was evaluated in a sepsis animal model by active or passive immunisation. Mice were immunized with antigen 3526-his in alum before challenge (active immunization) or administered anti-3526-his antibodies after challenge (passive immunisation). The sequence of 3526-his is based on the sequence of the native 3526 protein from the NMEC strain IHE3034. Mice were challenged with strains IHE3034, B616, IN1S or 9855/93. % PE (protective efficacy) was calculated as: 1−(% dead vaccinated/% dead control)×100.

| Challenge strain | Active immunisation | | Passive immunisation | |
|---|---|---|---|---|
| | % PE (survival) | P value | % PE (survival) | P value |
| IHE3034 (NMEC) | 70 (74/102) | <0.0001 | 100 (32/32) | <0.0001 |
| B616 (NMEC) | 85 (14/16) | 0.0002 | nd | nd |
| IN1S (SEPEC) | 50 (23/40) | <0.0001 | 50 (20/32) | 0.0026 |
| 9855/93 (SEPEC) | 35 (11/24) | 0.03 | nd | nd |

The results show that 3526 from ExPEC-NMEC strain IHE3034 confers protection in actively immunized mice against at least three additional ExPEC strains (one NMEC and two SEPEC). The passive immunization experiments confirm cross-protection against at least one additional ExPEC strain (SEPEC).

Example 4

Protection was evaluated in a sepsis animal model according to the following schedule:

| Active immunization | Passive immunization |
|---|---|
| CD1 mice (4 weeks old) are immunized s.c. 20 μg antigen + Freund's adjuvant: 3 doses at 0, 21, 35 days | Mice or rabbit immune serum is administered i.v. to CD1 mice |
| 14 days after last immunization (11 weeks old mice) mice are infected at a lethal dose ($LD_{80}$) with pathogenic E. coli strains. | 24 h after passive immunization mice are challenged i.p. with IHE3034 strain |

Blood is collected from the tail at 24 hours to evaluate bacteremia

Mortality is monitored for 4 days after the infection and $$\text{Protection rate is calculated as} = \frac{(\% \text{ dead } ctrl. - \% \text{ dead } immun.)}{\% \text{ dead } ctrl.} \times 100$$

| Candidate | Survival (%) Vacc. | Survival (%) no Vacc. | P value* |
|---|---|---|---|
| Orf3515 | 21/64 (33) | 5/67 (7) | 0.0003 |
| 405B | 17/55 (31) | 7/58 (12) | 0.01 |
| Upec1232 | 8/23 (34) | 2/28 (7) | 0.03 |

Example 5

In order to study the gene distribution, genetic variability and protein expression of antigen orf3526, as well as to evaluate the effective vaccine coverage, we studied three different collections of human and animal isolates including different pathogenic (ExPEC, ETEC, EPEC) and faecal strains. Briefly, Genomic DNA was prepared by culturing bacteria overnight at 37° C. in atmosphere humidified with 5% $CO_2$ in LB (Difco). Chromosomal DNA was prepared from 1.5 mL of culture using the GenElute Bacterial Genomic DNA Kit (Sigma) according to the manufacturer's instructions. DNA concentration was calculated by optical density determination at 260 nm. About 100 ng of chromosomal DNA was used as template for the amplification of antigen orf3526. The amplification enzyme used was the Phusion® DNA Polymerase (Finnzymes). All genes were amplified using primers external to the coding region. Primers were designed in conserved DNA region and the sequences are reported in Table 1. Antigen orf3526 was amplified using primers ECOK1_3385_1 and ECOK1_3385_22. PCR conditions were as follows: 35 cycles of denaturation at 98° C. for 10 s, annealing at 55° C. for 20 s, and elongation at 72° C. for 3 min. PCR products were purified with Agencourt® AMPure® protocol (Beckman Coulter) and sequenced on the capillary sequencer ABI3730x1 DNA Analyzers (Applied Biosystems). Sequences were assembled with Sequencher 4.8 (Gene Codes) and aligned and analyzed using the Vector NTI Suite 10.

TABLE 1

Primers list used for amplification and sequencing of orf3526 (Orf03343_1 to Orf03343_22 correspond to SEQ ID NOs 32 to 53)

| | |
|---|---|
| Orf03343_1 | TGATGCCGTTTTCTTAAGAATGGAGGAA |
| Orf03343_2 | GAGCCAGAACCTGTTCCTA |
| Orf03343_3 | GTAAAGCCATCGCTGGATTCA |
| Orf03343_4 | CCACCTCTTCATTGACCAGC |
| Orf03343_5 | CGGAACAGTTTTATCAGTAT |
| Orf03343_6 | CCCCGCGAACTTCATCAC |
| Orf03343_7 | GCAAGGTCTTTGCCGAGTATC |
| Orf03343_8 | TGATAAAAACTACTGGCTGGC |
| Orf03343_9 | GGTTACCGATAACCATCAG |
| Orf03343_10 | GCAGATACCAGCAAACCGA |
| Orf03343_11 | TCATCACGTTTTCCATGATCAGC |
| Orf03343_12 | GCGGATTTAGGCACCAACATTC |
| Orf03343_13 | GAATGTTGGTGCCTAAATCCGC |
| Orf03343_14 | GTGAACGTTTTAAAGCCCAGCTC |
| Orf03343_15 | AACTATATGGAAAAACCGCTGAC |
| Orf03343_16 | AAAGCGCCGTTCTATAAAGA |
| Orf03343_17 | TTATAGAACGGCGCTTTTAC |
| Orf03343_18 | CATCACCGATGGAGATCTGC |
| Orf03343_19 | AAGATGAACCGTGTCGCTGAC |
| Orf03343_20 | CTGGAACCTGTTCCAGTTGAT |
| Orf03343_21 | ATCAACTGGAACAGGTTCCAG |
| Orf03343_22 | TATTGCTGAAAAACATCAAAAAG |

Elisa Assay orf3526 antigen detection and relative quantification in supernatants (SN) was performed by an antibody-sandwich ELISA targeting orf3526 antigen with rabbit anti-orf3526 antigen polyclonal antibody and revealed by alkaline phosphatase-conjugated anti-rabbit antibody. Briefly, the wells of microtiter plates (Nunc, Maxi Sorp) were coated overnight at 4° C. with 0.22 µm-filtered bacterial supernatant. Unbound SN was washed out twice with a solution of PBS-Tween (0.05%) (PBS-T), and non-specific binding sites were blocked with a PBST-BSA (1%) solution for 1 h at 37° C. The plates were further washed another three times with PBS-T before rabbit anti-orf3526 polyclonal antibody serial dilutions were added to duplicate wells for 1 h 37 min at 37° C. After three washes with PBS-T, alkaline phosphatase-conjugated anti-rabbit polyclonal antibody was added. Subsequently, the microplates were incubated for 1 h at 37° C. and washed three times with PBST, before revelation by adding the enzyme substrate. After a 30-min incubation in the dark at room temperature, the reaction was stopped by adding 50 ul NaOH solution (3N). The plates were read at 405 nm in a microplate reader (TECAN).

Overall, ECOK1_3385 gene was present and expressed in more than 80% of the 417 strains analyzed, with an amino acid sequence identity never below 86%. In conclusion, the results presented here indicate that antigen orf3526 is well represented, conserved and expressed across pathogenic and faecal isolates indicating that this target may be a useful candidate for a broadly protective vaccine against *E. coli* (FIGS. 2(*a*), 2(*b*) and 2(*c*)).

Phylogenetic Reconstruction

Figure 3:
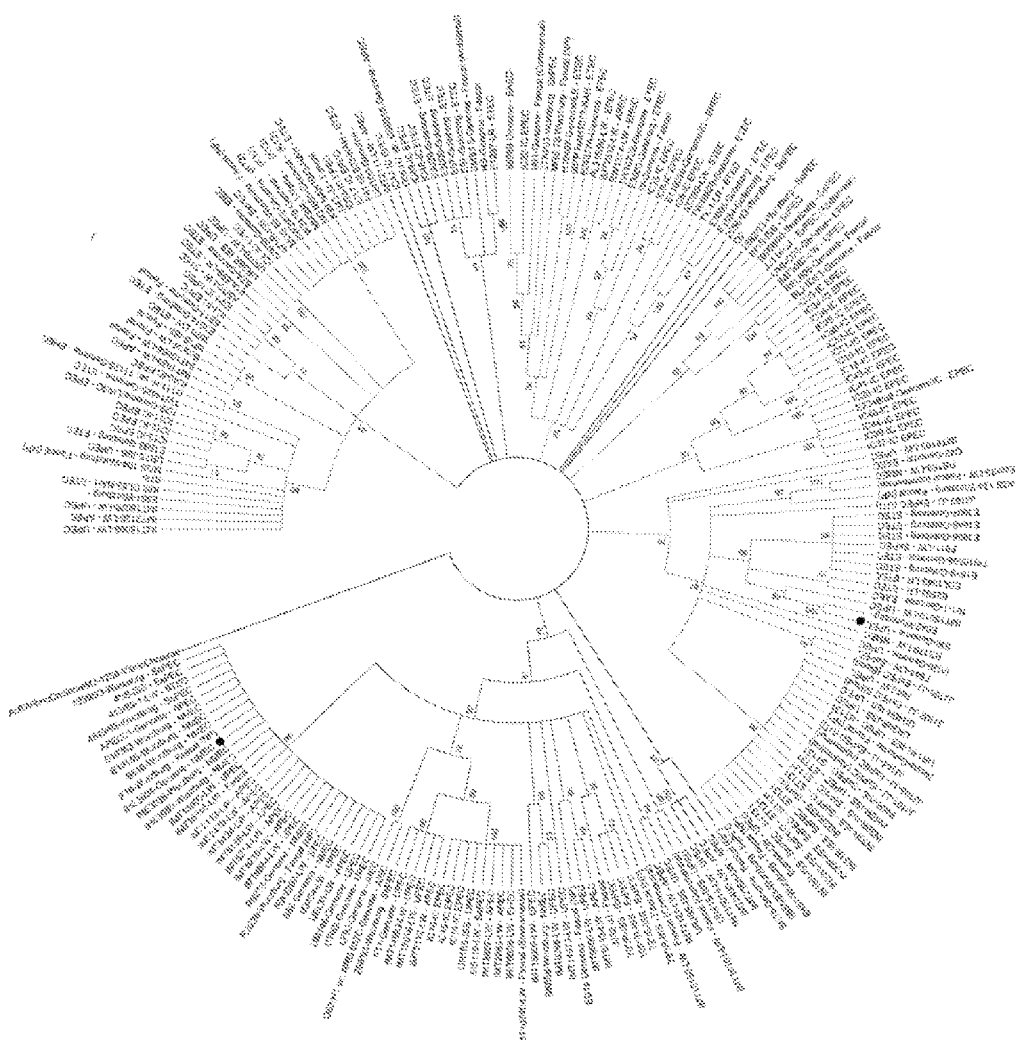
FIG. 3: Study of molecular diversity of orf3526: sequence alignment analysis of 217 sequences of orf3526 protein revealed a sequence identity ranging from 86% to 100%; the derived phylogenetic tree revealed the presence of 6 major variants. The phylogenetic tree was inferred using the Maximum likelihood method implemented in MEGA5 package.

Phylogenetic tree of 217 amino acid sequences of orf3526 antigen was computed using MEGA v.4 (ref Tamura K, Dudley J, Nei M, Kumar S (2007) MEGA4: Molecular Evolutionary Genetics Analysis (MEGA) software version 4.0. Mol Biol Evol 24: 1596-1599.) using the Neighbor Joining algorithm from distance matrices between protein sequences computed using the Maximum Composite Likelihood (ref Tamura K, Nei M, Kumar S (2004) Prospects for inferring very large phylogenies by using the neighbor-joining method. Proc Natl Acad Sci USA 101: 11030-11035.) (FIG. 3).

Example 6

Orf3526 is Protective in an Avian Model

Figure 4:
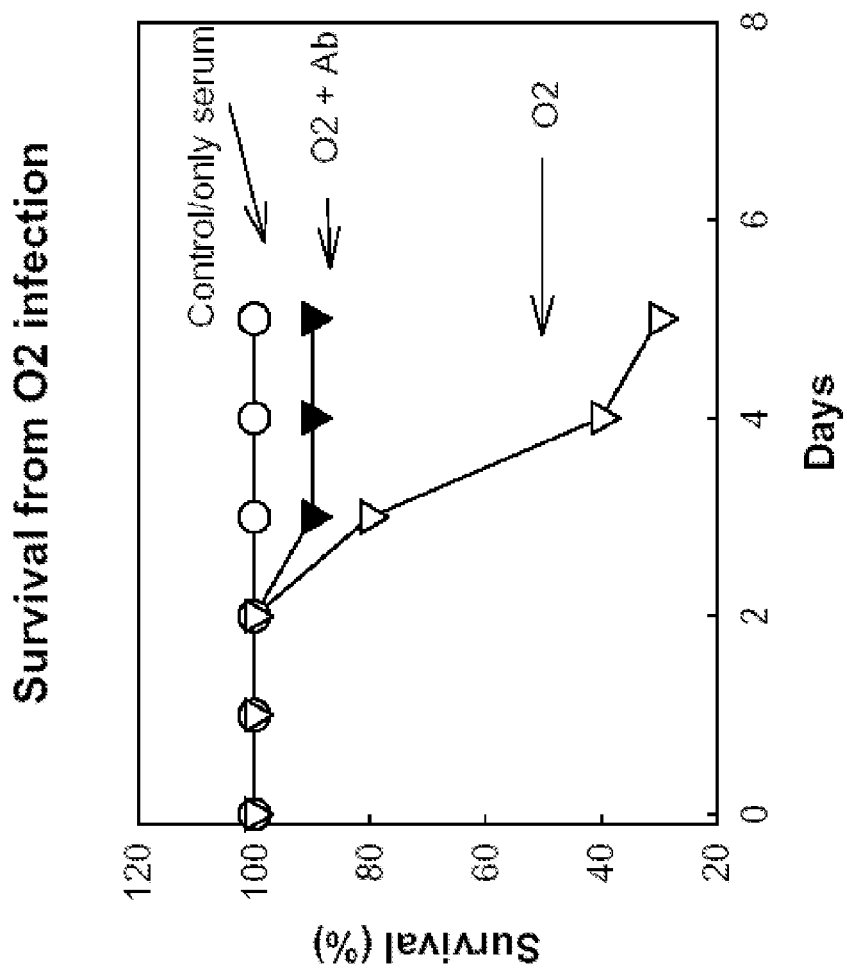
FIG. 4: Antibodies to antigen orf3526 were found to protect in passive immunization in an avian (chicken) model of sepsis.

Three day old chicks (Bar-On) were challenged i.p. with $5 \times 10^6$ of *E. coli* O2 strain 1772, in two injections of 0.2 ml each, 3 hours apart. Antibodies (anti-orf3526), 0.15 ml, were applied s.c. (neck) 20 min after the first injection. Antibodies to antigen orf3526 were found to protect in passive immunization in a chicken model of sepsis (FIG. 4).

Example 7

The purpose of this experiment was to evaluate the protective ability of conserved antigen orf3526 with and without LTK63 against diarrheal disease in piglets, caused by intestinal pathogenic K88 *E. coli* (ETEC).

Two studies were carried out:

1. 11NAHLW1019v: Production of Protein orf3526 Antiserum by Hyperimmunization (Phase I), Antiserum Oral Administration Pre-Challenge in Piglets (Phase II)

2. 11NAHLW1020v: ExPEC Antiserum Administration with Challenge Evaluation of orf3526 Protein The first experiment has been designed to generate anti-sera for the orf3526 protein with and without LTK63 in CD/CD swine followed by a pilot administration with minimum and maximum doses as well as controls to immunologically naive piglets to assess preliminary efficacy of anti-sera type products in the challenge model.

The second experiment is a randomized, blinded trial designed to evaluate the orf3526 protein given in the form of an anti-sera to immunologically naive piglets followed by oral K88 *E. coli* challenge.

The following material was utilised:
Purified recombinant orf3526 Protein
Purified recombinant orf3526 Protein+LTK63
Monoclonal Antibody to orf3526 for stability testing Challenge K88 challenge culture (lot no. TBD) was thawed at room temperature (~23 degrees C.); pooled together, diluted 1:2 with sterile Peptone Buffer, 2.0 ml and re-dispensed into 3 ml cryovials and frozen <−60 degrees C. A Post-freeze Viability Count was performed in accordance to SO 6.001, to establish the amount of antigen being administered.

At the time of farrowing, each piglet had the date and time of farrowing recorded on the Farrowing/Challenge Form. The piglets were ear tagged prior to processing, due to the need for the piglets' identification number in recording time and date of birth. Piglets were allowed to suckle ad libitum. Within 6 hours (+/−2 hours) of birth, piglets were weighed.

Immediately following processing, piglets meeting the Post-inclusion Removal/Withdrawal criteria were utilized for challenge study.

The diluted and re-dispensed K88 Challenge Culture (lot no. TBD) was thawed at room temperature (~23 degrees C.) and 2.0 ml administered orally to each piglet. Following challenge, piglets were placed back on the gilt.

The treatment outcome for Phase I was assessed by antibody titres to protein orf3526 in the sera collected from hyperimmunized pigs. The treatment outcome for Phase II was assessed by which group has the maximum protection from 2 doses of antisera orally pre-challenge; determined by the mortality/morbidity information gathered from clinical observations and necropsy results.

Example 8

Orf3526 Protection in a Murine Model of Intestinal Tract Colonization by Intragastric Infection with ETEC Strain GL53-K88

Mice received streptomycin (5 g/liter) in their drinking water (enriched with 6,7% fructose) 48 to 24 h prior to infection to eradicate normal resident bacteria flora. Following this, mice were infected by oral lavage with 109 CFU of a suspension of GL53 strain in a final volume of 400 ul. To reduce the effect of stomach acidity on the bacterial organism, bicarbonate was administered intragastrically 15 minutes prior to bacterial inoculation. 24 hours following infection, mice were euthanized and segments of ileum (2 cm) were harvested and homogenized. Serial dilutions of GL53, resistant to Kanamycin, are plated onto LB agar plates enriched with antibiotic. To confirm that the recovered bacteria were the inoculum strain, bacterial colonies are tested by PCR using primers encoding for LT holotoxin. To test the protective effect of antigen orf3526, mice were immunized intranasally on days 1, 7, 21, and 35 with antigen (20 ug) used alone or in combination with LTR72 as mucosal adjuvant (ratio 1:10). On day 49, mice were infected by oral lavage with 109 CFU of GL53 strain.

Figure 5:
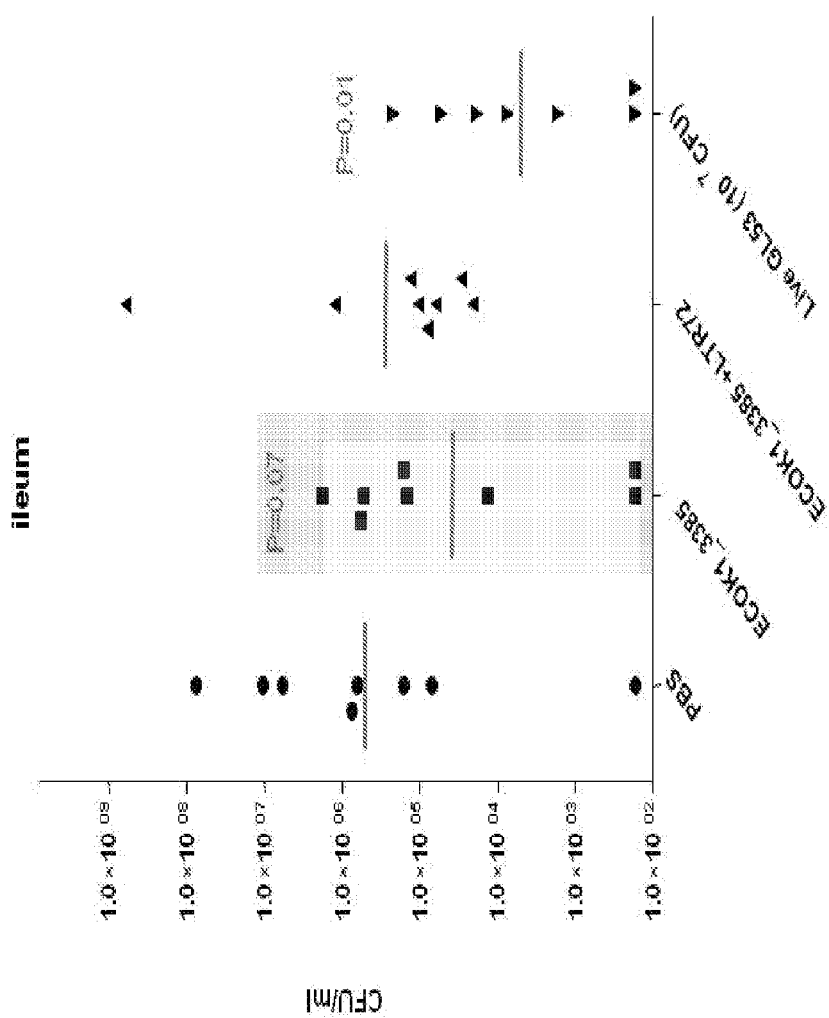
FIG. 5: Intranasal immunization with antigen orf3526 (ECOK1_3385) reduced colonization in ileum tract following challenge with ETEC strain GL53.

As shown in FIG. 5, intranasal immunization with antigen orf3526 reduced colonization in ileum tract following challenge with ETEC strain GL53. Thus, orf3526 is able to protect against challenge with the UPEC strain 536 in an UTI murine model.

Example 9

Antigen orf3526 was prepared and administered as previously described in combination with FCA, IC31, alum, MF59 or alone or in combination. Antigen orf3526 remained protective when administered with a variety of adjuvants:

| Candidates | animal model | | |
|---|---|---|---|
| | % survival immun. | % survival ctrl. | protection |
| pK1-3526 + FCA | 8/8 | 2/8 | 100 |
| pK1-3526 + IC31 | 7/8 | 1/8 | 86 |
| pK1-3526 + alum | 7/8 | 2/8 | 83 |
| pK1-3526 + MF59 | 6/8 | 0/8 | 75 |
| pK1-3526 + alum/IC31 | 8/8 | 2/8 | 100 |
| pK1-3526 + MF59/IC31 | 7/8 | 2/8 | 83 |
| pK1-3526ΔG + FCA | 10/10 | 1/10 | 100 |
| pK1-3526ΔGΔP + FCA | 9/10 | 1/10 | 89 |

Example 10

The protective effect of antigens 405B and upec1232 were determined using a UTI model of infection in mice:

The bacteria used to infect the mice were grown in filter-sterilized human urine and were passaged three times. The bacteria were incubated at 37° C., shaken at 200 rounds/min overnight, and centrifuged at 6,500×g for 10 min. The pellet was then suspended in phosphate-buffered saline (PBS) to a concentration of approximately 1010 CFU/ml.

Figure 6:
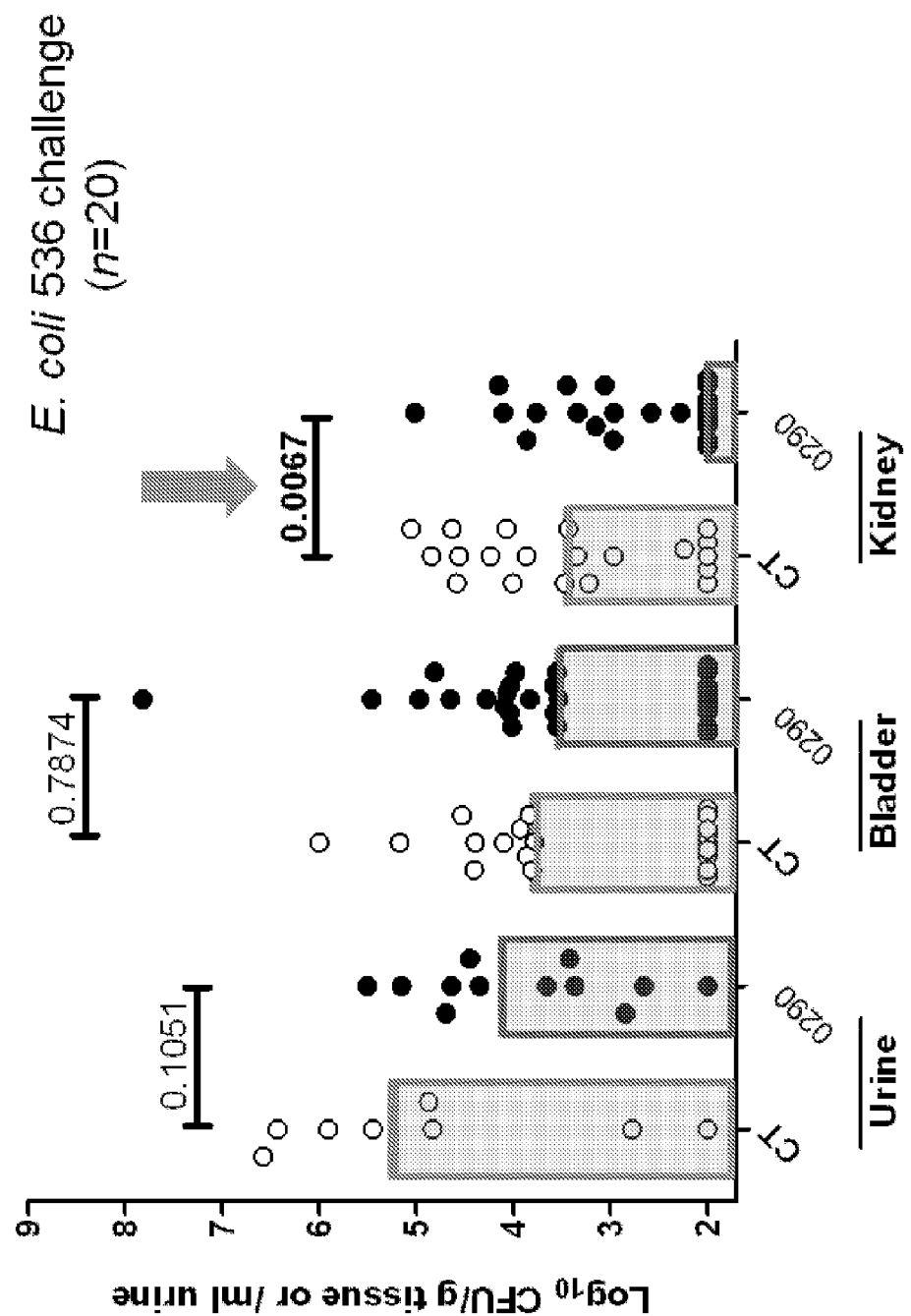
FIG. 6: Antigen 405B (ECOK1_0290) prevents kidney colonisation in a UTI model of infection.
Figure 7:
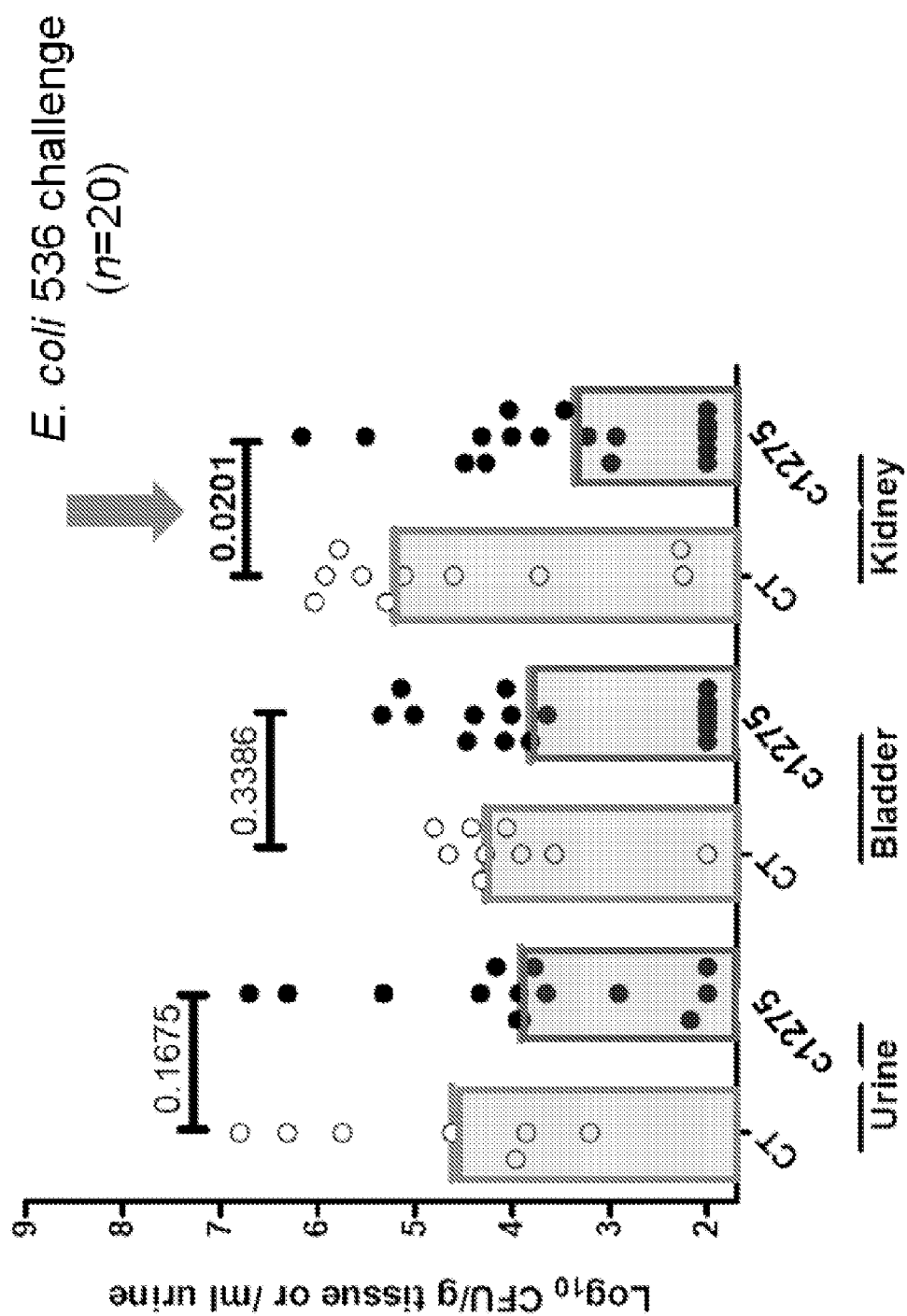
FIG. 7: Antigen upec1232 (c1275) prevents kidney colonisation in a UTI model of infection.

Mice were anesthetized by intraperitoneal administration of 0.08 ml of a mixture of Hypnorm (fentanyl citrate, 0.315 mg/ml; fluanisone, 10 mg/ml) and Stesolid (diazepam, 5 mg/ml) at a ratio of 5:1.5. Anesthetized mice were inoculated transurethrally with the bacterial suspension (E. coli 536) by use of plastic catheters. 0.05 ml of bacterial suspension was injected in the bladder over 5 s in order to avoid vesicoureteral reflux (12, 18). The catheter was removed immediately after inoculation. Urine from each mouse was collected in Eppendorf tubes by gentle compression of the abdomen, and the mice were killed by cervical dislocation. The organs were removed aseptically, the bladders were cut off near the urethra, and the kidneys were removed by blunt dissection to avoid bleeding. The organs were placed in cryotubes (Nunc 363452) containing a 750-µl suspension of collagenase (500 U/ml; Sigma C9891) and were stored at −80° C. Prior to homogenization, the infected organs were incubated for 1.5 h at room temperature and were then homogenized manually with inoculating loops and a whirl mixer. Bacteria from the inoculum, bacteria that were recovered from the urine samples and bacteria from either the bladder or one of the kidneys were measured. The results, illustrated in FIGS. 6 and 7 respectively, demonstrate that antigens 405B and upec1232 prevent kidney colonisation in a UTI model of infection.

Example 11

Mutants/Variants of Orf3526

Bacteria with one of each of three constructs expressing his-tagged variants of orf3526 were cultured in 30 ml of medium and induced to express the orf3526 variant at 25° C. (orf3526 without the leader peptide (3526), orf3526 with the N-terminus removed through the gly-ser linker or gly-ser region (ΔG3526), and orf3526 with the N-terminus removed through the proline rich region (ΔG3526)). The bacteria were harvested and lysed by sonication. The soluble fractions were isolated and loaded on an IMAC column. The column was washed three times with 20 mM imidazole buffer. The orf3526 variants were then eluted with three washes of 500 mM imidazole buffer. Removal of the N-terminus of orf3526 through the gly-ser linker or gly-ser region significantly increased solubility and yield of purified protein. The yield obtained was estimated by Bradford assay to be as follows: 0.18 mg of 3526 and 2.34 mg ΔG3526.

Example 12

Mutants/Variants of Orf3526

Figure 8:
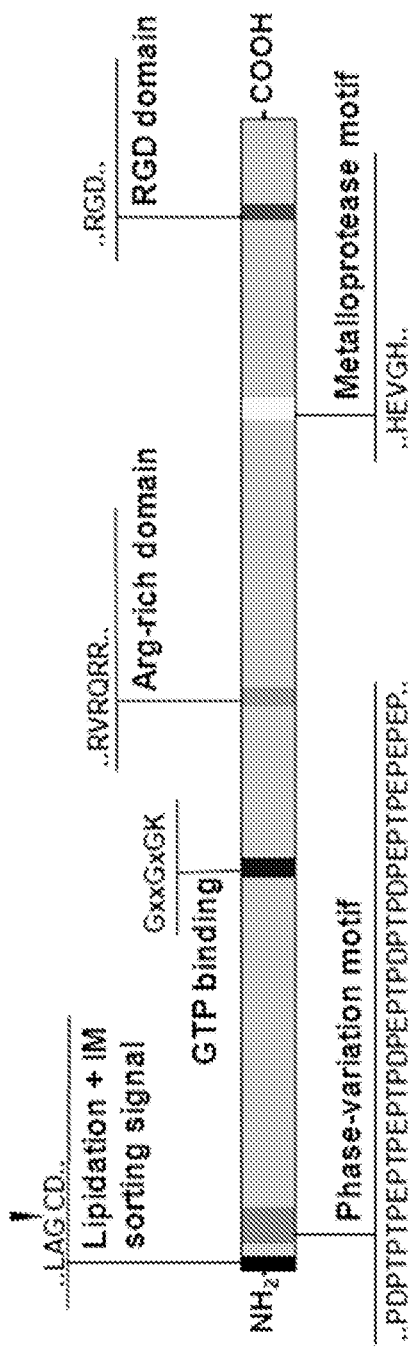
FIG. 8: Analysis of the orf3526 sequence revealed several conserved motifs.
Figure 9A:
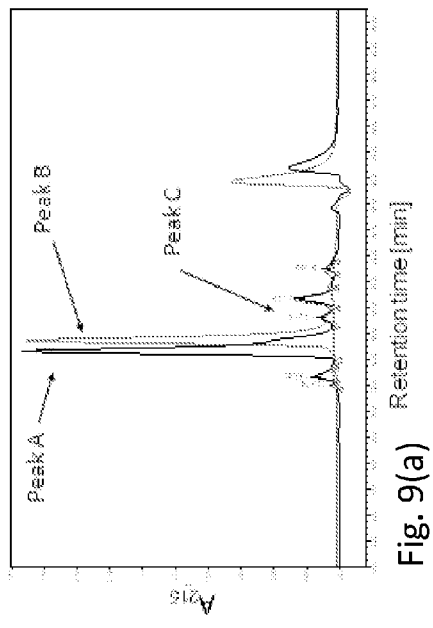
FIG. 9(a): Isoforms of DG3526TL were separated by SE-HPLC on a Tosoh G3000SWx1 column. The fraction that binds to butyl Sepharose appears less compact in SEC and forms peak A, while the form that binds to butyl Sepharose forms peak B. Peak C corresponds to an N-terminally truncated form.
Figure 9B:
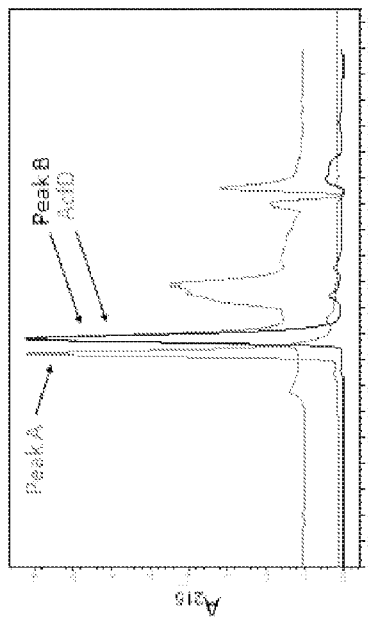
FIG. 9(b): To evaluate possible functional differences between DG3526TL and native 3526, the latter was purified from culture supernatant of ExPEC IHE3034 Running 3526 along with the isoforms of DG3526TL reveals that the native form coelutes with peak B, suggesting that native 3526 is i) compact and ii) a monomer.
Figure 10:
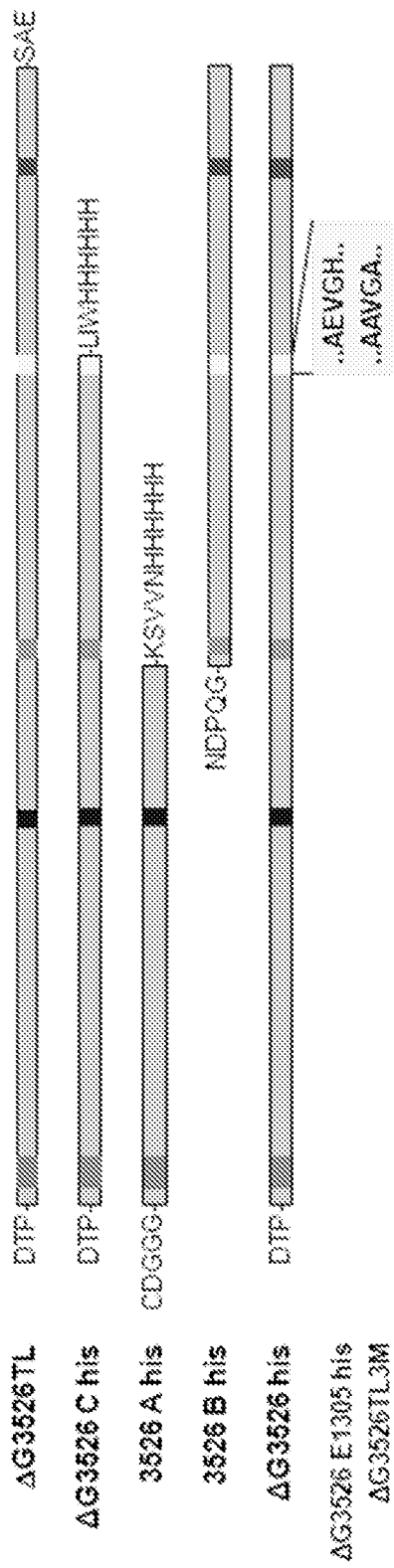
FIG. 10: Cartoon illustrating the seven mutants/variants of orf3526 utilised.
Figure 12:
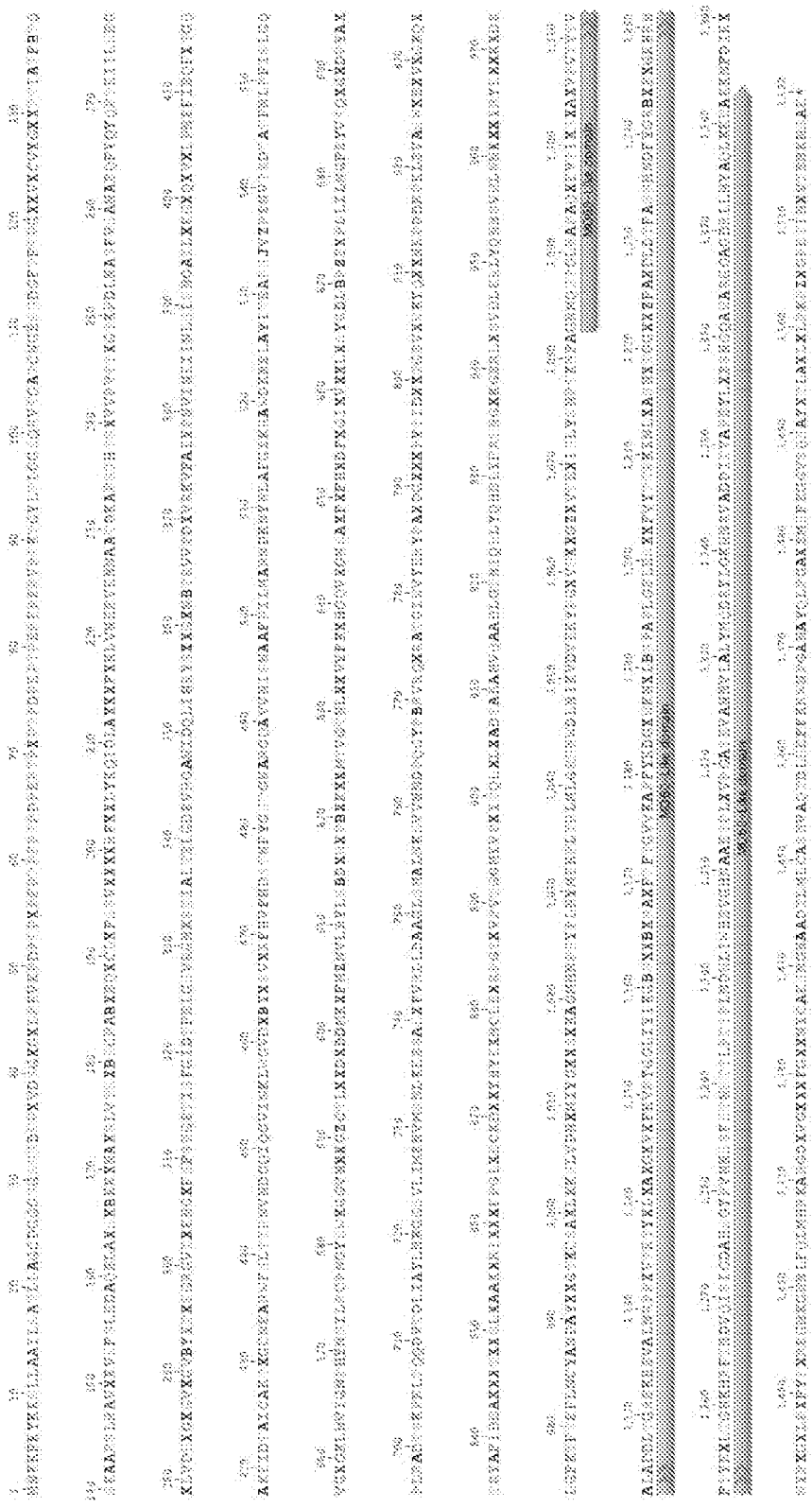
FIG. 12: orf3526 75% consensus sequence. Each specified residue is found at that position in at least 75% of the orf3526 sequences used to generate the consensus sequence. X represents any amino acid. The M060-Like domain is highlighted.
Figure 13:
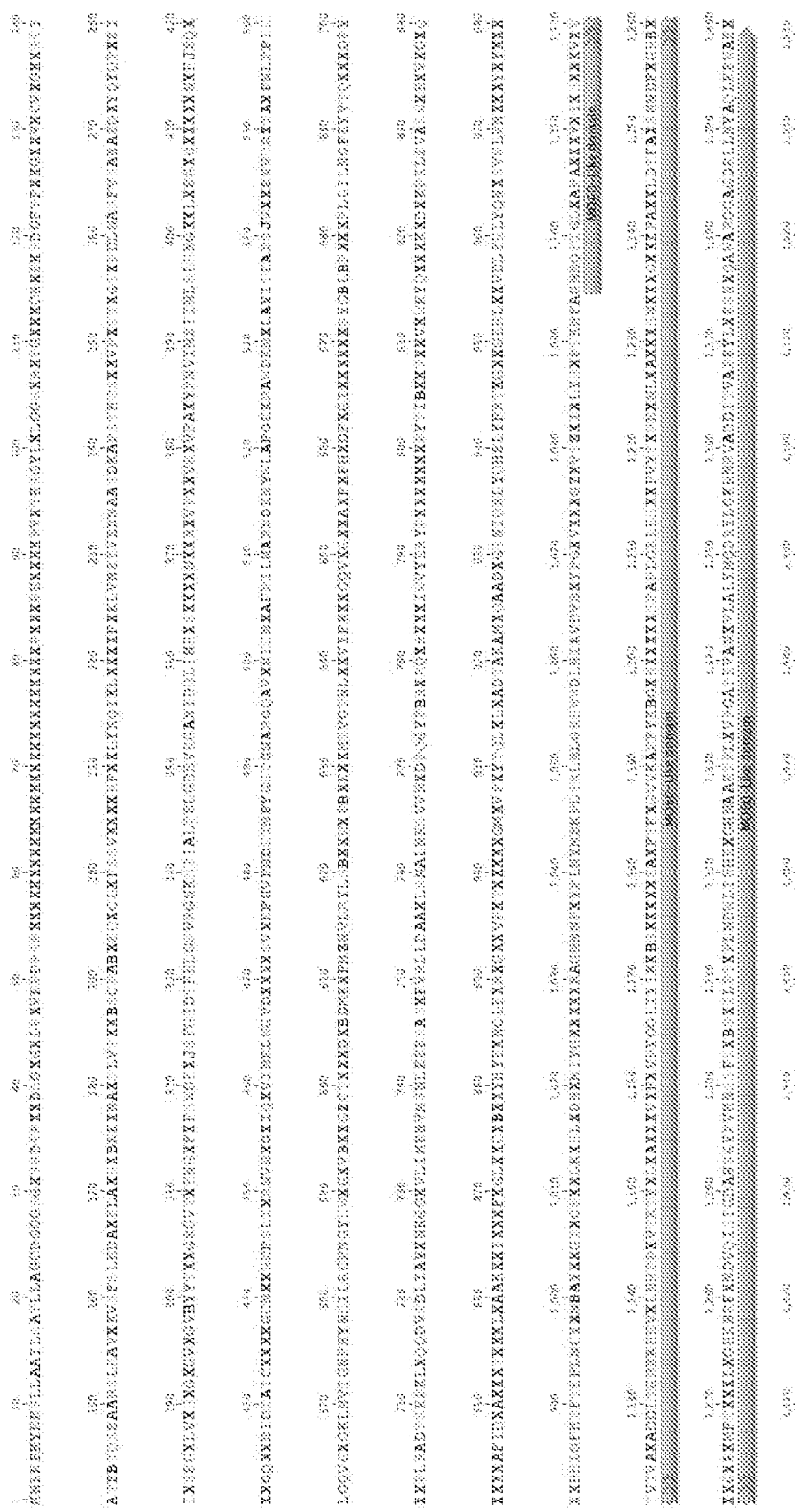
FIG. 13: orf3526 100% consensus sequence. Each specified residue is found at that position in all of the orf3526 sequences used to generate the consensus sequence. X represents any amino acid. The M060-Like domain is highlighted.

Although the function of orf3526 is not known, analysis of the orf3526 sequence revealed several conserved motifs, most notably a zinc binding motif, possibly part of a metallo-protease function, and an imperfect GTP binding motif (FIG. 8). Native orf3526 is a potential lipoprotein, also secreted into the culture supernatant. Sequence alignments studies show that the protein has homology to AcfD (accessory colonization factor) from *Vibrio cholera*. Native orf3526 is constitutively expressed and secreted by a Type 2 secretion system (T2SS). Seven mutants/variants of orf3526 were prepared as illustrated in FIG. 10.

Zinc content of the various orf3526 derivatives was determined by atomic absorption spectroscopy. Results, illustrated in FIG. 11, suggest the presence of a single zinc ion per protein molecule. The unexpected low zinc content of 3526 B his, actually containing the zinc binding motif, could be explained by misfolding of this truncated derivative, while the single amino acid exchange in the E1305 mutant apparently is not sufficient to completely abolish zinc binding (red boxes).

A purified triple mutant orf3526 (DG3526TL) protein was prepared wherein the amino acids at positions H1304, E1305 and H1308 according to SEQ ID 8 were substituted by another amino acid, specifically H1304A, E1305A and H1308A. Surprisingly, zinc affinity is almost completely lost in the DG3526TL triple mutant which comprised mutations in the zinc binding motif at amino acids 1304, 1305 and 1308 of SEQ ID 8 from the amino acid sequence HEVGH to AAVGA.

To allow functional and structural characterization, the soluble tagless recombinant protein DG3526TL (164 KDa) was purified by CaptoQ and butyl Sepharose chromatography. SE-HPLC/MALLS analysis revealed that DG3526TL exists in two isoforms (peaks A and B in FIG. 9*a*) and one truncated form (peak C in FIG. 9*a*). The isoforms can be separated on butyl Sepharose. However, without stabilization by glycerol, conversion of one form into the other was observed over time (FIGS. 9(*a*) and 9(*b*)). Thus, the triple mutant isoform is further advantageous in terms of purification.

The amino acid sequence of the triple mutant TL3M is:

```
>orf03526 Triple Mutant
                                          (SEQ ID 31)
MNKKFKYKKSLLAAILSATLLAGCDGGGSGSSSDTPSVDSGSGTLPEV

KPDPTPTPEPTPEPTPDPEPTPDPTPDPEPTPEPEPEPVPTKTGYLTL

GGSQRVTGATCNGESSDGFTFTPGNTVSCVVGSTTIATFNTQSEAARS

LRAVDKVSFSLEDAQELANSENKKTNAISLVTSSDSCPADAEQLCLTF

SSVVDRARFEKLYKQIDLATDNFSKLVNEEVENNAATDKAPSTHTSTV

VPVTTEGTKPDLNASFVSANAEQFYQYQPTEIILSEGQLVDSLGNGVA

GVDYYTNSGRGVTDENGKFSFSWGETISFGIDTFELGSVRGNKSTIAL

TELGDEVRGANIDQLIHRYSTTGQNNTRVVPDDVRKVFAEYPNVINEI

INLSLSNGATLDEGDQNVVLPNEFIEQFKTGQAKEIDTAICAKTDGCN

EARWFSLTTRNVNDGQIQGVINKLWGVDTNYQSVSKFHVFHDSTNFYG

STGNARGQAVVNISNSAFPILMARNDKNYWLAFGEKRAWDKNELAYIT

EAPSIVQPENVTRDTATFNLPFISLGQVGEGKLMVIGNPHYNSILRCP

NGYSWGGGVNSKGECTLSGDSDDMKHFMQNVLRYLSNDIWQPNTKSIM

TVGTNLENVYFKKAGQVLGNSAPFAFHEDFTGITVKQLTSYGDLNPEE

IPLLILNGFEYVTQWSGDPYAVPLRADTSKPKLTQQDVTDLIAYLNKG

GSVLIMENVMSNLKEESASSFVRLLDAAGLSMALNKSVVNNDPQGYPD

RVRQRRATGIWVYERYPAADGAQPPYTIDPNTGEVTWKYQQDNKPDDK
```

-continued

```
PKLEVASWQEEVEGKQVTRYAFIDEAEYTTEESLEAAKAKIFEKFPGL

QECKDSTYHYEINCLERRPGTDVPVTGGMYVPRYTQLNLDADTAKAMV

QAADLGTNIQRLYQHELYFRTKGSKGERLNSVDLERLYQNMSVWLWND

TKYRYEEGKEDELGFKTFTEFLNCYANDAYAGGTKCSADLKKSLVDNN

MIYGDGSSKAGMMNPSYPLNYMEKPLTRLMLGRSWWDLNIKVDVEKYP

GSVSAKGESVTENISLYSNPTKWFAGNMQSTGLWAPAQQDVTIKSSAS

VPVTVTVALADDLTGREKHEVALNRPPRVTKTYTLENGEVTFKVPYGG

ALIYIKGDSKDDVSANFTFTGVVKAPFYKDGEWKNDLDSPAPLGELES

ASFVYTTPKKNLEASNFTGGVAEFAKDLDTFASSMNDFYGRNDEDGKH

RMFTYKNLTGHKHRFTNDVQISIGDAHSGYPVMNSSFSTNSTTLPTTP

LNDWLIWAAVGANAAETPLNVPGATEVANNVLALYMQDRYLGKMNRVA

DDITVAPEYLDESNGQAWARGGAGDRLLMYAQLKEWAEENFDIKQWYP

DGELPKFYSDRKGMKGWNLFQLMHRKARGDDVGNSTFGGKNYCAESNG

NAADTLMLCASWVAQADLSEFFKKWNPGASAYQLPGATEMSFQGGVSS

SAYSTLASLKLPKPEKGPETINKVTEHKMSAE
```

Example 13

Antigen Combinations

His-tagged antigens were combined and administered with alum. The protection rate was calculated:

| Antigen(s) | Protection rate |
|---|---|
| Orf3526 (2 μg) | 61% |
| Orf3526 (2 μg) + 405B (10 μg) + upec-1232 (10 μg) | 87.5% |

Example 14

Antigen Combinations

Antigens were combined and administered with alum. Survival and protection rate were calculated following challenge with either IHE3034 (NMEC) or 9855/93 (SEPEC) ExPEC strains.

| Antigen(s) | IHE3034 challenge | | 9855/93 challenge | |
|---|---|---|---|---|
| | Survival with vaccination | Protection rate | Survival with vaccination | Protection rate |
| Orf3526 (2 µg) | 57/88 (64%) | 61% | n/a | n/a |
| Orf3526 (2 µg) + 405B (10 µg) + upec-1232 (10 µg) | 7/8 (87.5%) | 87.5% | n/a | n/a |
| Orf3526 (10 µg) | 11/16 (68%) | 63% | 14/23 (61%) | 48% |
| Orf3526 (10 µg) + 405B (10 µg) + upec-1232 (10 µg) | 7/8 (87.5%) | 87.5% | n/a | n/a |
| Orf3526C (0.2 µg) | 7/16 (44%) | 44% | n/a | n/a |
| Orf3526C (0.2 µg) + 405B (20 µg) | 5/8 (62.5%) | 62.5% | n/a | n/a |

Example 15

Protective Efficacy of 3625 in the Intestinal Colonization Model

Figure 14:
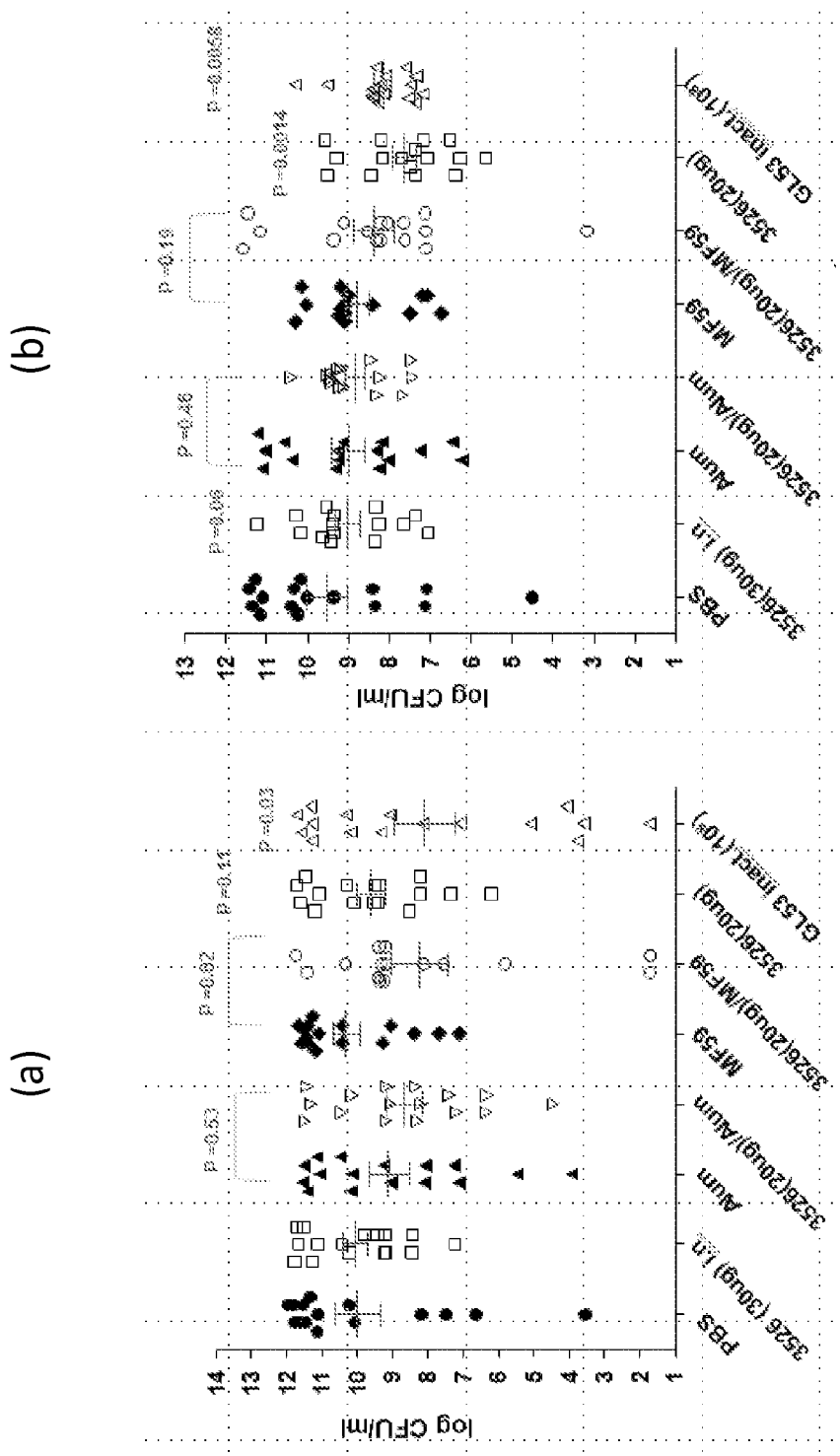
FIG. 14: Bacterial titres were significantly reduced after immunisation with 3526+alum, or after immunisation with 3526+MF59, compared to adjuvant alone. The results are confirmed in an experiment were mice were immunised on days 0 and 21 only (FIG. 14(b)).

Mice were immunized via the intramuscular route with the 3526 antigen with alum or MF59, on days 0, 21 and 35. Mice were challenged with GL53 (ETEC) on day 48 and bacterial titres were evaluated in the caecum. FIG. 14(a) shows that bacterial titres were significantly reduced after immunisation with 3526+alum, or after immunisation with 3526+MF59, compared to adjuvant alone. The results are confirmed in an experiment were mice were immunised on days 0 and 21 only (FIG. 14(b)).

Example 16

Figure 15:
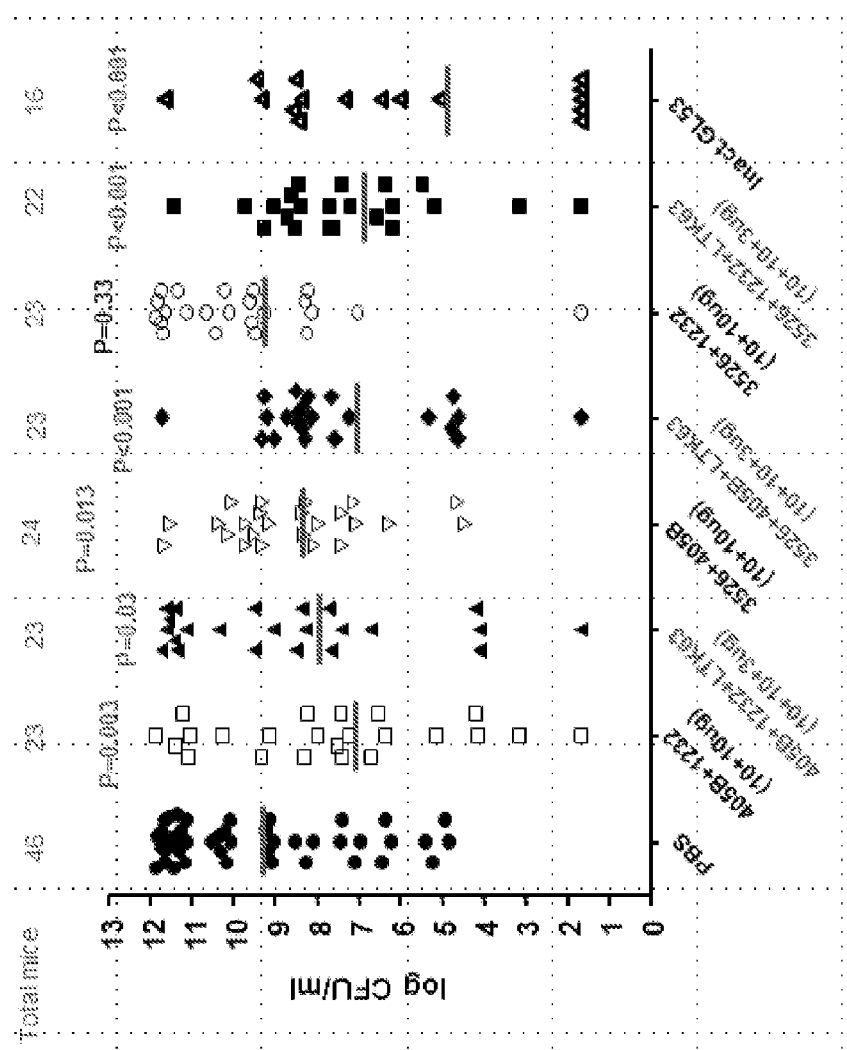
FIG. 15: 405B+3526+LTK63 and 3526+1232+LTK63 significantly reduces intestinal colonization by GL53 in the caecum, compared to LTK63 alone.

Protective Efficacy of Antigen Combinations in the Intestinal Colonization Model Mice were immunized with different combinations of antigens 405B, 1232 and 3526, with or without LTK63 (FIG. 15), on days 1, 21 and 35. Mice were challenged with GL53 (ETEC) and bacterial titres were evaluated in the caecum. The results show that 405B+3526+LTK63 and 3526+1232+LTK63 significantly reduces intestinal colonization by GL53 in the caecum, compared to LTK63 alone.

Example 17

Protective Efficacy of Isoforms A, B, and C of 3526

Mice were immunized with isoform A alone, isoform B alone, or a combination of isoforms A, B and C. Mice were challenged with IHE3034 and bacterial titres were evaluated. The results show that isoform B alone or combined with isoforms A and C confers greatest protective efficacy.

| 3526-His isoforms | Immunization dose | Survival | PE |
|---|---|---|---|
| [peak A] pur_131 | 20 ug | 44 (7/16) | 36 |
| [peak B] pur_131 | 20 ug | 69 (11/16) | 64.5 |
| [peak A, B, C] pur_131 | 20 ug | 62.5 (6/8) | 75 |
| [peak A, B, C] pur_131 | 5 ug | 87.5 (7/8) | 86 |
| [peak A] pur_131 | 5 ug | 37.5 (3/8) | 28.5 |
| [peak B] pur_131 | 5 ug | 87.5 (7/8) | 86 |

ADDITIONAL REFERENCES

[1] Bodanszky (1993) *Principles of Peptide Synthesis* (ISBN: 0387564314).
[2] Fields et al. (1997) Meth Enzymol 289: Solid-Phase Peptide Synthesis. ISBN: 0121821900.
[3] Chan & White (2000) *Fmoc Solid Phase Peptide Synthesis. ISBN:* 0199637245.
[4] Kullmann (1987) *Enzymatic Peptide Synthesis. ISBN:* 0849368413.
[5] Ibba (1996) *Biotechnol Genet Eng Rev* 13:197-216.
[6] *Vaccine Design: The Subunit and Adjuvant Approach* (eds. Powell & Newman) Plenum Press 1995 (ISBN 0-306-44867-X).
[7] Vaccine Adjuvants: Preparation Methods and Research Protocols (Volume 42 of Methods in Molecular Medicine series). ISBN: 1-59259-083-7. Ed. O'Hagan.
[8] *Vaccine Design* (1995) eds. Powell & Newman. ISBN: 030644867X. Plenum.
[9] WO90/14837.
[10] WO90/14837.
[11] Podda & Del Giudice (2003) *Expert Rev Vaccines* 2:197-203.
[12] Podda (2001) *Vaccine* 19: 2673-2680.
[13] *Vaccine Design: The Subunit and Adjuvant Approach* (eds. Powell & Newman) Plenum Press 1995 (ISBN 0-306-44867-X).
[14] Vaccine Adjuvants: Preparation Methods and Research Protocols (Volume 42 of Methods in Molecular Medicine series). ISBN: 1-59259-083-7. Ed. O'Hagan.
[15] U.S. Pat. No. 5,057,540.
[16] Niikura et al. (2002) *Virology* 293:273-280.
[17] Lenz et al. (2001) *J Immunol* 166:5346-5355.
[18] Pinto et al. (2003) *J Infect Dis* 188:327-338.
[19] Gerber et al. (2001) *J Virol* 75:4752-4760.
[20] WO03/024480.
[21] WO03/024481.
[22] Gluck et al. (2002) *Vaccine* 20:B10-B16.
[23] Meraldi et al. (2003) *Vaccine* 21:2485-2491.
[24] Pajak et al. (2003) *Vaccine* 21:836-842.
[25] Krieg (2003) *Nature Medicine* 9:831-835.

[26] McCluskie et al. (2002) *FEMS Immunology and Medical Microbiology* 32:179-185.
[27] WO98/40100.
[28] U.S. Pat. No. 6,207,646.
[29] U.S. Pat. No. 6,239,116.
[30] U.S. Pat. No. 6,429,199.
[31] Schellack et al. (2006) *Vaccine* 24:5461-72.
[32] Johnson et al. (1999) *Bioorg Med Chem Lett* 9:2273-2278.
[33] Evans et al. (2003) *Expert Rev Vaccines* 2:219-229.
[34] Beignon et al. (2002) *Infect Immun* 70:3012-3019.
[35] Pizza et al. (2001) *Vaccine* 19:2534-2541.
[36] Pizza et al. (2000) *Int J Med Microbiol* 290:455-461.
[37] Scharton-Kersten et al. (2000) *Infect Immun* 68:5306-5313.
[38] Ryan et al. (1999) *Infect Immun* 67:6270-6280.
[39] Partidos et al. (1999) *Immunol Lett* 67:209-216.
[40] Peppoloni et al. (2003) *Expert Rev Vaccines* 2:285-293.
[41] Pine et al. (2002) *J Control Release* 85:263-270.
[42] WO99/40936.
[43] WO99/44636.
[44] Singh et al] (2001) *J Cont Release* 70:267-276.
[45] WO99/27960.
[46] U.S. Pat. No. 6,090,406.
[47] U.S. Pat. No. 5,916,588.
[48] EP-A-0626169.
[49] WO99/52549.
[50] Andrianov et al. (1998) *Biomaterials* 19:109-115.
[51] Payne et al. (1998) *Adv Drug Delivery Review* 31:185-196.
[52] Stanley (2002) *Clin Exp Dermatol* 27:571-577.
[53] Jones (2003) *Curr Opin Investig Drugs* 4:214-218.
[54] WO99/11241.
[55] WO94/00153.
[56] WO98/57659.
[57] European patent applications 0835318, 0735898 and 0761231.
[58] Durant et al. (2007) *Infect Immun* 75:1916-25.
[59] WO02/081653.
[60] Gennaro (2000) *Remington: The Science and Practice of Pharmacy.* 20th edition, ISBN: 0683306472.
[61] *PCR (Introduction to Biotechniques Series)*, 2nd ed. (Newton & Graham eds., 1997, Springer Verlag).

SEQUENCE LISTING

```
<160> NUMBER OF SEQ ID NOS: 57

<210> SEQ ID NO 1
<211> LENGTH: 1242
<212> TYPE: DNA
<213> ORGANISM: Escherichia coli

<400> SEQUENCE: 1
gttgctgatg gtcagcaagc ctacacgctg acactgacag cggtggactc cgagggtaat      60
ccggtgacgg gagaagccag ccgcctgcga cttgttccgc aagacactaa tggtgtaacc     120
gttggtgcca tttcggaaat aaaaccaggg gtttacagcg ccacggtttc ttcgacccgt     180
gccggaaacg ttgttgtgcg tgccttcagc gagcagtatc agctgggcac attacaacaa     240
acgctgaagt ttgttgccgg gccgcttgat gcagcacatt cgtccatcac actgaatcct     300
gataaaccgg tggttggcgg tacagttacg gcaatctgga cggcaaaaga tgctaatgac     360
aaccctgtaa ctggcctcaa tccggatgca ccgtcattat cgggcgcagc tgctgctggt     420
tctacggcat caggctggac ggataatggc gacgggacct ggactgcgca gatttctctc     480
ggcactacgg cgggtgaatt agacgttatg ccgaagctca atgggcagga cgcggcagca     540
aatgcggcaa aagtaaccgt ggtggctgat gcattatctt caaaccagtc gaaagtctct     600
gtcgcagaag atcacgtaaa agccggtgaa agcacaaccg taacgctggt ggcgaaagat     660
gcgcatggca acgctatcag tggtctttcg ttgtcggcaa gtttgacggg gaccgcctct     720
gaaggggcga ccgtttccag ttggaccgaa aaaggtgacg gttcctatgt tgctacgtta     780
actacaggcg gaaagacggg cgagcttcgt gtcatgccgc tcttcaacgg ccagcctgca     840
gccaccgaag ccgcgcagct gactgttatt gccggagaga tgtcatcagc gaactctacg     900
cttgttgcgg acaataaaac tccaacggtt aaaacgacga cggaactcac cttcaccatg     960
aaggatgcgt acgggaatcc ggtcaccggg ctgaagccag atgcaccagt gtttagtggt    1020
gccgccagca cggggagtga gcgtccttca gcaggaaact ggacagagaa aggtaatggg    1080
gtctacgtgt cgaccttaac gctgggatct gccgcgggtc agttgtctgt gatgccgcga    1140
gtgaacggcc aaaatgccgt tgctcagcca ctggtgctga atgttgcagg tgacgcatct    1200
aaggctgaga ttcgtgatat gacagtgaag gttaataacc aa                       1242
```

<210> SEQ ID NO 2
<211> LENGTH: 414
<212> TYPE: PRT
<213> ORGANISM: Escherichia coli

<400> SEQUENCE: 2

```
Val Ala Asp Gly Gln Gln Ala Tyr Thr Leu Thr Leu Thr Ala Val Asp
1               5                   10                  15

Ser Glu Gly Asn Pro Val Thr Gly Glu Ala Ser Arg Leu Arg Leu Val
                20                  25                  30

Pro Gln Asp Thr Asn Gly Val Thr Val Gly Ala Ile Ser Glu Ile Lys
            35                  40                  45

Pro Gly Val Tyr Ser Ala Thr Val Ser Ser Thr Arg Ala Gly Asn Val
        50                  55                  60

Val Val Arg Ala Phe Ser Glu Gln Tyr Gln Leu Gly Thr Leu Gln Gln
65                  70                  75                  80

Thr Leu Lys Phe Val Ala Gly Pro Leu Asp Ala Ala His Ser Ser Ile
                85                  90                  95

Thr Leu Asn Pro Asp Lys Pro Val Val Gly Thr Val Thr Ala Ile
                100                 105                 110

Trp Thr Ala Lys Asp Ala Asn Asp Asn Pro Val Thr Gly Leu Asn Pro
                115                 120                 125

Asp Ala Pro Ser Leu Ser Gly Ala Ala Ala Gly Ser Thr Ala Ser
            130                 135                 140

Gly Trp Thr Asp Asn Gly Asp Gly Thr Trp Thr Ala Gln Ile Ser Leu
145                 150                 155                 160

Gly Thr Thr Ala Gly Glu Leu Asp Val Met Pro Lys Leu Asn Gly Gln
                165                 170                 175

Asp Ala Ala Ala Asn Ala Ala Lys Val Thr Val Val Ala Asp Ala Leu
                180                 185                 190

Ser Ser Asn Gln Ser Lys Val Ser Val Ala Glu Asp His Val Lys Ala
            195                 200                 205

Gly Glu Ser Thr Thr Val Thr Leu Val Ala Lys Asp Ala His Gly Asn
210                 215                 220

Ala Ile Ser Gly Leu Ser Leu Ser Ala Ser Leu Thr Gly Thr Ala Ser
225                 230                 235                 240

Glu Gly Ala Thr Val Ser Ser Trp Thr Glu Lys Gly Asp Gly Ser Tyr
                245                 250                 255

Val Ala Thr Leu Thr Thr Gly Gly Lys Thr Gly Glu Leu Arg Val Met
                260                 265                 270

Pro Leu Phe Asn Gly Gln Pro Ala Ala Thr Glu Ala Ala Gln Leu Thr
            275                 280                 285

Val Ile Ala Gly Glu Met Ser Ser Ala Asn Ser Thr Leu Val Ala Asp
            290                 295                 300

Asn Lys Thr Pro Thr Val Lys Thr Thr Thr Glu Leu Thr Phe Thr Met
305                 310                 315                 320

Lys Asp Ala Tyr Gly Asn Pro Val Thr Gly Leu Lys Pro Asp Ala Pro
                325                 330                 335

Val Phe Ser Gly Ala Ala Ser Thr Gly Ser Glu Arg Pro Ser Ala Gly
            340                 345                 350

Asn Trp Thr Glu Lys Gly Asn Gly Val Tyr Val Ser Thr Leu Thr Leu
            355                 360                 365
```

Gly Ser Ala Ala Gly Gln Leu Ser Val Met Pro Arg Val Asn Gly Gln
            370                 375                 380

Asn Ala Val Ala Gln Pro Leu Val Leu Asn Val Ala Gly Asp Ala Ser
385                 390                 395                 400

Lys Ala Glu Ile Arg Asp Met Thr Val Lys Val Asn Asn Gln
            405                 410

<210> SEQ ID NO 3
<211> LENGTH: 453
<212> TYPE: DNA
<213> ORGANISM: Escherichia coli

<400> SEQUENCE: 3
atgattcacc tgttcaaaac ctgcatgatt accgccttca ttctggggtt aacgtggtct      60
gccccactcc gggcacagga tcaacgttac atcagtatac gcaatacaga tacgatatgg    120
ctcccgggaa atatttgtgc ttaccagttc cggctggata atggcggaaa cgatgaagga    180
tttggccccc tcaccatcac tctgcaactc aaagacaaat atggtcagac gctggtgacc    240
agaaaaatgg aaacggaagc ctttggtgac agtaatgcca cgcgaaccac agacgcattt    300
ctggaaacgg agtgcgtgga aaatgtcgcc acaaccgaaa tcattaaagc aactgaagaa    360
agtaacggcc atcgtgtcag tctgccgtta tcggttttcg atccccagga ctaccatcca    420
ctgctgatta ccgtttccgg aaaaaacgtt aac                                 453

<210> SEQ ID NO 4
<211> LENGTH: 151
<212> TYPE: PRT
<213> ORGANISM: Escherichia coli

<400> SEQUENCE: 4

Met Ile His Leu Phe Lys Thr Cys Met Ile Thr Ala Phe Ile Leu Gly
1               5                   10                  15

Leu Thr Trp Ser Ala Pro Leu Arg Ala Gln Asp Gln Arg Tyr Ile Ser
            20                  25                  30

Ile Arg Asn Thr Asp Thr Ile Trp Leu Pro Gly Asn Ile Cys Ala Tyr
        35                  40                  45

Gln Phe Arg Leu Asp Asn Gly Asn Asp Glu Gly Phe Gly Pro Leu
    50                  55                  60

Thr Ile Thr Leu Gln Leu Lys Asp Lys Tyr Gly Gln Thr Leu Val Thr
65                  70                  75                  80

Arg Lys Met Glu Thr Glu Ala Phe Gly Asp Ser Asn Ala Thr Arg Thr
                85                  90                  95

Thr Asp Ala Phe Leu Glu Thr Glu Cys Val Glu Asn Val Ala Thr Thr
            100                 105                 110

Glu Ile Ile Lys Ala Thr Glu Glu Ser Asn Gly His Arg Val Ser Leu
        115                 120                 125

Pro Leu Ser Val Phe Asp Pro Gln Asp Tyr His Pro Leu Leu Ile Thr
    130                 135                 140

Val Ser Gly Lys Asn Val Asn
145                 150

<210> SEQ ID NO 5
<211> LENGTH: 378
<212> TYPE: DNA
<213> ORGANISM: Escherichia coli

<400> SEQUENCE: 5

```
caggatcaac gttacatcag tatacgcaat acagatacga tatggctccc gggaaatatt      60
tgtgcttacc agttccggct ggataatggc ggaaacgatg aaggatttgg ccccctcacc     120
atcactctgc aactcaaaga caaatatggt cagacgctgg tgaccagaaa aatggaaacg     180
gaagcctttg gtgacagtaa tgccacgcga accacagacg catttctgga aacggagtgc     240
gtggaaaatg tcgccacaac cgaaatcatt aaagcaactg aagaaagtaa cggccatcgt     300
gtcagtctgc cgttatcggt tttcgatccc caggactacc atccactgct gattaccgtt     360
tccggaaaaa acgttaac                                                    378
```

<210> SEQ ID NO 6
<211> LENGTH: 126
<212> TYPE: PRT
<213> ORGANISM: Escherichia coli

<400> SEQUENCE: 6

```
Gln Asp Gln Arg Tyr Ile Ser Ile Arg Asn Thr Asp Thr Ile Trp Leu
1               5                   10                  15
Pro Gly Asn Ile Cys Ala Tyr Gln Phe Arg Leu Asp Asn Gly Gly Asn
            20                  25                  30
Asp Glu Gly Phe Gly Pro Leu Thr Ile Thr Leu Gln Leu Lys Asp Lys
        35                  40                  45
Tyr Gly Gln Thr Leu Val Thr Arg Lys Met Glu Thr Glu Ala Phe Gly
    50                  55                  60
Asp Ser Asn Ala Thr Arg Thr Thr Asp Ala Phe Leu Glu Thr Glu Cys
65                  70                  75                  80
Val Glu Asn Val Ala Thr Thr Glu Ile Ile Lys Ala Thr Glu Glu Ser
                85                  90                  95
Asn Gly His Arg Val Ser Leu Pro Leu Ser Val Phe Asp Pro Gln Asp
            100                 105                 110
Tyr His Pro Leu Leu Ile Thr Val Ser Gly Lys Asn Val Asn
        115                 120                 125
```

<210> SEQ ID NO 7
<211> LENGTH: 4560
<212> TYPE: DNA
<213> ORGANISM: Escherichia coli

<400> SEQUENCE: 7

```
atgaataaga aatttaaata taagaaatcg cttttagcgg ctattttaag cgcaaccctg      60
ttagccggtt gtgatggtgg tggttcagga tcgtcctccg atacgccgtc tgtagattct     120
ggatcaggga ctttgccgga agtgaaaccc gatccaacac caaccccgga gccgacacct     180
gagccgacgc cggacccaga acctacgccg gatccaacac ctgatcctga gccgacacca     240
gaaccggagc cagaacctgt tcctacgaaa acgggttatc tgaccctggg cggaagccag     300
cgggtaactg gtgctacctg taatggtgaa tccagcgatg gctttacctt tacgccaggc     360
aataccgtga gttgtgtggt gggcagtacg accattgcaa cattcaacac ccagtcagaa     420
gctgcgcgta gcctgcgtgc ggttgacaaa gtgtcgttta cctggaggat cgcgcaggag     480
ctggcgaatt ctgaaaataa gaaaaccaac gccatctctc tggtgacgtc cagcgacagt     540
tgccccgcag atgcagaaca gctttgtctt actttctcgt cagtggttga tcgcgcgcga     600
tttgaaaaac tgtataagca aattgatctg gcaacagaca atttcagcaa gctggtcaat     660
```

```
gaagaggtgg aaaacaatgc tgcgactgat aaagcgccgt ccacccatac ctcaacggta    720
gtgccagtca cgacagaggg aacaaaaccg gatctgaacg cgtccttcgt gtcggctaac    780
gcggaacagt tttatcagta tcaacccact gaaatcattc tttccgaagg ccaactggtg    840
gatagcctgg ggaacggtgt tgctggcgtt gactactaca ccaattcagg ccgtggcgta    900
actgacgaaa acgtaaaatt ttcctttagc tggggcgaaa ccatctcctt tggtatcgat    960
acctttgaac tgggctcagt acgtggcaat aagtcgacca ttgcgctgac tgaattgggt   1020
gatgaagttc gcggggcaaa tatcgatcag ctcattcatc gttattcgac gactggtcaa   1080
aataatactc gtgttgttcc ggacgatgta cgcaaggtct tgccgaata tcccaacgtg   1140
atcaacgaga taatcaatct ttcgttatcc aacggtgcga cgctggatga aggcgatcaa   1200
aacgttgtgc tgcctaacga atttatcgag cagtttaaga cgggtcaggc caaagagatc   1260
gataccgcga tttgtgcgaa aaccgacggt tgtaacgagg ctcgctggtt ctcgctgaca   1320
acgcgcaatg ttaatgacgg ccagattcag ggcgttatta acaagctgtg gggcgtggat   1380
acgaactatc agtctgtcag caagttccac gtcttccatg actctaccaa cttctatggc   1440
agcaccggta acgcgcgcgg tcaggcggtg gtaaatatct ccaactcggc attcccgatt   1500
ctgatggcgc gtaatgataa aaactactgg ctggcgtttg cgaaaaacg cgcctgggat   1560
aaaaatgagc tggcgtacat tacggaagcg ccttccattg tgcagccaga gaacgttacg   1620
cgcgatactg cgactttcaa cctgccgttt atttcgctgg ggcaagtcgg tgaaggcaaa   1680
ctgatggtta tcggtaaccc gcactacaac agcatcctgc gttgcccgaa cggttacagt   1740
tggggcggtg gtgttaatag taaaggtgag tgtacgctca gcggtgattc tgatgacatg   1800
aagcacttta tgcagaacgt actgcgctac ttgtcaaatg acatctggca gccaaatacc   1860
aagagcatca tgactgtcgg caccaacctg gagaacgttt atttcaaaaa agcgggccag   1920
gtattgggaa atagtgcacc atttgctttc catgaggatt tcactggtat cacggttaaa   1980
cagttgacca gctatggcga tctgaatccg gaagagattc cgttgctgat cctcaacggc   2040
tttgaatatg tgactcagtg gtctggcgat ccctatgctg tgcctctgcg tgcagatacc   2100
agcaaaccga gctgactca gcaggatgtg accgatctga tcgcttatct gaacaaaggt   2160
ggctcggtgc tgatcatgga aaacgtgatg agcaatctta aggaagagag cgcgtccagt   2220
tttgtgcgtc tgctggatgc cgcgggtctg tcaatggctc tgaacaaatc ggtggtgaac   2280
aacgatccgc aagggtatcc ggatcgcgtt cgtcagcgtc gcgcgactgg catttgggtt   2340
tatgaacgtt atcctgctgc agacggcgcg caaccgccgt acaccatcga cccaaataca   2400
ggggaagtga cctggaaata ccagcaagac aacaagcctg atgacaagcc gaaactggaa   2460
gttgcgagct ggcaggagga agttgagggc aaacaggtaa cgcgttatgc ctttattgat   2520
gaagcggaat acacaacaga agaatctctg gaagcggcaa aggcaaaaat ctttgagaag   2580
tttcctgggt tacaggagtg taaggactcg acttaccatt acgagattaa ctgtttggag   2640
cgccgcccag gcacggatgt tccggtaaca ggtggcatgt atgttccgcg ctatacgcaa   2700
ctgaatcttg acgccgacac cgcgaaagcg atggtgcagg cggcggattt aggcaccaac   2760
attcagcgcc tgtatcagca tgagctttat ttccgtacca aaggcagtaa aggtgagcgt   2820
ctgaacagtg ttgatctgga acgtctgtac cagaacatgt cggtctggct gtggaacgat   2880
acgaaatatc gttacgaaga gggcaaggaa gatgagctgg gctttaaaac gttcaccgag   2940
ttcctgaact gctacgccaa tgatgccatt gcaggcggca ccagtgctct cgcagatctg   3000
aaaaaatcgc tggtcgataa caacatgatc tacggtgacg gtagcagcaa agcgggcatg   3060
```

```
atgaacccaa gctatccgct caactatatg gaaaaaccgc tgacgcgtct gatgctgggc      3120
cgttcctggt gggatctgaa cattaaggtt gatgtggaga agtacccagg atccgtatcg      3180
gcaaagggtg agagcgttac ggaaaacatc agcctgtact cgaatccgac caaatggttt      3240
gcgggtaaca tgcagtcaac cggcctgtgg caccggccc agcaggacgt caccattaag       3300
tcttcggcgt cagtcccagt gactgttacc gtggcgctgg ctgacgacct gactggacgt      3360
gagaagcatg aagttgcgct gaaccgtccg ccaagagtga ctaaaacgta tactctggag      3420
gctaacggtg aagtgacctt caaggtgcct tatggtggtc tgatttatat caagggcgac      3480
agtaaggatg atgtttctgc taacttcacc tttaccggtg tagtaaaagc gccgttctat      3540
aaagacggcg aatggaaaaa cgatctggac tcaccggcgc cgctgggcga gctggagtct      3600
gcgtcgttcg tctataccac gccgaagaag aaccttgagg ccagcaattt cactggtggt      3660
gtagcagaat cgctaaaga tctggatacc tttgccagct cgatgaatga cttctacggt        3720
cgtaatgatg aagacggtaa gcaccggatg tttacctata aaacttgac ggggcacaag        3780 catcgtttca ccaacgatgt gcagatctcc atcggtgatg cgcactcggg ttatccggta      3840
atgaacagca gcttctcgac gaacagcacc acgctgccga cgacgccgct gaacgactgg      3900
ctgatttggc acgaagtcgg tcataacgct gcagaaacac cgctgaacgt accgggtgca      3960
actgaagtgg cgaacaacgt gctggcgctg tacatgcagg atcgctatct cggtaagatg      4020
aaccgtgtcg ctgacgacat taccgtcgcg ccggaatatc tggacgagag caacggtcag      4080
gcctgggcgc gcggcggtgc gggtgaccgt ctgctgatgt acgcacagtt gaaggagtgg      4140
gcagaggaaa actttgatat caaacagtgg tatccagatg gtgagctgcc taagttctac      4200
agcgatcgta aagggatgaa gggctggaac ctgttccagt tgatgcaccg taaagcgcgc      4260
ggcgatgatg ttggtaacag caccttggt ggcaagaatt actgtgctga atccaatggt       4320
aacgctgccg acacgctgat gctgtgtgca tcctgggtcg ctcaggcgga tctttcggaa      4380
ttctttaaga aatggaatcc gggtgcaagt gcttaccagt tgccgggagc aacggagatg      4440
agtttccagg gcggtgtgag ctcttcggct tacagcacgc tggcgtcact caagctgccg      4500
aaaccggaaa aagggccgga aaccattaac aaggttaccg agcataagat gtctgccgag      4560
```

<210> SEQ ID NO 8
<211> LENGTH: 1520
<212> TYPE: PRT
<213> ORGANISM: Escherichia coli

<400> SEQUENCE: 8

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
            20                  25                  30

Ser Asp Thr Pro Ser Val Asp Ser Gly Ser Gly Thr Leu Pro Glu Val
        35                  40                  45

Lys Pro Asp Pro Thr Pro Thr Pro Glu Pro Thr Pro Glu Pro Thr Pro
    50                  55                  60

Asp Pro Glu Pro Thr Pro Asp Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
            100                 105                 110

```
Asp Gly Phe Thr Phe Thr Pro Gly Asn Thr Val Ser Cys Val Val Gly
        115                 120                 125

Ser Thr Thr Ile Ala Thr Phe Asn Thr Gln Ser Glu Ala Ala Arg Ser
    130                 135                 140

Leu Arg Ala Val Asp Lys Val Ser Phe Ser Leu Glu Asp Ala Gln Glu
145                 150                 155                 160

Leu Ala Asn Ser Glu Asn Lys Lys Thr Asn Ala Ile Ser Leu Val Thr
                165                 170                 175

Ser Ser Asp Ser Cys Pro Ala Asp Ala Glu Gln Leu Cys Leu Thr Phe
            180                 185                 190

Ser Ser Val Val Asp Arg Ala Arg Phe Glu Lys Leu Tyr Lys Gln Ile
        195                 200                 205

Asp Leu Ala Thr Asp Asn Phe Ser Lys Leu Val Asn Glu Glu Val Glu
    210                 215                 220

Asn Asn Ala Ala Thr Asp Lys Ala Pro Ser Thr His Thr Ser Thr Val
225                 230                 235                 240

Val Pro Val Thr Thr Glu Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265                 270

Ile Leu Ser Glu Gly Gln Leu Val Asp Ser Leu Gly Asn Gly Val Ala
        275                 280                 285

Gly Val Asp Tyr Tyr Thr Asn Ser Gly Arg Gly Val Thr Asp Glu Asn
    290                 295                 300

Gly Lys Phe Ser Phe Ser Trp Gly Glu Thr Ile Ser Phe Gly Ile Asp
305                 310                 315                 320

Thr Phe Glu Leu Gly Ser Val Arg Gly Asn Lys Ser Thr Ile Ala Leu
                325                 330                 335

Thr Glu Leu Gly Asp Glu Val Arg Gly Ala Asn Ile Asp Gln Leu Ile
            340                 345                 350

His Arg Tyr Ser Thr Thr Gly Gln Asn Asn Thr Arg Val Val Pro Asp
        355                 360                 365

Asp Val Arg Lys Val Phe Ala Glu Tyr Pro Asn Val Ile Asn Glu Ile
    370                 375                 380

Ile Asn Leu Ser Leu Ser Asn Gly Ala Thr Leu Asp Glu Gly Asp Gln
385                 390                 395                 400

Asn Val Val Leu Pro Asn Glu Phe Ile Glu Gln Phe Lys Thr Gly Gln
                405                 410                 415

Ala Lys Glu Ile Asp Thr Ala Ile Cys Ala Lys Thr Asp Gly Cys Asn
            420                 425                 430

Glu Ala Arg Trp Phe Ser Leu Thr Thr Arg Asn Val Asn Asp Gly Gln
        435                 440                 445

Ile Gln Gly Val Ile Asn Lys Leu Trp Gly Val Asp Thr Asn Tyr Gln
    450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ser
                485                 490                 495

Ala Phe Pro Ile Leu Met Ala Arg Asn Asp Lys Asn Tyr Trp Leu Ala
            500                 505                 510

Phe Gly Glu Lys Arg Ala Trp Asp Lys Asn Glu Leu Ala Tyr Ile Thr
        515                 520                 525
```

```
Glu Ala Pro Ser Ile Val Gln Pro Glu Asn Val Thr Arg Asp Thr Ala
            530                 535                 540

Thr Phe Asn Leu Pro Phe Ile Ser Leu Gly Gln Val Gly Glu Gly Lys
545                 550                 555                 560

Leu Met Val Ile Gly Asn Pro His Tyr Asn Ser Ile Leu Arg Cys Pro
                    565                 570                 575

Asn Gly Tyr Ser Trp Gly Gly Val Asn Ser Lys Gly Glu Cys Thr
            580                 585                 590

Leu Ser Gly Asp Ser Asp Met Lys His Phe Met Gln Asn Val Leu
            595                 600                 605

Arg Tyr Leu Ser Asn Asp Ile Trp Gln Pro Asn Thr Lys Ser Ile Met
            610                 615                 620

Thr Val Gly Thr Asn Leu Glu Asn Val Tyr Phe Lys Lys Ala Gly Gln
625                 630                 635                 640

Val Leu Gly Asn Ser Ala Pro Phe Ala Phe His Glu Asp Phe Thr Gly
                    645                 650                 655

Ile Thr Val Lys Gln Leu Thr Ser Tyr Gly Asp Leu Asn Pro Glu Glu
                    660                 665                 670

Ile Pro Leu Leu Ile Leu Asn Gly Phe Glu Tyr Val Thr Gln Trp Ser
                    675                 680                 685

Gly Asp Pro Tyr Ala Val Pro Leu Arg Ala Asp Thr Ser Lys Pro Lys
            690                 695                 700

Leu Thr Gln Gln Asp Val Thr Asp Leu Ile Ala Tyr Leu Asn Lys Gly
705                 710                 715                 720

Gly Ser Val Leu Ile Met Glu Asn Val Met Ser Asn Leu Lys Glu Glu
                    725                 730                 735

Ser Ala Ser Ser Phe Val Arg Leu Leu Asp Ala Ala Gly Leu Ser Met
            740                 745                 750

Ala Leu Asn Lys Ser Val Val Asn Asn Asp Pro Gln Gly Tyr Pro Asp
            755                 760                 765

Arg Val Arg Gln Arg Arg Ala Thr Gly Ile Trp Val Tyr Glu Arg Tyr
            770                 775                 780

Pro Ala Ala Asp Gly Ala Gln Pro Pro Tyr Thr Ile Asp Pro Asn Thr
785                 790                 795                 800

Gly Glu Val Thr Trp Lys Tyr Gln Gln Asp Asn Lys Pro Asp Asp Lys
                    805                 810                 815

Pro Lys Leu Glu Val Ala Ser Trp Gln Glu Val Glu Gly Lys Gln
            820                 825                 830

Val Thr Arg Tyr Ala Phe Ile Asp Glu Ala Glu Tyr Thr Thr Glu Glu
            835                 840                 845

Ser Leu Glu Ala Ala Lys Ala Lys Ile Phe Glu Lys Phe Pro Gly Leu
850                 855                 860

Gln Glu Cys Lys Asp Ser Thr Tyr His Tyr Glu Ile Asn Cys Leu Glu
865                 870                 875                 880

Arg Arg Pro Gly Thr Asp Val Pro Val Thr Gly Gly Met Tyr Val Pro
                    885                 890                 895

Arg Tyr Thr Gln Leu Asn Leu Asp Ala Asp Thr Ala Lys Ala Met Val
            900                 905                 910

Gln Ala Ala Asp Leu Gly Thr Asn Ile Gln Arg Leu Tyr Gln His Glu
            915                 920                 925

Leu Tyr Phe Arg Thr Lys Gly Ser Lys Gly Glu Arg Leu Asn Ser Val
            930                 935                 940

Asp Leu Glu Arg Leu Tyr Gln Asn Met Ser Val Trp Leu Trp Asn Asp
```

```
             945                 950                 955                 960
Thr Lys Tyr Arg Tyr Glu Glu Gly Lys Glu Asp Glu Leu Gly Phe Lys
                965                 970                 975
Thr Phe Thr Glu Phe Leu Asn Cys Tyr Ala Asn Asp Ala Tyr Ala Gly
                980                 985                 990
Gly Thr Lys Cys Ser Ala Asp Leu Lys Lys Ser Leu Val Asp Asn Asn
                995                 1000                1005
Met Ile Tyr Gly Asp Gly Ser Ser Lys Ala Gly Met Met Asn Pro Ser
            1010                1015                1020
Tyr Pro Leu Asn Tyr Met Glu Lys Pro Leu Thr Arg Leu Met Leu Gly
1025                1030                1035                1040
Arg Ser Trp Trp Asp Leu Asn Ile Lys Val Asp Val Glu Lys Tyr Pro
                1045                1050                1055
Gly Ser Val Ser Ala Lys Gly Glu Ser Val Thr Glu Asn Ile Ser Leu
                1060                1065                1070
Tyr Ser Asn Pro Thr Lys Trp Phe Ala Gly Asn Met Gln Ser Thr Gly
                1075                1080                1085
Leu Trp Ala Pro Ala Gln Gln Asp Val Thr Ile Lys Ser Ser Ala Ser
            1090                1095                1100
Val Pro Val Thr Val Thr Val Ala Leu Ala Asp Asp Leu Thr Gly Arg
1105                1110                1115                1120
Glu Lys His Glu Val Ala Leu Asn Arg Pro Pro Arg Val Thr Lys Thr
                1125                1130                1135
Tyr Thr Leu Glu Ala Asn Gly Glu Val Thr Phe Lys Val Pro Tyr Gly
                1140                1145                1150
Gly Leu Ile Tyr Ile Lys Gly Asp Ser Lys Asp Asp Val Ser Ala Asn
                1155                1160                1165
Phe Thr Phe Thr Gly Val Val Lys Ala Pro Phe Tyr Lys Asp Gly Glu
            1170                1175                1180
Trp Lys Asn Asp Leu Asp Ser Pro Ala Pro Leu Gly Glu Leu Glu Ser
1185                1190                1195                1200
Ala Ser Phe Val Tyr Thr Thr Pro Lys Lys Asn Leu Glu Ala Ser Asn
                1205                1210                1215
Phe Thr Gly Gly Val Ala Glu Phe Ala Lys Asp Leu Asp Thr Phe Ala
                1220                1225                1230
Ser Ser Met Asn Asp Phe Tyr Gly Arg Asn Asp Glu Asp Gly Lys His
            1235                1240                1245
Arg Met Phe Thr Tyr Lys Asn Leu Thr Gly His Lys His Arg Phe Thr
1250                1255                1260
Asn Asp Val Gln Ile Ser Ile Gly Asp Ala His Ser Gly Tyr Pro Val
1265                1270                1275                1280
Met Asn Ser Ser Phe Ser Thr Asn Ser Thr Thr Leu Pro Thr Thr Pro
            1285                1290                1295
Leu Asn Asp Trp Leu Ile Trp His Glu Val Gly His Asn Ala Ala Glu
                1300                1305                1310
Thr Pro Leu Asn Val Pro Gly Ala Thr Glu Val Ala Asn Asn Val Leu
            1315                1320                1325
Ala Leu Tyr Met Gln Asp Arg Tyr Leu Gly Lys Met Asn Arg Val Ala
            1330                1335                1340
Asp Asp Ile Thr Val Ala Pro Glu Tyr Leu Asp Glu Ser Asn Gly Gln
1345                1350                1355                1360
Ala Trp Ala Arg Gly Gly Ala Gly Asp Arg Leu Leu Met Tyr Ala Gln
                1365                1370                1375
```

Leu Lys Glu Trp Ala Glu Glu Asn Phe Asp Ile Lys Gln Trp Tyr Pro
         1380                1385                1390

Asp Gly Glu Leu Pro Lys Phe Tyr Ser Asp Arg Lys Gly Met Lys Gly
         1395                1400                1405

Trp Asn Leu Phe Gln Leu Met His Arg Lys Ala Arg Gly Asp Asp Val
    1410                1415                1420

Gly Asn Ser Thr Phe Gly Gly Lys Asn Tyr Cys Ala Glu Ser Asn Gly
1425                1430                1435                1440

Asn Ala Ala Asp Thr Leu Met Leu Cys Ala Ser Trp Val Ala Gln Ala
              1445                1450                1455

Asp Leu Ser Glu Phe Phe Lys Lys Trp Asn Pro Gly Ala Ser Ala Tyr
         1460                1465                1470

Gln Leu Pro Gly Ala Thr Glu Met Ser Phe Gln Gly Gly Val Ser Ser
         1475                1480                1485

Ser Ala Tyr Ser Thr Leu Ala Ser Leu Lys Leu Pro Lys Pro Glu Lys
         1490                1495                1500

Gly Pro Glu Thr Ile Asn Lys Val Thr Glu His Lys Met Ser Ala Glu
1505                1510                1515                1520

<210> SEQ ID NO 9
<211> LENGTH: 2214
<212> TYPE: DNA
<213> ORGANISM: Escherichia coli

<400> SEQUENCE: 9

```
tgtgatggtg gtggttcagg atcgtcctcc gatacgccgt ctgtagattc tggatcaggg    60
actttgccgg aagtgaaacc cgatccaaca ccaaccccgg agccgacacc tgagccgacg   120
ccggacccag aacctacgcc ggatccaaca cctgatcctg agccgacacc agaaccggag   180
ccagaacctg ttcctacgaa acgggttat ctgaccctgg cggaagcca gcgggtaact    240 ggtgctacct gtaatggtga atccagcgat ggctttacct ttacgccagg caataccgtg   300
agttgtgtgg tgggcagtac gaccattgca acattcaaca cccagtcaga agctgcgcgt   360
agcctgcgtg cggttgacaa agtgtcgttt agcctggagg acgcgcagga gctggcgaat   420
tctgaaaata agaaaaccaa cgccatctct ctggtgacgt ccagcgacag ttgccccgca   480
gatgcagaac agctttgtct tactttctcg tcagtggttg atcgcgcgcg atttgaaaaa   540
ctgtataagc aaattgatct ggcaacagac aatttcagca agctggtcaa tgaagaggtg   600
gaaaacaatg ctgcgactga taaagcgccg tccacccata cctcaacggt agtgccagtc   660
acgacagagg gaacaaaacc ggatctgaac gcgtccttcg tgtcggctaa cgcggaacag   720 tttttatcagt atcaacccac tgaaatcatt ctttccgaag ccaactggt ggatagcctg   780 gggaacggtg ttgctggcgt tgactactac accaattcag gccgtggcgt aactgacgaa   840
aacggtaaat tttcctttag ctggggcgaa accatctcct ttggtatcga tacctttgaa   900
ctgggctcag tacgtggcaa taagtcgacc attgcgctga ctgaattggg tgatgaagtt   960 cgcgggggcaa atatcgatca gctcattcat cgttattcga cgactggtca aataatact  1020 cgtgttgttc cggacgatgt acgcaaggtc tttgccgaat atcccaacgt gatcaacgag  1080
ataatcaatc tttcgttatc caacggtgcg acgctggatg aaggcgatca aaacgttgtg  1140
ctgcctaacg aatttatcga gcagtttaag acgggtcagg ccaaagagat cgataccgcg  1200
atttgtgcga aaaccgacgg ttgtaacgag gctcgctggt tctcgctgac aacgcgcaat  1260
gttaatgacg gccagattca gggcgttatt aacaagctgt ggggcgtgga tacgaactat  1320
```

```
cagtctgtca gcaagttcca cgtcttccat gactctacca acttctatgg cagcaccggt   1380
aacgcgcgcg gtcaggcggt ggtaaatatc tccaactcgg cattcccgat tctgatggcg   1440
cgtaatgata aaaactactg gctggcgttt ggcgaaaaac gcgcctggga taaaaatgag   1500
ctggcgtaca ttacggaagc gccttccatt gtgcagccag agaacgttac gcgcgatact   1560
gcgactttca acctgccgtt tatttcgctg ggcaagtcg gtgaaggcaa actgatggtt   1620
atcggtaacc cgcactacaa cagcatcctg cgttgcccga acggttacag ttggggcggt   1680
ggtgttaata gtaaaggtga gtgtacgctc agcggtgatt ctgatgacat gaagcacttt   1740
atgcagaacg tactgcgcta cttgtcaaat gacatctggc agccaaatac caagagcatc   1800
atgactgtcg gcaccaacct ggagaacgtt tatttcaaaa aagcgggcca ggtattggga   1860
aatagtgcac catttgcttt ccatgaggat ttcactggta tcacggttaa acagttgacc   1920
agctatggcg atctgaatcc ggaagagatt ccgttgctga tcctcaacgg ctttgaatat   1980
gtgactcagt ggtctggcga tccctatgct gtgcctctgc gtgcagatac cagcaaaccg   2040
aagctgactc agcaggatgt gaccgatctg atcgcttatc tgaacaaagg tggctcggtg   2100
ctgatcatgg aaaacgtgat gagcaatctt aaggaagaga gcgcgtccag ttttgtgcgt   2160
ctgctggatg ccgcgggtct gtcaatggct ctgaacaaat cggtggtgaa caac          2214
```

<210> SEQ ID NO 10
<211> LENGTH: 738
<212> TYPE: PRT
<213> ORGANISM: Escherichia coli

<400> SEQUENCE: 10

```
Cys Asp Gly Gly Gly Ser Gly Ser Ser Asp Thr Pro Ser Val Asp
 1               5                  10                  15

Ser Gly Ser Gly Thr Leu Pro Glu Val Lys Pro Asp Pro Thr Pro Thr
            20                  25                  30

Pro Glu Pro Thr Pro Glu Pro Thr Pro Asp Pro Glu Pro Thr Pro Asp
        35                  40                  45

Pro Thr Pro Asp Pro Glu Pro Thr Pro Glu Pro Glu Pro Val
    50                  55                  60

Pro Thr Lys Thr Gly Tyr Leu Thr Leu Gly Gly Ser Gln Arg Val Thr
65                  70                  75                  80

Gly Ala Thr Cys Asn Gly Glu Ser Ser Asp Gly Phe Thr Phe Thr Pro
                85                  90                  95

Gly Asn Thr Val Ser Cys Val Val Gly Ser Thr Thr Ile Ala Thr Phe
            100                 105                 110

Asn Thr Gln Ser Glu Ala Ala Arg Ser Leu Arg Ala Val Asp Lys Val
        115                 120                 125

Ser Phe Ser Leu Glu Asp Ala Gln Glu Leu Ala Asn Ser Glu Asn Lys
    130                 135                 140

Lys Thr Asn Ala Ile Ser Leu Val Thr Ser Ser Asp Ser Cys Pro Ala
145                 150                 155                 160

Asp Ala Glu Gln Leu Cys Leu Thr Phe Ser Ser Val Val Asp Arg Ala
                165                 170                 175

Arg Phe Glu Lys Leu Tyr Lys Gln Ile Asp Leu Ala Thr Asp Asn Phe
            180                 185                 190

Ser Lys Leu Val Asn Glu Glu Val Glu Asn Asn Ala Ala Thr Asp Lys
        195                 200                 205

Ala Pro Ser Thr His Thr Ser Thr Val Val Pro Val Thr Thr Glu Gly
```

```
            210                 215                 220
Thr Lys Pro Asp Leu Asn Ala Ser Phe Val Ser Ala Asn Ala Glu Gln
225                 230                 235                 240

Phe Tyr Gln Tyr Gln Pro Thr Glu Ile Ile Leu Ser Glu Gly Gln Leu
                245                 250                 255

Val Asp Ser Leu Gly Asn Gly Val Ala Gly Val Asp Tyr Tyr Thr Asn
                260                 265                 270

Ser Gly Arg Gly Val Thr Asp Glu Asn Gly Lys Phe Ser Phe Ser Trp
                275                 280                 285

Gly Glu Thr Ile Ser Phe Gly Ile Asp Thr Phe Glu Leu Gly Ser Val
                290                 295                 300

Arg Gly Asn Lys Ser Thr Ile Ala Leu Thr Glu Leu Gly Asp Glu Val
305                 310                 315                 320

Arg Gly Ala Asn Ile Asp Gln Leu Ile His Arg Tyr Ser Thr Thr Gly
                325                 330                 335

Gln Asn Asn Thr Arg Val Val Pro Asp Asp Val Arg Lys Val Phe Ala
                340                 345                 350

Glu Tyr Pro Asn Val Ile Asn Glu Ile Ile Asn Leu Ser Leu Ser Asn
                355                 360                 365

Gly Ala Thr Leu Asp Glu Gly Asp Gln Asn Val Val Leu Pro Asn Glu
                370                 375                 380

Phe Ile Glu Gln Phe Lys Thr Gly Gln Ala Lys Glu Ile Asp Thr Ala
385                 390                 395                 400

Ile Cys Ala Lys Thr Asp Gly Cys Asn Glu Ala Arg Trp Phe Ser Leu
                405                 410                 415

Thr Thr Arg Asn Val Asn Asp Gly Gln Ile Gln Gly Val Ile Asn Lys
                420                 425                 430

Leu Trp Gly Val Asp Thr Asn Tyr Gln Ser Val Ser Lys Phe His Val
                435                 440                 445

Phe His Asp Ser Thr Asn Phe Tyr Gly Ser Thr Gly Asn Ala Arg Gly
                450                 455                 460

Gln Ala Val Val Asn Ile Ser Asn Ser Ala Phe Pro Ile Leu Met Ala
465                 470                 475                 480

Arg Asn Asp Lys Asn Tyr Trp Leu Ala Phe Gly Glu Lys Arg Ala Trp
                485                 490                 495

Asp Lys Asn Glu Leu Ala Tyr Ile Thr Glu Ala Pro Ser Ile Val Gln
                500                 505                 510

Pro Glu Asn Val Thr Arg Asp Thr Ala Thr Phe Asn Leu Pro Phe Ile
                515                 520                 525

Ser Leu Gly Gln Val Gly Glu Gly Lys Leu Met Val Ile Gly Asn Pro
530                 535                 540

His Tyr Asn Ser Ile Leu Arg Cys Pro Asn Gly Tyr Ser Trp Gly Gly
545                 550                 555                 560

Gly Val Asn Ser Lys Gly Glu Cys Thr Leu Ser Gly Asp Ser Asp
                565                 570                 575

Met Lys His Phe Met Gln Asn Val Leu Arg Tyr Leu Ser Asn Asp Ile
                580                 585                 590

Trp Gln Pro Asn Thr Lys Ser Ile Met Thr Val Gly Thr Asn Leu Glu
                595                 600                 605

Asn Val Tyr Phe Lys Lys Ala Gly Gln Val Leu Gly Asn Ser Ala Pro
                610                 615                 620

Phe Ala Phe His Glu Asp Phe Thr Gly Ile Thr Val Lys Gln Leu Thr
625                 630                 635                 640
```

Ser Tyr Gly Asp Leu Asn Pro Glu Glu Ile Pro Leu Leu Ile Leu Asn
            645                 650                 655

Gly Phe Glu Tyr Val Thr Gln Trp Ser Gly Asp Pro Tyr Ala Val Pro
        660                 665                 670

Leu Arg Ala Asp Thr Ser Lys Pro Lys Leu Thr Gln Gln Asp Val Thr
            675                 680                 685

Asp Leu Ile Ala Tyr Leu Asn Lys Gly Gly Ser Val Leu Ile Met Glu
        690                 695                 700

Asn Val Met Ser Asn Leu Lys Glu Glu Ser Ala Ser Ser Phe Val Arg
705                 710                 715                 720

Leu Leu Asp Ala Ala Gly Leu Ser Met Ala Leu Asn Lys Ser Val Val
            725                 730                 735

Asn Asn

<210> SEQ ID NO 11
<211> LENGTH: 2277
<212> TYPE: DNA
<213> ORGANISM: Escherichia coli

<400> SEQUENCE: 11
gatccgcaag ggtatccgga tcgcgttcgt cagcgtcgcg cgactggcat ttgggtttat      60
gaacgttatc ctgctgcaga cggcgcgcaa ccgccgtaca ccatcgaccc aaatacaggg     120
gaagtgacct ggaaatacca gcaagacaac aagcctgatg acaagccgaa actggaagtt     180
gcgagctggc aggaggaagt tgagggcaaa caggtaacgc gttatgcctt tattgatgaa     240
gcggaataca caacagaaga atctctggaa gcggcaaagg caaaaatctt tgagaagttt     300
cctgggttac aggagtgtaa ggactcgact taccattacg agattaactg tttggagcgc     360
cgcccaggca cggatgttcc ggtaacaggt ggcatgtatg ttccgcgcta tacgcaactg     420
aatcttgacg ccgacaccgc gaaagcgatg gtgcaggcgg cggatttagg caccaacatt     480
cagcgcctgt atcagcatga gctttatttc cgtaccaaag gcagtaaagg tgagcgtctg     540
aacagtgttg atctggaacg tctgtaccag aacatgtcgg tctggctgtg gaacgatacg     600
aaatatcgtt acgaagaggg caaggaagat gagctgggct ttaaaacgtt caccgagttc     660
ctgaactgct acgccaatga tgcctatgca ggcggcacca gtgctccgc agatctgaaa     720 aaatcgctgg tcgataacaa catgatctac ggtgacggta gcagcaaagc gggcatgatg     780
aacccaagct atccgctcaa ctatatggaa aaaccgctga cgcgtctgat gctgggccgt     840
tcctggtggg atctgaacat taaggttgat gtggagaagt acccaggatc cgtatcggca     900
aagggtgaga gcgttacgga aaacatcagc ctgtactcga atccgaccaa atggtttgcg     960
ggtaacatgc agtcaaccgg cctgtgggca ccggcccagc aggacgtcac cattaagtct    1020
tcggcgtcag tcccagtgac tgttaccgtg gcgctggctg acgacctgac tggacgtgag    1080
aagcatgaag ttgcgctgaa ccgtccgcca gagtgactaa aacgtatac tctggaggct    1140 aacggtgaag tgaccttcaa ggtgccttat ggtggtctga tttatatcaa gggcgacagt    1200
aaggatgatg tttctgctaa cttcaccttt accggtgtag taaaagcgcc gttctataaa    1260
gacggcgaat ggaaaaacga tctggactca ccggcgccgc tgggcgagct ggagtctgcg    1320
tcgttcgtct ataccacgcc gaagaagaac cttgaggcca gcaatttcac tggtggtgta    1380
gcagaattcg ctaagatct ggatacctt gccagctcga tgaatgactt ctacggtcgt    1440
aatgatgaag acggtaagca ccggatgttt acctataaaa acttgacggg gcacaagcat    1500

```
cgtttcacca acgatgtgca gatctccatc ggtgatgcgc actcgggtta tccggtaatg   1560
aacagcagct tctcgacgaa cagcaccacg ctgccgacga cgccgctgaa cgactggctg   1620
atttggcacg aagtcggtca taacgctgca gaaacaccgc tgaacgtacc gggtgcaact   1680
gaagtggcga caacgtgct ggcgctgtac atgcaggatc gctatctcgg taagatgaac   1740
cgtgtcgctg acgacattac cgtcgcgccg aatatctgg acgagagcaa cggtcaggcc   1800
tgggcgcgcg cggtgcggg tgaccgtctg ctgatgtacg cacagttgaa ggagtgggca   1860
gaggaaaact ttgatatcaa acagtggtat ccagatggtg agctgcctaa gttctacagc   1920
gatcgtaaag ggatgaaggg ctggaacctg ttccagttga tgcaccgtaa agcgcgcggc   1980
gatgatgttg gtaacagcac ctttggtggc aagaattact gtgctgaatc caatggtaac   2040
gctgccgaca cgctgatgct gtgtgcatcc tgggtcgctc aggcggatct ttcggaattc   2100
tttaagaaat ggaatccggg tgcaagtgct taccagttgc cgggagcaac ggagatgagt   2160
ttccagggcg gtgtgagctc ttcggcttac agcacgctgg cgtcactcaa gctgccgaaa   2220
ccggaaaaag ggccggaaac cattaacaag gttaccgagc ataagatgtc tgccgag      2277

<210> SEQ ID NO 12
<211> LENGTH: 759
<212> TYPE: PRT
<213> ORGANISM: Escherichia coli

<400> SEQUENCE: 12

Asp Pro Gln Gly Tyr Pro Asp Arg Val Arg Gln Arg Ala Thr Gly
1               5                   10                  15

Ile Trp Val Tyr Glu Arg Tyr Pro Ala Ala Asp Gly Ala Gln Pro Pro
            20                  25                  30

Tyr Thr Ile Asp Pro Asn Thr Gly Glu Val Thr Trp Lys Tyr Gln Gln
        35                  40                  45

Asp Asn Lys Pro Asp Asp Lys Pro Lys Leu Glu Val Ala Ser Trp Gln
    50                  55                  60

Glu Glu Val Glu Gly Lys Gln Val Thr Arg Tyr Ala Phe Ile Asp Glu
65                  70                  75                  80

Ala Glu Tyr Thr Thr Glu Glu Ser Leu Glu Ala Lys Ala Lys Ile
                85                  90                  95

Phe Glu Lys Phe Pro Gly Leu Gln Glu Cys Lys Asp Ser Thr Tyr His
            100                 105                 110

Tyr Glu Ile Asn Cys Leu Glu Arg Arg Pro Gly Thr Asp Val Pro Val
        115                 120                 125

Thr Gly Gly Met Tyr Val Pro Arg Tyr Thr Gln Leu Asn Leu Asp Ala
    130                 135                 140

Asp Thr Ala Lys Ala Met Val Gln Ala Ala Asp Leu Gly Thr Asn Ile
145                 150                 155                 160

Gln Arg Leu Tyr Gln His Glu Leu Tyr Phe Arg Thr Lys Gly Ser Lys
                165                 170                 175

Gly Glu Arg Leu Asn Ser Val Asp Leu Glu Arg Leu Tyr Gln Asn Met
            180                 185                 190

Ser Val Trp Leu Trp Asn Asp Thr Lys Tyr Arg Tyr Glu Glu Gly Lys
        195                 200                 205

Glu Asp Glu Leu Gly Phe Lys Thr Phe Thr Glu Phe Leu Asn Cys Tyr
    210                 215                 220

Ala Asn Asp Ala Tyr Ala Gly Gly Thr Lys Cys Ser Ala Asp Leu Lys
225                 230                 235                 240
```

-continued

```
Lys Ser Leu Val Asp Asn Asn Met Ile Tyr Gly Asp Gly Ser Ser Lys
                245                 250                 255
Ala Gly Met Met Asn Pro Ser Tyr Pro Leu Asn Tyr Met Glu Lys Pro
            260                 265                 270
Leu Thr Arg Leu Met Leu Gly Arg Ser Trp Trp Asp Leu Asn Ile Lys
        275                 280                 285
Val Asp Val Glu Lys Tyr Pro Gly Ser Val Ser Ala Lys Gly Glu Ser
    290                 295                 300
Val Thr Glu Asn Ile Ser Leu Tyr Ser Asn Pro Thr Lys Trp Phe Ala
305                 310                 315                 320
Gly Asn Met Gln Ser Thr Gly Leu Trp Ala Pro Ala Gln Gln Asp Val
                325                 330                 335
Thr Ile Lys Ser Ser Ala Ser Val Pro Val Thr Val Thr Val Ala Leu
            340                 345                 350
Ala Asp Asp Leu Thr Gly Arg Glu Lys His Glu Val Ala Leu Asn Arg
        355                 360                 365
Pro Pro Arg Val Thr Lys Thr Tyr Thr Leu Glu Ala Asn Gly Glu Val
    370                 375                 380
Thr Phe Lys Val Pro Tyr Gly Gly Leu Ile Tyr Ile Lys Gly Asp Ser
385                 390                 395                 400
Lys Asp Asp Val Ser Ala Asn Phe Thr Phe Thr Gly Val Val Lys Ala
                405                 410                 415
Pro Phe Tyr Lys Asp Gly Glu Trp Lys Asn Asp Leu Asp Ser Pro Ala
            420                 425                 430
Pro Leu Gly Glu Leu Glu Ser Ala Ser Phe Val Tyr Thr Thr Pro Lys
        435                 440                 445
Lys Asn Leu Glu Ala Ser Asn Phe Thr Gly Gly Val Ala Glu Phe Ala
    450                 455                 460
Lys Asp Leu Asp Thr Phe Ala Ser Ser Met Asn Asp Phe Tyr Gly Arg
465                 470                 475                 480
Asn Asp Glu Asp Gly Lys His Arg Met Phe Thr Tyr Lys Asn Leu Thr
                485                 490                 495
Gly His Lys His Arg Phe Thr Asn Asp Val Gln Ile Ser Ile Gly Asp
            500                 505                 510
Ala His Ser Gly Tyr Pro Val Met Asn Ser Ser Phe Ser Thr Asn Ser
        515                 520                 525
Thr Thr Leu Pro Thr Thr Pro Leu Asn Asp Trp Leu Ile Trp His Glu
    530                 535                 540
Val Gly His Asn Ala Ala Glu Thr Pro Leu Asn Val Pro Gly Ala Thr
545                 550                 555                 560
Glu Val Ala Asn Asn Val Leu Ala Leu Tyr Met Gln Asp Arg Tyr Leu
                565                 570                 575
Gly Lys Met Asn Arg Val Ala Asp Asp Ile Thr Val Ala Pro Glu Tyr
            580                 585                 590
Leu Asp Glu Ser Asn Gly Gln Ala Trp Ala Arg Gly Ala Gly Asp
        595                 600                 605
Arg Leu Leu Met Tyr Ala Gln Leu Lys Glu Trp Ala Glu Glu Asn Phe
    610                 615                 620
Asp Ile Lys Gln Trp Tyr Pro Asp Gly Glu Leu Pro Lys Phe Tyr Ser
625                 630                 635                 640
Asp Arg Lys Gly Met Lys Gly Trp Asn Leu Phe Gln Leu Met His Arg
                645                 650                 655
Lys Ala Arg Gly Asp Asp Val Gly Asn Ser Thr Phe Gly Gly Lys Asn
```

```
                660             665             670
Tyr Cys Ala Glu Ser Asn Gly Asn Ala Ala Asp Thr Leu Met Leu Cys
            675                 680                 685
Ala Ser Trp Val Ala Gln Ala Asp Leu Ser Glu Phe Phe Lys Lys Trp
        690                 695                 700
Asn Pro Gly Ala Ser Ala Tyr Gln Leu Pro Gly Ala Thr Glu Met Ser
705                 710                 715                 720
Phe Gln Gly Gly Val Ser Ser Ser Ala Tyr Ser Thr Leu Ala Ser Leu
                725                 730                 735
Lys Leu Pro Lys Pro Glu Lys Gly Pro Glu Thr Ile Asn Lys Val Thr
            740                 745                 750
Glu His Lys Met Ser Ala Glu
            755

<210> SEQ ID NO 13
<211> LENGTH: 4461
<212> TYPE: DNA
<213> ORGANISM: Escherichia coli

<400> SEQUENCE: 13
```

| | | | | | |
|---|---|---|---|---|---|
| gatacgccgt | ctgtagattc | tggatcaggg | actttgccgg | aagtgaaacc | cgatccaaca | 60 |
| ccaaccccgg | agccgacacc | tgagccgacg | ccggacccag | aacctacgcc | ggatccaaca | 120 |
| cctgatcctg | agccgacacc | agaaccggag | ccagaacctg | ttcctacgaa | acgggttat | 180 |
| ctgaccctgg | cggaagcca | gcgggtaact | ggtgctacct | gtaatggtga | atccagcgat | 240 |
| ggctttacct | ttacgccagg | caataccgtg | agttgtgtgg | tgggcagtac | gaccattgca | 300 |
| acattcaaca | cccagtcaga | agctgcgcgt | agcctgcgtg | cggttgacaa | agtgtcgttt | 360 |
| agcctggagg | acgcgcagga | gctggcgaat | tctgaaaata | agaaaaccaa | cgccatctct | 420 |
| ctggtgacgt | ccagcgacag | ttgccccgca | gatgcagaac | agctttgtct | tactttctcg | 480 |
| tcagtggttg | atcgcgcgcg | atttgaaaaa | ctgtataagc | aaattgatct | ggcaacagac | 540 |
| aatttcagca | agctggtcaa | tgaagaggtg | gaaaacaatg | ctgcgactga | taaagcgccg | 600 |
| tccacccata | cctcaacggt | agtgccagtc | acgacagagg | gaacaaaacc | ggatctgaac | 660 |
| gcgtccttcg | tgtcggctaa | cgcggaacag | ttttatcagt | atcaacccac | tgaaatcatt | 720 |
| ctttccgaag | gccaactggt | ggatagcctg | gggaacggtg | ttgctggcgt | tgactactac | 780 |
| accaattcag | gccgtggcgt | aactgacgaa | aacggtaaat | tttcctttag | ctggggcgaa | 840 |
| accatctcct | ttggtatcga | tacctttgaa | ctgggctcag | tacgtggcaa | taagtcgacc | 900 |
| attgcgctga | ctgaattggg | tgatgaagtt | cgcggggcaa | atatcgatca | gctcattcat | 960 |
| cgttattcga | cgactggtca | aaataatact | cgtgttgttc | cggacgatgt | acgcaaggtc | 1020 |
| tttgccgaat | atcccaacgt | gatcaacgag | ataatcaatc | tttcgttatc | caacggtgcg | 1080 |
| acgctggatg | aaggcgatca | aaacgttgtg | ctgcctaacg | aatttatcga | gcagtttaag | 1140 |
| acgggtcagg | ccaaagagat | cgataccgcg | atttgtgcga | aaaccgacgg | ttgtaacgag | 1200 |
| gctcgctggt | tctcgctgac | aacgcgcaat | gttaatgacg | ccagattca | gggcgttatt | 1260 |
| aacaagctgt | ggggcgtgga | tacgaactat | cagtctgtca | gcaagttcca | cgtcttccat | 1320 |
| gactctacca | acttctatgg | cagcaccggt | aacgcgcgcg | gtcaggcggt | ggtaaatatc | 1380 |
| tccaactcgg | cattcccgat | tctgatggcg | cgtaatgata | aaaactactg | gctggcgttt | 1440 |
| ggcgaaaaac | gcgcctggga | taaaaatgag | ctggcgtaca | ttacggaagc | gccttccatt | 1500 |
| gtgcagccag | agaacgttac | gcgcgatact | gcgactttca | acctgccgtt | tatttcgctg | 1560 |

```
gggcaagtcg gtgaaggcaa actgatggtt atcggtaacc cgcactacaa cagcatcctg    1620
cgttgcccga acggttacag ttggggcggt ggtgttaata gtaaaggtga gtgtacgctc    1680
agcggtgatt ctgatgacat gaagcacttt atgcagaacg tactgcgcta cttgtcaaat    1740
gacatctggc agccaaatac caagagcatc atgactgtcg gcaccaacct ggagaacgtt    1800
tatttcaaaa aagcgggcca ggtattggga aatagtgcac catttgcttt ccatgaggat    1860
ttcactggta tcacggttaa acagttgacc agctatggcg atctgaatcc ggaagagatt    1920
ccgttgctga tcctcaacgg ctttgaatat gtgactcagt ggtctggcga tccctatgct    1980
gtgcctctgc gtgcagatac cagcaaaccg aagctgactc agcaggatgt gaccgatctg    2040
atcgcttatc tgaacaaagg tggctcggtg ctgatcatgg aaaacgtgat gagcaatctt    2100
aaggaagaga gcgcgtccag ttttgtgcgt ctgctggatg ccgcgggtct gtcaatggct    2160
ctgaacaaat cggtggtgaa caacgatccg caagggtatc cggatcgcgt tcgtcagcgt    2220
cgcgcgactg gcatttgggt ttatgaacgt tatcctgctg cagacggcgc gcaaccgccg    2280
tacaccatcg acccaaatac aggggaagtg acctggaaat accagcaaga caacaagcct    2340
gatgacaagc cgaaactgga agttgcgagc tggcaggagg aagttgaggg caaacaggta    2400
acgcgttatg cctttattga tgaagcggaa tacacaacag aagaatctct ggaagcggca    2460
aaggcaaaaa tctttgagaa gtttcctggg ttacaggagt gtaaggactc gacttaccat    2520
tacgagatta actgtttgga gcgccgccca ggcacggatg ttccggtaac aggtggcatg    2580
tatgttccgc gctatacgca actgaatctt gacgccgaca ccgcgaaagc gatggtgcag    2640
gcggcggatt taggcaccaa cattcagcgc ctgtatcagc atgagcttta tttccgtacc    2700
aaaggcagta aggtgagcg tctgaacagt gttgatctgg aacgtctgta ccagaacatg    2760
tcggtctggc tgtggaacga tacgaaatat cgttacgaag agggcaagga agatgagctg    2820
ggctttaaaa cgttcaccga gttcctgaac tgctacgcca atgatgccta tgcaggcggc    2880
accaagtgct ccgcagatct gaaaaaatcg ctggtcgata caacatgat ctacggtgac    2940 ggtagcagca aagcgggcat gatgaaccca agctatccgc tcaactatat ggaaaaaccg    3000
ctgacgcgtc tgatgctggg ccgttcctgg tgggatctga acattaaggt tgatgtggag    3060
aagtacccag atccgtatc ggcaaagggt gagagcgtta cggaaaacat cagcctgtac    3120
tcgaatccga ccaaatggtt tgcgggtaac atgcagtcaa ccggcctgtg ggcaccggcc    3180
cagcaggacg tcaccattaa gtcttcggcg tcagtcccag tgactgttac cgtggcgctg    3240
gctgacgacc tgactggacg tgagaagcat gaagttgcgc tgaaccgtcc gccaagagtg    3300
actaaaacgt atactctgga ggctaacggt gaagtgacct tcaaggtgcc ttatggtggt    3360
ctgatttata tcaagggcga cagtaaggat gatgtttctg ctaacttcac ctttaccggt    3420
gtagtaaaag cgccgttcta taaagacggc gaatggaaaa acgatctgga ctcaccggcg    3480
ccgctgggcg agctggagtc tgcgtcgttc gtctataca cgccgaagaa gaaccttgag    3540
gccagcaatt tcactggtgg tgtagcagaa ttcgctaaag atctggatac ctttgccagc    3600
tcgatgaatg acttctacgg tcgtaatgat gaagacggta agcaccggat gtttaccat    3660 aaaaacttga cggggcacaa gcatcgtttc accaacgatg tgcagatctc catcggtgat    3720
gcgcactcgg gttatccggt aatgaacagc agcttctcga cgaacagcac cacgctgccg    3780
acgacgccgc tgaacgactg gctgatttgg cacgaagtcg gtcataacgc tgcagaaaca    3840
ccgctgaacg taccgggtgc aactgaagtg gcgaacaacg tgctggcgct gtacatgcag    3900
```

-continued

```
gatcgctatc tcggtaagat gaaccgtgtc gctgacgaca ttaccgtcgc gccggaatat    3960
ctggacgaga gcaacggtca ggcctgggcg cgcggcggtg cgggtgaccg tctgctgatg    4020
tacgcacagt tgaaggagtg ggcagaggaa aactttgata tcaaacagtg gtatccagat    4080
ggtgagctgc ctaagttcta cagcgatcgt aaagggatga agggctggaa cctgttccag    4140
ttgatgcacc gtaaagcgcg cggcgatgat gttggtaaca gcacctttgg tggcaagaat    4200
tactgtgctg aatccaatgg taacgctgcc gacacgctga tgctgtgtgc atcctgggtc    4260
gctcaggcgg atctttcgga attctttaag aaatggaatc cgggtgcaag tgcttaccag    4320
ttgccgggag caacggagat gagtttccag ggcggtgtga gctcttcggc ttacagcacg    4380
ctggcgtcac tcaagctgcc gaaaccggaa aaagggccgg aaaccattaa caaggttacc    4440
gagcataaga tgtctgccga g                                              4461
```

<210> SEQ ID NO 14
<211> LENGTH: 1487
<212> TYPE: PRT
<213> ORGANISM: Escherichia coli

<400> SEQUENCE: 14

```
Asp Thr Pro Ser Val Asp Ser Gly Ser Gly Thr Leu Pro Glu Val Lys
1               5                   10                  15

Pro Asp Pro Thr Pro Thr Pro Glu Pro Thr Pro Glu Pro Thr Pro Asp
            20                  25                  30

Pro Glu Pro Thr Pro Asp Pro Thr Pro Asp Pro Glu Pro Thr Pro Glu
        35                  40                  45

Pro Glu Pro Glu Pro Val Pro Thr Lys Thr Gly Tyr Leu Thr Leu Gly
    50                  55                  60

Gly Ser Gln Arg Val Thr Gly Ala Thr Cys Asn Gly Glu Ser Ser Asp
65                  70                  75                  80

Gly Phe Thr Phe Thr Pro Gly Asn Thr Val Ser Cys Val Val Gly Ser
                85                  90                  95

Thr Thr Ile Ala Thr Phe Asn Thr Gln Ser Glu Ala Ala Arg Ser Leu
            100                 105                 110

Arg Ala Val Asp Lys Val Ser Phe Ser Leu Glu Asp Ala Gln Glu Leu
        115                 120                 125

Ala Asn Ser Glu Asn Lys Lys Thr Asn Ala Ile Ser Leu Val Thr Ser
    130                 135                 140

Ser Asp Ser Cys Pro Ala Asp Ala Glu Gln Leu Cys Leu Thr Phe Ser
145                 150                 155                 160

Ser Val Val Asp Arg Ala Arg Phe Glu Lys Leu Tyr Lys Gln Ile Asp
                165                 170                 175

Leu Ala Thr Asp Asn Phe Ser Lys Leu Val Asn Glu Glu Val Glu Asn
            180                 185                 190

Asn Ala Ala Thr Asp Lys Ala Pro Ser Thr His Thr Ser Thr Val Val
        195                 200                 205

Pro Val Thr Thr Glu Gly Thr Lys Pro Asp Leu Asn Ala Ser Phe Val
    210                 215                 220

Ser Ala Asn Ala Glu Gln Phe Tyr Gln Tyr Gln Pro Thr Glu Ile Ile
225                 230                 235                 240

Leu Ser Glu Gly Gln Leu Val Asp Ser Leu Gly Asn Gly Val Ala Gly
                245                 250                 255

Val Asp Tyr Tyr Thr Asn Ser Gly Arg Gly Val Thr Glu Asn Gly
            260                 265                 270
```

```
Lys Phe Ser Phe Ser Trp Gly Glu Thr Ile Ser Phe Gly Ile Asp Thr
            275                 280                 285

Phe Glu Leu Gly Ser Val Arg Gly Asn Lys Ser Thr Ile Ala Leu Thr
        290                 295                 300

Glu Leu Gly Asp Glu Val Arg Gly Ala Asn Ile Asp Gln Leu Ile His
305                 310                 315                 320

Arg Tyr Ser Thr Thr Gly Gln Asn Asn Thr Arg Val Val Pro Asp Asp
                325                 330                 335

Val Arg Lys Val Phe Ala Glu Tyr Pro Asn Val Ile Asn Glu Ile Ile
            340                 345                 350

Asn Leu Ser Leu Ser Asn Gly Ala Thr Leu Asp Glu Gly Asp Gln Asn
        355                 360                 365

Val Val Leu Pro Asn Glu Phe Ile Glu Gln Phe Lys Thr Gly Gln Ala
    370                 375                 380

Lys Glu Ile Asp Thr Ala Ile Cys Ala Lys Thr Asp Gly Cys Asn Glu
385                 390                 395                 400

Ala Arg Trp Phe Ser Leu Thr Thr Arg Asn Val Asn Asp Gly Gln Ile
                405                 410                 415

Gln Gly Val Ile Asn Lys Leu Trp Gly Val Asp Thr Asn Tyr Gln Ser
            420                 425                 430

Val Ser Lys Phe His Val Phe His Asp Ser Thr Asn Phe Tyr Gly Ser
        435                 440                 445

Thr Gly Asn Ala Arg Gly Gln Ala Val Val Asn Ile Ser Asn Ser Ala
    450                 455                 460

Phe Pro Ile Leu Met Ala Arg Asn Asp Lys Asn Tyr Trp Leu Ala Phe
465                 470                 475                 480

Gly Glu Lys Arg Ala Trp Asp Lys Asn Glu Leu Ala Tyr Ile Thr Glu
                485                 490                 495

Ala Pro Ser Ile Val Gln Pro Glu Asn Val Thr Arg Asp Thr Ala Thr
            500                 505                 510

Phe Asn Leu Pro Phe Ile Ser Leu Gly Gln Val Gly Glu Gly Lys Leu
        515                 520                 525

Met Val Ile Gly Asn Pro His Tyr Asn Ser Ile Leu Arg Cys Pro Asn
    530                 535                 540

Gly Tyr Ser Trp Gly Gly Val Asn Ser Lys Gly Glu Cys Thr Leu
545                 550                 555                 560

Ser Gly Asp Ser Asp Met Lys His Phe Met Gln Asn Val Leu Arg
                565                 570                 575

Tyr Leu Ser Asn Asp Ile Trp Gln Pro Asn Thr Lys Ser Ile Met Thr
            580                 585                 590

Val Gly Thr Asn Leu Glu Asn Val Tyr Phe Lys Lys Ala Gly Gln Val
        595                 600                 605

Leu Gly Asn Ser Ala Pro Phe Ala Phe His Glu Asp Phe Thr Gly Ile
    610                 615                 620

Thr Val Lys Gln Leu Thr Ser Tyr Gly Asp Leu Asn Pro Glu Ile
625                 630                 635                 640

Pro Leu Leu Ile Leu Asn Gly Phe Glu Tyr Val Thr Gln Trp Ser Gly
                645                 650                 655

Asp Pro Tyr Ala Val Pro Leu Arg Ala Asp Thr Ser Lys Pro Lys Leu
            660                 665                 670

Thr Gln Gln Asp Val Thr Asp Leu Ile Ala Tyr Leu Asn Lys Gly Gly
        675                 680                 685

Ser Val Leu Ile Met Glu Asn Val Met Ser Asn Leu Lys Glu Glu Ser
```

```
            690                 695                 700
Ala Ser Ser Phe Val Arg Leu Leu Asp Ala Ala Gly Leu Ser Met Ala
705                 710                 715                 720

Leu Asn Lys Ser Val Val Asn Asp Pro Gln Gly Tyr Pro Asp Arg
                725                 730                 735

Val Arg Gln Arg Arg Ala Thr Gly Ile Trp Val Tyr Glu Arg Tyr Pro
                740                 745                 750

Ala Ala Asp Gly Ala Gln Pro Pro Tyr Thr Ile Asp Pro Asn Thr Gly
                755                 760                 765

Glu Val Thr Trp Lys Tyr Gln Gln Asp Asn Lys Pro Asp Lys Pro
770                 775                 780

Lys Leu Glu Val Ala Ser Trp Gln Glu Val Gly Lys Gln Val
785                 790                 795                 800

Thr Arg Tyr Ala Phe Ile Asp Glu Ala Glu Tyr Thr Thr Glu Glu Ser
                805                 810                 815

Leu Glu Ala Ala Lys Ala Lys Ile Phe Glu Lys Phe Pro Gly Leu Gln
                820                 825                 830

Glu Cys Lys Asp Ser Thr Tyr His Tyr Glu Ile Asn Cys Leu Glu Arg
                835                 840                 845

Arg Pro Gly Thr Asp Val Pro Val Thr Gly Gly Met Tyr Val Pro Arg
                850                 855                 860

Tyr Thr Gln Leu Asn Leu Asp Ala Asp Thr Ala Lys Ala Met Val Gln
865                 870                 875                 880

Ala Ala Asp Leu Gly Thr Asn Ile Gln Arg Leu Tyr Gln His Glu Leu
                885                 890                 895

Tyr Phe Arg Thr Lys Gly Ser Lys Gly Glu Arg Leu Asn Ser Val Asp
                900                 905                 910

Leu Glu Arg Leu Tyr Gln Asn Met Ser Val Trp Leu Trp Asn Asp Thr
                915                 920                 925

Lys Tyr Arg Tyr Glu Glu Gly Lys Glu Asp Glu Leu Gly Phe Lys Thr
                930                 935                 940

Phe Thr Glu Phe Leu Asn Cys Tyr Ala Asn Asp Ala Tyr Ala Gly Gly
945                 950                 955                 960

Thr Lys Cys Ser Ala Asp Leu Lys Lys Ser Leu Val Asp Asn Asn Met
                965                 970                 975

Ile Tyr Gly Asp Gly Ser Ser Lys Ala Gly Met Met Asn Pro Ser Tyr
                980                 985                 990

Pro Leu Asn Tyr Met Glu Lys Pro Leu Thr Arg Leu Met Leu Gly Arg
                995                 1000                1005

Ser Trp Trp Asp Leu Asn Ile Lys Val Asp Val Glu Lys Tyr Pro Gly
                1010                1015                1020

Ser Val Ser Ala Lys Gly Glu Ser Val Thr Glu Asn Ile Ser Leu Tyr
1025                1030                1035                1040

Ser Asn Pro Thr Lys Trp Phe Ala Gly Asn Met Gln Ser Thr Gly Leu
                1045                1050                1055

Trp Ala Pro Ala Gln Gln Asp Val Thr Ile Lys Ser Ser Ala Ser Val
                1060                1065                1070

Pro Val Thr Val Thr Val Ala Leu Ala Asp Asp Leu Thr Gly Arg Glu
                1075                1080                1085

Lys His Glu Val Ala Leu Asn Arg Pro Pro Arg Val Thr Lys Thr Tyr
                1090                1095                1100

Thr Leu Glu Ala Asn Gly Glu Val Thr Phe Lys Val Pro Tyr Gly Gly
1105                1110                1115                1120
```

Leu Ile Tyr Ile Lys Gly Asp Ser Lys Asp Asp Val Ser Ala Asn Phe
                1125                1130                1135

Thr Phe Thr Gly Val Val Lys Ala Pro Phe Tyr Lys Asp Gly Glu Trp
                1140                1145                1150

Lys Asn Asp Leu Asp Ser Pro Ala Pro Leu Gly Glu Leu Glu Ser Ala
                1155                1160                1165

Ser Phe Val Tyr Thr Thr Pro Lys Lys Asn Leu Glu Ala Ser Asn Phe
                1170                1175                1180

Thr Gly Gly Val Ala Glu Phe Ala Lys Asp Leu Asp Thr Phe Ala Ser
1185                1190                1195                1200

Ser Met Asn Asp Phe Tyr Gly Arg Asn Asp Glu Asp Gly Lys His Arg
                1205                1210                1215

Met Phe Thr Tyr Lys Asn Leu Thr Gly His Lys His Arg Phe Thr Asn
                1220                1225                1230

Asp Val Gln Ile Ser Ile Gly Asp Ala His Ser Gly Tyr Pro Val Met
                1235                1240                1245

Asn Ser Ser Phe Ser Thr Asn Ser Thr Thr Leu Pro Thr Pro Thr Leu
                1250                1255                1260

Asn Asp Trp Leu Ile Trp His Glu Val Gly His Asn Ala Ala Glu Thr
1265                1270                1275                1280

Pro Leu Asn Val Pro Gly Ala Thr Glu Val Ala Asn Asn Val Leu Ala
                1285                1290                1295

Leu Tyr Met Gln Asp Arg Tyr Leu Gly Lys Met Asn Arg Val Ala Asp
                1300                1305                1310

Asp Ile Thr Val Ala Pro Glu Tyr Leu Asp Glu Ser Asn Gly Gln Ala
                1315                1320                1325

Trp Ala Arg Gly Gly Ala Gly Asp Arg Leu Leu Met Tyr Ala Gln Leu
                1330                1335                1340

Lys Glu Trp Ala Glu Glu Asn Phe Asp Ile Lys Gln Trp Tyr Pro Asp
1345                1350                1355                1360

Gly Glu Leu Pro Lys Phe Tyr Ser Asp Arg Lys Gly Met Lys Gly Trp
                1365                1370                1375

Asn Leu Phe Gln Leu Met His Arg Lys Ala Arg Gly Asp Asp Val Gly
                1380                1385                1390

Asn Ser Thr Phe Gly Gly Lys Asn Tyr Cys Ala Glu Ser Asn Gly Asn
                1395                1400                1405

Ala Ala Asp Thr Leu Met Leu Cys Ala Ser Trp Val Ala Gln Ala Asp
                1410                1415                1420

Leu Ser Glu Phe Phe Lys Lys Trp Asn Pro Gly Ala Ser Ala Tyr Gln
1425                1430                1435                1440

Leu Pro Gly Ala Thr Glu Met Ser Phe Gln Gly Gly Val Ser Ser Ser
                1445                1450                1455

Ala Tyr Ser Thr Leu Ala Ser Leu Lys Leu Pro Lys Pro Glu Lys Gly
                1460                1465                1470

Pro Glu Thr Ile Asn Lys Val Thr Glu His Lys Met Ser Ala Glu
                1475                1480                1485

<210> SEQ ID NO 15
<211> LENGTH: 4293
<212> TYPE: DNA
<213> ORGANISM: Escherichia coli

<400> SEQUENCE: 15
aaaacgggtt atctgaccct gggcggaagc cagcgggtaa ctggtgctac ctgtaatggt      60

-continued

```
gaatccagcg atggctttac ctttacgcca ggcaataccg tgagttgtgt ggtgggcagt      120
acgaccattg caacattcaa cacccagtca gaagctgcgc gtagcctgcg tgcggttgac      180
aaagtgtcgt ttagcctgga ggacgcgcag gagctggcga attctgaaaa taagaaaacc      240
aacgccatct ctctggtgac gtccagcgac agttgccccg cagatgcaga acagctttgt      300
cttactttct cgtcagtggt tgatcgcgcg cgatttgaaa aactgtataa gcaaattgat      360
ctggcaacag acaatttcag caagctggtc aatgaagagg tggaaaacaa tgctgcgact      420
gataaagcgc cgtccaccca tacctcaacg gtagtgccag tcacgacaga gggaacaaaa      480
ccggatctga acgcgtcctt cgtgtcggct aacgcgaaac agttttatca gtatcaaccc      540
actgaaatca ttcttccga aggccaactg gtggatagcc tggggaacgg tgttgctggc      600
gttgactact acaccaattc aggccgtggc gtaactgacg aaaacggtaa attttccttt      660
agctggggcg aaaccatctc ctttggtatc gatacctttg aactgggctc agtacgtggc      720
aataagtcga ccattgcgct gactgaattg ggtgatgaag ttcgcggggc aaatatcgat      780
cagctcattc atcgttattc gacgactggt caaaataata ctcgtgttgt tccggacgat      840
gtacgcaagg tctttgccga atatcccaac gtgatcaacg agataatcaa tctttcgtta      900
tccaacggtg cgacgctgga tgaaggcgat caaaacgttg tgctgcctaa cgaatttatc      960
gagcagttta agacgggtca ggccaaagag atcgataccg cgatttgtgc gaaaaccgac     1020
ggttgtaacg aggctcgctg gttctcgctg acaacgcgca atgttaatga cggccagatt     1080
cagggcgtta ttaacaagct gtggggcgtg gatacgaact atcagtctgt cagcaagttc     1140
cacgtcttcc atgactctac caacttctat ggcagcaccg gtaacgcgcg cggtcaggcg     1200
gtggtaaata tctccaactc ggcattcccg attctgatgg cgcgtaatga taaaaactac     1260
tggctggcgt ttggcgaaaa acgcgcctgg gataaaaatg agctggcgta cattacggaa     1320
gcgccttcca ttgtgcagcc agagaacgtt acgcgcgata ctgcgacttt caacctgccg     1380
tttatttcgc tggggcaagt cggtgaaggc aaactgatgg ttatcggtaa cccgcactac     1440
aacagcatcc tgcgttgccc gaacggttac agttggggcg gtggtgttaa tagtaaaggt     1500
gagtgtacgc tcagcggtga ttctgatgac atgaagcact ttatgcagaa cgtactgcgc     1560
tacttgtcaa atgacatctg gcagccaaat accaagagca tcatgactgt cggcaccaac     1620
ctggagaacg tttatttcaa aaaagcgggc caggtattgg gaaatagtgc accatttgct     1680
ttccatgagg atttcactgg tatcacggtt aaacagttga ccagctatgg cgatctgaat     1740
ccggaagaga ttccgttgct gatcctcaac ggctttgaat atgtgactca gtggtctggc     1800
gatccctatg ctgtgcctct gcgtgcagat accagcaaac cgaagctgac tcagcaggat     1860
gtgaccgatc tgatcgctta tctgaacaaa ggtggctcgg tgctgatcat ggaaaacgtg     1920
atgagcaatc ttaaggaaga gagcgcgtcc agttttgtgc gtctgctgga tgccgcgggt     1980
ctgtcaatgg ctctgaacaa atcggtggtg aacaacgatc cgcaagggta tccggatcgc     2040
gttcgtcagc gtcgcgcgac tggcatttgg gtttatgaac gttatcctgc tgcagacggc     2100
gcgcaaccgc cgtacaccat cgacccaaat acaggggaag tgacctggaa ataccagcaa     2160
gacaacaagc ctgatgacaa gccgaaactg gaagttgcga gctggcagga ggaagttgag     2220
ggcaaacagg taacgcgtta tgcctttatt gatgaagcgg aatacacaac agaagaatct     2280
ctggaagcgc aaaggcaaa atctttgag aagtttcctg ggttacagga gtgtaaggac     2340
tcgacttacc attacgagat taactgtttg gagcgccgcc caggcacgga tgttccggta     2400
```

| | |
|---|---|
| acaggtggca tgtatgttcc gcgctatacg caactgaatc ttgacgccga caccgcgaaa | 2460 |
| gcgatggtgc aggcggcgga tttaggcacc aacattcagc gcctgtatca gcatgagctt | 2520 |
| tatttccgta ccaaaggcag taaaggtgag cgtctgaaca gtgttgatct ggaacgtctg | 2580 |
| taccagaaca tgtcggtctg gctgtggaac gatacgaaat atcgttacga agagggcaag | 2640 |
| gaagatgagc tgggctttaa aacgttcacc gagttcctga actgctacgc caatgatgcc | 2700 |
| tatgcaggcg gcaccaagtg ctccgcagat ctgaaaaaat cgctggtcga taacaacatg | 2760 |
| atctacggtg acgtagcag caaagcgggc atgatgaacc caagctatcc gctcaactat | 2820 |
| atggaaaaac cgctgacgcg tctgatgctg ggccgttcct ggtgggatct gaacattaag | 2880 |
| gttgatgtgg agaagtaccc aggatccgta tcggcaaagg gtgagagcgt tacggaaaac | 2940 |
| atcagcctgt actcgaatcc gaccaaatgg tttgcgggta acatgcagtc aaccggcctg | 3000 |
| tgggcaccgg cccagcagga cgtcaccatt aagtcttcgg cgtcagtccc agtgactgtt | 3060 |
| accgtggcgc tggctgacga cctgactgga cgtgagaagc atgaagttgc gctgaaccgt | 3120 |
| ccgccaagag tgactaaaac gtatactctg gaggctaacg tgaagtgac cttcaaggtg | 3180 |
| ccttatggtg gtctgattta tcaagggc gacagtaagg atgatgtttc tgctaacttc | 3240 |
| acctttaccg gtgtagtaaa agcgccgttc tataaagacg gcgaatggaa aaacgatctg | 3300 |
| gactcaccgg cgccgctggg cgagctggag tctgcgtcgt tcgtctatac cacgccgaag | 3360 |
| aagaaccttg aggccagcaa tttcactggt ggtgtagcag aattcgctaa agatctggat | 3420 |
| acctttgcca gctcgatgaa tgacttctac ggtcgtaatg atgaagacgg taagcaccgg | 3480 |
| atgtttacct ataaaaactt gacggggcac aagcatcgtt tcaccaacga tgtgcagatc | 3540 |
| tccatcggtg atgcgcactc gggttatccg gtaatgaaca gcagcttctc gacgaacagc | 3600 |
| accacgctgc cgacgacgcc gctgaacgac tggctgattt ggcacgaagt cggtcataac | 3660 |
| gctgcagaaa caccgctgaa cgtaccgggt gcaactgaag tggcgaacaa cgtgctggcg | 3720 |
| ctgtacatgc aggatcgcta tctcggtaag atgaaccgtg tcgctgacga cattaccgtc | 3780 |
| gcgccggaat atctggacga gagcaacggt caggcctggg cgcgcggcgg tgcgggtgac | 3840 |
| cgtctgctga tgtacgcaca gttgaaggag tgggcagaga aaaactttga tatcaaacag | 3900 |
| tggtatccag atggtgagct gcctaagttc tacagcgatc gtaaagggat gaagggctgg | 3960 |
| aacctgttcc agttgatgca ccgtaaagcg cgcggcgatg atgttggtaa cagcaccttt | 4020 |
| ggtggcaaga attactgtgc tgaatccaat ggtaacgctg ccgacacgct gatgctgtgt | 4080 |
| gcatcctggg tcgctcaggc ggatctttcg gaattcttta agaaatggaa tccgggtgca | 4140 |
| agtgcttacc agttgccggg agcaacggag atgagtttcc agggcggtgt gagctcttcg | 4200 |
| gcttacagca cgctggcgtc actcaagctg ccgaaaccgg aaaagggcc ggaaaccatt | 4260 |
| aacaaggtta ccgagcataa gatgtctgcc gag | 4293 |

<210> SEQ ID NO 16
<211> LENGTH: 1431
<212> TYPE: PRT
<213> ORGANISM: Escherichia coli

<400> SEQUENCE: 16

Lys Thr Gly Tyr Leu Thr Leu Gly Gly Ser Gln Arg Val Thr Gly Ala
1               5                   10                  15

Thr Cys Asn Gly Glu Ser Ser Asp Gly Phe Thr Phe Thr Pro Gly Asn
            20                  25                  30

Thr Val Ser Cys Val Val Gly Ser Thr Thr Ile Ala Thr Phe Asn Thr

```
                35                  40                  45
Gln Ser Glu Ala Ala Arg Ser Leu Arg Ala Val Asp Lys Val Ser Phe
 50                  55                  60

Ser Leu Glu Asp Ala Gln Glu Leu Ala Asn Ser Glu Asn Lys Lys Thr
 65                  70                  75                  80

Asn Ala Ile Ser Leu Val Thr Ser Ser Asp Ser Cys Pro Ala Asp Ala
                 85                  90                  95

Glu Gln Leu Cys Leu Thr Phe Ser Ser Val Val Asp Arg Ala Arg Phe
            100                 105                 110

Glu Lys Leu Tyr Lys Gln Ile Asp Leu Ala Thr Asp Asn Phe Ser Lys
        115                 120                 125

Leu Val Asn Glu Glu Val Glu Asn Ala Ala Thr Asp Lys Ala Pro
    130                 135                 140

Ser Thr His Thr Ser Thr Val Val Pro Val Thr Thr Glu Gly Thr Lys
145                 150                 155                 160

Pro Asp Leu Asn Ala Ser Phe Val Ser Ala Asn Ala Glu Gln Phe Tyr
                165                 170                 175

Gln Tyr Gln Pro Thr Glu Ile Ile Leu Ser Glu Gly Gln Leu Val Asp
            180                 185                 190

Ser Leu Gly Asn Gly Val Ala Gly Val Asp Tyr Tyr Thr Asn Ser Gly
        195                 200                 205

Arg Gly Val Thr Asp Glu Asn Gly Lys Phe Ser Phe Ser Trp Gly Glu
    210                 215                 220

Thr Ile Ser Phe Gly Ile Asp Thr Phe Glu Leu Gly Ser Val Arg Gly
225                 230                 235                 240

Asn Lys Ser Thr Ile Ala Leu Thr Glu Leu Gly Asp Glu Val Arg Gly
                245                 250                 255

Ala Asn Ile Asp Gln Leu Ile His Arg Tyr Ser Thr Thr Gly Gln Asn
            260                 265                 270

Asn Thr Arg Val Val Pro Asp Asp Val Arg Lys Val Phe Ala Glu Tyr
        275                 280                 285

Pro Asn Val Ile Asn Glu Ile Ile Asn Leu Ser Leu Ser Asn Gly Ala
    290                 295                 300

Thr Leu Asp Glu Gly Asp Gln Asn Val Val Leu Pro Asn Glu Phe Ile
305                 310                 315                 320

Glu Gln Phe Lys Thr Gly Gln Ala Lys Glu Ile Asp Thr Ala Ile Cys
                325                 330                 335

Ala Lys Thr Asp Gly Cys Asn Glu Ala Arg Trp Phe Ser Leu Thr Thr
            340                 345                 350

Arg Asn Val Asn Asp Gly Gln Ile Gln Gly Val Ile Asn Lys Leu Trp
        355                 360                 365

Gly Val Asp Thr Asn Tyr Gln Ser Val Ser Lys Phe His Val Phe His
    370                 375                 380

Asp Ser Thr Asn Phe Tyr Gly Ser Thr Gly Asn Ala Arg Gly Gln Ala
385                 390                 395                 400

Val Val Asn Ile Ser Asn Ser Ala Phe Pro Ile Leu Met Ala Arg Asn
                405                 410                 415

Asp Lys Asn Tyr Trp Leu Ala Phe Gly Glu Lys Arg Ala Trp Asp Lys
            420                 425                 430

Asn Glu Leu Ala Tyr Ile Thr Glu Ala Pro Ser Ile Val Gln Pro Glu
        435                 440                 445

Asn Val Thr Arg Asp Thr Ala Thr Phe Asn Leu Pro Phe Ile Ser Leu
    450                 455                 460
```

```
Gly Gln Val Gly Glu Gly Lys Leu Met Val Ile Gly Asn Pro His Tyr
465                 470                 475                 480

Asn Ser Ile Leu Arg Cys Pro Asn Gly Tyr Ser Trp Gly Gly Val
            485                 490                 495

Asn Ser Lys Gly Glu Cys Thr Leu Ser Gly Asp Ser Asp Met Lys
            500                 505                 510

His Phe Met Gln Asn Val Leu Arg Tyr Leu Ser Asn Asp Ile Trp Gln
        515                 520                 525

Pro Asn Thr Lys Ser Ile Met Thr Val Gly Thr Asn Leu Glu Asn Val
        530                 535                 540

Tyr Phe Lys Lys Ala Gly Gln Val Leu Gly Asn Ser Ala Pro Phe Ala
545                 550                 555                 560

Phe His Glu Asp Phe Thr Gly Ile Thr Val Lys Gln Leu Thr Ser Tyr
            565                 570                 575

Gly Asp Leu Asn Pro Glu Glu Ile Pro Leu Ile Leu Asn Gly Phe
            580                 585                 590

Glu Tyr Val Thr Gln Trp Ser Gly Asp Pro Tyr Ala Val Pro Leu Arg
        595                 600                 605

Ala Asp Thr Ser Lys Pro Lys Leu Thr Gln Gln Asp Val Thr Asp Leu
        610                 615                 620

Ile Ala Tyr Leu Asn Lys Gly Gly Ser Val Leu Ile Met Glu Asn Val
625                 630                 635                 640

Met Ser Asn Leu Lys Glu Glu Ser Ala Ser Ser Phe Val Arg Leu Leu
            645                 650                 655

Asp Ala Ala Gly Leu Ser Met Ala Leu Asn Lys Ser Val Val Asn Asn
            660                 665                 670

Asp Pro Gln Gly Tyr Pro Asp Arg Val Arg Gln Arg Ala Thr Gly
            675                 680                 685

Ile Trp Val Tyr Glu Arg Tyr Pro Ala Ala Asp Gly Ala Gln Pro Pro
        690                 695                 700

Tyr Thr Ile Asp Pro Asn Thr Gly Glu Val Thr Trp Lys Tyr Gln Gln
705                 710                 715                 720

Asp Asn Lys Pro Asp Asp Lys Pro Lys Leu Glu Val Ala Ser Trp Gln
            725                 730                 735

Glu Glu Val Glu Gly Lys Gln Val Thr Arg Tyr Ala Phe Ile Asp Glu
            740                 745                 750

Ala Glu Tyr Thr Thr Glu Glu Ser Leu Glu Ala Ala Lys Ala Lys Ile
        755                 760                 765

Phe Glu Lys Phe Pro Gly Leu Gln Glu Cys Lys Asp Ser Thr Tyr His
        770                 775                 780

Tyr Glu Ile Asn Cys Leu Glu Arg Arg Pro Gly Thr Asp Val Pro Val
785                 790                 795                 800

Thr Gly Gly Met Tyr Val Pro Arg Tyr Thr Gln Leu Asn Leu Asp Ala
            805                 810                 815

Asp Thr Ala Lys Ala Met Val Gln Ala Asp Leu Gly Thr Asn Ile
        820                 825                 830

Gln Arg Leu Tyr Gln His Glu Leu Tyr Phe Arg Thr Lys Gly Ser Lys
        835                 840                 845

Gly Glu Arg Leu Asn Ser Val Asp Leu Glu Arg Leu Tyr Gln Asn Met
        850                 855                 860

Ser Val Trp Leu Trp Asn Asp Thr Lys Tyr Arg Tyr Glu Glu Gly Lys
865                 870                 875                 880
```

```
Glu Asp Glu Leu Gly Phe Lys Thr Phe Thr Glu Phe Leu Asn Cys Tyr
                885                 890                 895

Ala Asn Asp Ala Tyr Ala Gly Gly Thr Lys Cys Ser Ala Asp Leu Lys
            900                 905                 910

Lys Ser Leu Val Asp Asn Asn Met Ile Tyr Gly Asp Gly Ser Ser Lys
            915                 920                 925

Ala Gly Met Met Asn Pro Ser Tyr Pro Leu Asn Tyr Met Glu Lys Pro
        930                 935                 940

Leu Thr Arg Leu Met Leu Gly Arg Ser Trp Trp Asp Leu Asn Ile Lys
945                 950                 955                 960

Val Asp Val Glu Lys Tyr Pro Gly Ser Val Ser Ala Lys Gly Glu Ser
                965                 970                 975

Val Thr Glu Asn Ile Ser Leu Tyr Ser Asn Pro Thr Lys Trp Phe Ala
            980                 985                 990

Gly Asn Met Gln Ser Thr Gly Leu Trp Ala Pro Ala Gln Gln Asp Val
        995                 1000                1005

Thr Ile Lys Ser Ser Ala Ser Val Pro Val Thr Val Thr Val Ala Leu
    1010                1015                1020

Ala Asp Asp Leu Thr Gly Arg Glu Lys His Glu Val Ala Leu Asn Arg
1025                1030                1035                1040

Pro Pro Arg Val Thr Lys Thr Tyr Thr Leu Glu Ala Asn Gly Glu Val
                1045                1050                1055

Thr Phe Lys Val Pro Tyr Gly Gly Leu Ile Tyr Ile Lys Gly Asp Ser
                1060                1065                1070

Lys Asp Asp Val Ser Ala Asn Phe Thr Phe Thr Gly Val Val Lys Ala
            1075                1080                1085

Pro Phe Tyr Lys Asp Gly Glu Trp Lys Asn Asp Leu Asp Ser Pro Ala
            1090                1095                1100

Pro Leu Gly Glu Leu Glu Ser Ala Ser Phe Val Tyr Thr Thr Pro Lys
1105                1110                1115                1120

Lys Asn Leu Glu Ala Ser Asn Phe Thr Gly Gly Val Ala Glu Phe Ala
                1125                1130                1135

Lys Asp Leu Asp Thr Phe Ala Ser Ser Met Asn Asp Phe Tyr Gly Arg
            1140                1145                1150

Asn Asp Glu Asp Gly Lys His Arg Met Phe Thr Tyr Lys Asn Leu Thr
            1155                1160                1165

Gly His Lys His Arg Phe Thr Asn Asp Val Gln Ile Ser Ile Gly Asp
        1170                1175                1180

Ala His Ser Gly Tyr Pro Val Met Asn Ser Ser Phe Ser Thr Asn Ser
1185                1190                1195                1200

Thr Thr Leu Pro Thr Thr Pro Leu Asn Asp Trp Leu Ile Trp His Glu
            1205                1210                1215

Val Gly His Asn Ala Ala Glu Thr Pro Leu Asn Val Pro Gly Ala Thr
        1220                1225                1230

Glu Val Ala Asn Asn Val Leu Ala Leu Tyr Met Gln Asp Arg Tyr Leu
        1235                1240                1245

Gly Lys Met Asn Arg Val Ala Asp Asp Ile Thr Val Ala Pro Glu Tyr
        1250                1255                1260

Leu Asp Glu Ser Asn Gly Gln Ala Trp Ala Arg Gly Gly Ala Gly Asp
1265                1270                1275                1280

Arg Leu Leu Met Tyr Ala Gln Leu Lys Glu Trp Ala Glu Glu Asn Phe
                1285                1290                1295

Asp Ile Lys Gln Trp Tyr Pro Asp Gly Glu Leu Pro Lys Phe Tyr Ser
```

```
                  1300             1305                1310
Asp Arg Lys Gly Met Lys Gly Trp Asn Leu Phe Gln Leu Met His Arg
            1315                1320                1325

Lys Ala Arg Gly Asp Asp Val Gly Asn Ser Thr Phe Gly Gly Lys Asn
        1330                1335                1340

Tyr Cys Ala Glu Ser Asn Gly Asn Ala Ala Asp Thr Leu Met Leu Cys
1345                1350                1355                1360

Ala Ser Trp Val Ala Gln Ala Asp Leu Ser Glu Phe Phe Lys Lys Trp
                1365                1370                1375

Asn Pro Gly Ala Ser Ala Tyr Gln Leu Pro Gly Ala Thr Glu Met Ser
            1380                1385                1390

Phe Gln Gly Gly Val Ser Ser Ser Ala Tyr Ser Thr Leu Ala Ser Leu
                1395                1400                1405

Lys Leu Pro Lys Pro Glu Lys Gly Pro Glu Thr Ile Asn Lys Val Thr
            1410                1415                1420

Glu His Lys Met Ser Ala Glu
1425                1430

<210> SEQ ID NO 17
<211> LENGTH: 4491
<212> TYPE: DNA
<213> ORGANISM: Escherichia coli

<400> SEQUENCE: 17
tgtgatggtg gtggttcagg atcgtcctcc gatacgccgt ctgtagattc tggatcaggg     60
actttgccgg aagtgaaacc cgatccaaca ccaaccccgg agccgacacc tgagccgacg    120
ccggacccag aacctacgcc ggatccaaca cctgatcctg agccgacacc agaaccggag    180
ccagaacctg ttcctacgaa aacgggttat ctgaccctgg cggaagcca gcgggtaact    240 ggtgctacct gtaatggtga atccagcgat ggctttacct ttacgccagg caataccgtg    300
agttgtgtgg tgggcagtac gaccattgca acattcaaca cccagtcaga agctgcgcgt    360
agcctgcgtg cggttgacaa agtgtcgttt agcctggagg acgcgcagga gctggcgaat    420
tctgaaaata agaaaaccaa cgccatctct ctggtgacgt ccagcgacag ttgccccgca    480
gatgcagaac agctttgtct tactttctcg tcagtggttg atcgcgcgcg atttgaaaaa    540
ctgtataagc aaattgatct ggcaacagac aatttcagca agctggtcaa tgaagaggtg    600
gaaaacaatg ctgcgactga taaagcgccg tccacccata cctcaacggt agtgccagtc    660
acgacagagg gaacaaaacc ggatctgaac gcgtccttcg tgtcggctaa cgcggaacag    720
ttttatcagt atcaacccac tgaaatcatt ctttccgaag gccaactggt ggatagcctg    780
gggaacggtg ttgctggcgt tgactactac accaattcag gccgtggcgt aactgacgaa    840
aacggtaaat tttcctttag ctggggcgaa accatctcct ttggtatcga tacctttgaa    900
ctgggctcag tacgtggcaa taagtcgacc attgcgctga ctgaattggg tgatgaagtt    960 cgcgggcaa atatcgatca gctcattcat cgttattcga cgactggtca aaataatact   1020
cgtgttgttc cggacgatgt acgcaaggtc tttgccgaat atcccaacgt gatcaacgag   1080
ataatcaatc tttcgttatc caacggtgcg acgctggatg aaggcgatca aaacgttgtg   1140
ctgcctaacg aatttatcga gcagtttaag acgggtcagg ccaaagagat cgataccgcg   1200
atttgtgcga aaaccgacgg ttgtaacgag gctcgctggt tctcgctgac aacgcgcaat   1260
gttaatgacg gccagattca gggcgttatt aacaagctgt ggggcgtgga tacgaactat   1320
cagtctgtca gcaagttcca cgtcttccat gactctacca acttctatgg cagcaccggt   1380
```

-continued

```
aacgcgcgcg gtcaggcggt ggtaaatatc tccaactcgg cattcccgat tctgatggcg    1440
cgtaatgata aaaactactg gctggcgttt ggcgaaaaac gcgcctggga taaaaatgag    1500
ctggcgtaca ttacggaagc gccttccatt gtgcagccag agaacgttac gcgcgatact    1560
gcgactttca acctgccgtt tatttcgctg ggcaagtcg gtgaaggcaa actgatggtt     1620
atcggtaacc cgcactacaa cagcatcctg cgttgcccga acggttacag ttggggcggt    1680
ggtgttaata gtaaaggtga gtgtacgctc agcggtgatt ctgatgacat gaagcacttt    1740
atgcagaacg tactgcgcta cttgtcaaat gacatctggc agccaaatac caagagcatc    1800
atgactgtcg gcaccaacct ggagaacgtt tatttcaaaa aagcgggcca ggtattggga    1860
aatagtgcac catttgcttt ccatgaggat ttcactggta tcacggttaa acagttgacc    1920
agctatggcg atctgaatcc ggaagagatt ccgttgctga tcctcaacgg ctttgaatat    1980
gtgactcagt ggtctggcga tccctatgct gtgcctctgc gtgcagatac cagcaaaccg    2040
aagctgactc agcaggatgt gaccgatctg atcgcttatc tgaacaaagg tggctcggtg    2100
ctgatcatgg aaaacgtgat gagcaatctt aaggaagaga gcgcgtccag ttttgtgcgt    2160
ctgctggatg ccgcgggtct gtcaatggct ctgaacaaat cggtggtgaa caacgatccg    2220
caagggtatc cggatcgcgt tcgtcagcgt cgcgcgactg gcatttgggt ttatgaacgt    2280
tatcctgctg cagacggcgc gcaaccgccg tacaccatcg acccaaatac aggggaagtg    2340
acctggaaat accagcaaga caacaagcct gatgacaagc cgaaactgga agttgcgagc    2400
tggcaggagg aagttgaggg caaacaggta acgcgttatg cctttattga tgaagcggaa    2460
tacacaacag aagaatctct ggaagcggca aaggcaaaaa tctttgagaa gtttcctggg    2520
ttacaggagt gtaaggactc gacttaccat tacgagatta actgtttgga gcgccgccca    2580
ggcacggatg ttccggtaac aggtggcatg tatgttccgc gctatacgca actgaatctt    2640
gacgccgaca ccgcgaaagc gatggtgcag gcggcggatt taggcaccaa cattcagcgc    2700
ctgtatcagc atgagcttta tttccgtacc aaaggcagta aaggtgagcg tctgaacagt    2760
gttgatctgg aacgtctgta ccagaacatg tcggtctggc tgtggaacga tacgaaaatat    2820
cgttacgaag agggcaagga agatgagctg ggctttaaaa cgttcaccga gttcctgaac    2880
tgctacgcca atgatgccta tgcaggcggc accaagtgct ccgcagatct gaaaaaatcg    2940
ctggtcgata caacatgat  ctacggtgac ggtagcagca agcgggcat  gatgaaccca    3000
agctatccgc tcaactatat ggaaaaaccg ctgacgcgtc tgatgctggg ccgttcctgg    3060
tgggatctga acattaaggt tgatgtggag aagtacccag gatccgtatc ggcaaagggt    3120
gagagcgtta cggaaaacat cagcctgtac tcgaatccga ccaaatggtt tgcgggtaac    3180
atgcagtcaa ccgcctgtg  ggcaccggcc cagcaggacg tcaccattaa gtcttcggcg    3240
tcagtcccag tgactgttac cgtggcgctg gctgacgacc tgactggacg tgagaagcat    3300
gaagttgcgc tgaaccgtcc gccaagagtg actaaaacgt atactctgga ggctaacggt    3360
gaagtgacct tcaaggtgcc ttatggtggt ctgatttata tcaagggcga cagtaaggat    3420
gatgtttctg ctaacttcac ctttaccggt gtagtaaaag cgccgttcta taaagacggc    3480
gaatggaaaa acgatctgga ctcaccgcg  ccgctgggcg agctggagtc tgcgtcgttc    3540
gtctatacca cgccgaagaa gaaccttgag gccagcaatt tcactggtgg tgtagcagaa    3600
ttcgctaaag atctggatac ctttgccagc tcgatgaatg acttctacgg tcgtaatgat    3660
gaagacggta agcaccggat gtttacctat aaaaaacttga cggggcacaa gcatcgtttc    3720
```

-continued

```
accaacgatg tgcagatctc catcggtgat gcgcactcgg gttatccggt aatgaacagc    3780
agcttctcga cgaacagcac cacgctgccg acgacgccgc tgaacgactg gctgatttgg    3840
cacgaagtcg gtcataacgc tgcagaaaca ccgctgaacg taccgggtgc aactgaagtg    3900
gcgaacaacg tgctggcgct gtacatgcag gatcgctatc tcggtaagat gaaccgtgtc    3960
gctgacgaca ttaccgtcgc gccggaatat ctggacgaga gcaacggtca ggcctgggcg    4020
cgcggcggtg cgggtgaccg tctgctgatg tacgcacagt tgaaggagtg ggcagaggaa    4080
aactttgata tcaaacagtg gtatccagat ggtgagctgc ctaagttcta cagcgatcgt    4140
aaagggatga agggctggaa cctgttccag ttgatgcacc gtaaagcgcg cggcgatgat    4200
gttggtaaca gcacctttgg tggcaagaat tactgtgctg aatccaatgg taacgctgcc    4260
gacacgctga tgctgtgtgc atcctgggtc gctcaggcgg atctttcgga attctttaag    4320
aaatggaatc cgggtgcaag tgcttaccag ttgccgggag caacgagat gagtttccag    4380 ggcggtgtga gctcttcggc ttacagcacg ctggcgtcac tcaagctgcc gaaaccggaa    4440
aaagggccgg aaaccattaa caaggttacc gagcataaga tgtctgccga g            4491
```

<210> SEQ ID NO 18
<211> LENGTH: 1497
<212> TYPE: PRT
<213> ORGANISM: Escherichia coli

<400> SEQUENCE: 18

```
Cys Asp Gly Gly Gly Ser Gly Ser Ser Ser Asp Thr Pro Ser Val Asp
1               5                   10                  15

Ser Gly Ser Gly Thr Leu Pro Glu Val Lys Pro Asp Pro Thr Pro Thr
                20                  25                  30

Pro Glu Pro Thr Pro Glu Pro Thr Pro Asp Pro Glu Pro Thr Pro Asp
            35                  40                  45

Pro Thr Pro Asp Pro Glu Pro Thr Pro Glu Pro Glu Pro Glu Pro Val
        50                  55                  60

Pro Thr Lys Thr Gly Tyr Leu Thr Leu Gly Gly Ser Gln Arg Val Thr
65                  70                  75                  80

Gly Ala Thr Cys Asn Gly Glu Ser Ser Asp Gly Phe Thr Phe Thr Pro
                85                  90                  95

Gly Asn Thr Val Ser Cys Val Val Gly Ser Thr Thr Ile Ala Thr Phe
            100                 105                 110

Asn Thr Gln Ser Glu Ala Ala Arg Ser Leu Arg Ala Val Asp Lys Val
        115                 120                 125

Ser Phe Ser Leu Glu Asp Ala Gln Glu Leu Ala Asn Ser Glu Asn Lys
    130                 135                 140

Lys Thr Asn Ala Ile Ser Leu Val Thr Ser Ser Asp Ser Cys Pro Ala
145                 150                 155                 160

Asp Ala Glu Gln Leu Cys Leu Thr Phe Ser Ser Val Val Asp Arg Ala
                165                 170                 175

Arg Phe Glu Lys Leu Tyr Lys Gln Ile Asp Leu Ala Thr Asp Asn Phe
            180                 185                 190

Ser Lys Leu Val Asn Glu Glu Val Glu Asn Asn Ala Ala Thr Asp Lys
        195                 200                 205

Ala Pro Ser Thr His Thr Ser Thr Val Val Pro Val Thr Thr Glu Gly
    210                 215                 220

Thr Lys Pro Asp Leu Asn Ala Ser Phe Val Ser Ala Asn Ala Glu Gln
225                 230                 235                 240
```

-continued

```
Phe Tyr Gln Tyr Gln Pro Thr Glu Ile Ile Leu Ser Glu Gly Gln Leu
                245                 250                 255
Val Asp Ser Leu Gly Asn Gly Val Ala Gly Val Asp Tyr Tyr Thr Asn
            260                 265                 270
Ser Gly Arg Gly Val Thr Asp Glu Asn Gly Lys Phe Ser Phe Ser Trp
        275                 280                 285
Gly Glu Thr Ile Ser Phe Gly Ile Asp Thr Phe Glu Leu Gly Ser Val
    290                 295                 300
Arg Gly Asn Lys Ser Thr Ile Ala Leu Thr Glu Leu Gly Asp Glu Val
305                 310                 315                 320
Arg Gly Ala Asn Ile Asp Gln Leu Ile His Arg Tyr Ser Thr Thr Gly
                325                 330                 335
Gln Asn Asn Thr Arg Val Val Pro Asp Asp Val Arg Lys Val Phe Ala
            340                 345                 350
Glu Tyr Pro Asn Val Ile Asn Glu Ile Ile Asn Leu Ser Leu Ser Asn
        355                 360                 365
Gly Ala Thr Leu Asp Glu Gly Asp Gln Asn Val Val Leu Pro Asn Glu
    370                 375                 380
Phe Ile Glu Gln Phe Lys Thr Gly Gln Ala Lys Glu Ile Asp Thr Ala
385                 390                 395                 400
Ile Cys Ala Lys Thr Asp Gly Cys Asn Glu Ala Arg Trp Phe Ser Leu
                405                 410                 415
Thr Thr Arg Asn Val Asn Asp Gly Gln Ile Gln Gly Val Ile Asn Lys
            420                 425                 430
Leu Trp Gly Val Asp Thr Asn Tyr Gln Ser Val Ser Lys Phe His Val
        435                 440                 445
Phe His Asp Ser Thr Asn Phe Tyr Gly Ser Thr Gly Asn Ala Arg Gly
    450                 455                 460
Gln Ala Val Val Asn Ile Ser Asn Ser Ala Phe Pro Ile Leu Met Ala
465                 470                 475                 480
Arg Asn Asp Lys Asn Tyr Trp Leu Ala Phe Gly Glu Lys Arg Ala Trp
                485                 490                 495
Asp Lys Asn Glu Leu Ala Tyr Ile Thr Glu Ala Pro Ser Ile Val Gln
            500                 505                 510
Pro Glu Asn Val Thr Arg Asp Thr Ala Thr Phe Asn Leu Pro Phe Ile
        515                 520                 525
Ser Leu Gly Gln Val Gly Glu Gly Lys Leu Met Val Ile Gly Asn Pro
    530                 535                 540
His Tyr Asn Ser Ile Leu Arg Cys Pro Asn Gly Tyr Ser Trp Gly Gly
545                 550                 555                 560
Gly Val Asn Ser Lys Gly Glu Cys Thr Leu Ser Gly Asp Ser Asp Asp
                565                 570                 575
Met Lys His Phe Met Gln Asn Val Leu Arg Tyr Leu Ser Asn Asp Ile
            580                 585                 590
Trp Gln Pro Asn Thr Lys Ser Ile Met Thr Val Gly Thr Asn Leu Glu
        595                 600                 605
Asn Val Tyr Phe Lys Lys Ala Gly Gln Val Leu Gly Asn Ser Ala Pro
    610                 615                 620
Phe Ala Phe His Glu Asp Phe Thr Gly Ile Thr Val Lys Gln Leu Thr
625                 630                 635                 640
Ser Tyr Gly Asp Leu Asn Pro Glu Glu Ile Pro Leu Leu Ile Leu Asn
                645                 650                 655
Gly Phe Glu Tyr Val Thr Gln Trp Ser Gly Asp Pro Tyr Ala Val Pro
```

-continued

```
                660                 665                 670
Leu Arg Ala Asp Thr Ser Lys Pro Lys Leu Thr Gln Gln Asp Val Thr
            675                 680                 685

Asp Leu Ile Ala Tyr Leu Asn Lys Gly Gly Ser Val Leu Ile Met Glu
        690                 695                 700

Asn Val Met Ser Asn Leu Lys Glu Glu Ser Ala Ser Ser Phe Val Arg
705                 710                 715                 720

Leu Leu Asp Ala Ala Gly Leu Ser Met Ala Leu Asn Lys Ser Val Val
            725                 730                 735

Asn Asn Asp Pro Gln Gly Tyr Pro Asp Arg Val Arg Gln Arg Arg Ala
        740                 745                 750

Thr Gly Ile Trp Val Tyr Glu Arg Tyr Pro Ala Ala Asp Gly Ala Gln
            755                 760                 765

Pro Pro Tyr Thr Ile Asp Pro Asn Thr Gly Val Thr Trp Lys Tyr
        770                 775                 780

Gln Gln Asp Asn Lys Pro Asp Asp Lys Pro Lys Leu Glu Val Ala Ser
785                 790                 795                 800

Trp Gln Glu Glu Val Glu Gly Lys Gln Val Thr Arg Tyr Ala Phe Ile
            805                 810                 815

Asp Glu Ala Glu Tyr Thr Thr Glu Glu Ser Leu Glu Ala Ala Lys Ala
        820                 825                 830

Lys Ile Phe Glu Lys Phe Pro Gly Leu Gln Glu Cys Lys Asp Ser Thr
            835                 840                 845

Tyr His Tyr Glu Ile Asn Cys Leu Glu Arg Arg Pro Gly Thr Asp Val
        850                 855                 860

Pro Val Thr Gly Gly Met Tyr Val Pro Arg Tyr Thr Gln Leu Asn Leu
865                 870                 875                 880

Asp Ala Asp Thr Ala Lys Ala Met Val Gln Ala Ala Asp Leu Gly Thr
            885                 890                 895

Asn Ile Gln Arg Leu Tyr Gln His Glu Leu Tyr Phe Arg Thr Lys Gly
        900                 905                 910

Ser Lys Gly Glu Arg Leu Asn Ser Val Asp Leu Glu Arg Leu Tyr Gln
            915                 920                 925

Asn Met Ser Val Trp Leu Trp Asn Asp Thr Lys Tyr Arg Tyr Glu Glu
        930                 935                 940

Gly Lys Glu Asp Glu Leu Gly Phe Lys Thr Phe Thr Glu Phe Leu Asn
945                 950                 955                 960

Cys Tyr Ala Asn Asp Ala Tyr Ala Gly Gly Thr Lys Cys Ser Ala Asp
            965                 970                 975

Leu Lys Lys Ser Leu Val Asp Asn Asn Met Ile Tyr Gly Asp Gly Ser
        980                 985                 990

Ser Lys Ala Gly Met Met Asn Pro Ser Tyr Pro Leu Asn Tyr Met Glu
            995                 1000                1005

Lys Pro Leu Thr Arg Leu Met Leu Gly Arg Ser Trp Trp Asp Leu Asn
        1010                1015                1020

Ile Lys Val Asp Val Glu Lys Tyr Pro Gly Ser Val Ser Ala Lys Gly
1025                1030                1035                1040

Glu Ser Val Thr Glu Asn Ile Ser Leu Tyr Ser Asn Pro Thr Lys Trp
            1045                1050                1055

Phe Ala Gly Asn Met Gln Ser Thr Gly Leu Trp Ala Pro Ala Gln Gln
        1060                1065                1070

Asp Val Thr Ile Lys Ser Ser Ala Ser Val Pro Val Thr Val Thr Val
            1075                1080                1085
```

```
Ala Leu Ala Asp Asp Leu Thr Gly Arg Glu Lys His Glu Val Ala Leu
    1090                1095                1100

Asn Arg Pro Pro Arg Val Thr Lys Thr Tyr Thr Leu Glu Ala Asn Gly
1105                1110                1115                1120

Glu Val Thr Phe Lys Val Pro Tyr Gly Gly Leu Ile Tyr Ile Lys Gly
                1125                1130                1135

Asp Ser Lys Asp Asp Val Ser Ala Asn Phe Thr Phe Thr Gly Val Val
                1140                1145                1150

Lys Ala Pro Phe Tyr Lys Asp Gly Glu Trp Lys Asn Asp Leu Asp Ser
                1155                1160                1165

Pro Ala Pro Leu Gly Glu Leu Glu Ser Ala Ser Phe Val Tyr Thr Thr
                1170                1175                1180

Pro Lys Lys Asn Leu Glu Ala Ser Asn Phe Thr Gly Gly Val Ala Glu
1185                1190                1195                1200

Phe Ala Lys Asp Leu Asp Thr Phe Ala Ser Ser Met Asn Asp Phe Tyr
                1205                1210                1215

Gly Arg Asn Asp Glu Asp Gly Lys His Arg Met Phe Thr Tyr Lys Asn
                1220                1225                1230

Leu Thr Gly His Lys His Arg Phe Thr Asn Asp Val Gln Ile Ser Ile
                1235                1240                1245

Gly Asp Ala His Ser Gly Tyr Pro Val Met Asn Ser Ser Phe Ser Thr
                1250                1255                1260

Asn Ser Thr Thr Leu Pro Thr Thr Pro Leu Asn Asp Trp Leu Ile Trp
1265                1270                1275                1280

His Glu Val Gly His Asn Ala Ala Glu Thr Pro Leu Asn Val Pro Gly
                1285                1290                1295

Ala Thr Glu Val Ala Asn Asn Val Leu Ala Leu Tyr Met Gln Asp Arg
                1300                1305                1310

Tyr Leu Gly Lys Met Asn Arg Val Ala Asp Asp Ile Thr Val Ala Pro
                1315                1320                1325

Glu Tyr Leu Asp Glu Ser Asn Gly Gln Ala Trp Ala Arg Gly Gly Ala
                1330                1335                1340

Gly Asp Arg Leu Leu Met Tyr Ala Gln Leu Lys Glu Trp Ala Glu Glu
1345                1350                1355                1360

Asn Phe Asp Ile Lys Gln Trp Tyr Pro Asp Gly Glu Leu Pro Lys Phe
                1365                1370                1375

Tyr Ser Asp Arg Lys Gly Met Lys Gly Trp Asn Leu Phe Gln Leu Met
                1380                1385                1390

His Arg Lys Ala Arg Gly Asp Val Gly Asn Ser Thr Phe Gly Gly
                1395                1400                1405

Lys Asn Tyr Cys Ala Glu Ser Asn Gly Asn Ala Ala Asp Thr Leu Met
                1410                1415                1420

Leu Cys Ala Ser Trp Val Ala Gln Ala Asp Leu Ser Glu Phe Phe Lys
1425                1430                1435                1440

Lys Trp Asn Pro Gly Ala Ser Ala Tyr Gln Leu Pro Gly Ala Thr Glu
                1445                1450                1455

Met Ser Phe Gln Gly Gly Val Ser Ser Ser Ala Tyr Ser Thr Leu Ala
                1460                1465                1470

Ser Leu Lys Leu Pro Lys Pro Glu Lys Gly Pro Glu Thr Ile Asn Lys
                1475                1480                1485

Val Thr Glu His Lys Met Ser Ala Glu
                1490                1495
```

<210> SEQ ID NO 19
<211> LENGTH: 4491
<212> TYPE: DNA
<213> ORGANISM: Escherichia coli

<400> SEQUENCE: 19

| | | | | | |
|---|---|---|---|---|---|
| tgtgatggtg | gtggttcagg | atcgtcctcc | gatacgccgt | ctgtagattc | tggatcaggg | 60 |
| actttgccgg | aagtgaaacc | cgatccaaca | ccaaccccgg | agccgacacc | tgagccgacg | 120 |
| ccggacccag | aacctacgcc | ggatccaaca | cctgatcctg | agccgacacc | agaaccggag | 180 |
| ccagaacctg | ttcctacgaa | aacgggttat | ctgaccctgg | gcggaagcca | gcgggtaact | 240 |
| ggtgctacct | gtaatggtga | atccagcgat | ggctttacct | ttacgccagg | caataccgtg | 300 |
| agttgtgtgg | tgggcagtac | gaccattgca | acattcaaca | cccagtcaga | agctgcgcgt | 360 |
| agcctgcgtg | cggttgacaa | agtgtcgttt | agcctggagg | acgcgcagga | gctggcgaat | 420 |
| tctgaaaata | agaaaaccaa | cgccatctct | ctggtgacgt | ccagcgacag | ttgccccgca | 480 |
| gatgcagaac | agctttgtct | tactttctcg | tcagtggttg | atcgcgcgcg | atttgaaaaa | 540 |
| ctgtataagc | aaattgatct | ggcaacagac | aatttcagca | agctggtcaa | tgaagaggtg | 600 |
| gaaaacaatg | ctgcgactga | taaagcgccg | tccacccata | cctcaacggt | agtgccagtc | 660 |
| acgacagagg | gaacaaaacc | ggatctgaac | gcgtccttcg | tgtcggctaa | cgcggaacag | 720 |
| ttttatcagt | atcaacccac | tgaaatcatt | cttttccgaag | gccaactggt | ggatagcctg | 780 |
| gggaacggtg | ttgctggcgt | tgactactac | accaattcag | gccgtggcgt | aactgacgaa | 840 |
| aacggtaaat | tttcctttag | ctggggcgaa | accatctcct | tggtatcga | tacctttgaa | 900 |
| ctgggctcag | tacgtggcaa | taagtcgacc | attgcgctga | ctgaattggg | tgatgaagtt | 960 |
| cgcggggcaa | atatcgatca | gctcattcat | cgttattcga | cgactggtca | aaataatact | 1020 |
| cgtgttgttc | cggacgatgt | acgcaaggtc | tttgccgaat | atcccaacgt | gatcaacgag | 1080 |
| ataatcaatc | tttcgttatc | caacggtgcg | acgctggatg | aaggcgatca | aaacgttgtg | 1140 |
| ctgcctaacg | aatttatcga | gcagtttaag | acgggtcagg | ccaaagagat | cgataccgcg | 1200 |
| atttgtgcga | aaaccgacgg | ttgtaacgag | gctcgctggt | tctcgctgac | aacgcgcaat | 1260 |
| gttaatgacg | gccagattca | gggcgttatt | aacaagctgt | ggggcgtgga | tacgaactat | 1320 |
| cagtctgtca | gcaagttcca | cgtcttccat | gactctacca | acttctatgg | cagcaccggt | 1380 |
| aacgcgcgcg | gtcaggcggt | ggtaaatatc | tccaactcgg | cattcccgat | tctgatggcg | 1440 |
| cgtaatgata | aaaactactg | gctggcgttt | ggcgaaaaac | gcgcctggga | taaaaatgag | 1500 |
| ctggcgtaca | ttacggaagc | gccttccatt | gtgcagccag | agaacgttac | gcgcgatact | 1560 |
| gcgactttca | acctgccgtt | tatttcgctg | gggcaagtcg | gtgaaggcaa | actgatggtt | 1620 |
| atcggtaacc | cgcactacaa | cagcatcctg | cgttgcccga | acggttacag | ttggggcggt | 1680 |
| ggtgttaata | gtaaaggtga | gtgtacgctc | agcggtgatt | ctgatgacat | gaagcacttt | 1740 |
| atgcagaacg | tactgcgcta | cttgtcaaat | gacatctggc | agccaaatac | caagagcatc | 1800 |
| atgactgtcg | gcaccaacct | ggagaacgtt | tatttcaaaa | agcgggcca | ggtattggga | 1860 |
| aatagtgcac | catttgcttt | ccatgaggat | ttcactggta | tcacggttaa | acagttgacc | 1920 |
| agctatggcg | atctgaatcc | ggaagagatt | ccgttgctga | tcctcaacgg | ctttgaatat | 1980 |
| gtgactcagt | ggtctggcga | tcctatgct | gtgcctctgc | gtgcagatac | cagcaaaccg | 2040 |
| aagctgactc | agcaggatgt | gaccgatctg | atcgcttatc | tgaacaaagg | tggctcggtg | 2100 |
| ctgatcatgg | aaaacgtgat | gagcaatctt | aaggaagaga | gcgcgtccag | ttttgtgcgt | 2160 |

```
ctgctggatg ccgcgggtct gtcaatggct ctgaacaaat cggtggtgaa caacgatccg    2220
caagggtatc cggatcgcgt tcgtcagcgt cgcgcgactg gcatttgggt ttatgaacgt    2280
tatcctgctg cagacggcgc gcaaccgccg tacaccatcg acccaaatac aggggaagtg    2340
acctggaaat accagcaaga caacaagcct gatgacaagc cgaaactgga agttgcgagc    2400
tggcaggagg aagttgaggg caaacaggta acgcgttatg cctttattga tgaagcggaa    2460
tacacaacag aagaatctct ggaagcggca aaggcaaaaa tctttgagaa gtttcctggg    2520
ttacaggagt gtaaggactc gacttaccat tacgagatta actgtttgga gcgccgccca    2580
ggcacggatg ttccggtaac aggtggcatg tatgttccgc gctatacgca actgaatctt    2640
gacgccgaca ccgcgaaagc gatggtgcag gcggcggatt taggcaccaa cattcagcgc    2700
ctgtatcagc atgagcttta tttccgtacc aaaggcagta aaggtgagcg tctgaacagt    2760
gttgatctgg aacgtctgta ccagaacatg tcggtctggc tgtggaacga tacgaaatat    2820
cgttacgaag agggcaagga agatgagctg ggctttaaaa cgttcaccga gttcctgaac    2880
tgctacgcca atgatgccta tgcaggcggc accaagtgct ccgcagatct gaaaaaatcg    2940
ctggtcgata caacatgat ctacggtgac ggtagcagca aagcgggcat gatgaaccca    3000
agctatccgc tcaactatat ggaaaaaccg ctgacgcgtc tgatgctggg ccgttcctgg    3060
tgggatctga acattaaggt tgatgtggag aagtacccag gatccgtatc ggcaaagggt    3120
gagagcgtta cggaaaacat cagcctgtac tcgaatccga ccaaatggtt tgcgggtaac    3180
atgcagtcaa ccggcctgtg ggcaccggcc cagcaggacg tcaccattaa gtcttcggcg    3240
tcagtcccag tgactgttac cgtggcgctg gctgacgacc tgactggacg tgagaagcat    3300
gaagttgcgc tgaaccgtcc gccaagagtg actaaaacgt atactctgga ggctaacggt    3360
gaagtgacct tcaaggtgcc ttatggtggt ctgatttata tcaagggcga cagtaaggat    3420
gatgtttctg ctaacttcac ctttaccggt gtagtaaaag cgccgttcta taaagacggc    3480
gaatggaaaa acgatctgga ctcaccggcg ccgctgggcg agctggagtc tgcgtcgttc    3540
gtctatacca cgccgaagaa gaaccttgag gccagcaatt tcactggtgg tgtagcagaa    3600
ttcgctaaag atctggatac ctttgccagc tcgatgaatg acttctacgg tcgtaatgat    3660
gaagacggta agcaccggat gtttacctat aaaaacttga cggggcacaa gcatcgtttc    3720
accaacgatg tgcagatctc catcggtgat gcgcactcgg gttatccggt aatgaacagc    3780
agcttctcga cgaacagcac cacgctgccg acgacgccgc tgaacgactg gctgatttgg    3840
cacgcagtcg gtcataacgc tgcagaaaca ccgctgaacg taccgggtgc aactgaagtg    3900
gcgaacaacg tgctggcgct gtacatgcag gatcgctatc tcggtaagat gaaccgtgtc    3960
gctgacgaca ttaccgtcgc gccggaatat ctggacgaga gcaacggtca ggcctgggcg    4020
cgcggcggtg cgggtgaccg tctgctgatg tacgcacagt tgaaggagtg ggcagaggaa    4080
aactttgata tcaaacagtg gtatccagat ggtgagctgc ctaagttcta cagcgatcgt    4140
aaagggatga agggctggaa cctgttccag ttgatgcacc gtaaagcgcg cggcgatgat    4200
gttggtaaca gcacctttgg tggcaagaat tactgtgctg aatccaatgg taacgctgcc    4260
gacacgctga tgctgtgtgc atcctgggtc gctcaggcgg atcttcgga attctttaag    4320 aaatggaatc cgggtgcaag tgcttaccag ttgccgggag caacggagat gagtttccag    4380
ggcggtgtga gctcttcggc ttacagcacg ctggcgtcac tcaagctgcc gaaaccggaa    4440
aaagggccgg aaaccattaa caaggttacc gagcataaga tgtctgccga g             4491
```

<210> SEQ ID NO 20
<211> LENGTH: 1497
<212> TYPE: PRT
<213> ORGANISM: Escherichia coli

<400> SEQUENCE: 20

```
Cys Asp Gly Gly Gly Ser Gly Ser Ser Asp Thr Pro Ser Val Asp
1               5                   10                  15

Ser Gly Ser Gly Thr Leu Pro Glu Val Lys Pro Asp Pro Thr Pro
                20                  25                  30

Pro Glu Pro Thr Pro Glu Pro Thr Pro Asp Pro Glu Pro Thr Pro Asp
            35                  40                  45

Pro Thr Pro Asp Pro Glu Pro Thr Pro Glu Pro Glu Pro Glu Pro Val
        50                  55                  60

Pro Thr Lys Thr Gly Tyr Leu Thr Leu Gly Gly Ser Gln Arg Val Thr
65                  70                  75                  80

Gly Ala Thr Cys Asn Gly Glu Ser Ser Asp Gly Phe Thr Phe Thr Pro
                85                  90                  95

Gly Asn Thr Val Ser Cys Val Val Gly Ser Thr Thr Ile Ala Thr Phe
                100                 105                 110

Asn Thr Gln Ser Glu Ala Ala Arg Ser Leu Arg Ala Val Asp Lys Val
            115                 120                 125

Ser Phe Ser Leu Glu Asp Ala Gln Glu Leu Ala Asn Ser Glu Asn Lys
    130                 135                 140

Lys Thr Asn Ala Ile Ser Leu Val Thr Ser Ser Asp Ser Cys Pro Ala
145                 150                 155                 160

Asp Ala Glu Gln Leu Cys Leu Thr Phe Ser Ser Val Val Asp Arg Ala
                165                 170                 175

Arg Phe Glu Lys Leu Tyr Lys Gln Ile Asp Leu Ala Thr Asp Asn Phe
                180                 185                 190

Ser Lys Leu Val Asn Glu Val Glu Asn Asn Ala Ala Thr Asp Lys
    195                 200                 205

Ala Pro Ser Thr His Thr Ser Thr Val Val Pro Val Thr Thr Glu Gly
    210                 215                 220

Thr Lys Pro Asp Leu Asn Ala Ser Phe Val Ser Ala Asn Ala Glu Gln
225                 230                 235                 240

Phe Tyr Gln Tyr Gln Pro Thr Glu Ile Ile Leu Ser Glu Gly Gln Leu
                245                 250                 255

Val Asp Ser Leu Gly Asn Gly Val Ala Gly Val Asp Tyr Tyr Thr Asn
                260                 265                 270

Ser Gly Arg Gly Val Thr Asp Glu Asn Gly Lys Phe Ser Phe Ser Trp
    275                 280                 285

Gly Glu Thr Ile Ser Phe Gly Ile Asp Thr Phe Glu Leu Gly Ser Val
    290                 295                 300

Arg Gly Asn Lys Ser Thr Ile Ala Leu Thr Glu Leu Gly Asp Glu Val
305                 310                 315                 320

Arg Gly Ala Asn Ile Asp Gln Leu Ile His Arg Tyr Ser Thr Thr Gly
                325                 330                 335

Gln Asn Asn Thr Arg Val Val Pro Asp Val Arg Lys Val Phe Ala
            340                 345                 350

Glu Tyr Pro Asn Val Ile Asn Glu Ile Ile Asn Leu Ser Leu Ser Asn
        355                 360                 365

Gly Ala Thr Leu Asp Glu Gly Asp Gln Asn Val Val Leu Pro Asn Glu
    370                 375                 380
```

```
Phe Ile Glu Gln Phe Lys Thr Gly Gln Ala Lys Glu Ile Asp Thr Ala
385                 390                 395                 400

Ile Cys Ala Lys Thr Asp Gly Cys Asn Glu Ala Arg Trp Phe Ser Leu
            405                 410                 415

Thr Thr Arg Asn Val Asn Asp Gly Gln Ile Gln Gly Val Ile Asn Lys
            420                 425                 430

Leu Trp Gly Val Asp Thr Asn Tyr Gln Ser Val Ser Lys Phe His Val
        435                 440                 445

Phe His Asp Ser Thr Asn Phe Tyr Gly Ser Thr Gly Asn Ala Arg Gly
450                 455                 460

Gln Ala Val Val Asn Ile Ser Asn Ser Ala Phe Pro Ile Leu Met Ala
465                 470                 475                 480

Arg Asn Asp Lys Asn Tyr Trp Leu Ala Phe Gly Glu Lys Arg Ala Trp
            485                 490                 495

Asp Lys Asn Glu Leu Ala Tyr Ile Thr Glu Ala Pro Ser Ile Val Gln
            500                 505                 510

Pro Glu Asn Val Thr Arg Asp Thr Ala Thr Phe Asn Leu Pro Phe Ile
            515                 520                 525

Ser Leu Gly Gln Val Gly Glu Gly Lys Leu Met Val Ile Gly Asn Pro
530                 535                 540

His Tyr Asn Ser Ile Leu Arg Cys Pro Asn Gly Tyr Ser Trp Gly Gly
545                 550                 555                 560

Gly Val Asn Ser Lys Gly Glu Cys Thr Leu Ser Gly Asp Ser Asp Asp
            565                 570                 575

Met Lys His Phe Met Gln Asn Val Leu Arg Tyr Leu Ser Asn Asp Ile
            580                 585                 590

Trp Gln Pro Asn Thr Lys Ser Ile Met Thr Val Gly Thr Asn Leu Glu
        595                 600                 605

Asn Val Tyr Phe Lys Lys Ala Gly Gln Val Leu Gly Asn Ser Ala Pro
        610                 615                 620

Phe Ala Phe His Glu Asp Phe Thr Gly Ile Thr Val Lys Gln Leu Thr
625                 630                 635                 640

Ser Tyr Gly Asp Leu Asn Pro Glu Glu Ile Pro Leu Leu Ile Leu Asn
            645                 650                 655

Gly Phe Glu Tyr Val Thr Gln Trp Ser Gly Asp Pro Tyr Ala Val Pro
            660                 665                 670

Leu Arg Ala Asp Thr Ser Lys Pro Lys Leu Thr Gln Asp Val Thr
        675                 680                 685

Asp Leu Ile Ala Tyr Leu Asn Lys Gly Gly Ser Val Leu Ile Met Glu
        690                 695                 700

Asn Val Met Ser Asn Leu Lys Glu Glu Ser Ala Ser Ser Phe Val Arg
705                 710                 715                 720

Leu Leu Asp Ala Ala Gly Leu Ser Met Ala Leu Asn Lys Ser Val Val
            725                 730                 735

Asn Asn Asp Pro Gln Gly Tyr Pro Asp Arg Val Arg Gln Arg Arg Ala
            740                 745                 750

Thr Gly Ile Trp Val Tyr Glu Arg Tyr Pro Ala Ala Asp Gly Ala Gln
            755                 760                 765

Pro Pro Tyr Thr Ile Asp Pro Asn Thr Gly Glu Val Thr Trp Lys Tyr
        770                 775                 780

Gln Gln Asp Asn Lys Pro Asp Asp Lys Pro Lys Leu Glu Val Ala Ser
785                 790                 795                 800
```

```
Trp Gln Glu Glu Val Glu Gly Lys Gln Val Thr Arg Tyr Ala Phe Ile
                805                 810                 815

Asp Glu Ala Glu Tyr Thr Thr Glu Glu Ser Leu Glu Ala Ala Lys Ala
            820                 825                 830

Lys Ile Phe Glu Lys Phe Pro Gly Leu Gln Glu Cys Lys Asp Ser Thr
        835                 840                 845

Tyr His Tyr Glu Ile Asn Cys Leu Glu Arg Arg Pro Gly Thr Asp Val
    850                 855                 860

Pro Val Thr Gly Gly Met Tyr Val Pro Arg Tyr Thr Gln Leu Asn Leu
865                 870                 875                 880

Asp Ala Asp Thr Ala Lys Ala Met Val Gln Ala Ala Asp Leu Gly Thr
                885                 890                 895

Asn Ile Gln Arg Leu Tyr Gln His Glu Leu Tyr Phe Arg Thr Lys Gly
            900                 905                 910

Ser Lys Gly Glu Arg Leu Asn Ser Val Asp Leu Glu Arg Leu Tyr Gln
        915                 920                 925

Asn Met Ser Val Trp Leu Trp Asn Asp Thr Lys Tyr Arg Tyr Glu Glu
    930                 935                 940

Gly Lys Glu Asp Glu Leu Gly Phe Lys Thr Phe Thr Glu Phe Leu Asn
945                 950                 955                 960

Cys Tyr Ala Asn Asp Ala Tyr Ala Gly Gly Thr Lys Cys Ser Ala Asp
                965                 970                 975

Leu Lys Lys Ser Leu Val Asp Asn Asn Met Ile Tyr Gly Asp Gly Ser
            980                 985                 990

Ser Lys Ala Gly Met Met Asn Pro Ser Tyr Pro Leu Asn Tyr Met Glu
        995                 1000                1005

Lys Pro Leu Thr Arg Leu Met Leu Gly Arg Ser Trp Trp Asp Leu Asn
    1010                1015                1020

Ile Lys Val Asp Val Glu Lys Tyr Pro Gly Ser Val Ser Ala Lys Gly
1025                1030                1035                1040

Glu Ser Val Thr Glu Asn Ile Ser Leu Tyr Ser Asn Pro Thr Lys Trp
                1045                1050                1055

Phe Ala Gly Asn Met Gln Ser Thr Gly Leu Trp Ala Pro Ala Gln Gln
            1060                1065                1070

Asp Val Thr Ile Lys Ser Ser Ala Ser Val Pro Val Thr Val Thr Val
        1075                1080                1085

Ala Leu Ala Asp Asp Leu Thr Gly Arg Glu Lys His Glu Val Ala Leu
    1090                1095                1100

Asn Arg Pro Pro Arg Val Thr Lys Thr Tyr Thr Leu Glu Ala Asn Gly
1105                1110                1115                1120

Glu Val Thr Phe Lys Val Pro Tyr Gly Gly Leu Ile Tyr Ile Lys Gly
                1125                1130                1135

Asp Ser Lys Asp Asp Val Ser Ala Asn Phe Thr Phe Thr Gly Val Val
            1140                1145                1150

Lys Ala Pro Phe Tyr Lys Asp Gly Glu Trp Lys Asn Asp Leu Asp Ser
        1155                1160                1165

Pro Ala Pro Leu Gly Glu Leu Glu Ser Ala Ser Phe Val Tyr Thr Thr
    1170                1175                1180

Pro Lys Lys Asn Leu Glu Ala Ser Asn Phe Thr Gly Gly Val Ala Glu
1185                1190                1195                1200

Phe Ala Lys Asp Leu Asp Thr Phe Ala Ser Ser Met Asn Asp Phe Tyr
                1205                1210                1215

Gly Arg Asn Asp Glu Asp Gly Lys His Arg Met Phe Thr Tyr Lys Asn
```

```
                     1220                1225                1230
Leu Thr Gly His Lys His Arg Phe Thr Asn Asp Val Gln Ile Ser Ile
        1235                1240                1245
Gly Asp Ala His Ser Gly Tyr Pro Val Met Asn Ser Ser Phe Ser Thr
    1250                1255                1260
Asn Ser Thr Thr Leu Pro Thr Thr Pro Leu Asn Asp Trp Leu Ile Trp
1265                1270                1275                1280
His Ala Val Gly His Asn Ala Ala Glu Thr Pro Leu Asn Val Pro Gly
            1285                1290                1295
Ala Thr Glu Val Ala Asn Asn Val Leu Ala Leu Tyr Met Gln Asp Arg
        1300                1305                1310
Tyr Leu Gly Lys Met Asn Arg Val Ala Asp Ile Thr Val Ala Pro
    1315                1320                1325
Glu Tyr Leu Asp Glu Ser Asn Gly Gln Ala Trp Ala Arg Gly Gly Ala
        1330                1335                1340
Gly Asp Arg Leu Leu Met Tyr Ala Gln Leu Lys Glu Trp Ala Glu Glu
1345                1350                1355                1360
Asn Phe Asp Ile Lys Gln Trp Tyr Pro Asp Gly Glu Leu Pro Lys Phe
            1365                1370                1375
Tyr Ser Asp Arg Lys Gly Met Lys Gly Trp Asn Leu Phe Gln Leu Met
        1380                1385                1390
His Arg Lys Ala Arg Gly Asp Asp Val Gly Asn Ser Thr Phe Gly Gly
        1395                1400                1405
Lys Asn Tyr Cys Ala Glu Ser Asn Gly Asn Ala Ala Asp Thr Leu Met
    1410                1415                1420
Leu Cys Ala Ser Trp Val Ala Gln Ala Asp Leu Ser Glu Phe Phe Lys
1425                1430                1435                1440
Lys Trp Asn Pro Gly Ala Ser Ala Tyr Gln Leu Pro Gly Ala Thr Glu
                1445                1450                1455
Met Ser Phe Gln Gly Gly Val Ser Ser Ser Ala Tyr Ser Thr Leu Ala
            1460                1465                1470
Ser Leu Lys Leu Pro Lys Pro Glu Lys Gly Pro Glu Thr Ile Asn Lys
        1475                1480                1485
Val Thr Glu His Lys Met Ser Ala Glu
    1490                1495

<210> SEQ ID NO 21
<211> LENGTH: 4491
<212> TYPE: DNA
<213> ORGANISM: Escherichia coli

<400> SEQUENCE: 21
tgtgatggtg gtggttcagg atcgtcctcc gatacgccgt ctgtagattc tggatcaggg      60
actttgccgg aagtgaaacc cgatccaaca ccaaccccgg agccgacacc tgagccgacg     120
ccggacccag aacctacgcc ggatccaaca cctgatcctg agccgacacc agaaccggag     180
ccagaacctg ttcctacgaa aacgggttat ctgaccctgg gcggaagcca gcgggtaact     240
ggtgctacct gtaatggtga atccagcgat ggctttacct ttacgccagg caataccgtg     300
agttgtgtgg tgggcagtac gaccattgca acattcaaca cccagtcaga agctgcgcgt     360
agcctgcgtg cggttgacaa agtgtcgttt agcctggagg acgcgcagga gctggcgaat     420
tctgaaaata agaaaaccaa cgccatctct ctggtgacgt ccagcgacag ttgccccgca     480
gatgcagaac agctttgtct tactttctcg tcagtggttg atcgcgcgcg atttgaaaaa     540
```

```
ctgtataagc aaattgatct ggcaacagac aatttcagca agctggtcaa tgaagaggtg    600
gaaaacaatg ctgcgactga taaagcgccg tccacccata cctcaacggt agtgccagtc    660
acgacagagg gaacaaaacc ggatctgaac gcgtccttcg tgtcggctaa cgcggaacag    720
ttttatcagt atcaacccac tgaaatcatt cttttccgaag gccaactggt ggatagcctg    780
gggaacggtg ttgctggcgt tgactactac accaattcag gccgtggcgt aactgacgaa    840
aacggtaaat tttcctttag ctggggcgaa accatctcct ttggtatcga tacctttgaa    900
ctgggctcag tacgtggcaa taagtcgacc attgcgctga ctgaattggg tgatgaagtt    960
cgcggggcaa atatcgatca gctcattcat cgttattcga cgactggtca aaataatact   1020
cgtgttgttc cggacgatgt acgcaaggtc tttgccgaat atcccaacgt gatcaacgag   1080
ataatcaatc tttcgttatc caacggtgcg acgctggatg aaggcgatca aaacgttgtg   1140
ctgcctaacg aatttatcga gcagtttaag acgggtcagg ccaaagagat cgataccgcg   1200
atttgtgcga aaaccgacgg ttgtaacgag gctcgctggt tctcgctgac aacgcgcaat   1260
gttaatgacg gccagattca gggcgttatt aacaagctgt ggggcgtgga tacgaactat   1320
cagtctgtca gcaagttcca cgtcttccat gactctacca acttctatgg cagcaccggt   1380
aacgcgcgcg gtcaggcggt ggtaaatatc tccaactcgg cattcccgat tctgatggcg   1440
cgtaatgata aaaactactg gctggcgttt ggcgaaaaac gcgcctggga taaaaatgag   1500
ctggcgtaca ttacggaagc gccttccatt gtgcagccag agaacgttac gcgcgatact   1560
gcgactttca acctgccgtt tatttcgctg gggcaagtcg gtgaaggcaa actgatggtt   1620
atcggtaacc cgcactacaa cagcatcctg cgttgcccga acggttacag ttggggcggt   1680
ggtgttaata gtaaaggtga gtgtacgctc agcggtgatt ctgatgacat gaagcacttt   1740
atgcagaacg tactgcgcta cttgtcaaat gacatctggc agccaaatac caagagcatc   1800
atgactgtcg gcaccaacct ggagaacgtt tatttcaaaa aagcggggcca ggtattggga   1860 aatagtgcac catttgcttt ccatgaggat ttcactggta tcacggttaa acagttgacc   1920
agctatggcg atctgaatcc ggaagagatt ccgttgctga tcctcaacgg ctttgaatat   1980
gtgactcagt ggtctggcga tccctatgct gtgcctctgc gtgcagatac cagcaaaccg   2040
aagctgactc agcaggatgt gaccgatctg atcgcttatc tgaacaaagg tggctcggtg   2100
ctgatcatgg aaaacgtgat gagcaatctt aaggaagaga gcgcgtccag ttttgtgcgt   2160
ctgctggatg ccgcgggtct gtcaatggct ctgaacaaat cggtggtgaa caacgatccg   2220
caagggtatc cggatcgcgt tcgtcagcgt cgcgcgactg gcatttgggt ttatgaacgt   2280
tatcctgctg cagacggcgc gcaaccgccg tacaccatcg acccaaatac aggggaagtg   2340
acctggaaat accagcaaga caacaagcct gatgacaagc cgaaactgga agttgcgagc   2400
tggcaggagg aagttgaggg caaacaggta acgcgttatg cctttattga tgaagcggaa   2460
tacacaacag aagaatctct ggaagcggca aaggcaaaaa tctttgagaa gtttcctggg   2520
ttacaggagt gtaaggactc gacttaccat tacgagatta actgtttgga gcgccgccca   2580
ggcacggatg ttccggtaac aggtggcatg tatgttccgc gctatacgca actgaatctt   2640
gacgccgaca ccgcgaaagc gatggtgcag gcggcggatt taggcaccaa cattcagcgc   2700
ctgtatcagc atgagcttta tttccgtacc aaaggcagta aggtgagcg tctgaacagt   2760 gttgatctgg aacgtctgta ccagaacatg tcggtctggc tgtggaacga tacgaaatat   2820
cgttacgaag agggcaagga agatgagctg ggctttaaaa cgttcaccga gttcctgaac   2880
tgctacgcca atgatgccta tgcaggcggc accaagtgct ccgcagatct gaaaaaatcg   2940
```

```
ctggtcgata caacatgat ctacggtgac ggtagcagca aagcgggcat gatgaaccca    3000
agctatccgc tcaactatat ggaaaaaccg ctgacgcgtc tgatgctggg ccgttcctgg    3060
tgggatctga acattaaggt tgatgtggag aagtacccag gatccgtatc ggcaaagggt    3120
gagagcgtta cggaaaacat cagcctgtac tcgaatccga ccaaatggtt tgcgggtaac    3180
atgcagtcaa ccggcctgtg ggcaccggcc cagcaggacg tcaccattaa gtcttcggcg    3240
tcagtcccag tgactgttac cgtggcgctg gctgacgacc tgactggacg tgagaagcat    3300
gaagttgcgc tgaaccgtcc gccaagagtg actaaaacgt atactctgga ggctaacggt    3360
gaagtgacct tcaaggtgcc ttatggtggt ctgatttata tcaagggcga cagtaaggat    3420
gatgtttctg ctaacttcac ctttaccggt gtagtaaaag cgccgttcta taagacggc    3480
gaatggaaaa acgatctgga ctcaccggcg ccgctgggcg agctggagtc tgcgtcgttc    3540
gtctatacca cgccgaagaa gaaccttgag gccagcaatt tcactggtgg tgtagcagaa    3600
ttcgctaaag atctggatac ctttgccagc tcgatgaatg acttctacgg tcgtaatgat    3660
gaagacggta agcaccggat gtttacctat aaaaacttga cggggcacaa gcatcgtttc    3720
accaacgatg tgcagatctc catcggtgat gcgcactcgg gttatccggt aatgaacagc    3780
agcttctcga cgaacagcac cacgctgccg acgacgccgc tgaacgactg gctgatttgg    3840
cacgaagtcg gtcataacgc tgcagaaaca ccgctgaacg taccgggtgc aactgaagtg    3900
gcgaacaacg tgctggcgct gtacatgcag gatcgctatc tcggtaagat gaaccgtgtc    3960
gctgacgaca ttaccgtcgc gccggaatat ctggacgaga gcaacggtca ggcctgggcg    4020
cgcggcggtg cgggtgaccg tctgctgatg tacgcacagt tgaaggagtg ggcagaggaa    4080
aactttgata tcaaacagtg gtatccagat ggtgagctgc taagttcta cagcgatcgt    4140
aaagggatga agggctggaa cctgttccag ttgatgcacc gtaaagcgcg cggcgctgat    4200
gttggtaaca gcacctttgg tggcaagaat tactgtgctg aatccaatgg taacgctgcc    4260
gacacgctga tgctgtgtgc atcctgggtc gctcaggcgg atctttcgga attctttaag    4320
aaatggaatc cgggtgcaag tgcttaccag ttgccgggag caacggagat gagtttccag    4380
ggcggtgtga gctcttcggc ttacagcacg ctggcgtcac tcaagctgcc gaaaccggaa    4440
aaagggccgg aaaccattaa caaggttacc gagcataaga tgtctgccga g           4491
```

<210> SEQ ID NO 22
<211> LENGTH: 1497
<212> TYPE: PRT
<213> ORGANISM: Escherichia coli

<400> SEQUENCE: 22

Cys Asp Gly Gly Ser Gly Ser Ser Asp Thr Pro Ser Val Asp
1               5                   10                  15

Ser Gly Ser Gly Thr Leu Pro Glu Val Lys Pro Asp Pro Thr Pro Thr
            20                  25                  30

Pro Glu Pro Thr Pro Glu Pro Thr Pro Asp Pro Glu Pro Thr Pro Asp
        35                  40                  45

Pro Thr Pro Asp Pro Glu Pro Thr Pro Glu Pro Glu Pro Val
    50                  55                  60

Pro Thr Lys Thr Gly Tyr Leu Thr Leu Gly Gly Ser Gln Arg Val Thr
65                  70                  75                  80

Gly Ala Thr Cys Asn Gly Glu Ser Ser Asp Gly Phe Thr Phe Thr Pro
                85                  90                  95

```
Gly Asn Thr Val Ser Cys Val Val Gly Ser Thr Thr Ile Ala Thr Phe
                100                 105                 110

Asn Thr Gln Ser Glu Ala Ala Arg Ser Leu Arg Ala Val Asp Lys Val
            115                 120                 125

Ser Phe Ser Leu Glu Asp Ala Gln Glu Leu Ala Asn Ser Glu Asn Lys
        130                 135                 140

Lys Thr Asn Ala Ile Ser Leu Val Thr Ser Ser Asp Ser Cys Pro Ala
145                 150                 155                 160

Asp Ala Glu Gln Leu Cys Leu Thr Phe Ser Val Val Asp Arg Ala
                165                 170                 175

Arg Phe Glu Lys Leu Tyr Lys Gln Ile Asp Leu Ala Thr Asp Asn Phe
                180                 185                 190

Ser Lys Leu Val Asn Glu Val Glu Asn Asn Ala Ala Thr Asp Lys
        195                 200                 205

Ala Pro Ser Thr His Thr Ser Thr Val Val Pro Val Thr Thr Glu Gly
        210                 215                 220

Thr Lys Pro Asp Leu Asn Ala Ser Phe Val Ser Ala Asn Ala Glu Gln
225                 230                 235                 240

Phe Tyr Gln Tyr Gln Pro Thr Glu Ile Ile Leu Ser Glu Gly Gln Leu
                245                 250                 255

Val Asp Ser Leu Gly Asn Gly Val Ala Gly Val Asp Tyr Tyr Thr Asn
                260                 265                 270

Ser Gly Arg Gly Val Thr Asp Glu Asn Gly Lys Phe Ser Phe Ser Trp
            275                 280                 285

Gly Glu Thr Ile Ser Phe Gly Ile Asp Thr Phe Glu Leu Gly Ser Val
            290                 295                 300

Arg Gly Asn Lys Ser Thr Ile Ala Leu Thr Glu Leu Gly Asp Glu Val
305                 310                 315                 320

Arg Gly Ala Asn Ile Asp Gln Leu Ile His Arg Tyr Ser Thr Thr Gly
                325                 330                 335

Gln Asn Asn Thr Arg Val Val Pro Asp Asp Val Arg Lys Val Phe Ala
            340                 345                 350

Glu Tyr Pro Asn Val Ile Asn Glu Ile Ile Asn Leu Ser Leu Ser Asn
            355                 360                 365

Gly Ala Thr Leu Asp Glu Gly Asp Gln Asn Val Val Leu Pro Asn Glu
        370                 375                 380

Phe Ile Glu Gln Phe Lys Thr Gly Gln Ala Lys Glu Ile Asp Thr Ala
385                 390                 395                 400

Ile Cys Ala Lys Thr Asp Gly Cys Asn Glu Ala Arg Trp Phe Ser Leu
                405                 410                 415

Thr Thr Arg Asn Val Asn Asp Gly Gln Ile Gln Gly Val Ile Asn Lys
            420                 425                 430

Leu Trp Gly Val Asp Thr Asn Tyr Gln Ser Val Ser Lys Phe His Val
        435                 440                 445

Phe His Asp Ser Thr Asn Phe Tyr Gly Ser Thr Gly Asn Ala Arg Gly
        450                 455                 460

Gln Ala Val Val Asn Ile Ser Asn Ser Ala Phe Pro Ile Leu Met Ala
465                 470                 475                 480

Arg Asn Asp Lys Asn Tyr Trp Leu Ala Phe Gly Glu Lys Arg Ala Trp
                485                 490                 495

Asp Lys Asn Glu Leu Ala Tyr Ile Thr Glu Ala Pro Ser Ile Val Gln
            500                 505                 510

Pro Glu Asn Val Thr Arg Asp Thr Ala Thr Phe Asn Leu Pro Phe Ile
```

-continued

```
                515                 520                 525
Ser Leu Gly Gln Val Gly Glu Gly Lys Leu Met Val Ile Gly Asn Pro
    530                 535                 540

His Tyr Asn Ser Ile Leu Arg Cys Pro Asn Gly Tyr Ser Trp Gly Gly
545                 550                 555                 560

Gly Val Asn Ser Lys Gly Glu Cys Thr Leu Ser Gly Asp Ser Asp Asp
                565                 570                 575

Met Lys His Phe Met Gln Asn Val Leu Arg Tyr Leu Ser Asn Asp Ile
            580                 585                 590

Trp Gln Pro Asn Thr Lys Ser Ile Met Thr Val Gly Thr Asn Leu Glu
        595                 600                 605

Asn Val Tyr Phe Lys Lys Ala Gly Gln Val Leu Gly Asn Ser Ala Pro
    610                 615                 620

Phe Ala Phe His Glu Asp Phe Thr Gly Ile Thr Val Lys Gln Leu Thr
625                 630                 635                 640

Ser Tyr Gly Asp Leu Asn Pro Glu Glu Ile Pro Leu Leu Ile Leu Asn
                645                 650                 655

Gly Phe Glu Tyr Val Thr Gln Trp Ser Gly Asp Pro Tyr Ala Val Pro
            660                 665                 670

Leu Arg Ala Asp Thr Ser Lys Pro Lys Leu Thr Gln Asp Val Thr
        675                 680                 685

Asp Leu Ile Ala Tyr Leu Asn Lys Gly Gly Ser Val Leu Ile Met Glu
    690                 695                 700

Asn Val Met Ser Asn Leu Lys Glu Glu Ser Ala Ser Ser Phe Val Arg
705                 710                 715                 720

Leu Leu Asp Ala Ala Gly Leu Ser Met Ala Leu Asn Lys Ser Val Val
                725                 730                 735

Asn Asn Asp Pro Gln Gly Tyr Pro Asp Arg Val Arg Gln Arg Arg Ala
            740                 745                 750

Thr Gly Ile Trp Val Tyr Glu Arg Tyr Pro Ala Ala Asp Gly Ala Gln
        755                 760                 765

Pro Pro Tyr Thr Ile Asp Pro Asn Thr Gly Glu Val Thr Trp Lys Tyr
    770                 775                 780

Gln Gln Asp Asn Lys Pro Asp Asp Lys Pro Lys Leu Glu Val Ala Ser
785                 790                 795                 800

Trp Gln Glu Glu Val Glu Gly Lys Gln Val Thr Arg Tyr Ala Phe Ile
                805                 810                 815

Asp Glu Ala Glu Tyr Thr Thr Glu Glu Ser Leu Glu Ala Ala Lys Ala
            820                 825                 830

Lys Ile Phe Glu Lys Phe Pro Gly Leu Gln Glu Cys Lys Asp Ser Thr
        835                 840                 845

Tyr His Tyr Glu Ile Asn Cys Leu Glu Arg Arg Pro Gly Thr Asp Val
    850                 855                 860

Pro Val Thr Gly Gly Met Tyr Val Pro Arg Tyr Thr Gln Leu Asn Leu
865                 870                 875                 880

Asp Ala Asp Thr Ala Lys Ala Met Val Gln Ala Asp Leu Gly Thr
                885                 890                 895

Asn Ile Gln Arg Leu Tyr Gln His Glu Leu Tyr Phe Thr Lys Gly
            900                 905                 910

Ser Lys Gly Glu Arg Leu Asn Ser Val Asp Leu Glu Arg Leu Tyr Gln
        915                 920                 925

Asn Met Ser Val Trp Leu Trp Asn Asp Thr Lys Tyr Arg Tyr Glu Glu
    930                 935                 940
```

```
Gly Lys Glu Asp Glu Leu Gly Phe Lys Thr Phe Thr Glu Phe Leu Asn
945                 950                 955                 960

Cys Tyr Ala Asn Asp Ala Tyr Ala Gly Gly Thr Lys Cys Ser Ala Asp
            965                 970                 975

Leu Lys Lys Ser Leu Val Asp Asn Asn Met Ile Tyr Gly Asp Gly Ser
            980                 985                 990

Ser Lys Ala Gly Met Met Asn Pro Ser Tyr Pro Leu Asn Tyr Met Glu
            995                 1000                1005

Lys Pro Leu Thr Arg Leu Met Leu Gly Arg Ser Trp Trp Asp Leu Asn
    1010                1015                1020

Ile Lys Val Asp Val Glu Lys Tyr Pro Gly Ser Val Ser Ala Lys Gly
1025                1030                1035                1040

Glu Ser Val Thr Glu Asn Ile Ser Leu Tyr Ser Asn Pro Thr Lys Trp
                1045                1050                1055

Phe Ala Gly Asn Met Gln Ser Thr Gly Leu Trp Ala Pro Ala Gln Gln
                1060                1065                1070

Asp Val Thr Ile Lys Ser Ser Ala Ser Val Pro Val Thr Val Thr Val
            1075                1080                1085

Ala Leu Ala Asp Asp Leu Thr Gly Arg Glu Lys His Glu Val Ala Leu
    1090                1095                1100

Asn Arg Pro Pro Arg Val Thr Lys Thr Tyr Thr Leu Glu Ala Asn Gly
1105                1110                1115                1120

Glu Val Thr Phe Lys Val Pro Tyr Gly Gly Leu Ile Tyr Ile Lys Gly
                1125                1130                1135

Asp Ser Lys Asp Asp Val Ser Ala Asn Phe Thr Phe Thr Gly Val Val
            1140                1145                1150

Lys Ala Pro Phe Tyr Lys Asp Gly Glu Trp Lys Asn Asp Leu Asp Ser
            1155                1160                1165

Pro Ala Pro Leu Gly Glu Leu Glu Ser Ala Ser Phe Val Tyr Thr Thr
    1170                1175                1180

Pro Lys Lys Asn Leu Glu Ala Ser Asn Phe Thr Gly Gly Val Ala Glu
1185                1190                1195                1200

Phe Ala Lys Asp Leu Asp Thr Phe Ala Ser Ser Met Asn Asp Phe Tyr
            1205                1210                1215

Gly Arg Asn Asp Glu Asp Gly Lys His Arg Met Phe Thr Tyr Lys Asn
            1220                1225                1230

Leu Thr Gly His Lys His Arg Phe Thr Asn Asp Val Gln Ile Ser Ile
    1235                1240                1245

Gly Asp Ala His Ser Gly Tyr Pro Val Met Asn Ser Ser Phe Ser Thr
    1250                1255                1260

Asn Ser Thr Thr Leu Pro Thr Thr Pro Leu Asn Asp Trp Leu Ile Trp
1265                1270                1275                1280

His Glu Val Gly His Asn Ala Ala Glu Thr Pro Leu Asn Val Pro Gly
            1285                1290                1295

Ala Thr Glu Val Ala Asn Asn Val Leu Ala Leu Tyr Met Gln Asp Arg
    1300                1305                1310

Tyr Leu Gly Lys Met Asn Arg Val Ala Asp Asp Ile Thr Val Ala Pro
    1315                1320                1325

Glu Tyr Leu Asp Glu Ser Asn Gly Gln Ala Trp Ala Arg Gly Gly Ala
    1330                1335                1340

Gly Asp Arg Leu Leu Met Tyr Ala Gln Leu Lys Glu Trp Ala Glu Glu
1345                1350                1355                1360
```

```
Asn Phe Asp Ile Lys Gln Trp Tyr Pro Asp Gly Glu Leu Pro Lys Phe
            1365                1370                1375

Tyr Ser Asp Arg Lys Gly Met Lys Gly Trp Asn Leu Phe Gln Leu Met
        1380                1385                1390

His Arg Lys Ala Arg Gly Ala Asp Val Gly Asn Ser Thr Phe Gly Gly
        1395                1400                1405

Lys Asn Tyr Cys Ala Glu Ser Asn Gly Asn Ala Ala Asp Thr Leu Met
        1410                1415                1420

Leu Cys Ala Ser Trp Val Ala Gln Ala Asp Leu Ser Glu Phe Phe Lys
1425                1430                1435                1440

Lys Trp Asn Pro Gly Ala Ser Ala Tyr Gln Leu Pro Gly Ala Thr Glu
            1445                1450                1455

Met Ser Phe Gln Gly Gly Val Ser Ser Ser Ala Tyr Ser Thr Leu Ala
        1460                1465                1470

Ser Leu Lys Leu Pro Lys Pro Glu Lys Gly Pro Glu Thr Ile Asn Lys
        1475                1480                1485

Val Thr Glu His Lys Met Ser Ala Glu
    1490                1495
```

<210> SEQ ID NO 23
<211> LENGTH: 2184
<212> TYPE: DNA
<213> ORGANISM: Escherichia coli

<400> SEQUENCE: 23

```
gatacgccgt ctgtagattc tggatcaggg actttgccgg aagtgaaacc cgatccaaca    60
ccaaccccgg agccgacacc tgagccgacg ccggacccag aacctacgcc ggatccaaca   120
cctgatcctg agccgacacc agaaccggag ccagaacctg ttcctacgaa aacgggttat   180
ctgaccctgg gcggaagcca gcgggtaact ggtgctacct gtaatggtga atccagcgat   240
ggctttacct ttacgccagg caataccgtg agttgtgtgg tggcagtac gaccattgca    300
acattcaaca cccagtcaga agctgcgcgt agcctgcgtg cggttgacaa agtgtcgttt   360
agcctggagg acgcgcagga gctggcgaat tctgaaaata agaaaaccaa cgccatctct   420
ctggtgacgt ccagcgacag ttgccccgca gatgcagaac agctttgtct tactttctcg   480
tcagtggttg atcgcgcgcg atttgaaaaa ctgtataagc aaattgatct ggcaacagac   540
aatttcagca agctggtcaa tgaagaggtg aaaacaatg ctgcgactga taaagcgccg    600
tccacccata cctcaacggt agtgccagtc acgacagagg gaacaaaacc ggatctgaac   660
gcgtccttcg tgtcggctaa cgcggaacag ttttatcagt atcaacccac tgaaatcatt   720
ctttccgaag ccaactggt ggatagcctg gggaacggtg ttgctggcgt tgactactac    780
accaattcag gccgtggcgt aactgacgaa aacggtaaat tttcctttag ctggggcgaa   840
accatctcct ttggtatcga tacctttgaa ctgggctcag tacgtggcaa taagtcgacc   900
attgcgctga ctgaattggg tgatgaagtt cgcggggcaa atatcgatca gctcattcat   960
cgttattcga cgactggtca aaataatact cgtgttgttc cggacgatgt acgcaaggtc  1020
tttgccgaat atcccaacgt gatcaacgag ataatcaatc tttcgttatc caacggtgcg  1080
acgctggatg aaggcgatca aaacgttgtg ctgcctaacg aatttatcga gcagtttaag  1140
acgggtcagg ccaaagagat cgataccgcg atttgtgcga aaaccgacgg ttgtaacgag  1200
gctcgctggt ctcgctgac aacgcgcaat gttaatgacg ccagattca gggcgttatt    1260
aacaagctgt ggggcgtgga tacgaactat cagtctgtca gcaagttcca cgtcttccat  1320
```

```
gactctacca acttctatgg cagcaccggt aacgcgcgcg gtcaggcggt ggtaaatatc    1380
tccaactcgg cattcccgat tctgatggcg cgtaatgata aaaactactg gctggcgttt    1440
ggcgaaaaac gcgcctggga taaaaatgag ctggcgtaca ttacggaagc gccttccatt    1500
gtgcagccag agaacgttac gcgcgatact gcgactttca acctgccgtt tatttcgctg    1560
gggcaagtcg gtgaaggcaa actgatggtt atcggtaacc cgcactacaa cagcatcctg    1620
cgttgcccga acggttacag ttggggcggt ggtgttaata gtaaaggtga gtgtacgctc    1680
agcggtgatt ctgatgacat gaagcacttt atgcagaacg tactgcgcta cttgtcaaat    1740
gacatctggc agccaaatac caagagcatc atgactgtcg caccaacct ggagaacgtt    1800 tatttcaaaa aagcgggcca ggtattggga aatagtgcac catttgcttt ccatgaggat    1860
ttcactggta tcacggttaa acagttgacc agctatggcg atctgaatcc ggaagagatt    1920
ccgttgctga tcctcaacgg ctttgaatat gtgactcagt ggtctggcga tccctatgct    1980
gtgcctctgc gtgcagatac cagcaaaccg aagctgactc agcaggatgt gaccgatctg    2040
atcgcttatc tgaacaaagg tggctcggtg ctgatcatgg aaaacgtgat gagcaatctt    2100
aaggaagaga gcgcgtccag ttttgtgcgt ctgctggatg ccgcgggtct gtcaatggct    2160
ctgaacaaat cggtggtgaa caac                                           2184
```

<210> SEQ ID NO 24
<211> LENGTH: 728
<212> TYPE: PRT
<213> ORGANISM: Escherichia coli

<400> SEQUENCE: 24

```
Asp Thr Pro Ser Val Asp Ser Gly Ser Gly Thr Leu Pro Glu Val Lys
1               5                   10                  15

Pro Asp Pro Thr Pro Thr Pro Glu Pro Thr Pro Glu Pro Thr Pro Asp
            20                  25                  30

Pro Glu Pro Thr Pro Asp Pro Thr Pro Asp Pro Glu Pro Thr Pro Glu
        35                  40                  45

Pro Glu Pro Glu Pro Val Pro Thr Lys Thr Gly Tyr Leu Thr Leu Gly
    50                  55                  60

Gly Ser Gln Arg Val Thr Gly Ala Thr Cys Asn Gly Glu Ser Ser Asp
65                  70                  75                  80

Gly Phe Thr Phe Thr Pro Gly Asn Thr Val Ser Cys Val Val Gly Ser
                85                  90                  95

Thr Thr Ile Ala Thr Phe Asn Thr Gln Ser Glu Ala Ala Arg Ser Leu
            100                 105                 110

Arg Ala Val Asp Lys Val Ser Phe Ser Leu Glu Asp Ala Gln Glu Leu
        115                 120                 125

Ala Asn Ser Glu Asn Lys Lys Thr Asn Ala Ile Ser Leu Val Thr Ser
    130                 135                 140

Ser Asp Ser Cys Pro Ala Asp Ala Glu Gln Leu Cys Leu Thr Phe Ser
145                 150                 155                 160

Ser Val Val Asp Arg Ala Arg Phe Glu Lys Leu Tyr Lys Gln Ile Asp
                165                 170                 175

Leu Ala Thr Asp Asn Phe Ser Lys Leu Val Asn Glu Val Glu Asn
            180                 185                 190

Asn Ala Ala Thr Asp Lys Ala Pro Ser Thr His Thr Ser Thr Val Val
        195                 200                 205

Pro Val Thr Thr Glu Gly Thr Lys Pro Asp Leu Asn Ala Ser Phe Val
    210                 215                 220
```

```
Ser Ala Asn Ala Glu Gln Phe Tyr Gln Tyr Gln Pro Thr Glu Ile Ile
225                 230                 235                 240

Leu Ser Glu Gly Gln Leu Val Asp Ser Leu Gly Asn Gly Val Ala Gly
            245                 250                 255

Val Asp Tyr Tyr Thr Asn Ser Gly Arg Gly Val Thr Asp Glu Asn Gly
        260                 265                 270

Lys Phe Ser Phe Ser Trp Gly Glu Thr Ile Ser Phe Gly Ile Asp Thr
    275                 280                 285

Phe Glu Leu Gly Ser Val Arg Gly Asn Lys Ser Thr Ile Ala Leu Thr
290                 295                 300

Glu Leu Gly Asp Glu Val Arg Gly Ala Asn Ile Asp Gln Leu Ile His
305                 310                 315                 320

Arg Tyr Ser Thr Thr Gly Gln Asn Asn Thr Arg Val Val Pro Asp Asp
                325                 330                 335

Val Arg Lys Val Phe Ala Glu Tyr Pro Asn Val Ile Asn Glu Ile Ile
            340                 345                 350

Asn Leu Ser Leu Ser Asn Gly Ala Thr Leu Asp Glu Gly Asp Gln Asn
        355                 360                 365

Val Val Leu Pro Asn Glu Phe Ile Glu Gln Phe Lys Thr Gly Gln Ala
370                 375                 380

Lys Glu Ile Asp Thr Ala Ile Cys Ala Lys Thr Asp Gly Cys Asn Glu
385                 390                 395                 400

Ala Arg Trp Phe Ser Leu Thr Thr Arg Asn Val Asn Asp Gly Gln Ile
                405                 410                 415

Gln Gly Val Ile Asn Lys Leu Trp Gly Val Asp Thr Asn Tyr Gln Ser
            420                 425                 430

Val Ser Lys Phe His Val Phe His Asp Ser Thr Asn Phe Tyr Gly Ser
        435                 440                 445

Thr Gly Asn Ala Arg Gly Gln Ala Val Val Asn Ile Ser Asn Ser Ala
    450                 455                 460

Phe Pro Ile Leu Met Ala Arg Asn Asp Lys Asn Tyr Trp Leu Ala Phe
465                 470                 475                 480

Gly Glu Lys Arg Ala Trp Asp Lys Asn Glu Leu Ala Tyr Ile Thr Glu
                485                 490                 495

Ala Pro Ser Ile Val Gln Pro Glu Asn Val Thr Arg Asp Thr Ala Thr
            500                 505                 510

Phe Asn Leu Pro Phe Ile Ser Leu Gly Gln Val Gly Glu Gly Lys Leu
        515                 520                 525

Met Val Ile Gly Asn Pro His Tyr Asn Ser Ile Leu Arg Cys Pro Asn
530                 535                 540

Gly Tyr Ser Trp Gly Gly Val Asn Ser Lys Gly Glu Cys Thr Leu
545                 550                 555                 560

Ser Gly Asp Ser Asp Asp Met Lys His Phe Met Gln Asn Val Leu Arg
                565                 570                 575

Tyr Leu Ser Asn Asp Ile Trp Gln Pro Asn Thr Lys Ser Ile Met Thr
            580                 585                 590

Val Gly Thr Asn Leu Glu Asn Val Tyr Phe Lys Lys Ala Gly Gln Val
        595                 600                 605

Leu Gly Asn Ser Ala Pro Phe Ala Phe His Glu Asp Phe Thr Gly Ile
    610                 615                 620

Thr Val Lys Gln Leu Thr Ser Tyr Gly Asp Leu Asn Pro Glu Glu Ile
625                 630                 635                 640
```

```
              Pro Leu Leu Ile Leu Asn Gly Phe Glu Tyr Val Thr Gln Trp Ser Gly
                              645                 650                 655

Asp Pro Tyr Ala Val Pro Leu Arg Ala Asp Thr Ser Lys Pro Lys Leu
                          660                 665                 670

Thr Gln Gln Asp Val Thr Asp Leu Ile Ala Tyr Leu Asn Lys Gly Gly
                      675                 680                 685

Ser Val Leu Ile Met Glu Asn Val Met Ser Asn Leu Lys Glu Glu Ser
                  690                 695                 700

Ala Ser Ser Phe Val Arg Leu Leu Asp Ala Ala Gly Leu Ser Met Ala
              705                 710                 715                 720

Leu Asn Lys Ser Val Val Asn Asn
                              725

<210> SEQ ID NO 25
<211> LENGTH: 3810
<212> TYPE: DNA
<213> ORGANISM: Escherichia coli

<400> SEQUENCE: 25
```

| | | | | | |
|---|---|---|---|---|---|
| gatacgccgt | ctgtagattc | tggatcaggg | actttgccgg | aagtgaaacc | cgatccaaca | 60 |
| ccaaccccgg | agccgacacc | tgagccgacg | ccggacccag | aacctacgcc | ggatccaaca | 120 |
| cctgatcctg | agccgacacc | agaaccggag | ccagaacctg | ttcctacgaa | acgggttat | 180 |
| ctgaccctgg | gcggaagcca | gcgggtaact | ggtgctacct | gtaatggtga | atccagcgat | 240 |
| ggctttacct | ttacgccagg | caataccgtg | agttgtgtgg | tgggcagtac | gaccattgca | 300 |
| acattcaaca | cccagtcaga | agctgcgcgt | agcctgcgtg | cggttgacaa | agtgtcgttt | 360 |
| agcctggagg | acgcgcagga | gctggcgaat | tctgaaaata | agaaaaccaa | cgccatctct | 420 |
| ctggtgacgt | ccagcgacag | ttgccccgca | gatgcagaac | agctttgtct | tactttctcg | 480 |
| tcagtggttg | atcgcgcgcg | atttgaaaaa | ctgtataagc | aaattgatct | ggcaacagac | 540 |
| aatttcagca | agctggtcaa | tgaagaggtg | aaaacaatg | ctgcgactga | taaagcgccg | 600 |
| tccacccata | cctcaacggt | agtgccagtc | acgacagagg | gaacaaaacc | ggatctgaac | 660 |
| gcgtccttcg | tgtcggctaa | cgcggaacag | ttttatcagt | atcaacccac | tgaaatcatt | 720 |
| ctttccgaag | ccaactggt | ggatagcctg | gggaacggtg | ttgctggcgt | tgactactac | 780 |
| accaattcag | gccgtggcgt | aactgacgaa | aacggtaaat | tttcctttag | ctggggcgaa | 840 |
| accatctcct | ttggtatcga | tacctttgaa | ctgggctcag | tacgtggcaa | taagtcgacc | 900 |
| attgcgctga | ctgaattggg | tgatgaagtt | cgcggggcaa | atatcgatca | gctcattcat | 960 |
| cgttattcga | cgactggtca | aaataatact | cgtgttgttc | cggacgatgt | acgcaaggtc | 1020 |
| tttgccgaat | atcccaacgt | gatcaacgag | ataatcaatc | tttcgttatc | caacggtgcg | 1080 |
| acgctggatg | aaggcgatca | aaacgttgtg | ctgcctaacg | aatttatcga | gcagtttaag | 1140 |
| acgggtcagg | ccaaagagat | cgataccgcg | atttgtgcga | aaccgacgg | ttgtaacgag | 1200 |
| gctcgctggt | tctcgctgac | aacgcgcaat | gttaatgacg | ccagattca | gggcgttatt | 1260 |
| aacaagctgt | ggggcgtgga | tacgaactat | cagtctgtca | gcaagttcca | cgtcttccat | 1320 |
| gactctacca | acttctatgg | cagcaccggt | aacgcgcgcg | tcaggcggt | ggtaaatatc | 1380 |
| tccaactcgg | cattcccgat | tctgatggcg | cgtaatgata | aaaactactg | gctggcgttt | 1440 |
| ggcgaaaaac | gcgcctggga | taaaaatgag | ctgcgtaca | ttacggaagc | gccttccatt | 1500 |
| gtgcagccag | agaacgttac | gcgcgatact | gcgactttca | acctgccgtt | tatttcgctg | 1560 |
| gggcaagtcg | gtgaaggcaa | actgatggtt | atcggtaacc | cgcactacaa | cagcatcctg | 1620 |

-continued

```
cgttgcccga acggttacag ttggggcggt ggtgttaata gtaaaggtga gtgtacgctc    1680
agcggtgatt ctgatgacat gaagcacttt atgcagaacg tactgcgcta cttgtcaaat    1740
gacatctggc agccaaatac caagagcatc atgactgtcg gcaccaacct ggagaacgtt    1800
tatttcaaaa aagcgggcca ggtattggga aatagtgcac catttgcttt ccatgaggat    1860
ttcactggta tcacggttaa acagttgacc agctatggcg atctgaatcc ggaagagatt    1920
ccgttgctga tcctcaacgg ctttgaatat gtgactcagt ggtctggcga tccctatgct    1980
gtgcctctgc gtgcagatac cagcaaaccg aagctgactc agcaggatgt gaccgatctg    2040
atcgcttatc tgaacaaagg tggctcggtg ctgatcatgg aaaacgtgat gagcaatctt    2100
aaggaagaga gcgcgtccag ttttgtgcgt ctgctggatg ccgcgggtct gtcaatggct    2160
ctgaacaaat cggtggtgaa caacgatccg caagggtatc cggatcgcgt tcgtcagcgt    2220
cgcgcgactg gcatttgggt ttatgaacgt tatcctgctg cagacggcgc gcaaccgccg    2280
tacaccatcg acccaaatac aggggaagtg acctggaaat accagcaaga caacaagcct    2340
gatgacaagc cgaaactgga agttgcgagc tggcaggagg aagttgaggg caaacaggta    2400
acgcgttatg cctttattga tgaagcggaa tacacaacag aagaatctct ggaagcggca    2460
aaggcaaaaa tctttgagaa gtttcctggg ttacaggagt gtaaggactc gacttaccat    2520
tacgagatta actgtttgga gcgccgccca ggcacggatg ttccggtaac aggtggcatg    2580
tatgttccgc gctatacgca actgaatctt gacgccgaca ccgcgaaagc gatggtgcag    2640
gcggcggatt taggcaccaa cattcagcgc ctgtatcagc atgagcttta tttccgtacc    2700
aaaggcagta aggtgagcg tctgaacagt gttgatctgg aacgtctgta ccagaacatg    2760
tcggtctggc tgtggaacga tacgaaatat cgttacgaag agggcaagga agatgagctg    2820
ggctttaaaa cgttcaccga gttcctgaac tgctacgcca atgatgccta tgcaggcggc    2880
accaagtgct ccgcagatct gaaaaaatcg ctggtcgata caacatgat ctacggtgac    2940 ggtagcagca aagcgggcat gatgaaccca agctatccgc tcaactatat ggaaaaaccg    3000
ctgacgcgtc tgatgctggg ccgttcctgg tgggatctga acattaaggt tgatgtggag    3060
aagtacccag gatccgtatc ggcaaagggt gagagcgtta cggaaaacat cagcctgtac    3120
tcgaatccga ccaaatggtt tgcgggtaac atgcagtcaa ccggcctgtg ggcaccggcc    3180
cagcaggacg tcaccattaa gtcttcggcg tcagtcccag tgactgttac cgtggcgctg    3240
gctgacgacc tgactggacg tgagaagcat gaagttgcgc tgaaccgtcc gccaagagtg    3300
actaaaacgt atactctgga ggctaacggt gaagtgacct tcaaggtgcc ttatggtggt    3360 ctgattata tcaagggcga cagtaaggat gatgtttctg ctaacttcac ctttaccggt    3420
gtagtaaaag cgccgttcta taagacggc gaatggaaaa acgatctgga ctcaccggcg    3480
ccgctgggcg agctggagtc tgcgtcgttc gtctatacca cgccgaagaa gaaccttgag    3540
gccagcaatt tcactggtgg tgtagcagaa ttcgctaaag atctggatac ctttgccagc    3600
tcgatgaatg acttctacgg tcgtaatgat gaagacggta agcaccggat gtttacctat    3660
aaaaacttga cggggcacaa gcatcgtttc accaacgatg tgcagatctc catcggtgat    3720
gcgcactcgg gttatccggt aatgaacagc agcttctcga cgaacagcac cacgctgccg    3780
acgacgccgc tgaacgactg gctgatttgg                                     3810
```

<210> SEQ ID NO 26
<211> LENGTH: 1270
<212> TYPE: PRT

-continued

<213> ORGANISM: Escherichia coli

<400> SEQUENCE: 26

Asp Thr Pro Ser Val Asp Ser Gly Ser Gly Thr Leu Pro Glu Val Lys
1               5                   10                  15

Pro Asp Pro Thr Pro Thr Pro Glu Pro Thr Pro Glu Pro Thr Pro Asp
            20                  25                  30

Pro Glu Pro Thr Pro Asp Pro Thr Pro Asp Pro Glu Pro Thr Pro Glu
        35                  40                  45

Pro Glu Pro Glu Pro Val Pro Thr Lys Thr Gly Tyr Leu Thr Leu Gly
    50                  55                  60

Gly Ser Gln Arg Val Thr Gly Ala Thr Cys Asn Gly Glu Ser Ser Asp
65                  70                  75                  80

Gly Phe Thr Phe Thr Pro Gly Asn Thr Val Ser Cys Val Val Gly Ser
                85                  90                  95

Thr Thr Ile Ala Thr Phe Asn Thr Gln Ser Glu Ala Ala Arg Ser Leu
            100                 105                 110

Arg Ala Val Asp Lys Val Ser Phe Ser Leu Glu Asp Ala Gln Glu Leu
        115                 120                 125

Ala Asn Ser Glu Asn Lys Lys Thr Asn Ala Ile Ser Leu Val Thr Ser
    130                 135                 140

Ser Asp Ser Cys Pro Ala Asp Ala Glu Gln Leu Cys Leu Thr Phe Ser
145                 150                 155                 160

Ser Val Val Asp Arg Ala Arg Phe Glu Lys Leu Tyr Lys Gln Ile Asp
                165                 170                 175

Leu Ala Thr Asp Asn Phe Ser Lys Leu Val Asn Glu Val Glu Asn
            180                 185                 190

Asn Ala Ala Thr Asp Lys Ala Pro Ser Thr His Thr Ser Thr Val Val
    195                 200                 205

Pro Val Thr Thr Glu Gly Thr Lys Pro Asp Leu Asn Ala Ser Phe Val
210                 215                 220

Ser Ala Asn Ala Glu Gln Phe Tyr Gln Tyr Gln Pro Thr Glu Ile Ile
225                 230                 235                 240

Leu Ser Glu Gly Gln Leu Val Asp Ser Leu Gly Asn Gly Val Ala Gly
                245                 250                 255

Val Asp Tyr Tyr Thr Asn Ser Gly Arg Gly Val Thr Asp Glu Asn Gly
            260                 265                 270

Lys Phe Ser Phe Ser Trp Gly Glu Thr Ile Ser Phe Gly Ile Asp Thr
    275                 280                 285

Phe Glu Leu Gly Ser Val Arg Gly Asn Lys Ser Thr Ile Ala Leu Thr
290                 295                 300

Glu Leu Gly Asp Glu Val Arg Gly Ala Asn Ile Asp Gln Leu Ile His
305                 310                 315                 320

Arg Tyr Ser Thr Thr Gly Gln Asn Asn Thr Arg Val Val Pro Asp Asp
                325                 330                 335

Val Arg Lys Val Phe Ala Glu Tyr Pro Asn Val Ile Asn Glu Ile Ile
            340                 345                 350

Asn Leu Ser Leu Ser Asn Gly Ala Thr Leu Asp Glu Gly Asp Gln Asn
    355                 360                 365

Val Val Leu Pro Asn Glu Phe Ile Glu Gln Phe Lys Thr Gly Gln Ala
370                 375                 380

Lys Glu Ile Asp Thr Ala Ile Cys Ala Lys Thr Asp Gly Cys Asn Glu
385                 390                 395                 400

Ala Arg Trp Phe Ser Leu Thr Thr Arg Asn Val Asn Asp Gly Gln Ile
            405                 410                 415

Gln Gly Val Ile Asn Lys Leu Trp Gly Val Asp Thr Asn Tyr Gln Ser
        420                 425                 430

Val Ser Lys Phe His Val Phe His Asp Ser Thr Asn Phe Tyr Gly Ser
        435                 440                 445

Thr Gly Asn Ala Arg Gly Gln Ala Val Val Asn Ile Ser Asn Ser Ala
        450                 455                 460

Phe Pro Ile Leu Met Ala Arg Asn Asp Lys Asn Tyr Trp Leu Ala Phe
465                 470                 475                 480

Gly Glu Lys Arg Ala Trp Asp Lys Asn Glu Leu Ala Tyr Ile Thr Glu
                485                 490                 495

Ala Pro Ser Ile Val Gln Pro Glu Asn Val Thr Arg Asp Thr Ala Thr
                500                 505                 510

Phe Asn Leu Pro Phe Ile Ser Leu Gly Gln Val Gly Glu Gly Lys Leu
            515                 520                 525

Met Val Ile Gly Asn Pro His Tyr Asn Ser Ile Leu Arg Cys Pro Asn
        530                 535                 540

Gly Tyr Ser Trp Gly Gly Val Asn Ser Lys Gly Glu Cys Thr Leu
545                 550                 555                 560

Ser Gly Asp Ser Asp Asp Met Lys His Phe Met Gln Asn Val Leu Arg
                565                 570                 575

Tyr Leu Ser Asn Asp Ile Trp Gln Pro Asn Thr Lys Ser Ile Met Thr
            580                 585                 590

Val Gly Thr Asn Leu Glu Asn Val Tyr Phe Lys Lys Ala Gly Gln Val
            595                 600                 605

Leu Gly Asn Ser Ala Pro Phe Ala Phe His Glu Asp Phe Thr Gly Ile
    610                 615                 620

Thr Val Lys Gln Leu Thr Ser Tyr Gly Asp Leu Asn Pro Glu Glu Ile
625                 630                 635                 640

Pro Leu Leu Ile Leu Asn Gly Phe Glu Tyr Val Thr Gln Trp Ser Gly
                645                 650                 655

Asp Pro Tyr Ala Val Pro Leu Arg Ala Asp Thr Ser Lys Pro Lys Leu
            660                 665                 670

Thr Gln Gln Asp Val Thr Asp Leu Ile Ala Tyr Leu Asn Lys Gly Gly
        675                 680                 685

Ser Val Leu Ile Met Glu Asn Val Met Ser Asn Leu Lys Glu Glu Ser
        690                 695                 700

Ala Ser Ser Phe Val Arg Leu Leu Asp Ala Ala Gly Leu Ser Met Ala
705                 710                 715                 720

Leu Asn Lys Ser Val Val Asn Asn Asp Pro Gln Gly Tyr Pro Asp Arg
                725                 730                 735

Val Arg Gln Arg Arg Ala Thr Gly Ile Trp Val Tyr Glu Arg Tyr Pro
            740                 745                 750

Ala Ala Asp Gly Ala Gln Pro Pro Tyr Thr Ile Asp Pro Asn Thr Gly
        755                 760                 765

Glu Val Thr Trp Lys Tyr Gln Gln Asp Asn Lys Pro Asp Asp Lys Pro
    770                 775                 780

Lys Leu Glu Val Ala Ser Trp Gln Glu Glu Glu Gly Lys Gln Val
785                 790                 795                 800

Thr Arg Tyr Ala Phe Ile Asp Glu Ala Glu Tyr Thr Thr Glu Glu Ser
                805                 810                 815

Leu Glu Ala Ala Lys Ala Lys Ile Phe Glu Lys Phe Pro Gly Leu Gln

```
              820                 825                 830
Glu Cys Lys Asp Ser Thr Tyr His Tyr Glu Ile Asn Cys Leu Glu Arg
            835                 840                 845

Arg Pro Gly Thr Asp Val Pro Val Thr Gly Met Tyr Val Pro Arg
        850                 855                 860

Tyr Thr Gln Leu Asn Leu Asp Ala Asp Thr Ala Lys Ala Met Val Gln
865                 870                 875                 880

Ala Ala Asp Leu Gly Thr Asn Ile Gln Arg Leu Tyr Gln His Glu Leu
                885                 890                 895

Tyr Phe Arg Thr Lys Gly Ser Lys Gly Glu Arg Leu Asn Ser Val Asp
            900                 905                 910

Leu Glu Arg Leu Tyr Gln Asn Met Ser Val Trp Leu Trp Asn Asp Thr
            915                 920                 925

Lys Tyr Arg Tyr Glu Glu Gly Lys Glu Asp Leu Gly Phe Lys Thr
        930                 935                 940

Phe Thr Glu Phe Leu Asn Cys Tyr Ala Asn Asp Ala Tyr Ala Gly Gly
945                 950                 955                 960

Thr Lys Cys Ser Ala Asp Leu Lys Lys Ser Leu Val Asp Asn Asn Met
                965                 970                 975

Ile Tyr Gly Asp Gly Ser Ser Lys Ala Gly Met Met Asn Pro Ser Tyr
                980                 985                 990

Pro Leu Asn Tyr Met Glu Lys Pro Leu Thr Arg Leu Met Leu Gly Arg
            995                 1000                1005

Ser Trp Trp Asp Leu Asn Ile Lys Val Asp Val Glu Lys Tyr Pro Gly
        1010                1015                1020

Ser Val Ser Ala Lys Gly Glu Ser Val Thr Glu Asn Ile Ser Leu Tyr
1025                1030                1035                1040

Ser Asn Pro Thr Lys Trp Phe Ala Gly Asn Met Gln Ser Thr Gly Leu
                1045                1050                1055

Trp Ala Pro Ala Gln Gln Asp Val Thr Ile Lys Ser Ser Ala Ser Val
                1060                1065                1070

Pro Val Thr Val Thr Val Ala Leu Ala Asp Asp Leu Thr Gly Arg Glu
            1075                1080                1085

Lys His Glu Val Ala Leu Asn Arg Pro Pro Arg Val Thr Lys Thr Tyr
        1090                1095                1100

Thr Leu Glu Ala Asn Gly Glu Val Thr Phe Lys Val Pro Tyr Gly Gly
1105                1110                1115                1120

Leu Ile Tyr Ile Lys Gly Asp Ser Lys Asp Asp Val Ser Ala Asn Phe
                1125                1130                1135

Thr Phe Thr Gly Val Val Lys Ala Pro Phe Tyr Lys Asp Gly Glu Trp
            1140                1145                1150

Lys Asn Asp Leu Asp Ser Pro Ala Pro Leu Gly Glu Leu Glu Ser Ala
            1155                1160                1165

Ser Phe Val Tyr Thr Thr Pro Lys Lys Asn Leu Glu Ala Ser Asn Phe
        1170                1175                1180

Thr Gly Gly Val Ala Glu Phe Ala Lys Asp Leu Asp Thr Phe Ala Ser
1185                1190                1195                1200

Ser Met Asn Asp Phe Tyr Gly Arg Asn Asp Glu Asp Gly Lys His Arg
            1205                1210                1215

Met Phe Thr Tyr Lys Asn Leu Thr Gly His Lys His Arg Phe Thr Asn
            1220                1225                1230

Asp Val Gln Ile Ser Ile Gly Asp Ala His Ser Gly Tyr Pro Val Met
            1235                1240                1245
```

Asn Ser Ser Phe Ser Thr Asn Ser Thr Thr Leu Pro Thr Thr Pro Leu
    1250                1255                1260

Asn Asp Trp Leu Ile Trp
1265                1270

<210> SEQ ID NO 27
<211> LENGTH: 4563
<212> TYPE: DNA
<213> ORGANISM: Escherichia coli

<400> SEQUENCE: 27

| | | | | | |
|---|---|---|---|---|---|
| atgaataaga | aatttaaata | taagaaatcg | cttttagcgg | ctattttaag | cgcaaccctg | 60 |
| ttagccggtt | gtgatggtgg | tggttcagga | tcgtcctccg | atacgccgtc | tgtagattct | 120 |
| ggatcaggga | ctttgccgga | agtgaaaccc | gatccaacac | caaccccgga | gccgacacct | 180 |
| gagccgacgc | cggacccaga | acctacgccg | gatccaacac | ctgatcctga | gccgacacca | 240 |
| gaaccggagc | cagaacctgt | tcctacgaaa | acgggttatc | tgaccctggg | cggaagccag | 300 |
| cgggtaactg | gtgctacctg | taatggtgaa | tccagcgatg | gctttacctt | tacgccaggc | 360 |
| aataccgtga | gttgtgtggt | gggcagtacg | accattgcaa | cattcaacac | ccagtcagaa | 420 |
| gctgcgcgta | gcctgcgtgc | ggttgacaaa | gtgtcgttta | gcctggagga | cgcgcaggag | 480 |
| ctggcgaatt | ctgaaaataa | gaaaccaac | gccatctctc | tggtgacgtc | cagcgacagt | 540 |
| tgccccgcag | atgcagaaca | gctttgtctt | actttctcgt | cagtggttga | tcgcgcgcga | 600 |
| tttgaaaaac | tgtataagca | aattgatctg | gcaacagaca | atttcagcaa | gctggtcaat | 660 |
| gaagaggtgg | aaaacaatgc | tgcgactgat | aaagcgccgt | ccacccatac | ctcaacggta | 720 |
| gtgccagtca | cgacagaggg | aacaaaaccg | gatctgaacg | cgtccttcgt | gtcggctaac | 780 |
| gcggaacagt | tttatcagta | tcaacccact | gaaatcattc | tttccgaagg | ccaactggtg | 840 |
| gatagcctgg | ggaacggtgt | tgctggcgtt | gactactaca | ccaattcagg | ccgtggcgta | 900 |
| actgacgaaa | acggtaaatt | tcctttagc | tggggcgaaa | ccatctcctt | tggtatcgat | 960 |
| acctttgaac | tgggctcagt | acgtggcaat | aagtcgacca | ttgcgctgac | tgaattgggt | 1020 |
| gatgaagttc | gcggggcaaa | tatcgatcag | ctcattcatc | gttattcgac | gactggtcaa | 1080 |
| ataatactc | gtgttgttcc | ggacgatgta | cgcaaggtct | tgccgaata | tcccaacgtg | 1140 |
| atcaacgaga | taatcaatct | ttcgttatcc | aacggtgcga | cgctggatga | aggcgatcaa | 1200 |
| aacgttgtgc | tgcctaacga | atttatcgag | cagtttaaga | cgggtcaggc | caaagagatc | 1260 |
| gataccgcga | tttgtgcgaa | aaccgacggt | tgtaacgagg | ctcgctggtt | ctcgctgaca | 1320 |
| acgcgcaatg | ttaatgacgg | ccagattcag | ggcgttatta | caagctgtg | gggcgtggat | 1380 |
| acgaactatc | agtctgtcag | caagttccac | gtcttccatg | actctaccaa | cttctatggc | 1440 |
| agcaccggta | acgcgcgcgg | tcaggcggtg | gtaaatatct | ccaactcggc | attcccgatt | 1500 |
| ctgatggcgc | gtaatgataa | aaactactgg | ctggcgtttg | gcgaaaaacg | cgcctgggat | 1560 |
| aaaaatgagc | tggcgtacat | tacggaagcg | ccttccattg | tgcagccaga | gaacgttacg | 1620 |
| cgcgatactg | cgactttcaa | cctgccgttt | atttcgctgg | ggcaagtcgg | tgaaggcaaa | 1680 |
| ctgatggtta | tcggtaaccc | gcactacaac | agcatcctgc | gttgccccgaa | cggttacagt | 1740 |
| tggggcggtg | gtgttaatag | taaaggtgag | tgtacgctca | gcggtgattc | tgatgacatg | 1800 |
| aagcacttta | tgcagaacgt | actgcgctac | ttgtcaaatg | acatctggca | gccaaatacc | 1860 |
| aagagcatca | tgactgtcgg | caccaacctg | gagaacgttt | atttcaaaaa | agcgggccag | 1920 |

-continued

```
gtattgggaa atagtgcacc atttgctttc catgaggatt tcactggtat cacggttaaa    1980
cagttgacca gctatggcga tctgaatccg aagagattc cgttgctgat cctcaacggc    2040
tttgaatatg tgactcagtg gtctggcgat ccctatgctg tgcctctgcg tgcagatacc    2100
agcaaaccga agctgactca gcaggatgtg accgatctga tcgcttatct gaacaaaggt    2160
ggctcggtgc tgatcatgga aaacgtgatg agcaatctta aggaagagag cgcgtccagt    2220
tttgtgcgtc tgctggatgc cgcgggtctg tcaatggctc tgaacaaatc ggtggtgaac    2280
aacgatccgc aagggtatcc ggatcgcgtt cgtcagcgtc gcgcgactgg catttgggtt    2340
tatgaacgtt atcctgctgc agacggcgcg caaccgccgt acaccatcga cccaaataca    2400
ggggaagtga cctggaaata ccagcaagac aacaagcctg atgacaagcc gaaactggaa    2460
gttgcgagct ggcaggagga agttgagggc aaacaggtaa cgcgttatgc ctttattgat    2520
gaagcggaat acacaacaga agaatctctg gaagcggcaa aggcaaaaat ctttgagaag    2580
tttcctgggt tacaggagtg taaggactcg acttaccatt acgagattaa ctgtttggag    2640
cgccgcccag gcacggatgt tccggtaaca ggtggcatgt atgttccgcg ctatacgcaa    2700
ctgaatcttg acgccgacac cgcgaaagcg atggtgcagg cggcggattt aggcaccaac    2760
attcagcgcc tgtatcagca tgagctttat ttccgtacca aaggcagtaa aggtgagcgt    2820
ctgaacagtg ttgatctgga acgtctgtac cagaacatgt cggtctggct gtggaacgat    2880
acgaaatatc gttacgaaga gggcaaggaa gatgagctgg gctttaaaac gttcaccgag    2940
ttcctgaact gctacgccaa tgatgcctat gcaggcggca ccaagtgctc cgcagatctg    3000
aaaaaatcgc tggtcgataa caacatgatc tacggtgacg gtagcagcaa agcgggcatg    3060
atgaacccaa gctatccgct caactatatg gaaaaaccgc tgacgcgtct gatgctgggc    3120
cgttcctggt gggatctgaa cattaaggtt gatgtggaga agtacccagg atccgtatcg    3180
gcaaagggtg agagcgttac ggaaaacatc agcctgtact cgaatccgac caaatggttt    3240
gcgggtaaca tgcagtcaac cggcctgtgg gcaccggccc agcaggacgt caccattaag    3300
tcttcggcgt cagtcccagt gactgttacc gtggcgctgg ctgacgacct gactggacgt    3360
gagaagcatg aagttgcgct gaaccgtccg ccaagagtga ctaaaacgta tactctggag    3420
gctaacggtg aagtgacctt caaggtgcct tatggtggtc tgatttatat caagggcgac    3480
agtaaggatg atgtttctgc taacttcacc tttaccggtg tagtaaaagc gccgttctat    3540
aaagacggcg aatggaaaaa cgatctggac tcaccggcgc cgctgggcga gctggagtct    3600
gcgtcgttcg tctataccac gccgaagaag aaccttgagg ccagcaattt cactggtggt    3660
gtagcagaat cgctaaaga tctggatacc tttgccagct cgatgaatga cttctacggt    3720
cgtaatgatg aagacggtaa gcaccggatg tttacctata aaaacttgac ggggcacaag    3780
catcgtttca ccaacgatgt gcagatctcc atcggtgatg cgcactcggg ttatccggta    3840
atgaacagca gcttctcgac gaacagcacc acgctgccga cgacgccgct gaacgactgg    3900
ctgatttggc acgaagtcgg tcataacgct gcagaaacac cgctgaacgt accgggtgca    3960
actgaagtgg cgaacaacgt gctggcgctg tacatgcagg atcgctatct cggtaagatg    4020
aaccgtgtcg ctgacgacat taccgtcgcg ccggaatatc tggacgagag caacggtcag    4080
gcctgggcgc gcggcggtgc gggtgaccgt ctgctgatgt acgcacagtt gaaggagtgg    4140
gcagaggaaa actttgatat caaacagtgg tatccagatg gtgagctgcc taagttctac    4200
agcgatcgta aagggatgaa gggctggaac ctgttccagt tgatgcaccg taaagcgcgc    4260
ggcgatgatg ttggtaacag cacctttggt ggcaagaatt actgtgctga atccaatggt    4320
```

```
aacgctgccg acacgctgat gctgtgtgca tcctgggtcg ctcaggcgga tctttcggaa      4380
ttctttaaga aatggaatcc gggtgcaagt gcttaccagt tgccgggagc aacggagatg      4440
agtttccagg gcggtgtgag ctcttcggct tacagcacgc tggcgtcact caagctgccg      4500
aaaccggaaa aagggccgga aaccattaac aaggttaccg agcataagat gtctgccgag      4560
taa                                                                   4563

<210> SEQ ID NO 28
<211> LENGTH: 1520
<212> TYPE: PRT
<213> ORGANISM: Escherichia coli

<400> SEQUENCE: 28

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
            20                  25                  30

Ser Asp Thr Pro Ser Val Asp Ser Gly Ser Gly Thr Leu Pro Glu Val
        35                  40                  45

Lys Pro Asp Pro Thr Pro Thr Pro Glu Pro Thr Pro Glu Pro Thr Pro
    50                  55                  60

Asp Pro Glu Pro Thr Pro Asp Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
            100                 105                 110

Asp Gly Phe Thr Phe Thr Pro Gly Asn Thr Val Ser Cys Val Val Gly
        115                 120                 125

Ser Thr Thr Ile Ala Thr Phe Asn Thr Gln Ser Glu Ala Ala Arg Ser
130                 135                 140

Leu Arg Ala Val Asp Lys Val Ser Phe Ser Leu Glu Asp Ala Gln Glu
145                 150                 155                 160

Leu Ala Asn Ser Glu Asn Lys Lys Thr Asn Ala Ile Ser Leu Val Thr
                165                 170                 175

Ser Ser Asp Ser Cys Pro Ala Asp Ala Glu Gln Leu Cys Leu Thr Phe
            180                 185                 190

Ser Ser Val Val Asp Arg Ala Arg Phe Glu Lys Leu Tyr Lys Gln Ile
        195                 200                 205

Asp Leu Ala Thr Asp Asn Phe Ser Lys Leu Val Asn Glu Glu Val Glu
    210                 215                 220

Asn Asn Ala Ala Thr Asp Lys Ala Pro Ser Thr His Thr Ser Thr Val
225                 230                 235                 240

Val Pro Val Thr Thr Glu Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265                 270

Ile Leu Ser Glu Gly Gln Leu Val Asp Ser Leu Gly Asn Gly Val Ala
        275                 280                 285

Gly Val Asp Tyr Tyr Thr Asn Ser Gly Arg Gly Val Thr Asp Glu Asn
    290                 295                 300

Gly Lys Phe Ser Phe Ser Trp Gly Glu Thr Ile Ser Phe Gly Ile Asp
305                 310                 315                 320
```

Thr Phe Glu Leu Gly Ser Val Arg Gly Asn Lys Ser Thr Ile Ala Leu
            325                 330                 335

Thr Glu Leu Gly Asp Glu Val Arg Gly Ala Asn Ile Asp Gln Leu Ile
            340                 345                 350

His Arg Tyr Ser Thr Thr Gly Gln Asn Asn Thr Arg Val Val Pro Asp
            355                 360                 365

Asp Val Arg Lys Val Phe Ala Glu Tyr Pro Asn Val Ile Asn Glu Ile
370                 375                 380

Ile Asn Leu Ser Leu Ser Asn Gly Ala Thr Leu Asp Glu Gly Asp Gln
385                 390                 395                 400

Asn Val Val Leu Pro Asn Glu Phe Ile Glu Gln Phe Lys Thr Gly Gln
            405                 410                 415

Ala Lys Glu Ile Asp Thr Ala Ile Cys Ala Lys Thr Asp Gly Cys Asn
            420                 425                 430

Glu Ala Arg Trp Phe Ser Leu Thr Thr Arg Asn Val Asn Asp Gly Gln
            435                 440                 445

Ile Gln Gly Val Ile Asn Lys Leu Trp Gly Val Asp Thr Asn Tyr Gln
            450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ser
            485                 490                 495

Ala Phe Pro Ile Leu Met Ala Arg Asn Asp Lys Asn Tyr Trp Leu Ala
            500                 505                 510

Phe Gly Glu Lys Arg Ala Trp Asp Lys Asn Glu Leu Ala Tyr Ile Thr
            515                 520                 525

Glu Ala Pro Ser Ile Val Gln Pro Glu Asn Val Thr Arg Asp Thr Ala
            530                 535                 540

Thr Phe Asn Leu Pro Phe Ile Ser Leu Gly Gln Val Gly Glu Gly Lys
545                 550                 555                 560

Leu Met Val Ile Gly Asn Pro His Tyr Asn Ser Ile Leu Arg Cys Pro
            565                 570                 575

Asn Gly Tyr Ser Trp Gly Gly Val Asn Ser Lys Gly Glu Cys Thr
            580                 585                 590

Leu Ser Gly Asp Ser Asp Met Lys His Phe Met Gln Asn Val Leu
            595                 600                 605

Arg Tyr Leu Ser Asn Asp Ile Trp Gln Pro Asn Thr Lys Ser Ile Met
            610                 615                 620

Thr Val Gly Thr Asn Leu Glu Asn Val Tyr Phe Lys Lys Ala Gly Gln
625                 630                 635                 640

Val Leu Gly Asn Ser Ala Pro Phe Ala Phe His Glu Asp Phe Thr Gly
            645                 650                 655

Ile Thr Val Lys Gln Leu Thr Ser Tyr Gly Asp Leu Asn Pro Glu Glu
            660                 665                 670

Ile Pro Leu Leu Ile Leu Asn Gly Phe Glu Tyr Val Thr Gln Trp Ser
            675                 680                 685

Gly Asp Pro Tyr Ala Val Pro Leu Arg Ala Asp Thr Ser Lys Pro Lys
            690                 695                 700

Leu Thr Gln Gln Asp Val Thr Asp Leu Ile Ala Tyr Leu Asn Lys Gly
705                 710                 715                 720

Gly Ser Val Leu Ile Met Glu Asn Val Met Ser Asn Leu Lys Glu Glu
            725                 730                 735

Ser Ala Ser Ser Phe Val Arg Leu Leu Asp Ala Ala Gly Leu Ser Met

```
                    740                 745                 750
Ala Leu Asn Lys Ser Val Val Asn Asn Asp Pro Gln Gly Tyr Pro Asp
                755                 760                 765

Arg Val Arg Gln Arg Arg Ala Thr Gly Ile Trp Val Tyr Glu Arg Tyr
            770                 775                 780

Pro Ala Ala Asp Gly Ala Gln Pro Pro Tyr Thr Ile Asp Pro Asn Thr
785                 790                 795                 800

Gly Glu Val Thr Trp Lys Tyr Gln Gln Asp Asn Lys Pro Asp Asp Lys
                805                 810                 815

Pro Lys Leu Glu Val Ala Ser Trp Gln Glu Val Glu Gly Lys Gln
            820                 825                 830

Val Thr Arg Tyr Ala Phe Ile Asp Glu Ala Glu Tyr Thr Thr Glu Glu
                835                 840                 845

Ser Leu Glu Ala Ala Lys Ala Lys Ile Phe Glu Lys Phe Pro Gly Leu
            850                 855                 860

Gln Glu Cys Lys Asp Ser Thr Tyr His Tyr Glu Ile Asn Cys Leu Glu
865                 870                 875                 880

Arg Arg Pro Gly Thr Asp Val Pro Val Thr Gly Gly Met Tyr Val Pro
                885                 890                 895

Arg Tyr Thr Gln Leu Asn Leu Asp Ala Asp Thr Ala Lys Ala Met Val
            900                 905                 910

Gln Ala Ala Asp Leu Gly Thr Asn Ile Gln Arg Leu Tyr Gln His Glu
            915                 920                 925

Leu Tyr Phe Arg Thr Lys Gly Ser Lys Gly Glu Arg Leu Asn Ser Val
            930                 935                 940

Asp Leu Glu Arg Leu Tyr Gln Asn Met Ser Val Trp Leu Trp Asn Asp
945                 950                 955                 960

Thr Lys Tyr Arg Tyr Glu Glu Gly Lys Glu Asp Glu Leu Gly Phe Lys
                965                 970                 975

Thr Phe Thr Glu Phe Leu Asn Cys Tyr Ala Asn Asp Ala Tyr Ala Gly
            980                 985                 990

Gly Thr Lys Cys Ser Ala Asp Leu Lys Lys Ser Leu Val Asp Asn Asn
            995                 1000                1005

Met Ile Tyr Gly Asp Gly Ser Ser Lys Ala Gly Met Met Asn Pro Ser
            1010                1015                1020

Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
                1045                1050                1055

Gly Ser Val Ser Ala Lys Gly Glu Ser Val Thr Glu Asn Ile Ser Leu
            1060                1065                1070

Tyr Ser Asn Pro Thr Lys Trp Phe Ala Gly Asn Met Gln Ser Thr Gly
            1075                1080                1085

Leu Trp Ala Pro Ala Gln Gln Asp Val Thr Ile Lys Ser Ser Ala Ser
            1090                1095                1100

Val Pro Val Thr Val Thr Val Ala Leu Ala Asp Asp Leu Thr Gly Arg
1105                1110                1115                1120

Glu Lys His Glu Val Ala Leu Asn Arg Pro Pro Arg Val Thr Lys Thr
                1125                1130                1135

Tyr Thr Leu Glu Ala Asn Gly Glu Val Thr Phe Lys Val Pro Tyr Gly
            1140                1145                1150

Gly Leu Ile Tyr Ile Lys Gly Asp Ser Lys Asp Val Ser Ala Asn
            1155                1160                1165
```

Phe Thr Phe Thr Gly Val Val Lys Ala Pro Phe Tyr Lys Asp Gly Glu
        1170                1175                1180

Trp Lys Asn Asp Leu Asp Ser Pro Ala Pro Leu Gly Glu Leu Glu Ser
1185                1190                1195                1200

Ala Ser Phe Val Tyr Thr Thr Pro Lys Lys Asn Leu Glu Ala Ser Asn
            1205                1210                1215

Phe Thr Gly Gly Val Ala Glu Phe Ala Lys Asp Leu Asp Thr Phe Ala
            1220                1225                1230

Ser Ser Met Asn Asp Phe Tyr Gly Arg Asn Asp Glu Asp Gly Lys His
        1235                1240                1245

Arg Met Phe Thr Tyr Lys Asn Leu Thr Gly His Lys His Arg Phe Thr
        1250                1255                1260

Asn Asp Val Gln Ile Ser Ile Gly Asp Ala His Ser Gly Tyr Pro Val
1265                1270                1275                1280

Met Asn Ser Ser Phe Ser Thr Asn Ser Thr Thr Leu Pro Thr Thr Pro
            1285                1290                1295

Leu Asn Asp Trp Leu Ile Trp His Glu Val Gly His Asn Ala Ala Glu
        1300                1305                1310

Thr Pro Leu Asn Val Pro Gly Ala Thr Glu Val Ala Asn Asn Val Leu
        1315                1320                1325

Ala Leu Tyr Met Gln Asp Arg Tyr Leu Gly Lys Met Asn Arg Val Ala
        1330                1335                1340

Asp Asp Ile Thr Val Ala Pro Glu Tyr Leu Asp Glu Ser Asn Gly Gln
1345                1350                1355                1360

Ala Trp Ala Arg Gly Gly Ala Gly Asp Arg Leu Leu Met Tyr Ala Gln
            1365                1370                1375

Leu Lys Glu Trp Ala Glu Glu Asn Phe Asp Ile Lys Gln Trp Tyr Pro
        1380                1385                1390

Asp Gly Glu Leu Pro Lys Phe Tyr Ser Asp Arg Lys Gly Met Lys Gly
        1395                1400                1405

Trp Asn Leu Phe Gln Leu Met His Arg Lys Ala Arg Gly Asp Asp Val
        1410                1415                1420

Gly Asn Ser Thr Phe Gly Gly Lys Asn Tyr Cys Ala Glu Ser Asn Gly
1425                1430                1435                1440

Asn Ala Ala Asp Thr Leu Met Leu Cys Ala Ser Trp Val Ala Gln Ala
            1445                1450                1455

Asp Leu Ser Glu Phe Phe Lys Lys Trp Asn Pro Gly Ala Ser Ala Tyr
        1460                1465                1470

Gln Leu Pro Gly Ala Thr Glu Met Ser Phe Gln Gly Val Ser Ser
        1475                1480                1485

Ser Ala Tyr Ser Thr Leu Ala Ser Leu Lys Leu Pro Lys Pro Glu Lys
        1490                1495                1500

Gly Pro Glu Thr Ile Asn Lys Val Thr Glu His Lys Met Ser Ala Glu
1505                1510                1515                1520

<210> SEQ ID NO 29
<211> LENGTH: 975
<212> TYPE: DNA
<213> ORGANISM: Escherichia coli

<400> SEQUENCE: 29
atgatcacct caccaccaaa acgcggaatg gcactggtcg tggtgctggt attgctggcg    60
gttatgatgc tggtgaccat cacgctttcc gggcggatgc agcaacaact tgggcgaacg   120

-continued

```
cgcagccagc aggagtacca gcaggcgctg tggtacagcg ccagtgcaga aagcctggcg      180
ctgagcgcgc tcagtctgag cctgaaaaat gaaaagcgtg tgcatctggc acaaccgtgg      240
gcttctggcc cgcgtttttt cccactgccg caggggcaaa ttgccgtcac tctgcgtgac      300
gcacaggcct gctttaacct gaatgccctc gctcagccga cgacggcgtc gcgtccgctc      360
gcggtacaac aactgattgc cctgatctcg cgcctcgatg tgcctgctta tcgggccgaa      420
ctgatagccg aaagcctgtg ggagtttatt gacgaagacc gcagcgtgca gacgcgtctg      480
ggtcgtgaag acagcgagta tctcgcccgc tcggtgccgt tctacgccgc taatcaaccg      540
ctggctgata tcagcgagat gcgcgtggtg cagggaatgg acgccgggct ttatcaaaaa      600
ctgaaaccgt tggtctgtgc gctgccgatg gcccgccagc aaatcaacat caatacatta      660
gatgtcacgc aaagtgtgat tcttgaggcg ctgtttgacc cgtggttaag ccctgttcag      720
gcgcgggcat tattacaaca acgtccggcg aagggctggg aagatgtcga tcagtttctt      780
gctcagccgc tacttgcaga cgtcgatgag cgtactaaaa aacagctaaa aaccatcctg      840
agcgtggaca gcaattactt ctggctgcgt tcagatatca ccgtgaatga gattgaactg      900
acgatgaatt cgttaattgt ccgcatgggc ccacaacact tttctgttct ctggcatcag      960
acaggagaaa gtgag                                                      975
```

<210> SEQ ID NO 30
<211> LENGTH: 325
<212> TYPE: PRT
<213> ORGANISM: Escherichia coli

<400> SEQUENCE: 30

```
Met Ile Thr Ser Pro Pro Lys Arg Gly Met Ala Leu Val Val Val Leu
1               5                   10                  15

Val Leu Leu Ala Val Met Met Leu Val Thr Ile Thr Leu Ser Gly Arg
            20                  25                  30

Met Gln Gln Gln Leu Gly Arg Thr Arg Ser Gln Gln Glu Tyr Gln Gln
        35                  40                  45

Ala Leu Trp Tyr Ser Ala Ser Ala Glu Ser Leu Ala Leu Ser Ala Leu
    50                  55                  60

Ser Leu Ser Leu Lys Asn Glu Lys Arg Val His Leu Ala Gln Pro Trp
65                  70                  75                  80

Ala Ser Gly Pro Arg Phe Phe Pro Leu Pro Gln Gly Gln Ile Ala Val
                85                  90                  95

Thr Leu Arg Asp Ala Gln Ala Cys Phe Asn Leu Asn Ala Leu Ala Gln
            100                 105                 110

Pro Thr Thr Ala Ser Arg Pro Leu Ala Val Gln Gln Leu Ile Ala Leu
        115                 120                 125

Ile Ser Arg Leu Asp Val Pro Ala Tyr Arg Ala Glu Leu Ile Ala Glu
    130                 135                 140

Ser Leu Trp Glu Phe Ile Asp Glu Asp Arg Ser Val Gln Thr Arg Leu
145                 150                 155                 160

Gly Arg Glu Asp Ser Glu Tyr Leu Ala Arg Ser Val Pro Phe Tyr Ala
                165                 170                 175

Ala Asn Gln Pro Leu Ala Asp Ile Ser Glu Met Arg Val Val Gln Gly
            180                 185                 190

Met Asp Ala Gly Leu Tyr Gln Lys Leu Lys Pro Leu Val Cys Ala Leu
        195                 200                 205

Pro Met Ala Arg Gln Gln Ile Asn Ile Asn Thr Leu Asp Val Thr Gln
    210                 215                 220
```

```
Ser Val Ile Leu Glu Ala Leu Phe Asp Pro Trp Leu Ser Pro Val Gln
225                 230                 235                 240

Ala Arg Ala Leu Leu Gln Gln Arg Pro Ala Lys Gly Trp Glu Asp Val
                245                 250                 255

Asp Gln Phe Leu Ala Gln Pro Leu Leu Ala Asp Val Ala Glu Arg Thr
            260                 265                 270

Lys Lys Gln Leu Lys Thr Ile Leu Ser Val Asp Ser Asn Tyr Phe Trp
        275                 280                 285

Leu Arg Ser Asp Ile Thr Val Asn Glu Ile Glu Leu Thr Met Asn Ser
    290                 295                 300

Leu Ile Val Arg Met Gly Pro Gln His Phe Ser Val Leu Trp His Gln
305                 310                 315                 320

Thr Gly Glu Ser Glu
                325

<210> SEQ ID NO 31
<211> LENGTH: 1520
<212> TYPE: PRT
<213> ORGANISM: Escherichia coli

<400> SEQUENCE: 31

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
                20                  25                  30

Ser Asp Thr Pro Ser Val Asp Ser Gly Ser Gly Thr Leu Pro Glu Val
            35                  40                  45

Lys Pro Asp Pro Thr Pro Thr Pro Glu Pro Thr Pro Glu Pro Thr Pro
    50                  55                  60

Asp Pro Glu Pro Thr Pro Asp Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
                100                 105                 110

Asp Gly Phe Thr Phe Thr Pro Gly Asn Thr Val Ser Cys Val Val Gly
            115                 120                 125

Ser Thr Thr Ile Ala Thr Phe Asn Thr Gln Ser Glu Ala Ala Arg Ser
    130                 135                 140

Leu Arg Ala Val Asp Lys Val Ser Phe Ser Leu Glu Asp Ala Gln Glu
145                 150                 155                 160

Leu Ala Asn Ser Glu Asn Lys Lys Thr Asn Ala Ile Ser Leu Val Thr
                165                 170                 175

Ser Ser Asp Ser Cys Pro Ala Asp Ala Glu Gln Leu Cys Leu Thr Phe
            180                 185                 190

Ser Ser Val Val Asp Arg Ala Arg Phe Glu Lys Leu Tyr Lys Gln Ile
    195                 200                 205

Asp Leu Ala Thr Asp Asn Phe Ser Lys Leu Val Asn Glu Glu Val Glu
    210                 215                 220

Asn Asn Ala Ala Thr Asp Lys Ala Pro Ser Thr His Thr Ser Thr Val
225                 230                 235                 240

Val Pro Val Thr Thr Glu Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
```

-continued

```
                260             265             270
Ile Leu Ser Glu Gly Gln Leu Val Asp Ser Leu Gly Asn Gly Val Ala
            275             280             285

Gly Val Asp Tyr Tyr Thr Asn Ser Gly Arg Gly Val Thr Asp Glu Asn
        290             295             300

Gly Lys Phe Ser Phe Ser Trp Gly Glu Thr Ile Ser Phe Gly Ile Asp
305             310             315             320

Thr Phe Glu Leu Gly Ser Val Arg Gly Asn Lys Ser Thr Ile Ala Leu
                325             330             335

Thr Glu Leu Gly Asp Glu Val Arg Gly Ala Asn Ile Asp Gln Leu Ile
            340             345             350

His Arg Tyr Ser Thr Thr Gly Gln Asn Asn Thr Arg Val Val Pro Asp
        355             360             365

Asp Val Arg Lys Val Phe Ala Glu Tyr Pro Asn Val Ile Asn Glu Ile
    370             375             380

Ile Asn Leu Ser Leu Ser Asn Gly Ala Thr Leu Asp Glu Gly Asp Gln
385             390             395             400

Asn Val Val Leu Pro Asn Glu Phe Ile Glu Gln Phe Lys Thr Gly Gln
                405             410             415

Ala Lys Glu Ile Asp Thr Ala Ile Cys Ala Lys Thr Asp Gly Cys Asn
            420             425             430

Glu Ala Arg Trp Phe Ser Leu Thr Thr Arg Asn Val Asn Asp Gly Gln
        435             440             445

Ile Gln Gly Val Ile Asn Lys Leu Trp Gly Val Asp Thr Asn Tyr Gln
    450             455             460

Ser Val Ser Lys Phe His Val Phe His Asp Ser Thr Asn Phe Tyr Gly
465             470             475             480

Ser Thr Gly Asn Ala Arg Gly Gln Ala Val Val Asn Ile Ser Asn Ser
                485             490             495

Ala Phe Pro Ile Leu Met Ala Arg Asn Asp Lys Asn Tyr Trp Leu Ala
            500             505             510

Phe Gly Glu Lys Arg Ala Trp Asp Lys Asn Glu Leu Ala Tyr Ile Thr
        515             520             525

Glu Ala Pro Ser Ile Val Gln Pro Glu Asn Val Thr Arg Asp Thr Ala
    530             535             540

Thr Phe Asn Leu Pro Phe Ile Ser Leu Gly Gln Val Gly Glu Gly Lys
545             550             555             560

Leu Met Val Ile Gly Asn Pro His Tyr Asn Ser Ile Leu Arg Cys Pro
                565             570             575

Asn Gly Tyr Ser Trp Gly Gly Val Asn Ser Lys Gly Glu Cys Thr
            580             585             590

Leu Ser Gly Asp Ser Asp Met Lys His Phe Met Gln Asn Val Leu
        595             600             605

Arg Tyr Leu Ser Asn Asp Ile Trp Gln Pro Asn Thr Lys Ser Ile Met
    610             615             620

Thr Val Gly Thr Asn Leu Glu Asn Val Tyr Phe Lys Lys Ala Gly Gln
625             630             635             640

Val Leu Gly Asn Ser Ala Pro Phe Ala Phe His Glu Asp Phe Thr Gly
                645             650             655

Ile Thr Val Lys Gln Leu Thr Ser Tyr Gly Asp Leu Asn Pro Glu Glu
            660             665             670

Ile Pro Leu Leu Ile Leu Asn Gly Phe Glu Tyr Val Thr Gln Trp Ser
        675             680             685
```

```
Gly Asp Pro Tyr Ala Val Pro Leu Arg Ala Asp Thr Ser Lys Pro Lys
    690             695                 700

Leu Thr Gln Gln Asp Val Thr Asp Leu Ile Ala Tyr Leu Asn Lys Gly
705             710                 715                 720

Gly Ser Val Leu Ile Met Glu Asn Val Met Ser Asn Leu Lys Glu Glu
                725                 730                 735

Ser Ala Ser Ser Phe Val Arg Leu Leu Asp Ala Ala Gly Leu Ser Met
            740                 745                 750

Ala Leu Asn Lys Ser Val Val Asn Asn Asp Pro Gln Gly Tyr Pro Asp
        755                 760                 765

Arg Val Arg Gln Arg Arg Ala Thr Gly Ile Trp Val Tyr Glu Arg Tyr
    770                 775                 780

Pro Ala Ala Asp Gly Ala Gln Pro Pro Tyr Thr Ile Asp Pro Asn Thr
785             790                 795                 800

Gly Glu Val Thr Trp Lys Tyr Gln Gln Asp Asn Lys Pro Asp Asp Lys
                805                 810                 815

Pro Lys Leu Glu Val Ala Ser Trp Gln Glu Val Glu Gly Lys Gln
            820                 825                 830

Val Thr Arg Tyr Ala Phe Ile Asp Glu Ala Glu Tyr Thr Thr Glu Glu
    835                 840                 845

Ser Leu Glu Ala Ala Lys Ala Lys Ile Phe Glu Lys Phe Pro Gly Leu
850                 855                 860

Gln Glu Cys Lys Asp Ser Thr Tyr His Tyr Glu Ile Asn Cys Leu Glu
865                 870                 875                 880

Arg Arg Pro Gly Thr Asp Val Pro Val Thr Gly Gly Met Tyr Val Pro
                885                 890                 895

Arg Tyr Thr Gln Leu Asn Leu Asp Ala Asp Thr Ala Lys Ala Met Val
            900                 905                 910

Gln Ala Ala Asp Leu Gly Thr Asn Ile Gln Arg Leu Tyr Gln His Glu
        915                 920                 925

Leu Tyr Phe Arg Thr Lys Gly Ser Lys Gly Glu Arg Leu Asn Ser Val
    930                 935                 940

Asp Leu Glu Arg Leu Tyr Gln Asn Met Ser Val Trp Leu Trp Asn Asp
945             950                 955                 960

Thr Lys Tyr Arg Tyr Glu Glu Gly Lys Glu Asp Glu Leu Gly Phe Lys
                965                 970                 975

Thr Phe Thr Glu Phe Leu Asn Cys Tyr Ala Asn Asp Ala Tyr Ala Gly
            980                 985                 990

Gly Thr Lys Cys Ser Ala Asp Leu Lys Lys Ser Leu Val Asp Asn Asn
        995                 1000                1005

Met Ile Tyr Gly Asp Gly Ser Ser Lys Ala Gly Met Met Asn Pro Ser
    1010                1015                1020

Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
                1045                1050                1055

Gly Ser Val Ser Ala Lys Gly Glu Ser Val Thr Glu Asn Ile Ser Leu
            1060                1065                1070

Tyr Ser Asn Pro Thr Lys Trp Phe Ala Gly Asn Met Gln Ser Thr Gly
        1075                1080                1085

Leu Trp Ala Pro Ala Gln Gln Asp Val Thr Ile Lys Ser Ser Ala Ser
    1090                1095                1100
```

```
Val Pro Val Thr Val Thr Val Ala Leu Ala Asp Asp Leu Thr Gly Arg
1105                1110                1115                1120

Glu Lys His Glu Val Ala Leu Asn Arg Pro Pro Arg Val Thr Lys Thr
            1125                1130                1135

Tyr Thr Leu Glu Ala Asn Gly Glu Val Thr Phe Lys Val Pro Tyr Gly
        1140                1145                1150

Gly Leu Ile Tyr Ile Lys Gly Asp Ser Lys Asp Asp Val Ser Ala Asn
            1155                1160                1165

Phe Thr Phe Thr Gly Val Val Lys Ala Pro Phe Tyr Lys Asp Gly Glu
        1170                1175                1180

Trp Lys Asn Asp Leu Asp Ser Pro Ala Pro Leu Gly Glu Leu Glu Ser
1185                1190                1195                1200

Ala Ser Phe Val Tyr Thr Thr Pro Lys Lys Asn Leu Glu Ala Ser Asn
            1205                1210                1215

Phe Thr Gly Gly Val Ala Glu Phe Ala Lys Asp Leu Asp Thr Phe Ala
        1220                1225                1230

Ser Ser Met Asn Asp Phe Tyr Gly Arg Asn Asp Glu Asp Gly Lys His
            1235                1240                1245

Arg Met Phe Thr Tyr Lys Asn Leu Thr Gly His Lys His Arg Phe Thr
    1250                1255                1260

Asn Asp Val Gln Ile Ser Ile Gly Asp Ala His Ser Gly Tyr Pro Val
1265                1270                1275                1280

Met Asn Ser Ser Phe Ser Thr Asn Ser Thr Thr Leu Pro Thr Thr Pro
            1285                1290                1295

Leu Asn Asp Trp Leu Ile Trp Ala Ala Val Gly Ala Asn Ala Ala Glu
        1300                1305                1310

Thr Pro Leu Asn Val Pro Gly Ala Thr Glu Val Ala Asn Asn Val Leu
        1315                1320                1325

Ala Leu Tyr Met Gln Asp Arg Tyr Leu Gly Lys Met Asn Arg Val Ala
        1330                1335                1340

Asp Asp Ile Thr Val Ala Pro Glu Tyr Leu Asp Glu Ser Asn Gly Gln
1345                1350                1355                1360

Ala Trp Ala Arg Gly Gly Ala Gly Asp Arg Leu Leu Met Tyr Ala Gln
            1365                1370                1375

Leu Lys Glu Trp Ala Glu Glu Asn Phe Asp Ile Lys Gln Trp Tyr Pro
        1380                1385                1390

Asp Gly Glu Leu Pro Lys Phe Tyr Ser Asp Arg Lys Gly Met Lys Gly
            1395                1400                1405

Trp Asn Leu Phe Gln Leu Met His Arg Lys Ala Arg Gly Asp Asp Val
1410                1415                1420

Gly Asn Ser Thr Phe Gly Gly Lys Asn Tyr Cys Ala Glu Ser Asn Gly
1425                1430                1435                1440

Asn Ala Ala Asp Thr Leu Met Leu Cys Ala Ser Trp Val Ala Gln Ala
            1445                1450                1455

Asp Leu Ser Glu Phe Phe Lys Lys Trp Asn Pro Gly Ala Ser Ala Tyr
        1460                1465                1470

Gln Leu Pro Gly Ala Thr Glu Met Ser Phe Gln Gly Gly Val Ser Ser
        1475                1480                1485

Ser Ala Tyr Ser Thr Leu Ala Ser Leu Lys Leu Pro Lys Pro Glu Lys
        1490                1495                1500

Gly Pro Glu Thr Ile Asn Lys Val Thr Glu His Lys Met Ser Ala Glu
1505                1510                1515                1520
```

```
<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
tgatgccgtt ttcttaagaa tggaggaa                                       28

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
gagccagaac ctgttccta                                                 19

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
gtaaagccat cgctggattc a                                              21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ccacctcttc attgaccagc                                                20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cggaacagtt ttatcagtat                                                20

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
ccccgcgaac ttcatcac                                                  18

<210> SEQ ID NO 38
<211> LENGTH: 21
<212> TYPE: DNA
<213> ORGANISM: Artificial Sequence
<220> FEATURE:
<223> OTHER INFORMATION: Primer
```

<400> SEQUENCE: 38
gcaaggtctt tgccgagtat c                                    21

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
tgataaaaac tactggctgg c                                    21

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
ggttaccgat aaccatcag                                       19

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
gcagatacca gcaaaccga                                       19

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
tcatcacgtt ttccatgatc agc                                  23

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
gcggatttag gcaccaacat tc                                   22

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
gaatgttggt gcctaaatcc gc                                   22

<210> SEQ ID NO 45
<211> LENGTH: 23

```
<212> TYPE: DNA
<213> ORGANISM: Artificial Sequence
<220> FEATURE:
<223> OTHER INFORMATION: Primer

<400> SEQUENCE: 45
gtgaacgttt taaagcccag ctc                                          23

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
aactatatgg aaaaaccgct gac                                          23

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
aaagcgccgt tctataaaga                                              20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ttatagaacg gcgcttttac                                              20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
catcaccgat ggagatctgc                                              20

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
aagatgaacc gtgtcgctga c                                            21

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
```
ctggaacctg ttccagttga t                                              21

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
atcaactgga acaggttcca g                                              21

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
tattgctgaa aaacatcaaa aag                                            23

<210> SEQ ID NO 54
<211> LENGTH: 1521
<212> TYPE: PRT
<213> ORGANISM: Escherichia coli
<220> FEATURE:
<221> NAME/KEY: misc_feature
<222> LOCATION: 37, 42, 44, 55, 71, 121, 122, 124, 127,
      129, 130, 150, 164, 166, 170, 173, 179, 186, 189,
      192, 197, 198, 199, 200, 203, 204, 213, 214, 215,
      217, 240, 247, 279, 284, 286, 289, 296, 303, 307,
      358, 359, 361, 370, 397, 400, 402, 404, 414, 430,
      462, 465, 468, 559, 583, 588, 589, 595, 596, 598,
      603, 616, 618, 621, 623, 624, 632, 633, 638, 643,
      648, 650, 653, 656, 659, 661, 662, 664, 674, 688,
      690, 695, 741, 774, 788, 791, 792, 793, 799, 800,
      805, 810, 811, 826, 828, 830, 834, 844, 845, 846,
      848, 849, 852, 856, 859, 860, 861, 866, 871, 872,
      877, 882, 887, 898, 903, 905, 937, 943, 961, 962,
      963, 968, 969, 971, 992, 993, 996, 1000, 1009, 1014,
      1015, 1017, 1059, 1062, 1063, 1066, 1070, 1096, 1101,
      1103, 1105, 1133, 1139, 1141, 1143, 1145, 1147, 1163,
      1164, 1166, 1169, 1185, 1189, 1202, 1203, 1214, 1218,
      1222, 1223, 1227, 1244, 1246, 1256, 1317, 1356, 1390,
      1394, 1396, 1399, 1403, 1424, 1427, 1428, 1429, 1432,
      1433, 1479, 1493, 1497, 1499, 1505, 1512
<223> OTHER INFORMATION: 'Xaa' is any amino acid
<220> FEATURE:
<221> NAME/KEY: misc_feature
<222> LOCATION: 534
<223> OTHER INFORMATION: 'Xaa' is Ile or Leu

<400> SEQUENCE: 54

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
            20                  25                  30

Ser Asp Thr Pro Xaa Val Asp Ser Gly Xaa Gly Xaa Leu Pro Glu Val
        35                  40                  45

Lys Pro Asp Pro Thr Pro Xaa Pro Glu Pro Thr Pro Glu Pro Thr Pro
    50                  55                  60

Asp Pro Glu Pro Thr Pro Xaa Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser

```
                100             105             110
Asp Gly Phe Thr Phe Thr Pro Gly Xaa Xaa Val Xaa Cys Val Xaa Gly
            115                 120                 125

Xaa Xaa Thr Thr Ile Ala Thr Phe Asx Thr Gln Ser Glu Ala Ala Arg
        130                 135                 140

Ser Leu Arg Ala Val Xaa Lys Val Ser Phe Ser Leu Glu Asp Ala Gln
145                 150                 155                 160

Glu Leu Ala Xaa Ser Xaa Asx Lys Lys Xaa Asn Ala Xaa Ser Leu Val
                165                 170                 175

Thr Ser Xaa Asx Ser Cys Pro Ala Asx Xaa Glu Gln Xaa Cys Leu Xaa
            180                 185                 190

Phe Ser Ser Val Xaa Xaa Xaa Arg Phe Xaa Xaa Leu Tyr Lys Gln
        195                 200                 205

Ile Asp Leu Ala Xaa Xaa Xaa Phe Xaa Lys Leu Val Asn Glu Glu Val
        210                 215                 220

Glu Asn Ala Ala Thr Asp Lys Ala Pro Ser Thr His Thr Ser Xaa
225                 230                 235                 240

Val Val Pro Val Thr Thr Xaa Gly Thr Lys Pro Asp Leu Asn Ala Ser
            245                 250                 255

Phe Val Ser Ala Asn Ala Glu Gln Phe Tyr Gln Tyr Gln Pro Thr Glu
            260                 265                 270

Ile Ile Leu Ser Glu Gly Xaa Leu Val Asp Ser Xaa Gly Xaa Gly Val
            275                 280                 285

Xaa Gly Val Asx Tyr Tyr Thr Xaa Ser Gly Arg Gly Val Thr Xaa Glu
        290                 295                 300

Asn Gly Xaa Phe Ser Phe Ser Trp Gly Glu Thr Ile Ser Phe Gly Ile
305                 310                 315                 320

Asp Thr Phe Glu Leu Gly Ser Val Arg Gly Asn Lys Ser Thr Ile Ala
            325                 330                 335

Leu Thr Glu Leu Gly Asp Glu Val Arg Gly Ala Asn Ile Asp Gln Leu
            340                 345                 350

Ile His Arg Tyr Ser Xaa Xaa Gly Xaa Asn Asx Thr Arg Val Val Pro
            355                 360                 365

Asp Xaa Val Arg Lys Val Phe Ala Glu Tyr Pro Asn Val Ile Asn Glu
        370                 375                 380

Ile Ile Asn Leu Ser Leu Ser Asn Gly Ala Thr Leu Xaa Glu Gly Xaa
385                 390                 395                 400

Gln Xaa Val Xaa Leu Pro Asn Glu Phe Ile Glu Gln Phe Xaa Thr Gly
            405                 410                 415

Gln Ala Lys Glu Ile Asp Thr Ala Ile Cys Ala Lys Thr Xaa Gly Cys
            420                 425                 430

Asn Glu Ala Arg Trp Phe Ser Leu Thr Thr Arg Asn Val Asn Asp Gly
            435                 440                 445

Gln Ile Gln Gly Val Ile Asn Lys Leu Trp Gly Val Asp Xaa Asx Tyr
            450                 455                 460

Xaa Ser Val Xaa Lys Phe His Val Phe His Asp Ser Thr Asn Phe Tyr
465                 470                 475                 480

Gly Ser Thr Gly Asn Ala Arg Gly Gln Ala Val Val Asn Ile Ser Asn
            485                 490                 495

Ala Ala Phe Pro Ile Leu Met Ala Arg Asn Asp Lys Asn Tyr Trp Leu
            500                 505                 510

Ala Phe Gly Glu Lys Arg Ala Trp Asp Lys Asn Glu Leu Ala Tyr Ile
            515                 520                 525
```

```
Thr Glu Ala Pro Ser Xaa Val Glx Pro Glu Asn Val Thr Arg Asp Thr
            530                 535                 540

Ala Thr Phe Asn Leu Pro Phe Ile Ser Leu Gly Gln Val Gly Xaa Gly
545                 550                 555                 560

Lys Leu Met Val Ile Gly Asn Pro His Tyr Asn Ser Ile Leu Arg Cys
                565                 570                 575

Pro Asn Gly Tyr Ser Trp Xaa Gly Val Asn Xaa Xaa Gly Glx Cys
            580                 585                 590

Thr Leu Xaa Xaa Asp Xaa Asp Met Lys Xaa Phe Met Glx Asn Val
            595                 600                 605

Leu Arg Tyr Leu Ser Asx Asp Xaa Trp Xaa Pro Asx Xaa Lys Xaa Xaa
            610                 615                 620

Met Thr Val Gly Thr Asn Leu Xaa Xaa Val Tyr Phe Lys Xaa His Gly
625                 630                 635                 640

Gln Val Xaa Gly Asn Ser Ala Xaa Phe Xaa Phe His Xaa Asp Phe Xaa
                645                 650                 655

Gly Ile Xaa Val Xaa Xaa Leu Xaa Ser Tyr Gly Asp Leu Asx Pro Glx
                660                 665                 670

Glu Xaa Pro Leu Leu Ile Leu Asn Gly Phe Glu Tyr Val Thr Gln Xaa
            675                 680                 685

Gly Xaa Asp Pro Tyr Ala Xaa Pro Leu Arg Ala Asp Thr Ser Lys Pro
690                 695                 700

Lys Leu Thr Gln Gln Asp Val Thr Asp Leu Ile Ala Tyr Leu Asn Lys
705                 710                 715                 720

Gly Gly Ser Val Leu Ile Met Glu Asn Val Met Ser Asn Leu Lys Glu
                725                 730                 735

Glu Ser Ala Ser Xaa Phe Val Arg Leu Leu Asp Ala Ala Gly Leu Ser
            740                 745                 750

Met Ala Leu Asn Lys Ser Val Val Asn Asn Asp Pro Gln Gly Tyr Pro
            755                 760                 765

Asx Arg Val Arg Gln Xaa Arg Ala Thr Gly Ile Trp Val Tyr Glu Arg
            770                 775                 780

Tyr Pro Ala Xaa Asp Gly Xaa Xaa Xaa Pro Tyr Thr Ile Asp Xaa Xaa
785                 790                 795                 800

Thr Gly Glu Val Xaa Trp Lys Tyr Gln Xaa Xaa Asn Lys Pro Asp Asp
                805                 810                 815

Lys Pro Lys Leu Glu Val Ala Ser Trp Xaa Glu Xaa Val Xaa Gly Lys
            820                 825                 830

Gln Xaa Thr Arg Tyr Ala Phe Ile Asp Glu Ala Xaa Xaa Xaa Thr Xaa
            835                 840                 845

Xaa Ser Leu Xaa Ala Ala Lys Xaa Lys Ile Xaa Xaa Xaa Phe Pro Gly
850                 855                 860

Leu Xaa Glu Cys Lys Asp Xaa Xaa Tyr His Tyr Glu Xaa Asn Cys Leu
865                 870                 875                 880

Glu Xaa Arg Pro Gly Thr Xaa Val Pro Val Thr Gly Gly Met Tyr Val
            885                 890                 895

Pro Xaa Tyr Thr Gln Leu Xaa Leu Xaa Ala Asp Thr Ala Lys Ala Met
            900                 905                 910

Val Gln Ala Ala Asp Leu Gly Thr Asn Ile Gln Arg Leu Tyr Gln His
            915                 920                 925

Glu Leu Tyr Phe Arg Thr Asn Gly Xaa Lys Gly Glu Arg Leu Xaa Ser
930                 935                 940
```

```
Val Asp Leu Glu Arg Leu Tyr Gln Asn Met Ser Val Trp Leu Trp Asn
945                 950                 955                 960

Xaa Xaa Xaa Tyr Arg Tyr Glu Xaa Xaa Lys Xaa Asp Glu Leu Gly Phe
            965                 970                 975

Lys Thr Phe Thr Glu Phe Leu Asn Cys Tyr Ala Asn Asp Ala Tyr Xaa
            980                 985                 990

Xaa Gly Thr Xaa Cys Ser Ala Xaa Leu Lys Lys Ser Leu Val Asp Asn
        995                 1000                1005

Xaa Met Ile Tyr Gly Xaa Xaa Ser Xaa Lys Ala Gly Met Met Asn Pro
    1010                1015                1020

Ser Tyr Pro Leu Asn Tyr Met Glu Lys Pro Leu Thr Arg Leu Met Leu
1025                1030                1035                1040

Gly Arg Ser Trp Trp Asp Leu Asn Ile Lys Val Asp Val Glu Lys Tyr
                1045                1050                1055

Pro Gly Xaa Val Ser Xaa Xaa Gly Glx Xaa Val Thr Glu Xaa Ile Ser
            1060                1065                1070

Leu Tyr Ser Asn Pro Thr Lys Trp Phe Ala Gly Asn Met Gln Ser Thr
            1075                1080                1085

Gly Leu Trp Ala Pro Ala Gln Xaa Glu Val Thr Ile Xaa Ser Xaa Ala
            1090                1095                1100

Xaa Val Pro Val Thr Val Thr Val Ala Leu Ala Asp Asp Leu Thr Gly
1105                1110                1115                1120

Arg Glu Lys His Glu Val Ala Leu Asn Arg Pro Pro Xaa Val Thr Lys
                1125                1130                1135

Thr Tyr Xaa Leu Xaa Ala Xaa Gly Xaa Val Xaa Phe Lys Val Pro Tyr
            1140                1145                1150

Gly Gly Leu Ile Tyr Ile Lys Gly Asx Ser Xaa Xaa Asx Xaa Ser Ala
            1155                1160                1165

Xaa Phe Thr Phe Thr Gly Val Val Lys Ala Pro Phe Tyr Lys Asp Gly
    1170                1175                1180

Xaa Trp Lys Asn Xaa Leu Asx Ser Pro Ala Pro Leu Gly Glu Leu Glu
1185                1190                1195                1200

Ser Xaa Xaa Phe Val Tyr Thr Thr Pro Lys Lys Asn Leu Xaa Ala Ser
            1205                1210                1215

Asn Xaa Thr Gly Gly Xaa Xaa Glx Phe Ala Xaa Asp Leu Asp Thr Phe
            1220                1225                1230

Ala Ser Ser Met Asn Asp Phe Tyr Gly Arg Asx Xaa Glu Xaa Gly Lys
            1235                1240                1245

His Arg Met Phe Thr Tyr Lys Xaa Leu Thr Gly His Lys His Arg Phe
            1250                1255                1260

Thr Asn Asp Val Gln Ile Ser Ile Gly Asp Ala His Ser Gly Tyr Pro
1265                1270                1275                1280

Val Met Asn Ser Ser Phe Ser Thr Asn Ser Thr Thr Leu Pro Thr Thr
            1285                1290                1295

Pro Leu Asn Asp Trp Leu Ile Trp His Glu Val Gly Asn Ala Ala
            1300                1305                1310

Glu Thr Pro Leu Xaa Val Pro Gly Ala Thr Glu Val Ala Asn Asn Val
            1315                1320                1325

Leu Ala Leu Tyr Met Gln Asp Arg Tyr Leu Gly Lys Met Asn Arg Val
            1330                1335                1340

Ala Asp Asp Ile Thr Val Ala Pro Glu Tyr Leu Xaa Glu Ser Asn Gly
1345                1350                1355                1360

Gln Ala Trp Ala Arg Gly Gly Ala Gly Asp Arg Leu Leu Met Tyr Ala
```

-continued

```
                        1365                1370                1375

Gln Leu Lys Glu Trp Ala Glu Lys Asn Phe Asp Ile Lys Xaa Trp Tyr
            1380                1385                1390

Pro Xaa Gly Xaa Leu Pro Xaa Phe Tyr Ser Xaa Arg Glu Gly Met Lys
        1395                1400                1405

Gly Trp Asn Leu Phe Gln Leu Met His Arg Lys Ala Arg Gly Asp Xaa
    1410                1415                1420

Val Gly Xaa Xaa Xaa Phe Gly Xaa Xaa Asn Tyr Cys Ala Glu Ser Asn
1425                1430                1435                1440

Gly Asn Ala Ala Asp Thr Leu Met Leu Cys Ala Ser Trp Val Ala Gln
                1445                1450                1455

Thr Asp Leu Ser Glu Phe Phe Lys Lys Trp Asn Pro Gly Ala Asn Ala
            1460                1465                1470

Tyr Gln Leu Pro Gly Ala Xaa Glu Met Ser Phe Glu Gly Gly Val Ser
        1475                1480                1485

Gln Ser Ala Tyr Xaa Thr Leu Ala Xaa Leu Xaa Leu Pro Lys Pro Glx
    1490                1495                1500

Xaa Gly Pro Glu Thr Ile Asn Xaa Val Thr Glu His Lys Met Ser Ala
1505                1510                1515                1520

Glu
```

<210> SEQ ID NO 55
<211> LENGTH: 1538
<212> TYPE: PRT
<213> ORGANISM: Escherichia coli
<220> FEATURE:
<221> NAME/KEY: misc_feature
<222> LOCATION: 31, 37, 38, 42, 44, 47, 55, 56, 57, 58, 59,
60, 61, 62, 63, 64, 65, 66, 67, 68, 69, 70, 71, 72,
73, 74, 75, 76, 77, 78, 79, 80, 81, 83, 84, 85, 88,
89, 90, 91, 94, 101, 106, 108, 111, 112, 113, 116,
118, 125, 126, 128, 129, 131, 134, 136, 137, 157,
167, 171, 173, 177, 180, 185, 186, 193, 196, 199,
204, 205, 206, 207, 210, 211, 217, 219, 220, 221,
222, 224, 247, 248, 251, 254, 257, 272, 278, 282,
286, 289, 291, 293, 296, 303, 304, 310, 314, 316,
322, 363, 365, 366, 367, 368, 370, 371, 373, 376,
377, 380, 384, 401, 402, 404, 407, 409, 410, 411,
412, 413, 415, 420, 421, 422, 425, 426, 434, 435,
436, 437, 441, 442, 449, 454, 456, 459, 469, 470,
472, 475, 499, 504, 531, 543, 544, 550, 553, 566,
590, 592, 595, 596, 601, 602, 603, 605, 610, 622,
623, 625, 628, 630, 631, 639, 640, 645, 646, 650,
652, 653, 655, 657, 660, 663, 666, 667, 668, 669,
670, 671, 679, 680, 681, 695, 696, 697, 701, 702,
714, 725, 730, 748, 757, 769, 778, 781, 783, 784,
785, 794, 795, 796, 797, 798, 799, 800, 806, 807,
809, 810, 812, 817, 818, 819, 821, 823, 833, 835,
837, 839, 841, 842, 843, 844, 849, 851, 852, 853,
855, 856, 857, 859, 863, 864, 866, 867, 868, 870,
873, 874, 876, 878, 879, 884, 889, 891, 893, 894,
897, 899, 900, 901, 902, 903, 906, 909, 914, 916,
924, 929, 946, 948, 949, 954, 955, 965, 972, 973,
974, 976, 978, 979, 980, 982, 998, 1003, 1004, 1007,
1010, 1011, 1014, 1017, 1020, 1025, 1026, 1027, 1028,
1029, 1037, 1067, 1071, 1073, 1074, 1075, 1078, 1082,
1084, 1088, 1103, 1107, 1108, 1109, 1111, 1113, 1115,
1116, 1117, 1119, 1126, 1139, 1145, 1151, 1153, 1155,
1156, 1157, 1159, 1161, 1172, 1175, 1176, 1177, 1178,
1179, 1182, 1186, 1198, 1200, 1201, 1202, 1203, 1204,
1215, 1216, 1221, 1224, 1227, 1229, 1230, 1231, 1234,
1235, 1236, 1238, 1239, 1243, 1244, 1250, 1256, 1260,
1261, 1262, 1264, 1266, 1270, 1271, 1272, 1274, 1281,
1304, 1307, 1312, 1323, 1333, 1343, 1372, 1376, 1400,
1405, 1406, 1410, 1412, 1413, 1416, 1418, 1420, 1422,
1438, 1441, 1443, 1444, 1445, 1446, 1449, 1450, 1460,
1463, 1474, 1478, 1488, 1495, 1496, 1499, 1501, 1502,
1505, 1506, 1510, 1514, 1515, 1516, 1518, 1521, 1522, 1526, 1527, 1529, 1533, 1534, 1536, 1537
<223> OTHER INFORMATION: 'Xaa' is any amino acid
<220> FEATURE:
<221> NAME/KEY: misc_feature
<222> LOCATION: 323, 417, 541
<223> OTHER INFORMATION: 'Xaa' is Ile or Leu

<400> SEQUENCE: 55

| | | | | | | | | | | | | | | |
|---|---|---|---|---|---|---|---|---|---|---|---|---|---|---|
| Met | Asn | Lys | Lys | Phe | Lys | Tyr | Lys | Lys | Ser | Leu | Leu | Ala | Ala | Ile | Leu |
| 1 | | | | 5 | | | | | 10 | | | | | 15 | |
| Ser | Ala | Thr | Leu | Leu | Ala | Gly | Cys | Asp | Gly | Gly | Gly | Ser | Gly | Xaa | Ser |
| | | | 20 | | | | | 25 | | | | | 30 | | |
| Ser | Asp | Thr | Pro | Xaa | Xaa | Asp | Ser | Gly | Xaa | Gly | Xaa | Leu | Pro | Xaa | Val |
| | | 35 | | | | | 40 | | | | | 45 | | | |
| Lys | Pro | Asp | Pro | Thr | Pro | Xaa | Xaa | Xaa | Xaa | Xaa | Xaa | Xaa | Xaa | Xaa | |
| 50 | | | | | 55 | | | | | 60 | | | | | |
| Xaa | Xaa | Xaa | Xaa | Xaa | Xaa | Xaa | Xaa | Xaa | Xaa | Xaa | Xaa | Xaa | Xaa | Xaa | |
| 65 | | | | | 70 | | | | | 75 | | | | | 80 |
| Xaa | Pro | Xaa | Xaa | Xaa | Pro | Glu | Xaa | Xaa | Xaa | Pro | Val | Xaa | Thr | Lys | |
| | | | | 85 | | | | | 90 | | | | | 95 | |
| Thr | Gly | Tyr | Leu | Xaa | Leu | Gly | Gly | Ser | Xaa | Arg | Xaa | Thr | Gly | Xaa | Xaa |
| | | | 100 | | | | | 105 | | | | | 110 | | |
| Xaa | Cys | Asn | Xaa | Glu | Xaa | Ser | Asp | Gly | Phe | Thr | Phe | Xaa | Xaa | Gly | Xaa |
| | | 115 | | | | | 120 | | | | | 125 | | | |
| Xaa | Val | Xaa | Cys | Val | Xaa | Gly | Xaa | Xaa | Thr | Thr | Ile | Ala | Thr | Phe | Asx |
| | 130 | | | | | 135 | | | | | 140 | | | | |
| Thr | Gln | Ser | Glu | Ala | Ala | Arg | Ser | Leu | Arg | Ala | Val | Xaa | Lys | Val | Ser |
| 145 | | | | | 150 | | | | | 155 | | | | | 160 |
| Phe | Ser | Leu | Glu | Asp | Ala | Xaa | Glu | Leu | Ala | Xaa | Ser | Xaa | Asx | Lys | Lys |
| | | | | 165 | | | | | 170 | | | | | 175 | |
| Xaa | Asn | Ala | Xaa | Ser | Leu | Val | Thr | Xaa | Xaa | Asx | Ser | Cys | Pro | Ala | Asx |
| | | | 180 | | | | | 185 | | | | | 190 | | |
| Xaa | Glu | Gln | Xaa | Cys | Leu | Xaa | Phe | Ser | Ser | Val | Xaa | Xaa | Xaa | Xaa | Arg |
| | | 195 | | | | | 200 | | | | | 205 | | | |
| Phe | Xaa | Xaa | Leu | Tyr | Lys | Gln | Ile | Xaa | Leu | Xaa | Xaa | Xaa | Xaa | Phe | Xaa |
| | 210 | | | | | 215 | | | | | 220 | | | | |
| Lys | Leu | Val | Asn | Glu | Glu | Val | Glu | Asn | Asn | Ala | Ala | Thr | Asp | Lys | Ala |
| 225 | | | | | 230 | | | | | 235 | | | | | 240 |
| Pro | Ser | Thr | His | Thr | Ser | Xaa | Xaa | Val | Pro | Xaa | Thr | Thr | Xaa | Gly | Thr |
| | | | | 245 | | | | | 250 | | | | | 255 | |
| Xaa | Pro | Asp | Leu | Asn | Ala | Ser | Phe | Val | Ser | Ala | Asn | Ala | Glu | Gln | Xaa |
| | | | 260 | | | | | 265 | | | | | 270 | | |
| Tyr | Gln | Tyr | Gln | Pro | Xaa | Glu | Ile | Ile | Xaa | Ser | Glu | Gly | Xaa | Leu | Val |
| | | 275 | | | | | 280 | | | | | 285 | | | |
| Xaa | Ser | Xaa | Gly | Xaa | Gly | Val | Xaa | Gly | Val | Asx | Tyr | Tyr | Thr | Xaa | Xaa |
| | 290 | | | | | 295 | | | | | 300 | | | | |
| Gly | Arg | Gly | Val | Thr | Xaa | Glu | Asn | Gly | Xaa | Phe | Xaa | Phe | Ser | Trp | Gly |
| 305 | | | | | 310 | | | | | 315 | | | | | 320 |
| Glu | Xaa | Xaa | Ser | Phe | Gly | Ile | Asp | Thr | Phe | Glu | Leu | Gly | Ser | Val | Arg |
| | | | | 325 | | | | | 330 | | | | | 335 | |
| Gly | Asn | Lys | Ser | Thr | Ile | Ala | Leu | Thr | Glu | Leu | Gly | Asp | Glu | Val | Arg |
| | | | 340 | | | | | 345 | | | | | 350 | | |
| Gly | Ala | Asn | Ile | Asp | Gln | Leu | Ile | His | Arg | Xaa | Ser | Xaa | Xaa | Xaa | Xaa |
| | | 355 | | | | | 360 | | | | | 365 | | | |
| Asn | Xaa | Xaa | Arg | Xaa | Val | Pro | Xaa | Xaa | Val | Arg | Xaa | Val | Phe | Ala | Xaa |

```
                370             375             380
Tyr Pro Asn Val Ile Asn Glu Ile Ile Asn Leu Ser Leu Ser Asn Gly
385                 390                 395                 400

Xaa Xaa Leu Xaa Glu Gly Xaa Gln Xaa Xaa Xaa Xaa Asn Xaa Phe
                405                 410                 415

Xaa Glu Gln Xaa Xaa Xaa Gly Gln Xaa Xaa Glu Ile Asp Thr Ala Ile
                    420                 425                 430

Cys Xaa Xaa Xaa Xaa Gly Cys Asn Xaa Xaa Arg Trp Phe Ser Leu Thr
                435                 440                 445

Xaa Arg Asn Val Asn Xaa Gly Xaa Ile Gln Xaa Val Ile Asn Lys Leu
                450                 455                 460

Trp Gly Val Asp Xaa Xaa Tyr Xaa Ser Val Xaa Lys Phe His Val Phe
465                 470                 475                 480

His Asp Ser Thr Asn Phe Tyr Gly Ser Thr Gly Asn Ala Arg Gly Gln
                    485                 490                 495

Ala Val Xaa Asn Ile Ser Asn Xaa Ala Phe Pro Ile Leu Met Ala Arg
                500                 505                 510

Asn Asp Lys Asn Tyr Trp Leu Ala Phe Gly Glu Lys Arg Ala Trp Asp
                515                 520                 525

Lys Asn Xaa Leu Ala Tyr Ile Thr Glu Ala Pro Ser Xaa Val Xaa Xaa
                530                 535                 540

Glu Asn Val Thr Arg Xaa Thr Ala Xaa Phe Asn Leu Pro Phe Ile Ser
545                 550                 555                 560

Leu Gly Gln Val Gly Xaa Gly Lys Leu Met Val Ile Gly Asn Pro His
                    565                 570                 575

Tyr Asn Ser Ile Leu Arg Cys Pro Asn Gly Tyr Ser Trp Xaa Gly Xaa
                580                 585                 590

Val Asx Xaa Xaa Gly Glx Cys Thr Xaa Xaa Xaa Asp Xaa Asx Asp Met
                595                 600                 605

Lys Xaa Phe Met Glx Asn Val Leu Arg Tyr Leu Ser Asx Xaa Xaa Trp
                610                 615                 620

Xaa Pro Asx Xaa Lys Xaa Xaa Met Thr Val Gly Thr Asn Leu Xaa Xaa
625                 630                 635                 640

Val Tyr Phe Lys Xaa Xaa Gly Gln Val Xaa Gly Xaa Xaa Ala Xaa Phe
                    645                 650                 655

Xaa Phe His Xaa Asp Phe Xaa Gly Ile Xaa Xaa Xaa Xaa Xaa Xaa Ser
                660                 665                 670

Tyr Gly Asx Leu Asx Pro Xaa Xaa Xaa Pro Leu Leu Ile Leu Asn Gly
                675                 680                 685

Phe Glu Tyr Val Thr Gln Xaa Xaa Xaa Asp Pro Tyr Xaa Xaa Pro Leu
690                 695                 700

Arg Ala Asp Thr Ser Lys Pro Lys Leu Xaa Gln Gln Asp Val Thr Asp
705                 710                 715                 720

Leu Ile Ala Tyr Xaa Asn Lys Gly Gly Xaa Val Leu Ile Met Glu Asn
                    725                 730                 735

Val Met Ser Asn Leu Lys Glu Glu Ser Ala Ser Xaa Phe Val Arg Leu
                740                 745                 750

Leu Asp Ala Ala Xaa Leu Ser Met Ala Leu Asn Lys Ser Val Val Asn
                755                 760                 765

Xaa Asp Pro Gln Gly Tyr Pro Asx Arg Xaa Arg Gln Xaa Arg Xaa Xaa
                770                 775                 780

Xaa Ile Trp Val Tyr Glu Arg Tyr Pro Xaa Xaa Xaa Xaa Xaa Xaa Xaa
785                 790                 795                 800
```

```
Pro Tyr Thr Ile Asx Xaa Xaa Thr Xaa Xaa Val Xaa Trp Lys Tyr Gln
            805                 810                 815

Xaa Xaa Xaa Lys Xaa Asp Xaa Lys Pro Lys Leu Glu Val Ala Ser Trp
            820                 825                 830

Xaa Glu Xaa Val Xaa Gly Xaa Gln Xaa Xaa Xaa Ala Phe Ile Asp
            835                 840                 845

Xaa Ala Xaa Xaa Xaa Thr Xaa Xaa Xaa Leu Xaa Ala Ala Lys Xaa Xaa
        850                 855                 860

Ile Xaa Xaa Xaa Phe Xaa Gly Leu Xaa Cys Xaa Asx Xaa Xaa Tyr
865             870                 875                 880

His Tyr Glu Xaa Asn Cys Leu Glu Xaa Arg Xaa Gly Xaa Xaa Val Pro
            885                 890                 895

Xaa Thr Xaa Xaa Xaa Xaa Xaa Gly Met Xaa Val Pro Xaa Tyr Thr Gln
            900                 905                 910

Leu Xaa Leu Xaa Ala Asp Thr Ala Lys Ala Met Xaa Gln Ala Ala Asp
        915                 920                 925

Xaa Gly Thr Asn Ile Gln Arg Leu Tyr Gln His Glu Leu Tyr Phe Arg
        930                 935                 940

Thr Xaa Gly Xaa Xaa Gly Glu Arg Leu Xaa Xaa Val Asp Leu Glu Arg
945             950                 955                 960

Leu Tyr Gln Asn Xaa Ser Val Trp Leu Trp Asn Xaa Xaa Xaa Tyr Xaa
            965                 970                 975

Tyr Xaa Xaa Xaa Lys Xaa Asp Glu Leu Gly Phe Lys Thr Phe Thr Glu
        980                 985                 990

Phe Leu Asn Cys Tyr Xaa Asn Asx Ala Tyr Xaa Xaa Gly Thr Xaa Cys
            995                 1000                1005

Ser Xaa Xaa Leu Lys Xaa Ser Leu Xaa Asp Asn Xaa Met Ile Tyr Gly
        1010                1015                1020

Xaa Xaa Xaa Xaa Xaa Lys Ala Gly Met Met Asn Pro Xaa Tyr Pro Leu
1025            1030                1035                1040

Asn Tyr Met Glu Lys Pro Leu Thr Arg Leu Met Leu Gly Arg Ser Trp
            1045                1050                1055

Trp Asp Leu Asn Ile Lys Val Asp Val Glu Xaa Tyr Pro Gly Xaa Val
            1060                1065                1070

Xaa Xaa Xaa Gly Glx Xaa Val Thr Glx Xaa Ile Xaa Leu Tyr Ser Xaa
        1075                1080                1085

Pro Thr Lys Trp Phe Ala Gly Asn Met Gln Ser Thr Gly Leu Xaa Ala
        1090                1095                1100

Pro Ala Xaa Xaa Xaa Val Xaa Ile Xaa Ser Xaa Xaa Xaa Val Xaa Val
1105            1110                1115                1120

Thr Val Thr Val Ala Xaa Ala Asp Asp Leu Thr Gly Arg Glu Lys His
            1125                1130                1135

Glu Val Xaa Leu Asn Arg Pro Pro Xaa Val Thr Lys Thr Tyr Xaa Leu
            1140                1145                1150

Xaa Ala Xaa Xaa Xaa Val Xaa Phe Xaa Val Pro Tyr Gly Gly Leu Ile
        1155                1160                1165

Tyr Ile Lys Xaa Asx Ser Xaa Xaa Xaa Xaa Ser Ala Xaa Phe Thr
1170            1175                1180

Phe Xaa Gly Val Val Lys Ala Pro Phe Tyr Lys Asx Gly Xaa Trp Xaa
1185            1190                1195                1200

Xaa Xaa Xaa Xaa Ser Pro Ala Pro Leu Gly Glu Leu Glu Ser Xaa Xaa
                1205                1210                1215
```

```
Phe Val Tyr Thr Xaa Pro Lys Xaa Asn Leu Xaa Ala Xaa Xaa Xaa Ser
        1220              1225                1230

Asn Xaa Xaa Xaa Gly Xaa Xaa Glx Phe Ala Xaa Xaa Leu Asp Thr Phe
    1235                1240                1245

Ala Xaa Ser Met Asn Asp Phe Xaa Gly Arg Asx Xaa Xaa Xaa Gly Xaa
    1250                1255                1260

His Xaa Met Phe Thr Xaa Xaa Xaa Leu Xaa Gly His Lys His Arg Phe
1265            1270                1275                1280

Xaa Asn Asp Val Gln Ile Ser Ile Gly Asp Ala His Ser Gly Tyr Pro
            1285                1290                1295

Val Met Asn Ser Ser Phe Ser Xaa Asx Ser Xaa Thr Leu Pro Thr Xaa
        1300                1305                1310

Pro Leu Asn Asp Trp Leu Ile Trp His Glu Xaa Gly His Asn Ala Ala
        1315                1320                1325

Glu Thr Pro Leu Xaa Val Pro Gly Ala Thr Glu Val Ala Asn Xaa Val
        1330                1335                1340

Leu Ala Leu Tyr Met Gln Asp Arg Tyr Leu Gly Lys Met Asn Arg Val
1345            1350                1355                1360

Ala Asp Asp Ile Thr Val Ala Pro Glu Tyr Leu Xaa Glu Ser Asn Xaa
            1365                1370                1375

Gln Ala Trp Ala Arg Gly Gly Ala Gly Asp Arg Leu Leu Met Tyr Ala
        1380                1385                1390

Gln Leu Lys Glu Trp Ala Glu Xaa Asn Phe Asp Ile Xaa Xaa Trp Tyr
        1395                1400                1405

Pro Xaa Gly Xaa Xaa Leu Pro Xaa Phe Xaa Ser Xaa Arg Xaa Gly Met
    1410                1415                1420

Lys Gly Trp Asn Leu Phe Gln Leu Met His Arg Lys Ala Xaa Gly Asp
1425            1430                1435                1440

Xaa Val Xaa Xaa Xaa Xaa Phe Gly Xaa Xaa Asn Tyr Cys Ala Glu Ser
            1445                1450                1455

Asn Gly Asn Xaa Ala Asp Xaa Leu Met Leu Cys Ala Ser Trp Val Ala
        1460                1465                1470

Gln Xaa Asp Leu Ser Xaa Phe Phe Lys Lys Trp Asn Pro Gly Ala Xaa
        1475                1480                1485

Ala Tyr Gln Leu Pro Gly Xaa Xaa Glu Met Xaa Phe Xaa Xaa Gly Val
        1490                1495                1500

Xaa Xaa Ser Ala Tyr Xaa Thr Leu Ala Xaa Xaa Xaa Leu Xaa Lys Pro
1505            1510                1515                1520

Xaa Xaa Gly Pro Glu Xaa Xaa Asn Xaa Val Thr Glu Xaa Xaa Met Xaa
            1525                1530                1535

Xaa Glu

<210> SEQ ID NO 56
<211> LENGTH: 26
<212> TYPE: DNA
<213> ORGANISM: Artificial Sequence
<220> FEATURE:
<223> OTHER INFORMATION: immunostimulatory oligonucleotide
<220> FEATURE:
<221> NAME/KEY: modified_base
<222> LOCATION: 1, 3, 5, 7, 9, 11, 13, 15, 17, 19, 21, 23, 25
<223> OTHER INFORMATION: 'n' is 'i' (Inosine)

<400> SEQUENCE: 56 ncncncnc ncncncnc ncncnc                                          26
```

```
<210> SEQ ID NO 57
<211> LENGTH: 11
<212> TYPE: PRT
<213> ORGANISM: Artificial Sequence
<220> FEATURE:
<223> OTHER INFORMATION: polycationic oligopeptide

<400> SEQUENCE: 57

Lys Leu Lys Leu Leu Leu Leu Leu Lys Leu Lys
1               5                   10
```

The invention claimed is:

1. An immunogenic composition comprising a combination of
   (i) an immunologically effective amount of an isolated bacterial Ig-like domain protein fragment (orf405B) comprising
      (i-a) an amino acid sequence having at least 95% sequence identity to SEQ ID NO: 2, or
      (i-b) a fragment of SEQ ID NO: 2, wherein the fragment of SEQ ID NO: 2 consists of at least 20 consecutive amino acids and the fragment includes a B cell epitope of the amino acid sequence of SEQ ID NO: 2,
   wherein concentration of the isolated protein recited in (i) is at least 0.2 µg per unit dose, and
   (ii) an immunologically effective amount of an isolated putative Lipoprotein (orf3526) comprising
      (ii-a) an amino acid sequence having at least 95% sequence identity to SEQ ID NO: 8, or
      (ii-b) a fragment of SEQ ID NO: 8, wherein the fragment of SEQ ID NO: 8 consists of at least 20 consecutive amino acids and the fragment includes a B cell epitope of the amino acid sequence of SEQ ID NO: 8,
   wherein concentration of the isolated protein recited in (ii) is at least 0.2 µg per unit dose.

2. The immunogenic composition of claim 1 which further comprises at least one bacterial toxin.

3. The immunogenic composition of claim 2 wherein the bacterial toxin is an *Escherichia coli* toxin.

4. The immunogenic composition of claim 3 wherein the bacterial toxin is modified heat-labile toxin of *Escherichia coli* (LTK63).

5. The immunogenic composition of claim 1 (ii-a) wherein the putative Lipoprotein (orf3526) is a mutant protein wherein at least one amino acid at positions 1304, 1305, 1306, 1307 and/or 1308 with reference to SEQ ID NO: 8 is/are substituted by another amino acid and wherein the zinc binding activity of the mutant orf3526 protein is reduced by at least 50%→relative to wild-type orf3526.

6. The immunogenic composition of claim 1 which further comprises one or more pharmaceutically acceptable carriers, diluents and/or adjuvants.

7. The immunogenic composition of claim 6 which is a vaccine composition.

* * * * *